US011801301B2

(12) United States Patent
Deisseroth et al.

(10) Patent No.: US 11,801,301 B2
(45) Date of Patent: Oct. 31, 2023

(54) LIGHT-RESPONSIVE POLYPEPTIDES AND METHODS OF USE THEREOF

(71) Applicant: The Board of Trustees of the Leland Stanford Junior University, Stanford, CA (US)

(72) Inventors: Karl A. Deisseroth, Stanford, CA (US); Andre Berndt, Mountain View, CA (US); Soo Yeun Lee, Palo Alto, CA (US); Charu Ramakrishnan, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 805 days.

(21) Appl. No.: 15/756,936

(22) PCT Filed: Sep. 14, 2016

(86) PCT No.: PCT/US2016/051684
§ 371 (c)(1),
(2) Date: Jul. 31, 2018

(87) PCT Pub. No.: WO2017/048808
PCT Pub. Date: Mar. 23, 2017

(65) Prior Publication Data
US 2018/0250402 A1    Sep. 6, 2018

Related U.S. Application Data

(60) Provisional application No. 62/218,971, filed on Sep. 15, 2015.

(51) Int. Cl.
| | |
|---|---|
| *C07K 14/00* | (2006.01) |
| *C12N 15/79* | (2006.01) |
| *C07H 21/04* | (2006.01) |
| *A61K 41/00* | (2020.01) |
| *A61N 5/06* | (2006.01) |
| *C07K 14/405* | (2006.01) |
| *A61K 38/00* | (2006.01) |
| *C12N 15/86* | (2006.01) |
| *C12N 15/85* | (2006.01) |

(52) U.S. Cl.
CPC ............... *A61K 41/00* (2013.01); *A61N 5/06* (2013.01); *A61N 5/062* (2013.01); *C07K 14/00* (2013.01); *C07K 14/405* (2013.01); *A61K 38/00* (2013.01); *C07K 2319/01* (2013.01); *C07K 2319/04* (2013.01); *C12N 15/85* (2013.01); *C12N 15/86* (2013.01); *C12N 2750/14143* (2013.01)

(58) Field of Classification Search
CPC ........ A61K 41/00; A61K 38/00; C07K 14/00; C07K 2319/01; C07K 2319/04; C12N 15/85; C12N 15/86; C07H 21/04
See application file for complete search history.

(56) References Cited

U.S. PATENT DOCUMENTS

| | | |
|---|---|---|
| 8,759,492 B2 | 6/2014 | Lin et al. |
| 2011/0165681 A1 | 7/2011 | Boyden et al. |
| 2012/0034691 A1 | 2/2012 | Looger et al. |
| 2012/0121542 A1 | 5/2012 | Chuong et al. |
| 2012/0214188 A1 | 8/2012 | Klapoetke et al. |
| 2013/0066402 A1 | 3/2013 | Lin et al. |
| 2013/0224756 A1 | 8/2013 | Cohen et al. |
| 2013/0317569 A1 | 11/2013 | Deisseroth et al. |
| 2014/0101785 A1 | 4/2014 | Looger et al. |
| 2015/0202456 A1 | 7/2015 | Andersen et al. |
| 2015/0226755 A1 | 8/2015 | Ai et al. |
| 2015/0246242 A1 | 9/2015 | Delp et al. |

FOREIGN PATENT DOCUMENTS

| | | |
|---|---|---|
| CN | 101663066 A | 3/2010 |
| CN | 103313752 A | 9/2013 |
| WO | WO 2009/119782 | 10/2009 |
| WO | WO 2015/148974 | 10/2015 |
| WO | WO 2016/090172 | 6/2016 |
| WO | WO 2017/087542 | 5/2017 |

OTHER PUBLICATIONS

Gradinaru, (Brain Cell Biology, (36): 129-139, 2008). (Year: 2008).*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Cruz et al., 2017, Methods in Molecular Biology, vol. 1654, Chapter 5, pp. 55-75.*
Kato et al., (2012) "Crystal structure of the channelrhodopsin light-gated cation channel," Nature 482, 369-374.
Plazzo et al., (2012) "Bioinformatic and Mutational Analysis of Channelrhodopsin-2 Protein Cation-conducting Pathway," The journal of Biological Chemistry, 287(7): 4818-4825.
Wietek et al., (2014) "Conversion of Channelrhodopsin into a Light-Gated Chloride Channel," Science, 344, 409-412.
Lin et al.; "ReaChR: a Red-Shifted Variant of Channelrhodopsin Enables Deep Transcranial Optogenetic Excitation"; Nature Neuroscience; vol. 16, No. 10, pp. 1499-1508 (Sep. 1, 2013).

(Continued)

*Primary Examiner* — Shin Lin Chen
(74) *Attorney, Agent, or Firm* — Rudy J. Ng; Bozicevic, Field & Francis LLP

(57) ABSTRACT

The present disclosure provides variant light-responsive polypeptides, and nucleic acids comprising nucleotide sequences encoding the light-responsive polypeptides. The present disclosure provides methods, devices, and systems for controlling the activity of a cell expressing a variant light-responsive polypeptide of the present disclosure.

8 Claims, 72 Drawing Sheets

Specification includes a Sequence Listing.

(56) References Cited

OTHER PUBLICATIONS

Arenkiel, et al. "In vivo light-induced activation of neural circuitry in transgenic mice expressing Channelrhodopsin-2", Neuron, 2007, 54:205-218.
Chadman (2009) "Criteria for validating mouse models of psychiatric diseases," American J. of Medical Genetics, vol. 150B, Issue 1, p. 1-11.
Cardin, et al. (2010) "Targeted optogenetic stimulation and recording of neurons in vivo using cell-type-specific expression of Channelrhodopsin-2"; Nature Protocols; vol. 5, No. 2, pp. 247-254.
Deisseroth (2006) "Next-generation optical technologies for illuminating genetically targeted brain circuits," The Journal of Neuroscience, vol. 26, No. 41, pp. 10380-10386.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
MGI description of "Exploration behavior", 2018 1 page.
Nester and Hyman (2013) "Animal models of neuropsychiatric disorders," Nat. Neuroscience 13(10) p. 1161-1169.
Powell, et al. (2006) "Schizophrenia-Relevant Behavioral Testing in Rodent Models: A Uniquely Human Disorder?" Biol. Psychiatry; vol. 59, pp. 1198-1207.
Simmons et al. (2008) "Localization and function of NK3 subtype Tachykinin receptors of layer pyramidal neurons of the guinea-pig medial prefrontal cortex", Neuroscience, vol. 156, No. 4: pp. 987-994.
Stuber (2010) Dissecting the neural circuitry of addiction and psychiatric disease with optogenetics; Neuropsychopharmacology; vol. 35, No. 1, pp. 341-342 (2010).
Wang, et al., (2007) "High-speed mapping of synaptic connectivity using photostimulation in Channelrhodopsin-2 transgenic mice", PNAS, vol. 104, No. 19, pp. 8143-8148.
Wikipedia description of optogenetics, 2018 1 page.

\* cited by examiner

FIG. 1
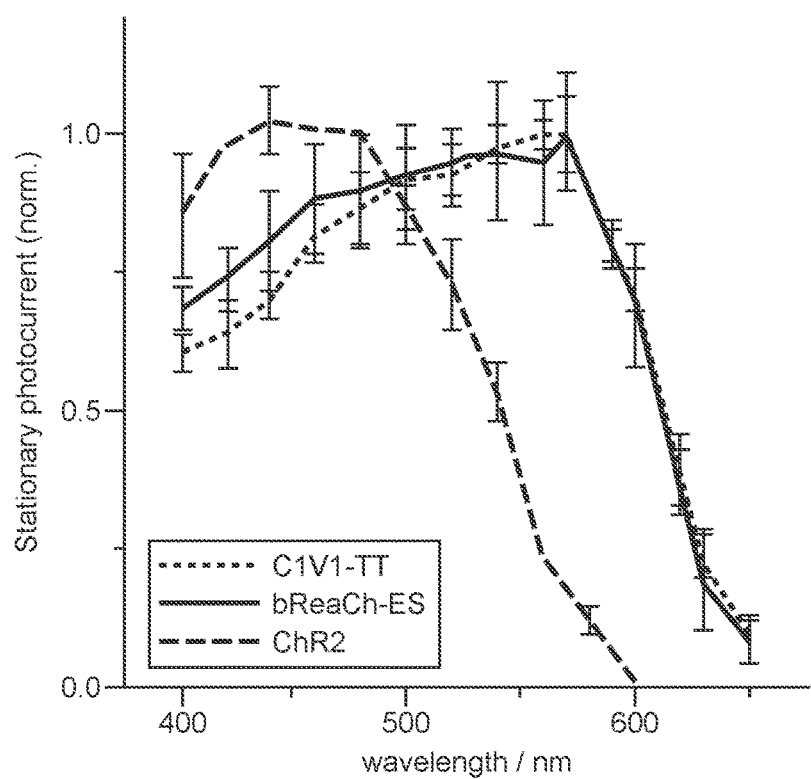

FIG. 1 (Cont.)
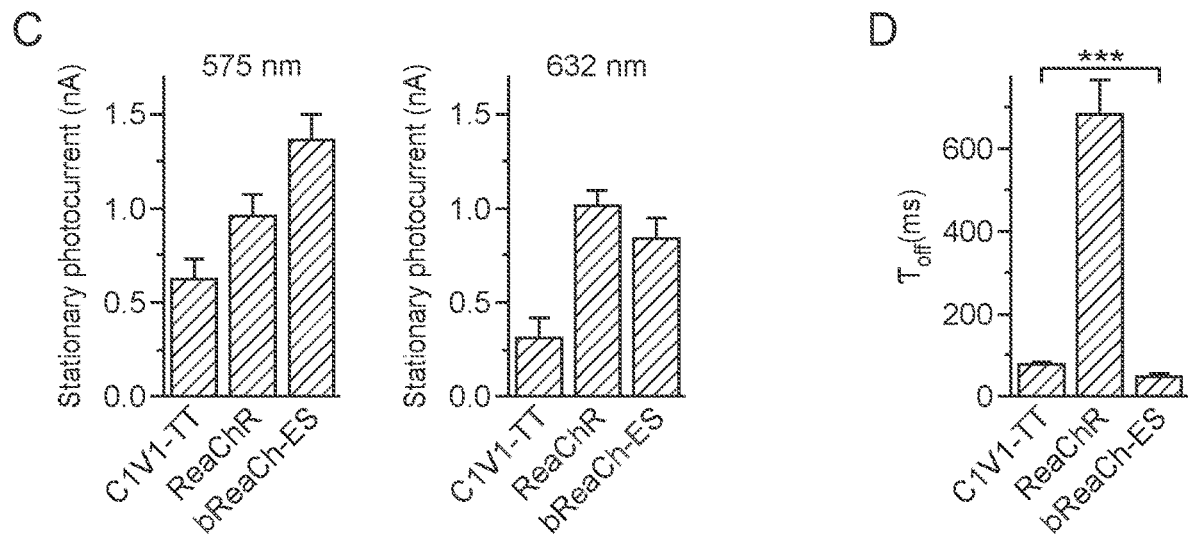
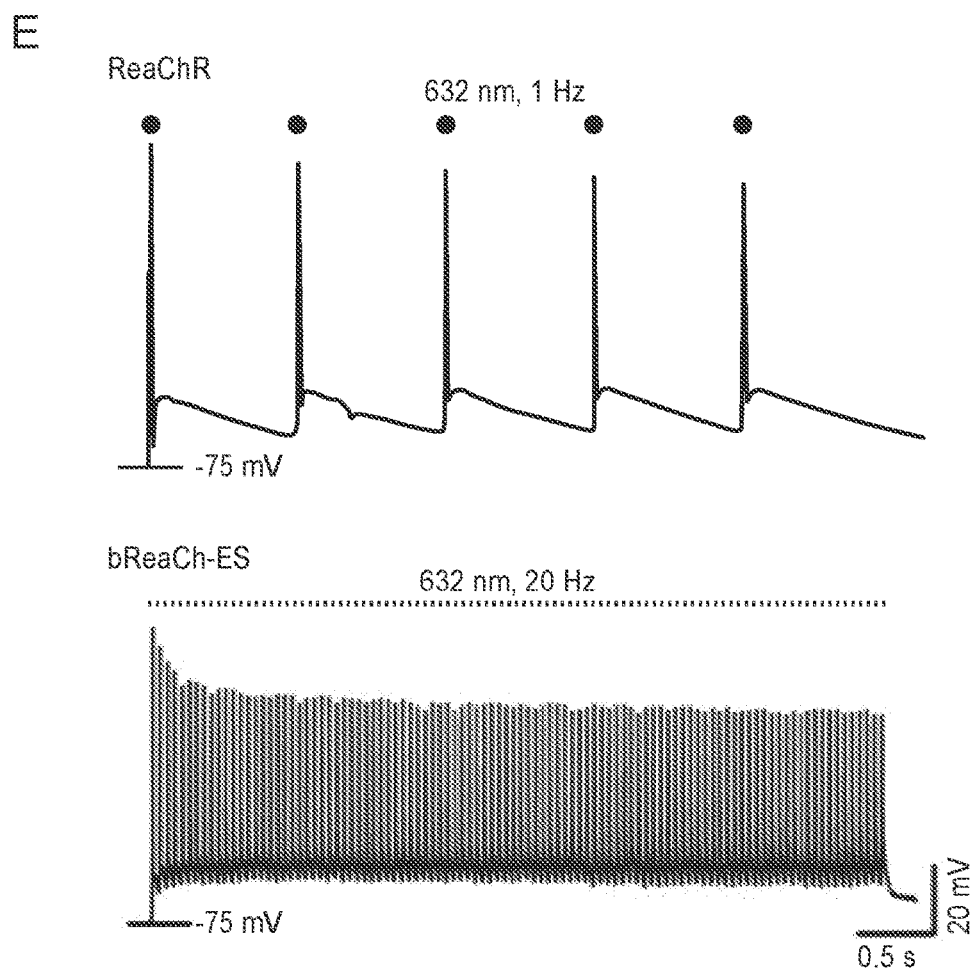

FIG. 2
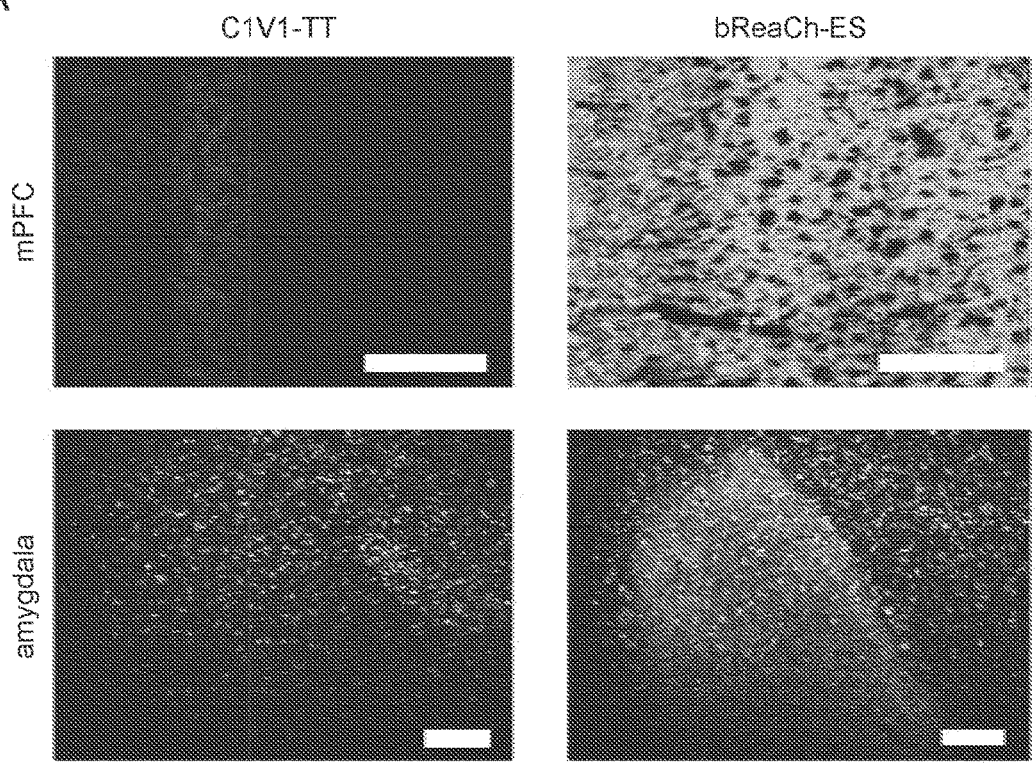
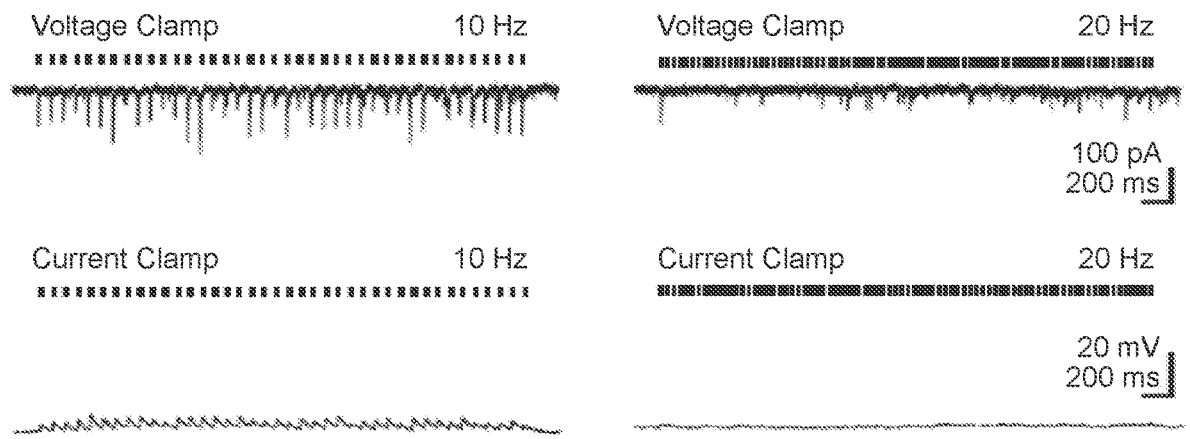

FIG. 3
A
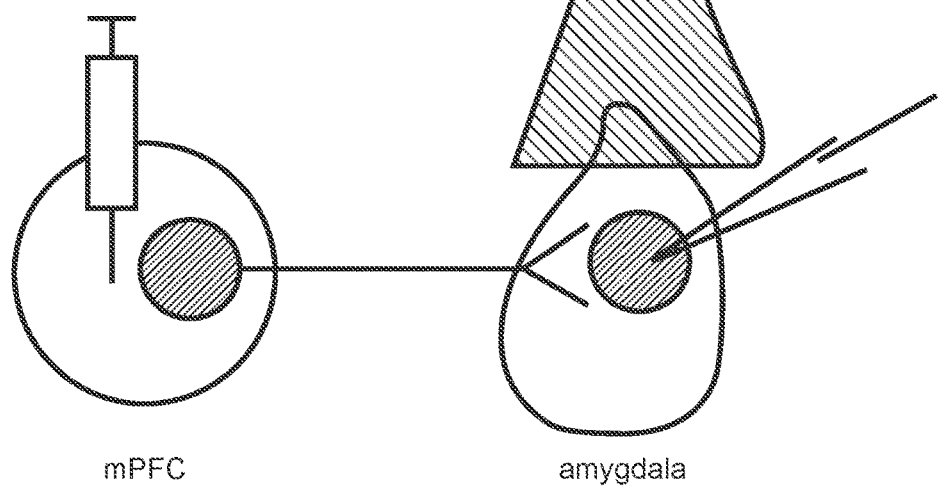
B
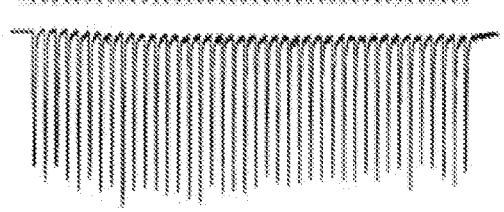
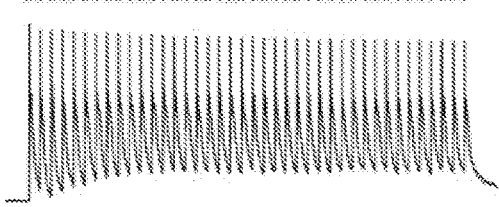
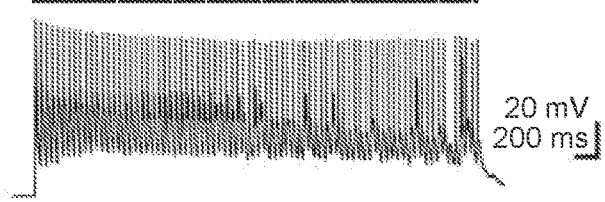

FIG. 4A

Amino acid sequence of ReaChR (SEQ ID NO:1)
MVSRRPWLLALALAVALAAGSAGASTGSDATVPVATQDGPDYVFHRAHER
MLFQTSYTLENNGSVICIPNNGQCFCLAWLKSNGTNAEKLAANILQWVVFA
LSVACLGWYAYQAWRATCGWEEVYVALIEMMKSIIEAFHEFDSPATLWLSSG
NGVVWMRYGEWLLTCPVILIHLSNLTGLKDDYSKRTMGLLVSDVGCIVWGA
TSAMCTGWTKILFFLISLSYGMYTYFHAAKVYIEAFHTVPKGLCRQLVRAM
AWLFFVSWGMFPVLFLLGPEGFGHISPYGSAIGHSILDLIAKNMWGVLGNYL
RVKIHEHILLYGDIRKKQKITIAGQEMEVETLVAEEEDKYESS
E = amino acid 163

FIG. 4B

Amino acid sequence of ReaChRE-S (SEQ ID NO:2)
MVSRRPWLLALALAVALAAGSAGASTGSDATVPVATQDGPDYVFHRAHER
MLFQTSYTLENNGSVICIPNNGQCFCLAWLKSNGTNAEKLAANILQWVVFA
LSVACLGWYAYQAWRATCGWEEVYVALIEMMKSIIEAFHEFDSPATLWLSSG
NGVVWMRYGSWLLTCPVILIHLSNLTGLKDDYSKRTMGLLVSDVGCIVWGA
TSAMCTGWTKILFFLISLSYGMYTYFHAAKVYIEAFHTVPKGLCRQLVRAM
AWLFFVSWGMFPVLFLLGPEGFGHISPYGSAIGHSILDLIAKNMWGVLGNYL
RVKIHEHILLYGDIRKKQKITIAGQEMEVETLVAEEEDKYESS
S = amino acid 163

FIG. 4C

Amino acid sequence of bReaChE-S (SEQ ID NO:3)
MDYGGALSAVGLFQTSYTLENNGSVICIPNNGQCFCLAWLKSNGTNAEKLA
ANILQWVVFALSVACLGWYAYQAWRATCGWEEVYVALIEMMKSIIEAFHEF
DSPATLWLSSGNGVVWMRYGSWLLTCPVILIHLSNLTGLKDDYSKRTMGLLV
SDVGCIVWGATSAMCTGWTKILFFLISLSYGMYTYFHAAKVYIEAFHTVPKG
LCRQLVRAMAWLFFVSWGMFPVLFLLGPEGFGHISPYGSAIGHSILDLIAKN
MWGVLGNYLRVKIHEHILLYGDIRKKQKITIAGQEMEVETLVAEEED
S = amino acid 123

FIG. 4D bReaChE-S + trafficking sequence + ER export sequence (SEQ ID NO:4)
MDYGGALSAVGLFQTSYTLENNGSVICIPNNGQCFCLAWLKSNGTNAEKLA
ANILQWVVFALSVACLGWYAYQAWRATCGWEEVYVALIEMMKSIIEAFHEF
DSPATLWLSSGNGVVWMRYGSWLLTCPVILIHLSNLTGLKDDYSKRTMGLLV
SDVGCIVWGATSAMCTGWTKILFFLISLSYGMYTFHAAKVYIEAFHTVPKG
LCRQLVRAMAWLFFVSWGMFPVLFLLGPEGFGHISPYGSAIGHSILDLIAKN
MWGVLGNYLRVKIHEHILLYGDIRKKQKITIAGQEMEVETLVAEEEDAAAKS
RITSEGEYIPLDQIDINVFCYENEV
S = amino acid 123
Boxed outline = trafficking sequence
Boxed outline and underlined = ER export sequence

FIG. 4E

Amino acid sequence of bReaChE-S no signal sequence (SEQ ID NO:5)
LFQTSYTLENNGSVICIPNNGQCFCLAWLKSNGTNAEKLAANILQWVVFALS
VACLGWYAYQAWRATCGWEEVYVALIEMMKSIIEAFHEFDSPATLWLSSGN
GVVWMRYGSWLLTCPVILIHLSNLTGLKDDYSKRTMGLLVSDVGCIVWGAT
SAMCTGWTKILFFLISLSYGMYTYFHAAKVYIEAFHTVPKGLCRQLVRAMA
WLFFVSWGMFPVLFLLGPEGFGHISPYGSAIGHSILDLIAKNMWGVLGNYLR
VKIHEHILLYGDIRKKQKITIAGQEMEVETLVAEEED
S = amino acid 112

FIG. 4F

Amino acid sequence of bReaChE-S no signal sequence + trafficking sequence + ER
export (SEQ ID NO:6)
LFQTSYTLENNGSVICIPNNGQCFCLAWLKSNGTNAEKLAANILQWVVFALS
VACLGWYAYQAWRATCGWEEVYVALIEMMKSIIEAFHEFDSPATLWLSSGN
GVVWMRYGSWLLTCPVILIHLSNLTGLKDDYSKRTMGLLVSDVGCIVWGAT
SAMCTGWTKILFFLISLSYGMYTYFHAAKVYIEAFHTVPKGLCRQLVRAMA
WLFFVSWGMFPVLFLLGPEGFGHISPYGSAIGHSILDLIAKNMWGVLGNYLR
VKIHEHILLYGDIRKKQKITIAGQEMEVETLVAEEEDAAAKSRITSEGEYIPLD
QIDINVFCYENEV
S = amino acid 112
Boxed outline = trafficking sequence
Boxed outline and underlined = ER export sequence

FIG. 5A

GCaMPK (SEQ ID NO:7)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKYTDSEEEIGEAFRVFDKDGNGYISAAELR
HVMTNLGEKLTDEEVDEMIREADIDGDGQVNYEEFVQMMTAK

FIG. 5B

GCaMP2 (SEQ ID NO:8)
MRGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTSEEEIREAFRVFDKDGNGYISAAELRH
VMTNLGEKLTDEEVDEMIREADIDGDGQVNYEEFVQMMTAK

FIG. 5C

GCaMP2.1 (SEQ ID NO:9)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 5D

GCaMP2.2a (SEQ ID NO:10)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 5E

GCaMP2.2b (SEQ ID NO:11)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSTQCKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 5F

GCaMP2.3 (SEQ ID NO:12)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGNGTIDFPEFLTMMARKMKDTDSEEEIREAFRVFDKDGNGYISAAELRH
VMTNLGEKLTDEEVDEMIREADIDGDGQVNYEEFVQMMTAK

FIG. 5G

GCaMP2.4 (SEQ ID NO:13)
MGSHHHHHHGMASMTGGQQMGRDLYDDDDKDLATMVDSSRRKWNKTG
HAVRAIGRLSSLENVYIMADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKDTDSEEEIREAFRVFDKDGNGYISAAELRH
VMTNLGEKLTDEEVDEMIREADIDGDGQVNYEEFVQMMTAK

FIG. 5H

GCaMP3 (SEQ ID NO:14)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNTRDQ
LTEEQIAEFKEAFSLFDKDGDGTITTKELGTVMRSLGQNPTEAELQDMINEV
DADGDGTIDFPEFLTMMARKMKDTDSEEEIREAFRVFDKDGNGYISAAELRH
VMTNLGEKLTDEEVDEMIREADIDGDGQVNYEEFVQMMTAK

FIG. 5I

GCaMP5g (SEQ ID NO:15)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYTDSEEEIREAFRVFDKDGNGYISAAELRHV
MTNLGEKLTDEEVDEMIREADIDGDGQVNYEEFVQMMTAK

FIG. 5J

GCaMP6m (SEQ ID NO:16)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKGSYRDTEEEIREAFGVFDKDGNGYISAAELRHV
MTNLGEKLTDEEVDEMIREADIDGDGQVNYEEFVQMMTAK

FIG. 5K

GCaMP6s (SEQ ID NO:17)
MGSHHHHHHGMASMTGGQQMGRDLYDDDDKDLATMVDSSRRKWNKTG
HAVRAIGRLSSLENVYIKADKQKNGIKANFHIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEAFSLFDKDGDGTITTKELGTVMRSLGQNPTEAELQDMINEVD
ADGDGTIDFPEFLTMMARKMKYRDTEEEIREAFGVFDKDGNGYISAAELRH
VMTNLGEKLTDEEVDEMIREADIDGDGQVNYEEFVQMMTAK

FIG. 5L

GCaMP6f (SEQ ID NO:18)
MGSHHHHHHGMASMTGGQQMGRDLYDDDDKDLATMVDSSRRKWNKTG
HAVRAIGRLSSLENVYIKADKQKNGIKANFKIRHNIEDGGVQLAYHYQQNTP
IGDGPVLLPDNHYLSVQSKLSKDPNEKRDHMVLLEFVTAAGITLGMDELYK
GGTGGSMVSKGEELFTGVVPILVELDGDVNGHKFSVSGEGEGDATYGKLTL
KFICTTGKLPVPWPTLVTTLTYGVQCFSRYPDHMKQHDFFKSAMPEGYIQER
TIFFKDDGNYKTRAEVKFEGDTLVNRIELKGIDFKEDGNILGHKLEYNLPDQL
TEEQIAEFKEEFSLFDKDGDGTITTKELGTVMRSLGQNPTEAELQDMINEVD
ADGDGTIDFPEFLTMMARKMKYRDTEEEIREAFGVFDKDGNGYISAAELRH
VMTNLGEKLTDEEVDEMIREADIDGDGQVNYEEFVQMMTAK

FIG. 5M

GEM-GECO1 (GenBank ID: JN258409) (SEQ ID NO:19)
MVDSSRRKWNKTGHAVRAIGRLSSPENVYIKADEQKNGIKAYFKIRHNIEGG
GVQLAYHYQQITPIGDGPVLLPDNHYLSVQSILSKDPNEKRDHMVLLEFVTA
AGITLGMDELYKGGSGGMVSKGEELFTGVVPIQVELDGDVNGHKFSVSGEG
EGDATYGKLTLKFICTTGKLPVPWPTLVTTLSYGVQCFSRYPDHMKQHDFFK
SAMPEGYIQERTIFFKDDGNYKTRAEVKFEGDTLVNRIELKGIDFKEDGNILG
HKLEYSTRDQLTEEQIAEFKEAFSLFDKDGDGTITTKELGTVMRSLGQNPTE
AELQDMINEVDADGDGTIDFPEFLTMMAPKMQDTDSEEEIREAFRVFDKDG
NGYIGAAELRHVMTNLGEKLTDEEVDEMIRVADIDGDGQVNYEEFVQMMT
AK

FIG. 5N

GEX-GECO1 (GenBank ID: JN258410) (SEQ ID NO:20)
MVDSSRRKWNKTGHAVRAIGRLSSLENVYIKADEQKNGIKANFKIRHNIEDG
GVQLAYHYQQNTPIGDGPVLLPDNHYLSVQSILSKDPNEKRDHMVLLEFVT
AAGITLGMDELYKGGTGGSMVSKGEELFTGVVPIQVELDGDVNGHKFSVSG
EGEGDATYGKLTLKFICTTGKLPVPWPTLVTTLSYGVQCFSRYPDHMKQHDF
FKSAMPEGYIQERTIFFKDDGNYKTRAEVKFEGDTLVNRIELKGIDFKEDGNI
LGHKLEYNTRDQLTEEQIAELKEAFSLFDKDGDGTITTKELGTVMRSLGQNP
TEAELQDMINEVDADGDGTIDLPEFQTMMARKMNDTDSEEEIREAFRVFDK
DGNGYIGAAELRHVMTNLGEKLTDEEVDEMIRVADIDGDGQVNYEEFVQM
MTAK

FIG. 5O

R-GECO1 (GenBank ID: JN258411) (SEQ ID NO:21)
MVDSSRRKWNKAGHAVRAIGRLSSPVVSERMYPEDGALKSEIKKGLRLKDG
GHYAAEVKTTYKAKKPVQLPGAYIVDIKLDIVSHNEDYTIVEQCERAEGRHS
TGGMDELYKGGTGGSLVSKGEEDNMAIIKEFMRFKVHMEGSVNGHEFEIEG
EGEGRPYEAFQTAKLKVTKGGPLPFAWDILSPQFMYGSKAYIKHPADIPDYF
KLSFPEGFRWERVMNFEDGGIIHVNQDSSLQDGVFIYKVKLRGTNFPPDGPV
MQKKTMGWEATRDQLTEEQIAEFKEAFSLFDKDGDGTITTKELGTVMRSLG
QNPTEAELQDMINEVDADGDGTFDFPEFLTMMARKMNDTDSEEEIREAFRV
FDKDGNGYIGAAELRHVMTDLGEKLTDEEVDEMIRVADIDGDGQVNYEEFV
QMMTAK

FIG. 5P

B-GECO1 (GenBank ID: JN258412) (SEQ ID NO:22)
MVDSPRRKWNKTGHAVRAIGRLSSPENVYIKADKQKNGIKANFKIRHNIEG
GGVQLAYHYQQNTPIGDGPVLLPDNHYLSVQSILSKDPNEKRDHMVLLEFV
TAAGITLGMDELYKGGTGGSESMVSKGEELFTGVVPIQVELDGDVNGHKFS
VSGEGEGDATYGKLTLKFICTTGKLPVPWPTLVTTLSHGVQCFSRYPDHMKQ
HDFFKSAMPGGYIQERTIFFKDDGNYKTRAEVKFEGDTLVNRIELKGIDFKED
GNILGHKLEYNTRGQLTEEQIAEFKEAFSLFDKDGDGTITTKELGTVMRSLG
QNPTEAELQDMINEVDADGDGTIDFPEFLTMMAPKMQDTDSEEEIREAFRVF
DKDGNGYIGAAELRHVMTNLGEKLTDEEVDEMIREADIDGDGQVNYEEFV
QMMTAK

FIG. 5Q

G-GECO1 (GenBank ID: JN258413) (SEQ ID NO:23)
MVDSSRRKWNKTGHAVRAIGRLSSLENVYIKADKQKNGIKANFKIRHNIED
GGVQLAYHYQQNTPIGDGPVLLPDNHYLSVQSILSKDPNEKRDHMVLLEFV
TAAGITLGMDELYKGGTGGSMVSKGEELFTGVVPIQVELDGDVNGHKFSVS
GEGEGDATYGKLTLKFICTTGKLPVPWPTLVTTLTYGVQCFSRYPDHMKQHD
FFKSAMPEGYIQERTIFFKDDGNYKTRAEVKFEGDTLVNRIELKGIDFKEDGN
ILGHKLEYNTRDQLTEEQIAEFKEAFSLFDKDGDGTITTKELGTVMRSLGQNP
TEAELQDMINEVDADGDGTIDFPEFLTMMARKMKDTDSEEEIREAFRVFDK
DGNGYIGAAELRHVMTNLGEKLTDEEVDEMIRVADIDGDGQVNYEEFVQM
MTAK

FIG. 5R

G-GECO1.1 (GenBank ID: JN258414) (SEQ ID NO:24)
MVDSSRRKWNKTGHAVRAIGRLSSLENVYIKADEQKNGIKAYFKIRHNIEGG
GVQLAYHYQQNTPIGDGPVLLPDNHYLSVQSILSKDPNEKRDHMVLLEFVT
AAGITLGMDELYKGGTGGSMVSKGEELFTGVVPIQVELDGDVNGHKFSVSG
EGEGDATYGKLTLKFICTTGKLPVPWPTLVTTLTYGVQCFSRYPDHMKQHDF
FKSAMPEGYIQERTIFFKDDGNYKTRAEVKFEGDTLVNRIELKGIDFKEDGNI
LGHKLEYNTRDQLTEEQIAEFKEAFSLFDKDGDGTITTKELGTVMRSLGQNP
TEAELQDMINEVDADGDGTIDFPEFLTMMARKMNDTDSEEEIREAFRVFDK
DGNGYIGAAELRHVMTNLGEKLTDEEVDEMIRVADIDGDGQVNYEEFVQM
MTAK

FIG. 5S

G-GECO1.2 (GenBank ID: JN258415) (SEQ ID NO:25)
MVDSSRRKWNKTGHAVRAIGRLSSLENVYIKADEQKNGIKAYFKIRHNIEGG
GVQLAYHYQQNTPIGDGPVLLPDNHYLSVQSMLSKDPNEKRDHMVLLEFVT
AAGITLGMDELYKGGTGGSESMVSKGEELFTGVVPIQVELDGDVNGHKFSV
SGEGEGDATYGKLTLKFICTTGKLPVPWPTLVTTLTYGVQCFSRYPDHMKQH
DFFKSAMPEGYIQERTIFFKGDGNYKTRAEVKFEGDTLVNRIELKGIDFKEDG
NILGHKLEYNTRDQLTEEQIAEFKEAFSLFDKDGDGTITTKELGTVMRSLGQ
NPTEAELQDMINEVDADGDGTIDFPEFLTMMARKMKDTDSEEEIREAFRVFD
KDGNGYIGAAELRHVMTNLGEKLTDEEVDEMIRVADIDGDGQVNYEEFVQ
MMTAK

FIG. 6A

TN-XXL (SEQ ID NO:26)
MVSKGEELFTGVVPILVELDGDVNGHKFSVRGEGEGDATNGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSK
LSKDPNEKRDHMVLLEFVTAARMLSEEELANCFRIFDKDANGFIDIEELGEIL
RATGEHVTEEDIEDLMKDSDKNNDGRIDFDEFLKMMEGVQGTSEEELANCF
RIFDKDANGFIDIEELGEILRATGEHVTEEDIEDLMKDSDKNNDGRIDFDEFL
KMMEGVQELMGGVQLADHYQQNTPIGDGPVLLPDNHYLSYQSKLSKDPNE
KRDHMVLLEFVTAAGITLGMDELYKGGTGGSMVSKGEELFTGVVPILVELD
GDVNGHKFSVRGEGEGDATNGKLTLKFICTTGKLPVPWPTLVTTLGYGLMC
FARYPDHMKQHDFFKSAMPEGYVQERTIFFKDDGNYKTRAEVKFEGDTLVN
RIELKGIDFKEDGNILGHKLEYNYNSHNVYIMADKQKNGIKANFKIRHNIED

FIG. 6B

YC3.6 (SEQ ID NO:27)
MVSKGEELFTGVVPILVELDGDVNGHRFSVSGEGEGDATYGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSA
LSKDPNEKRDHMVLLEFVTAARMHDQLTEEQIAEFKEAFSLFDKDGDGTITT
KELGTVMRSLGQNPTEAELQDMINEVDADGNGTIYFPEFLTMMARKMKDT
DSEEEIREAFRVFDKDGNGYISAAQLRHVMTNLGEKLTDEEVDEMIREADID
GDGQVNYEEFVQMMTAKGGKRRWKKNFIAVSAANRFKKISSSGALELMDG
GVQLADHYQQNTPIGDGPVLLPDNHYLSYQSALSKDPNEKRDHMVLLEFVT
AAGITLGMDELYKGGSGGMVSKGEELFTGVVPILVELDGDVNGHKFSVSGE
GEGDATYGKLTLKLICTTGKLPVPWPTLVTTLGYGLQCFARYPDHMKQHDFF
KSAMPEGYVQERTIFFKDDGNYKTRAEVKFEGDTLVNRIELKGIDFKEDGNI
LGHKLEYNYNSHNVYITADKQKNGIKANFKIRHNIELSRGPGTSAEIYACRLE
ISN

FIG. 6C

D3CPVenus polypeptide (SEQ ID NO:28)
MVSKGEELFTGVVPILVELDGDVNGHRFSVSGEGEGDATYGKLTLKFICTTG
KLPVPWPTLVTTLTWGVQCFSRYPDHMKQHDFFKSAMPEGYVQERTIFFKD
DGNYKTRAEVKFEGDTLVNRIELKGIDFKEDGNILGHKLEYNYISHNVYITA
DKQKNGIKAHFKIRHNIEDGSVQLADHYQQNTPIGDGPVLLPDNHYLSTQSA
LSKDPNEKRDHMVLLEFVTAARMHDQLTEEQIAEFKEAFSLLDKDGDGTITT
KELGTALRSLGQNPTEAELQDMINEVDADGNGTIYFPEFLTMMARKMKDTD
SEEEIREAFRVFDKDGNGYISAAELRHVMTNLGEKLTDEEVDEMIREADIDG
DGQVNYEEFVQMMTAKGGKRRWQKTGHAVRAFGRLKKISSSGALELMDG
GVQLADHYQQNTPIGDGPVLLPDNHYLSYQSALSKDPNEKRDHMVLLEFVT
AAGITLGMDELYKGGSGGMVSKGEELFTGVVPILVELDGDVNGHKFSVSGE
GEGDATYGKLTLKLICTTGKLPVPWPTLVTTLGYGLQCFARYPDHMKQHDFF
KSAMPEGYVQERTIFFKDDGNYKTRAEVKFEGDTLVNRIELKGIDFKEDGNI
LGHKLEYNYNSHNVYITADKQKNGIKANFKIRHNIE

FIG. 7A

Amino acid sequence of ChR1 (SEQ ID NO:29)
MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVILIHLSNLTGLANDYNKRTMGLLVSDIGTIVWGTTAALSKG
YVRVIFFLMGLCYGIYTFFNAAKVYIEAYHTVPKGICRDLVRYLAWLYFCSW
AMFPVLFLLGPEGFGHINQFNSAIAHAILDLASKNAWSMMGHFLRVKIHEHI
LLYGDIRKKQKVNVAGQEMEVETMVHEEDD

FIG. 7B

Amino acid sequence of ChR2 (SEQ ID NO:30)
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTCPVILIHLSNLTGLSNDYSRRTMGLLV
SDIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 7C

Amino acid sequence of ChR2 SFO (SEQ ID NO:31)
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTSPVILIHLSNLTGLSNDYSRRTMGLLV
SDIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 7D

Amino acid sequence of ChR2 SSFO (SEQ ID NO:32)
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFFEF
KNPSMLYLATGHRVQWLRYAEWLLTSPVILIHLSNLTGLSNDYSRRTMGLLV
SAIGTIVWGATSAMATGYVKVIFFCLGLCYGANTFFHAAKAYIEGYHTVPKG
RCRQVVTGMAWLFFVSWGMFPILFILGPEGFGVLSVYGSTVGHTIIDLMSKN
CWGLLGHYLRVLIHEHILIHGDIRKTTKLNIGGTEIEVETLVEDEAEAGAVP

FIG. 7E

Amino acid sequence of VChR1 (SEQ ID NO:33)
MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTCPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 7F

Amino acid sequence of VChR1 SFO (SEQ ID NO:34)
MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTSPVLLIHLSNLTGLKDDYSKRTMGLLVSDVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 7G

Amino acid sequence of VChR1 SSFO (SEQ ID NO:35)

MDYPVARSLIVRYPTDLGNGTVCMPRGQCYCEGWLRSRGTSIEKTIAITLQW
VVFALSVACLGWYAYQAWRATCGWEEVYVALIEMMKSIIEAFHEFDSPATLW
LSSGNGVVWMRYGEWLLTCPVLLIHLSNLTGLKDDYSKRTMGLLVSAVGCI
VWGATSAMCTGWTKILFFLISLSYGMYTYFHAAKVYIEAFHTVPKGICRELV
RVMAWTFFVAWGMFPVLFLLGTEGFGHISPYGSAIGHSILDLIAKNMWGVLG
NYLRVKIHEHILLYGDIRKKQKITIAGQEMEVETLVAEEED

FIG. 7H

Amino acid sequence of C1V1 (SEQ ID NO:36)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVLLIHLSNLTGLKDDYSKRTMGLLVSDVGCIVWGATSAMCT
GWTKILFFLISLSYGMYTYFHAAKVYIEAFHTVPKGICRELVRVMAWTFFVA
WGMFPVLFLLGTEGFGHISPYGSAIGHSILDLIAKNMWGVLGNYLRVKIHEH
ILLYGDIRKKQKITIAGQEMEVETLVAEEED

FIG. 7I

Amino acid sequence of C1C2 (SEQ ID NO:37)

MSRRPWLLALALAVALAAGSAGASTGSDATVPVATQDGPDYVFHRAHERML
FQTSYTLENNGSVICIPNNGQCFCLAWLKSNGTNAEKLAANILQWITFALSAL
CLMFYGYQTWKSTCGWEEIYVATIEMIKFIIEYFHEFDEPAVIYSSNGNKTVW
LRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVS
WGMFPILFILGPEGFGVLSVYGSTVGHTIIDLMSKNCWGLLGHYLRVLIHEHI
LIHGDIRKTTKLNIGGTEIEVETLVEDEAEAGAV

FIG. 7J

Amino acid sequence of SdChR (SEQ ID NO:38)
MGGAPAPDAHSAPPGNDSAGGSEYHAPAGYQVNPPYHPVHGYEEQCSSIYI
YYGALWEQETARGFQWFAVFLSALFLAFYGWHAYKASVGWEEVYVCSVEL
IKVILEIYFEFTSPAMLFLYGGNITPWLRYAEWLLTCPVILIHLSNITGLSEEYN
KRTMALLVSDLGTICMGVTAALATGWVKWLFYCIGLVYGTQTFYNAGIIYV
ESYYIMPAGGCKKLVLAMTAVYYSSWLMFPGLFIFGPEGMHTLSVAGSTIGH
TIADLLSKNIWGLLGHFLRIKIHEHIIMYGDIRRPVSSQFLGRKVDVLAFVTEE
DKV

FIG. 7K

Amino acid sequence of CnChR2 (SEQ ID NO:39)
MEPVLGLASTAVRELTAGGSGNPYESYKPPEDPCALTPFGCLTNFWCDPQFG
LADAKYDYCYVKAAYGELAIVETSRLPWLYSHGSDAEHQGALAMQWMAF
ALCIICLVFYAYHSWKATTGWEEVYVCVVELVKVLLEIYKEFESPASIYLPTA
NAALWLRYGEWLLTCPVILIHLSNITGLKDDYNKRTMQLLVSDIGCVVWGIT
AAFSVGWLKWVFFVLGLLYGSNTYFHAAKVYIESYHTVPKGHCRLIVRLMA
YCFYVAWTMYPILFILGPEGLGHMSAYMSTALHGVADMLSKQIWGLLGHHL
RVKIFEHILIHGDIRKTTTMQVGGQMVQVEEMVDEEDEDTI

FIG. 7L

Amino acid sequence of CsChrimson (SEQ ID NO:40)
MSRLVAASWLLALLLCGITSTTTASSAPAASSTDGTAAAAVSHYAMNGFDEL
AKGAVVPEDHFVCGPADKCYCSAWLHSRGTPGEKIGAQVCQWIAFSIAIALL
TFYGFSAWKATCGWEEVYVCCVEVLFVTLEIFKEFSSPATVYLSTGNHAYCL
RYFEWLLSCPVILIKLSNLSGLKNDYSKRTMGLIVSCVGMIVFGMAAGLATD
WLKWLLYIVSCIYGGYMYFQAAKCYVEANHSVPKGHCRMVVKLMAYAYF
ASWGSYPILWAVGPEGLLKLSPYANSIGHSICDIIAKEFWTFLAHHLRIKIHEHI
LIHGDIRKTTKMEIGGEEVEVEEFVEEEDEDTV

FIG. 7M

Amino acid sequence of ShChR1 (SEQ ID NO:41)

METAATMTHAFISAVPSAEATIRGLLSAAAVVTPAADAHGETSNATTAGADH
GCFPHINHGTELQHKIAVGLQWFTVIVAIVQLIFYGWHSFKATTGWEEVYVC
VIELVKCFIELFHEVDSPATVYQTNGGAVIWLRYSMWLLTCPVILIHLSNLTGL
HEEYSKRTMTILVTDIGNIVWGITAAFTKGPLKILFFMIGLFYGVTCFFQIAKV
YIESYHTLPKGVCRKICKIMAYVFFCSWLMFPVMFIAGHEGLGLITPYTSGIG
HLILDLISKNTWGFLGHHLRVKIHEHILIHGDIRKTTTINVAGENMEIETFVDE
EEEGGV

FIG. 7N

Amino acid sequence of Arch (SEQ ID NO:42)

MDPIALQAGYDLLGDGRPETLWLGIGTLLMLIGTFYFLVRGWGVTDKDARE
YYAVTILVPGIASAAYLSMFFGIGLTEVTGGEMLDIYYARYADWLFTTPLLL
LDLALLAKVDRVTIGTLVGVDALMIVTGLIGALSHTAIARYSWWLFSTICMIV
VLYFLATSLRSAAKERGPEVASTFNTLTALVLVLWTAYPILWIIGTEGAGVVGL
GIETLLFMVLDVTAKVGFGFILLRSRAILGDTEAPEPSAGADVSAAD

FIG. 7O

Amino acid sequence of ArchT (SEQ ID NO:43)

MDPIALQAGYDLLGDGRPETLWLGIGTLLMLIGTFYFIVKGWGVTDKEARE
YYSITILVPGIASAAYLSMFFGIGLTEVTVAGEVLDIYYARYADWLFTTPLLLL
DLALLAKVDRVSIGTLVGVDALMIVTGLIGALSHTPLARYSWWLFSTICMIV
VLYFLATSLRAAAKERGPEVASTFNTLTALVLVLWTAYPILWIIGTEGAGVVGL
GIETLLFMVLDVTAKVGFGFILLRSRAILGDTEAPEP

FIG. 7P

Amino acid sequence of GtR3 (SEQ ID NO:44)

ASSFGKALLEFVFIVFACITLLLGINAAKSKAASRVLFPATFVTGIASIAYFSMA
SGGGWVIAPDCRQLFVARYLDWLITTPLLIDLGLVAGVSRWDIMALCLSDV
LMIATGAFGSLTVGNVKWVWWFFGMCWFLHIIFALGKSWAEAAKAKGGDS
ASVYSKIAGITVITWFCYPVVWVFAEGFGNFSVTFEVLIYGVLDVISKAVFGLI
LMSGAATGYESI

FIG. 7Q

Amino acid sequence of Oxy (SEQ ID NO:45)
MAPLAQDWTYAEWSAVYNALSFGIAGMGSATIFFWLQLPNVTKNYRTALTIT
GIVTLIATYHYFRIFNSWVAAFNVGLGVNGAYEVTVSGTPFNDAYRYVDWLL
TVPLLLVELILVMKLPAKETVCLAWTLGIASAVMVALGYPGEIQDDLSVRWF
WWACAMVPFVYVVGTLVVGLGAATAKQPEGVVDLVSAARYLTVVSWLTYP
FVYIVKNIGLAGSTATMYEQIGYSAADVTAKAVFGVLIWAIANAKSRLEEEG
KLRA

FIG. 7R

Amino acid sequence of Mac (SEQ ID NO:46)
MIVDQFEEVLMKTSQLFPLPTATQSAQPTHVAPVPTVLPDTPIYETVGDSGSK
TLWVVFVLMLIASAAFTALSWKIPVNRRLYHVITTIITLTAALSYFAMATGHG
VALNKIVIRTQHDHVPDTYETVYRQVYYARYIDWAITTPLLLLDLGLLAGMS
GAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYA
VLDVLAKGVFGAWLLVTHANLRESDVELNGFWANGLNREGAIRIGEDDGA

FIG. 7S

Amino acid sequence of NpHR (SEQ ID NO:47)
VTQRELFEFVLNDPLLASSLYINIALAGLSILLFVFMTRGLDDPRAKLIAVSTIL
VPVVSIASYTGLASGLTISVLEMPAGHFAEGSSVMLGGEEVDGVVTMWGRY
LTWALSTPMILLALGLLAGSNATKLFTAITFDIAMCVTGLAAALTTSSHLMRW
FWYAISCACFLVVLYILLVEWAQDAKAAGTADMFNTLKLLTVVMWLGYPIV
WALGVEGIAVLPVGVTSWGYSFLDIVAKYIFAFLLLNYLTSNESVVSGSILDV
PSASGTPADD

FIG. 7T

Amino acid sequence of DsChR (SEQ ID NO:48)

MRRRESQLAYLCLFVLIAGWAPRLTESAPDLAERRPPSERNTPYANIKKVPNI
TEPNANVQLDGWALYQDFYYLAGSDKEWVVGPSDQCYCRAWSKSHGTDR
EGEAAVVWAYIVFAICIVQLVYFMFAAWKATVGWEEVYVNIIELVHIALVIWV
EFDKPAMLYLNDGQMVPWLRYSAWLLSCPVILIHLSNLTGLKGDYSKRTMG
LLVSDIGTIVFGTSAALAPPNHVKVILFTIGLLYGLFTFFTAAKVYIEAYHTVP
KGQCRNLVRAMAWTYFVSWAMFPILFILGREGFGHITYFGSSIGHFILEIFSKN
LWSLLGHGLRYRIRQHIIIHGNLTKKNKINIAGDNVEVEEYVDSNDKDSDV

FIG. 7U

Amino acid sequence of Champ (SEQ ID NO:49)

MDPIALQAGYDLLGDGRPETLWLGIGTLLMLIGTFYFLVRGWGVTDKDARE
YYAVTILVPGIASAAYLSMFFGIGLTEVTVGGEMLDIYYARYADWLFTTPLLL
LDLALLAKVDRVTIGTLVGVDALMIVTGLIGALSHTAIARYSWWLFSTICMIV
VLYFLATSLRSAAKERGPEVASTFNTLTALVLVLWTAYPILWIIGTEGAGVVGL
GIETLLFMVLDVTAKVGFGFILLRSRAILGDTEAPEPSAGADVSAADKSRITSE
GEYIPLDQIDINVGAPGSGATNFSLLKQAGDVEENPGPMDLKESPSEGSLQPS
SIQIFANTSTLHGIRHIFVYGPLTIRRVLWAVAFVGSLGLLLVESSERVSYYFSY
QHVTKVDEVVAQSLVFPAVTLCNLNGFRFSRLTTNDLYHAGELLALLDVNLQ
IPDPHLADPTVLEALRQKANFKHYKPKQFSMLEFLHRVGHDLKDMMLYCKF
KGQECGHQDFTTVFTKYGKCYMFNSGEDGKPLLTTVKGGTGNGLEIMLDIQ
QDEYLPIWGETEETTFEAGVKVQIHSQSEPPFIQELGFGVAPGFQTFVATQEQR
LTYLPPPWGECRSSEMGLDFFPVYSITACRIDCETRYIVENCNCRMVHMPGD
APFCTPEQHKECAEPALGLLAEKDSNYCLCRTPCNLTRYNKELSMVKIPSKTS
AKYLEKKFNKSEKYISENILVLDIFFEALNYETIEQKKAYEVAALLGDIGGQM
GLFIGASLLTILELFDYIYELIKEKLLDLLGKEEEGSHDENMSTCDTMPNHSE
TISHTVNVPLQTALGTLEEIACAAAKSRITSEGEYIPLDQIDINVVSKGEELFTG
VVPILVELDGDVNGHKFSVSGEGEGDATYGKLTLKFICTTGKLPVPWPTLVT
TFGYGLQCFARYPDHMKQHDFFKSAMPEGYVQERTIFFKDDGNYKTRAEVK
FEGDTLVNRIELKGIDFREDGNILGHKLEYNYNSHNVYIMADKQKNGIKVNF
KIRHNIEDGSVQLADHYQQNTPIGDGPVLLPDNHYLSYQSALSKDPNEKRDH
MVLLEFVTAAGITLGMDELYKFCYENEV

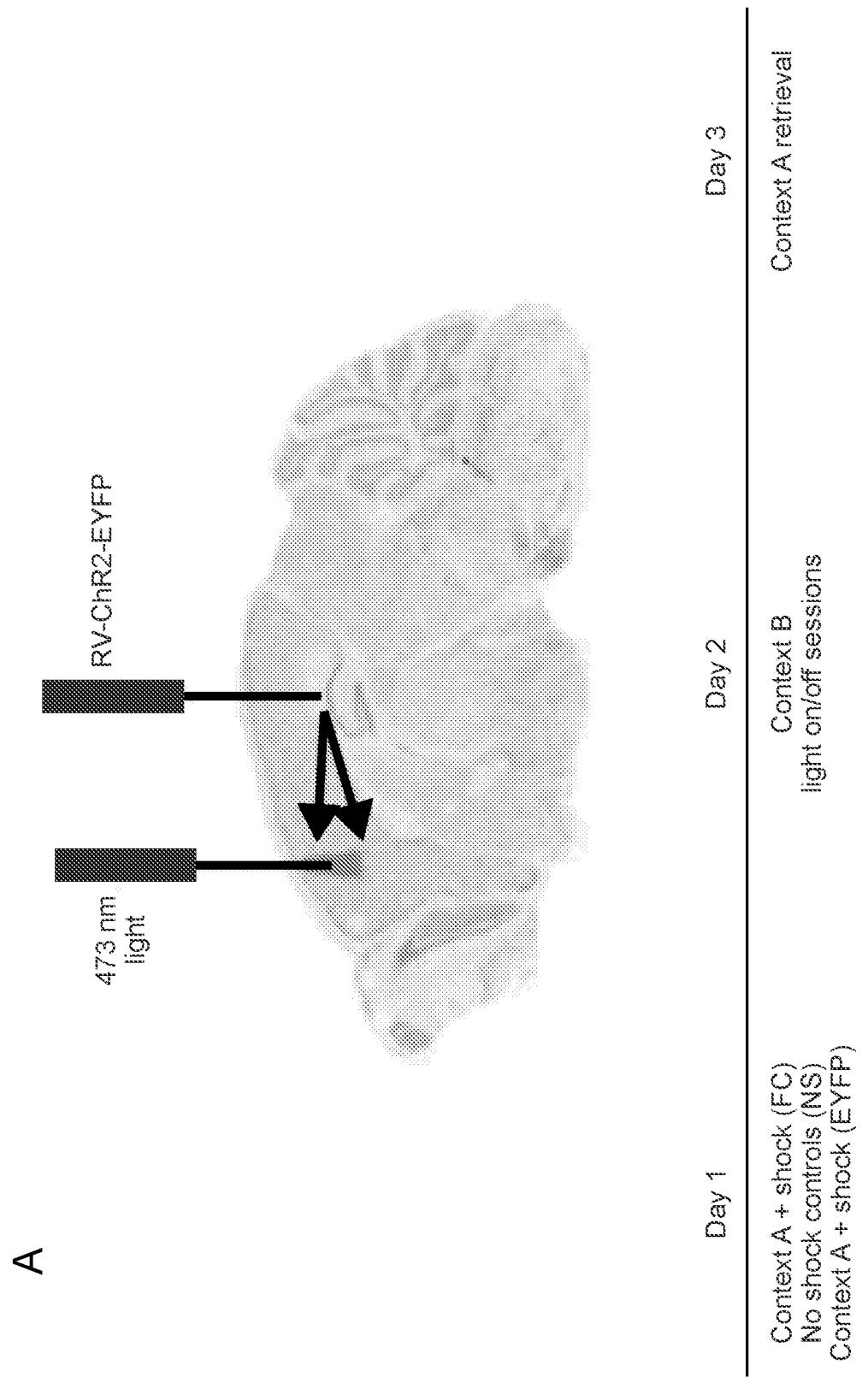

FIG. 13 (Cont.)
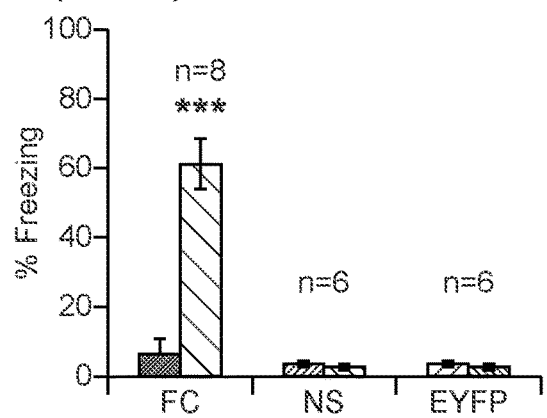
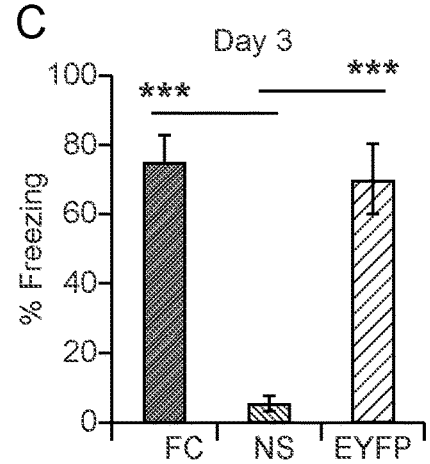
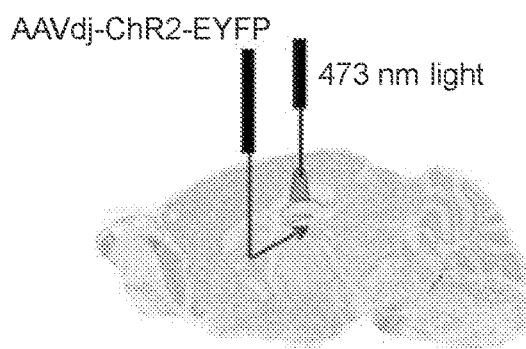
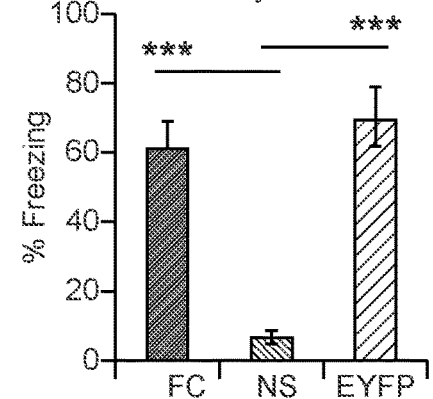
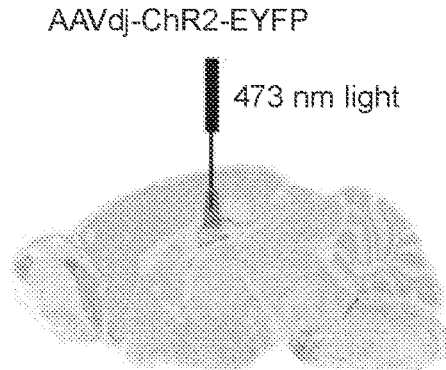
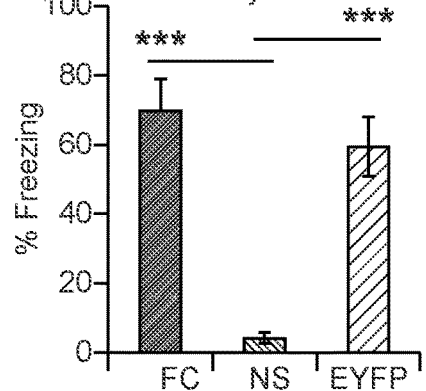

FIG. 13 (Cont.)
F
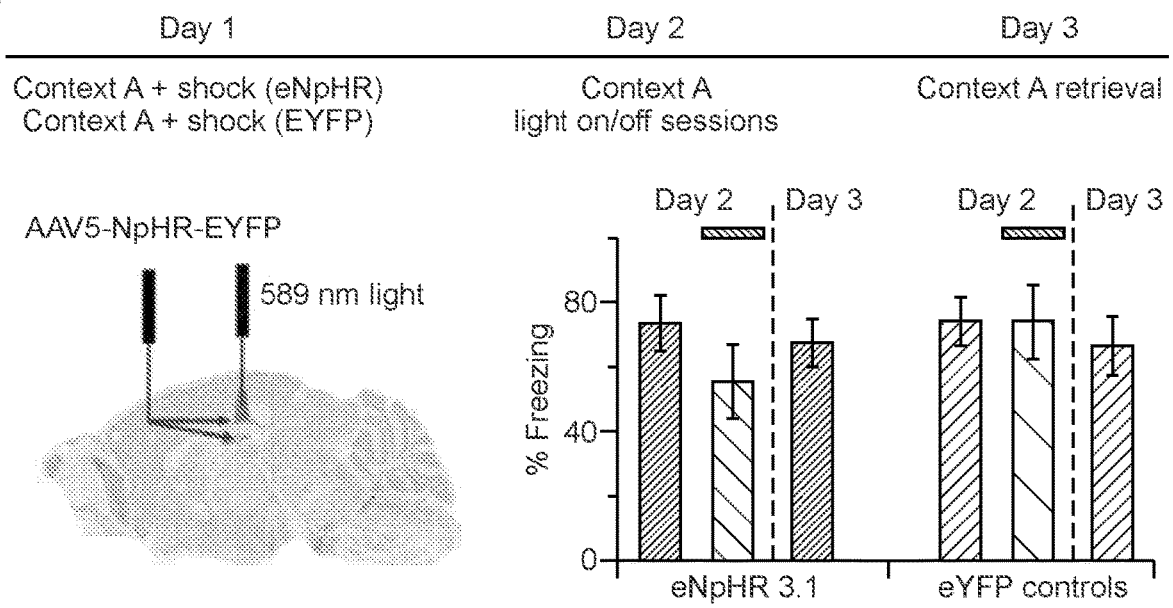
G
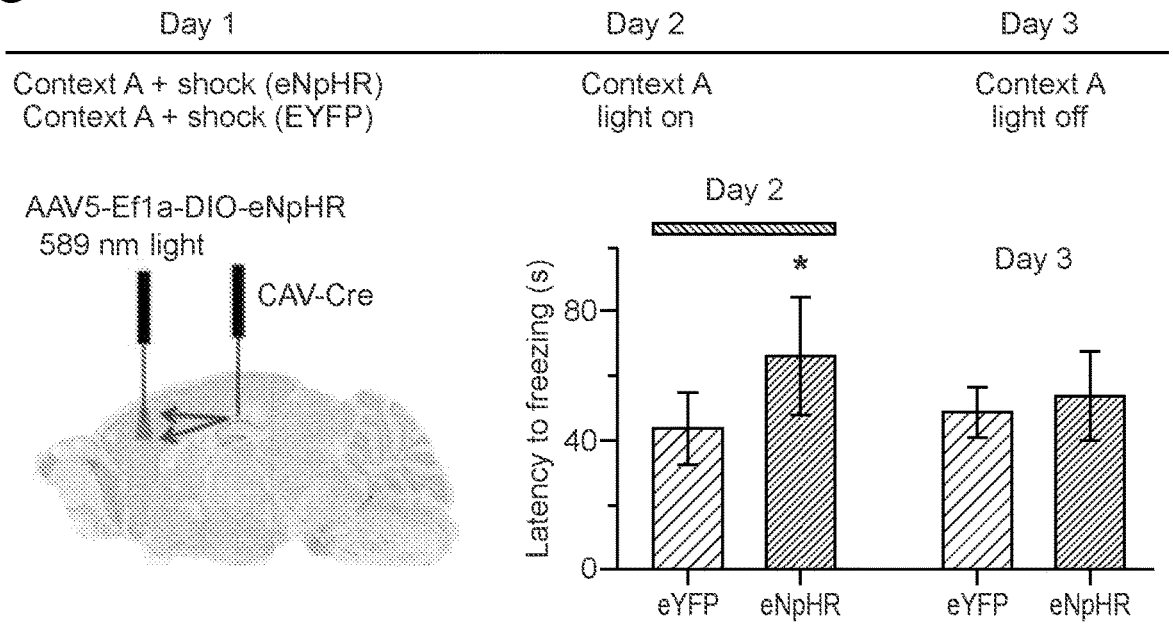

| Day 1 | Day 2 | Day 12, 13, 14 | Day 15 | Day 16 | Day 17 |
|---|---|---|---|---|---|
| Context A + shock (FC)<br>No shock controls (NS)<br>Context A + shock (EYFP) | Context B<br>Light on/off sessions | Context A<br>Extinction | Context C<br>Light on/off sessions | Context A<br>Fear training | Context D<br>Light on/off sessions |

A

FIG. 14 (Cont.)
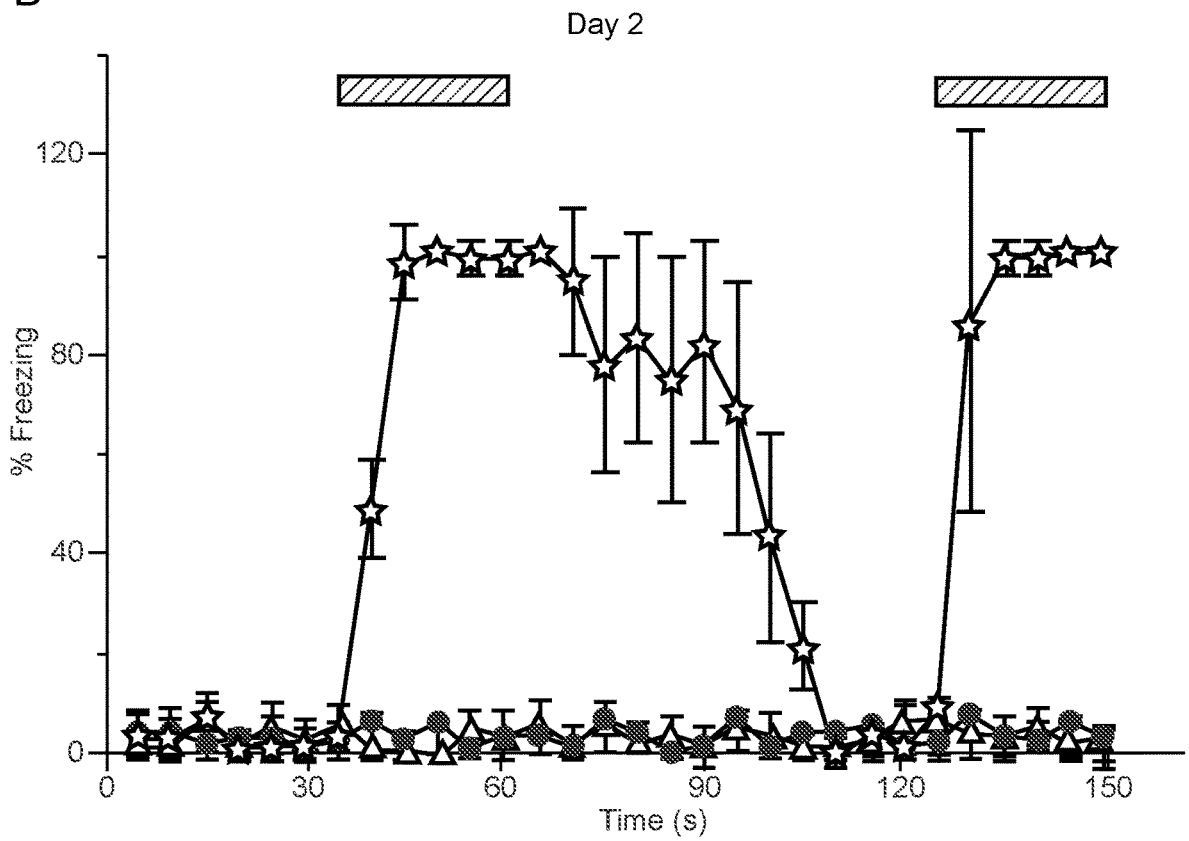
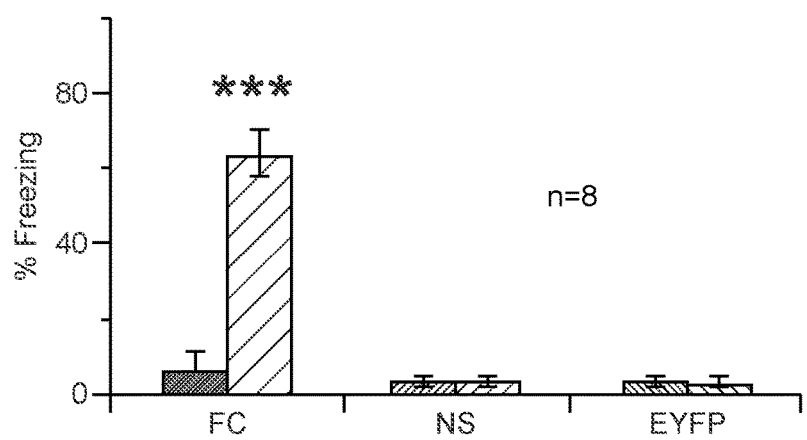

FIG. 14 (Cont.)
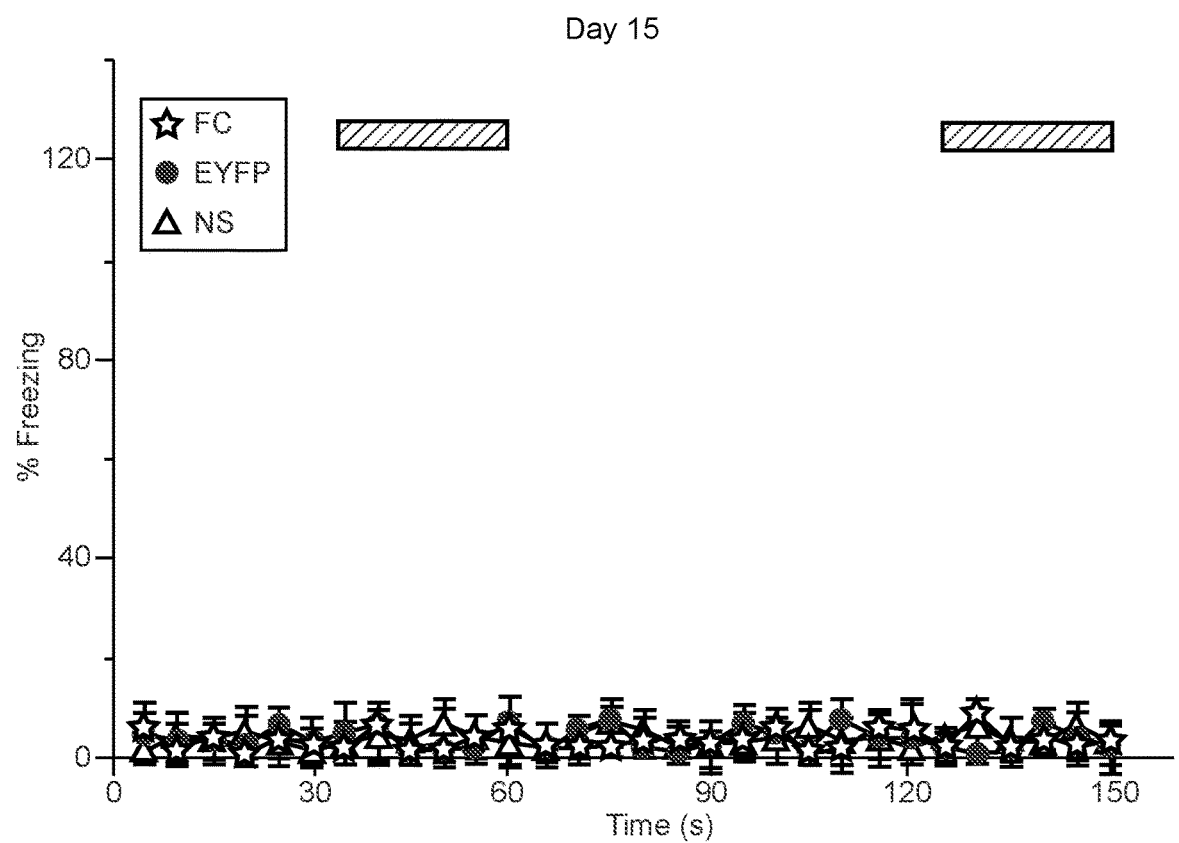
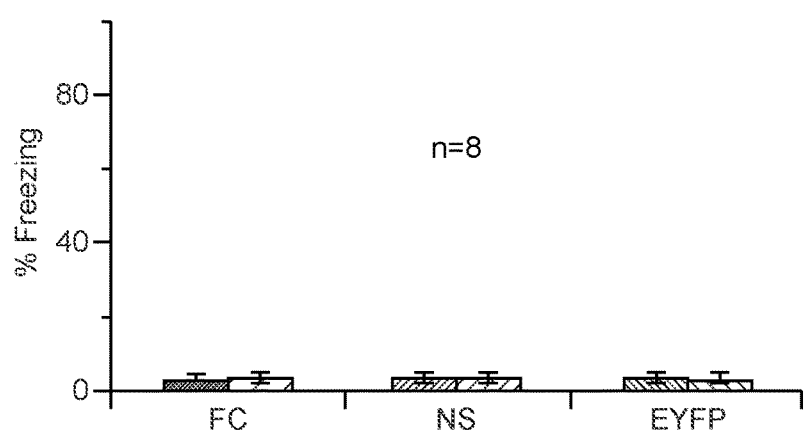

FIG. 14 (Cont.)
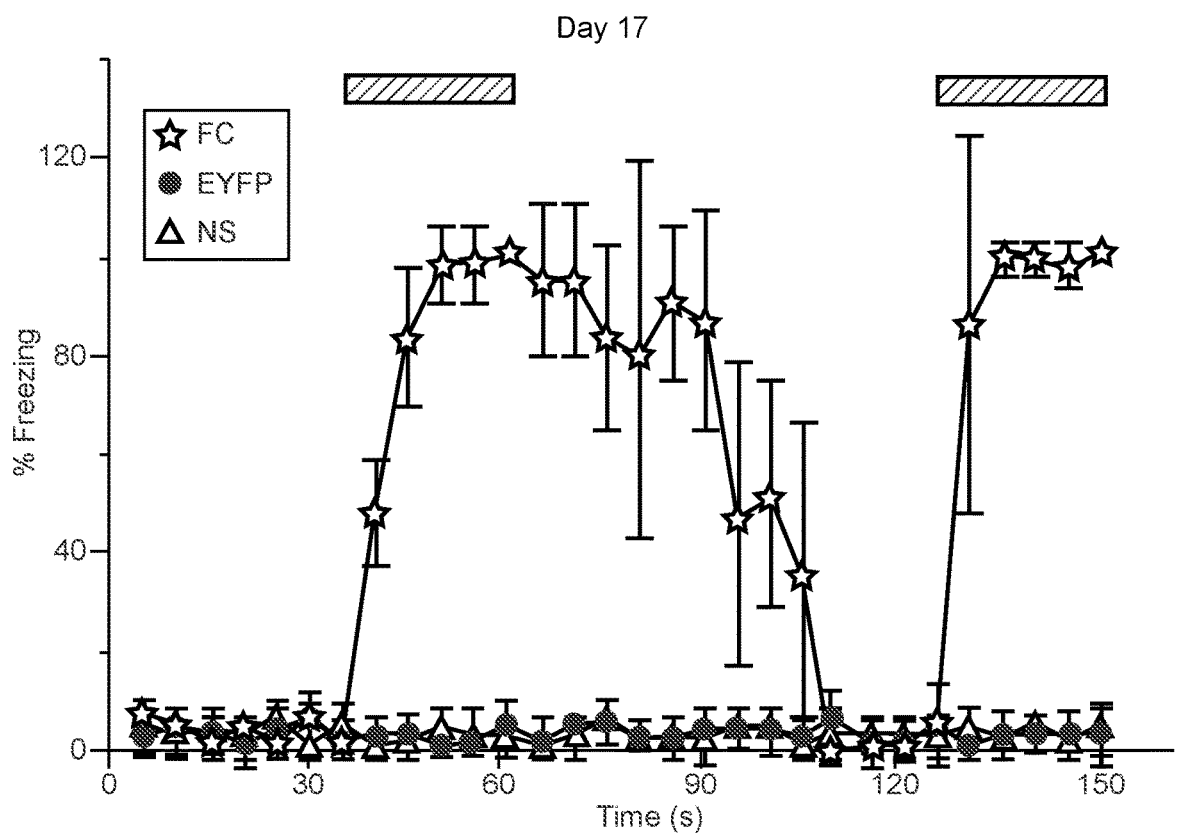
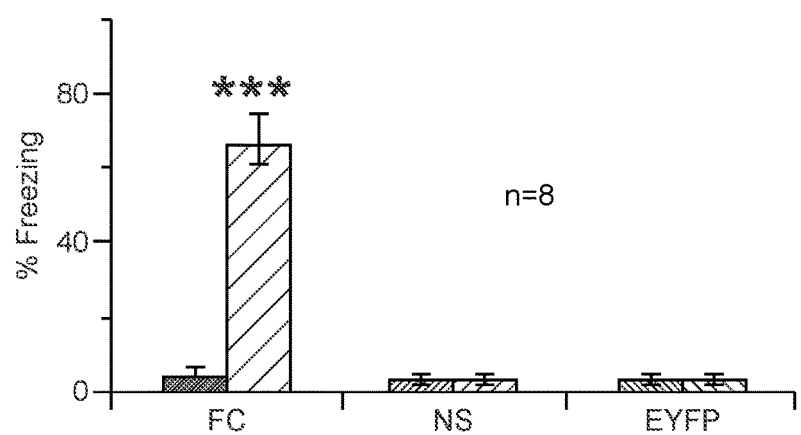

FIG. 14 (Cont.)
E
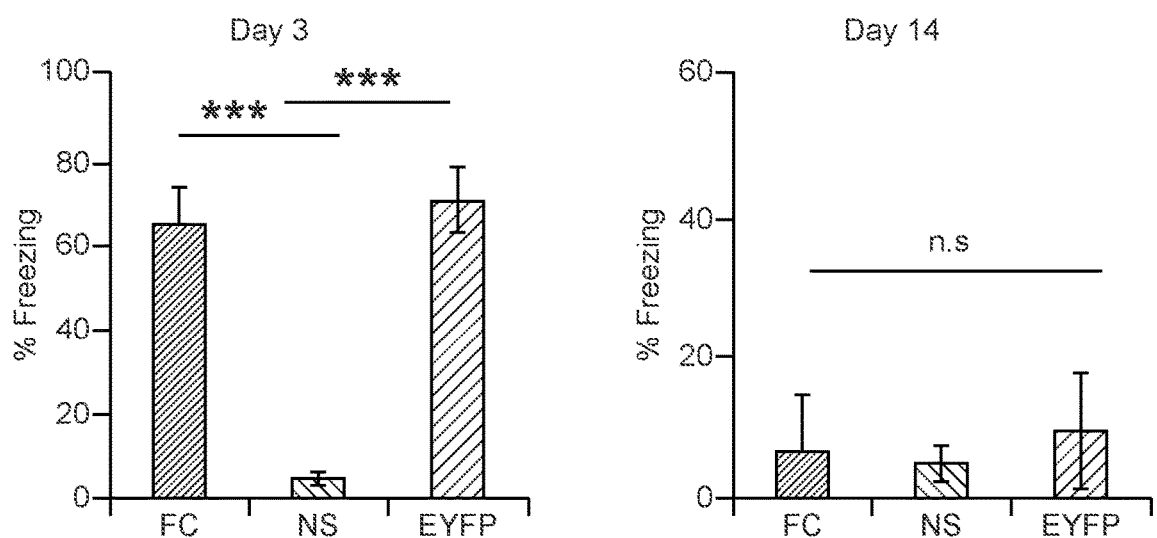
F
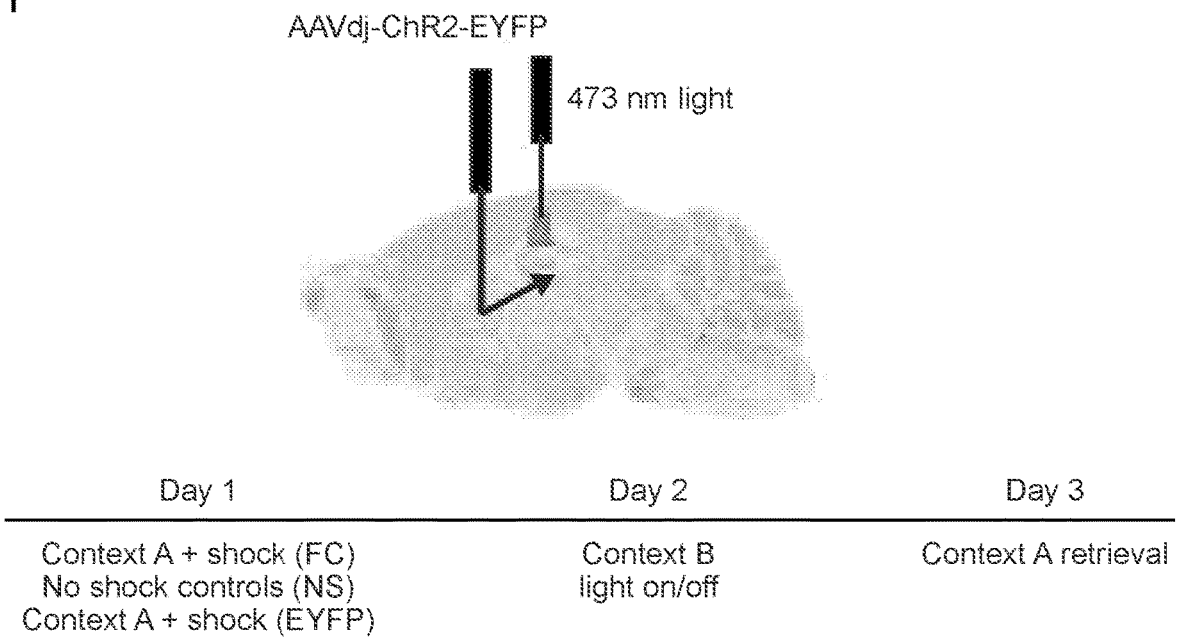

FIG. 14 (Cont.)
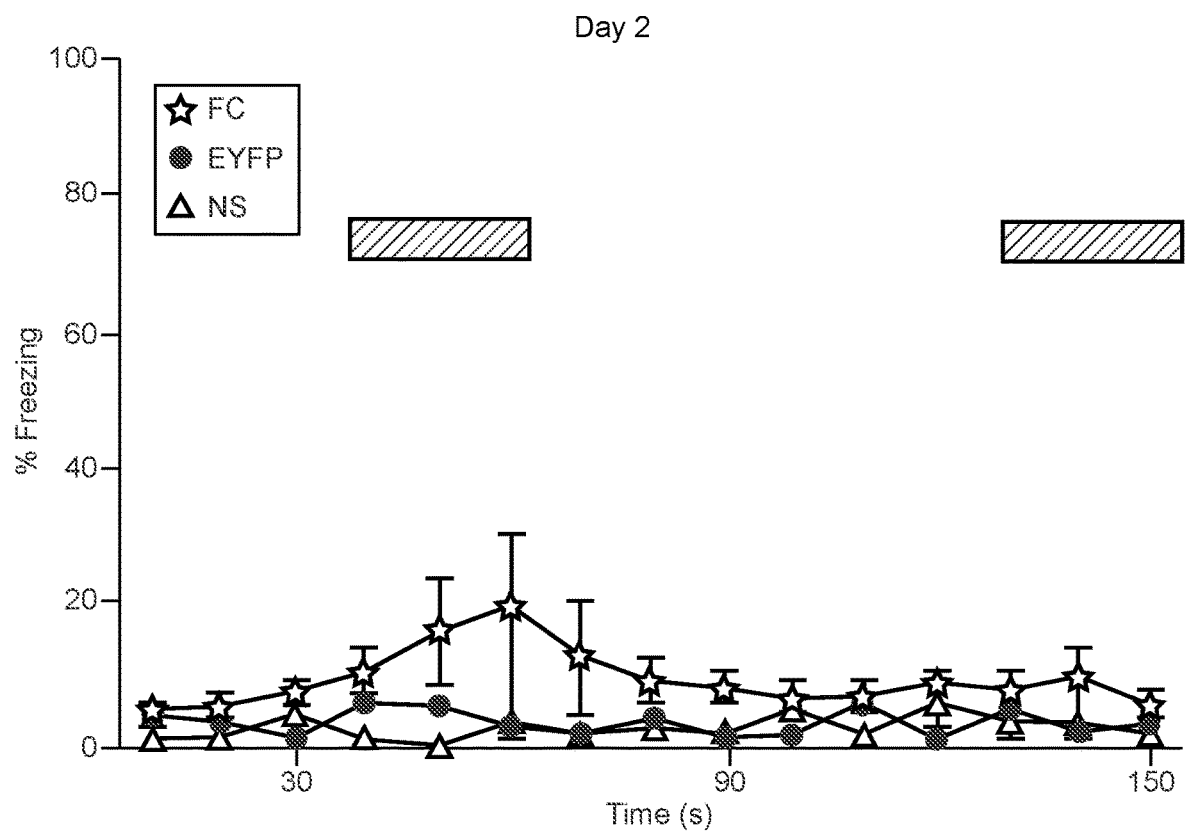
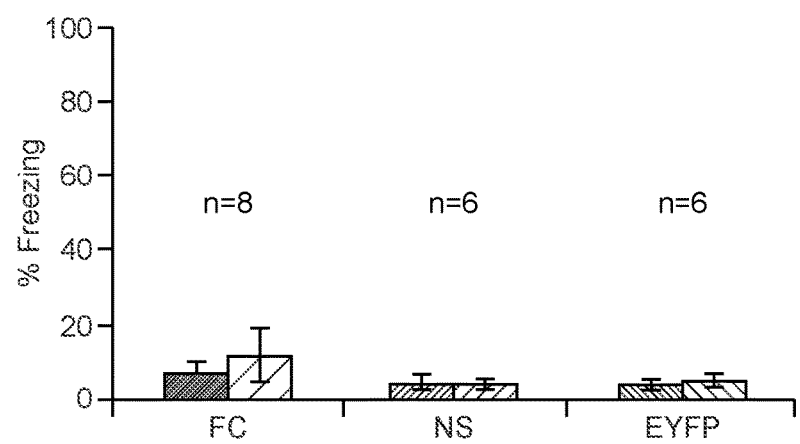

H

| Day 1 | Day 2 | Day 3 |
|---|---|---|
| Context A + shock (FC)<br>No shock controls (NS)<br>Context A + shock (EYFP) | Context B<br>light on/off sessions | Context A<br>retrieval |

FIG. 14 (Cont.)
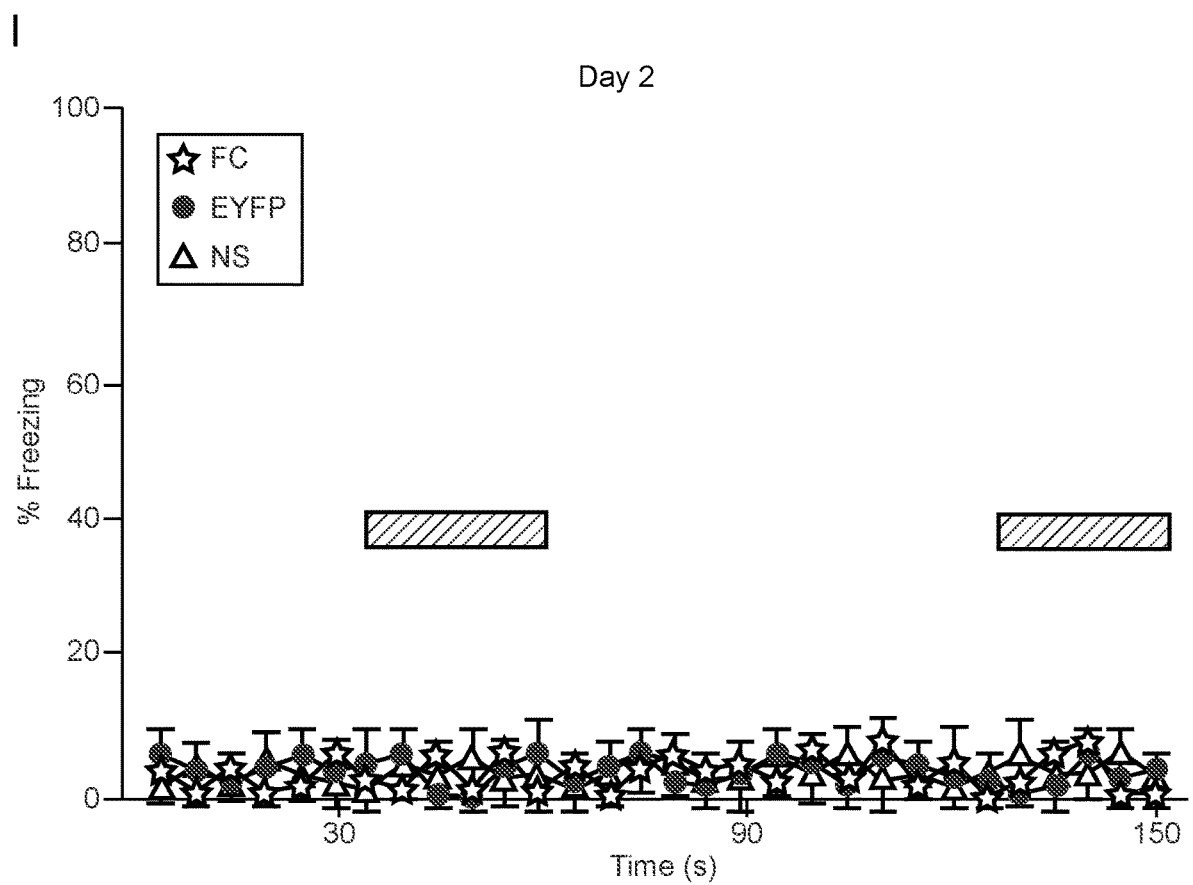
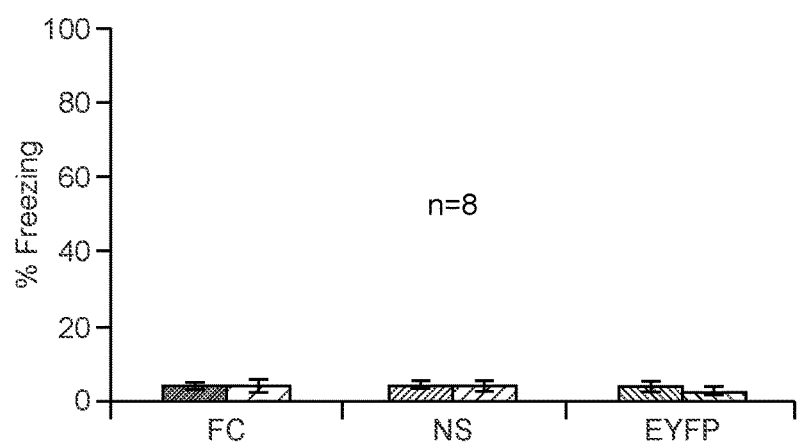

FIG. 14 (Cont.)
J
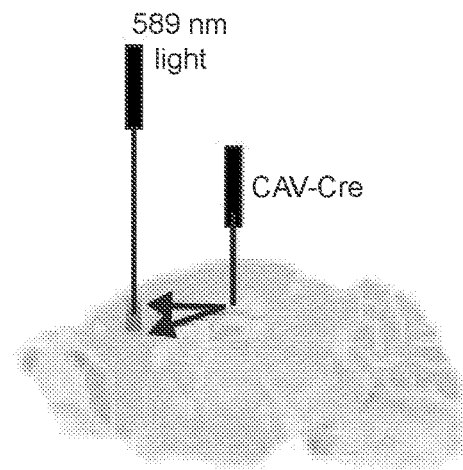
| Day 1 | Day 2 | Day 3 |
|---|---|---|
| Context A + shock (eNpHR) | Context A | Context A |
| Context A + shock (EYFP) | light on/off sessions | retrieval |
| Day 1 | Day 2 |
|---|---|
| Tone + shock (eNpHR) | Cued retrieval with |
| Tone + shock (EYFP) | light on/off sessions |
K 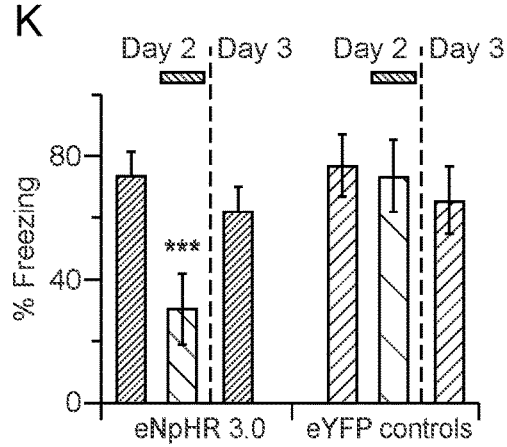
L 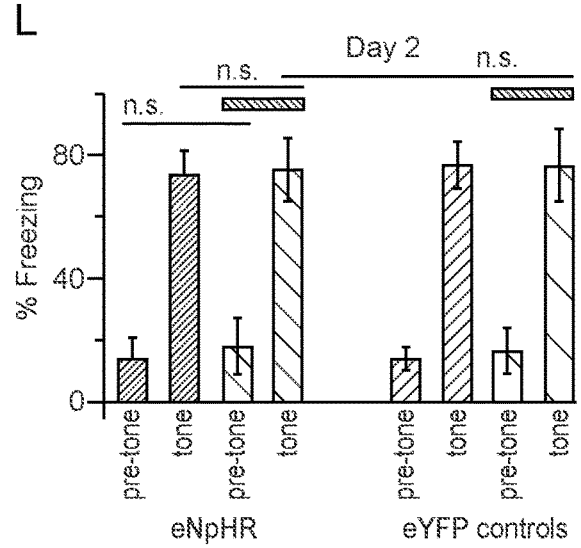

FIG. 16 (Cont.)
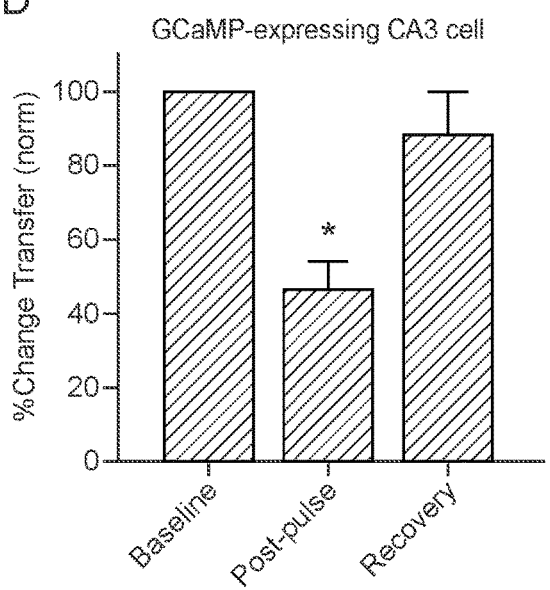
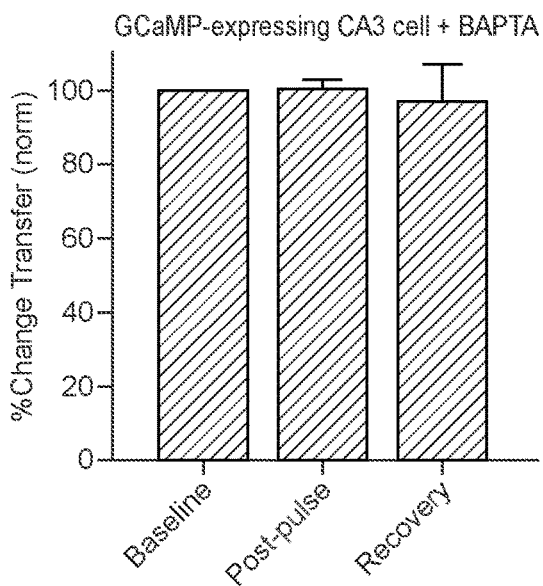
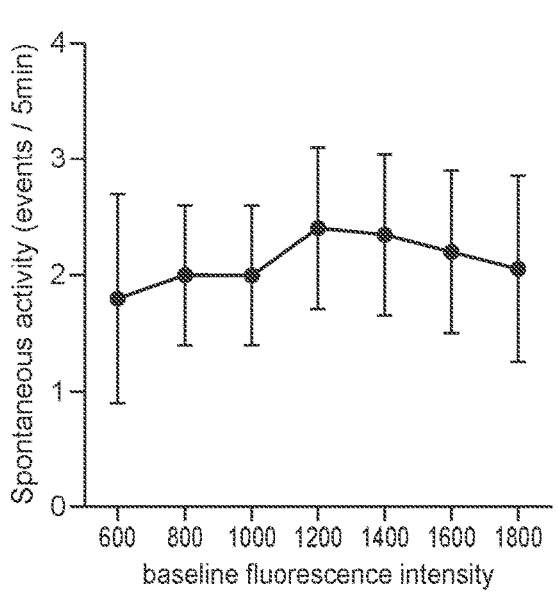
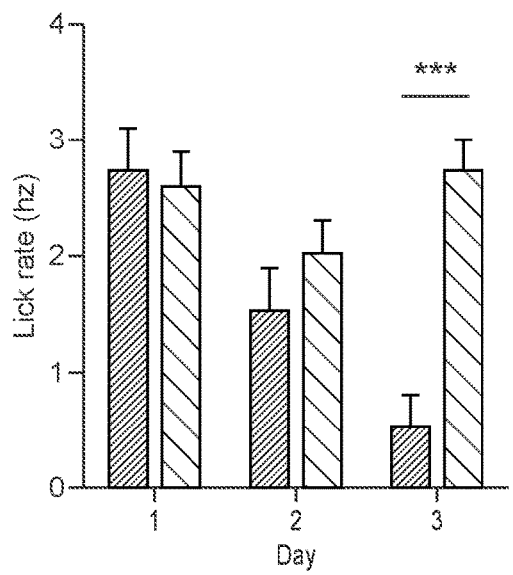

FIG. 17 (Cont.)
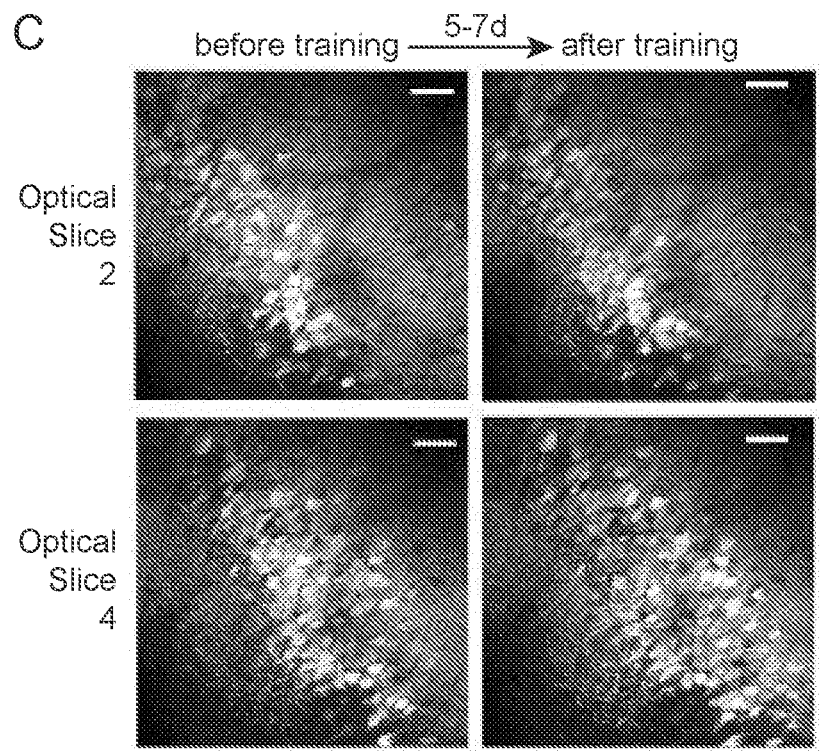
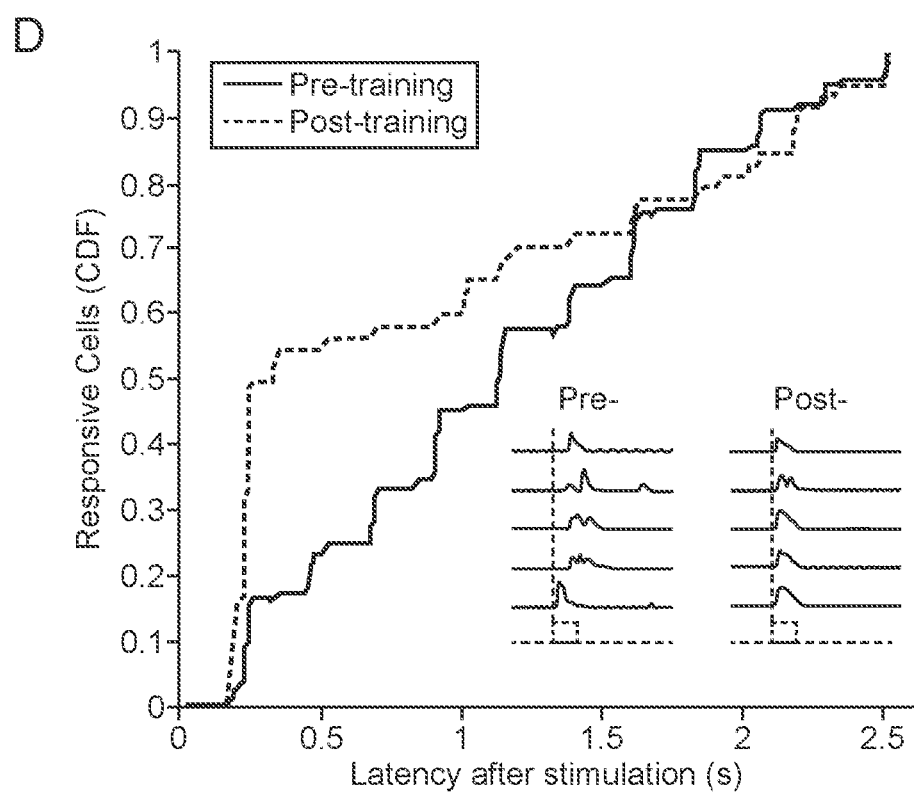

FIG. 17 (Cont.)
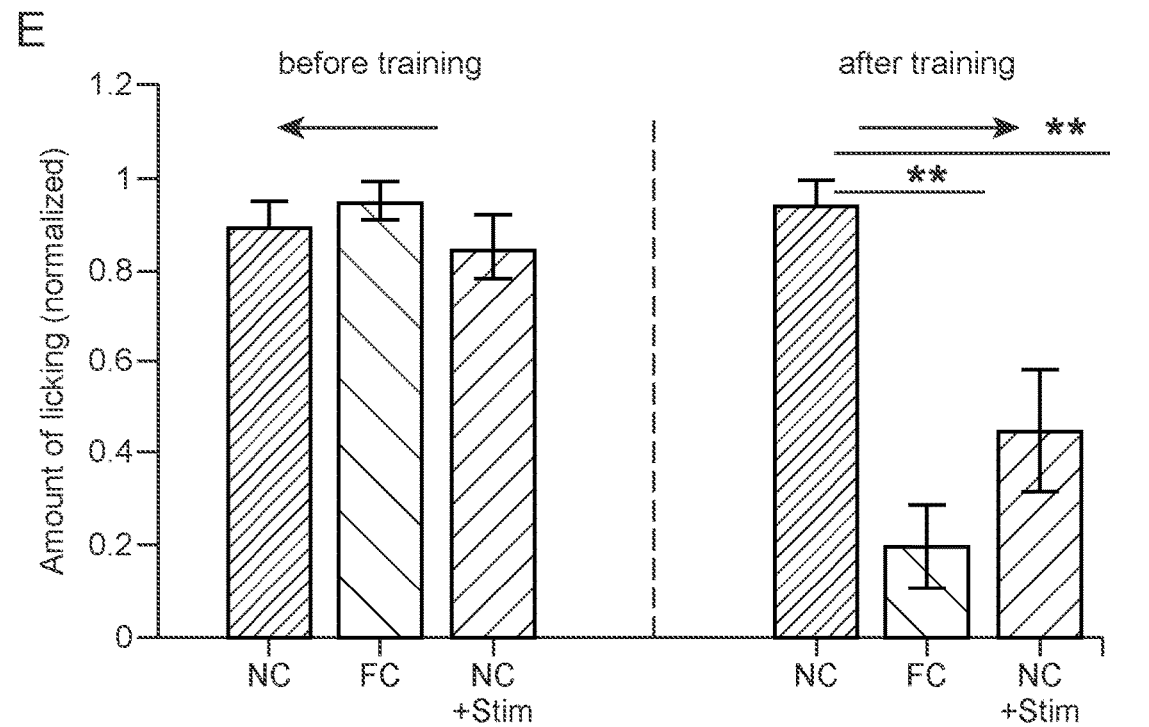
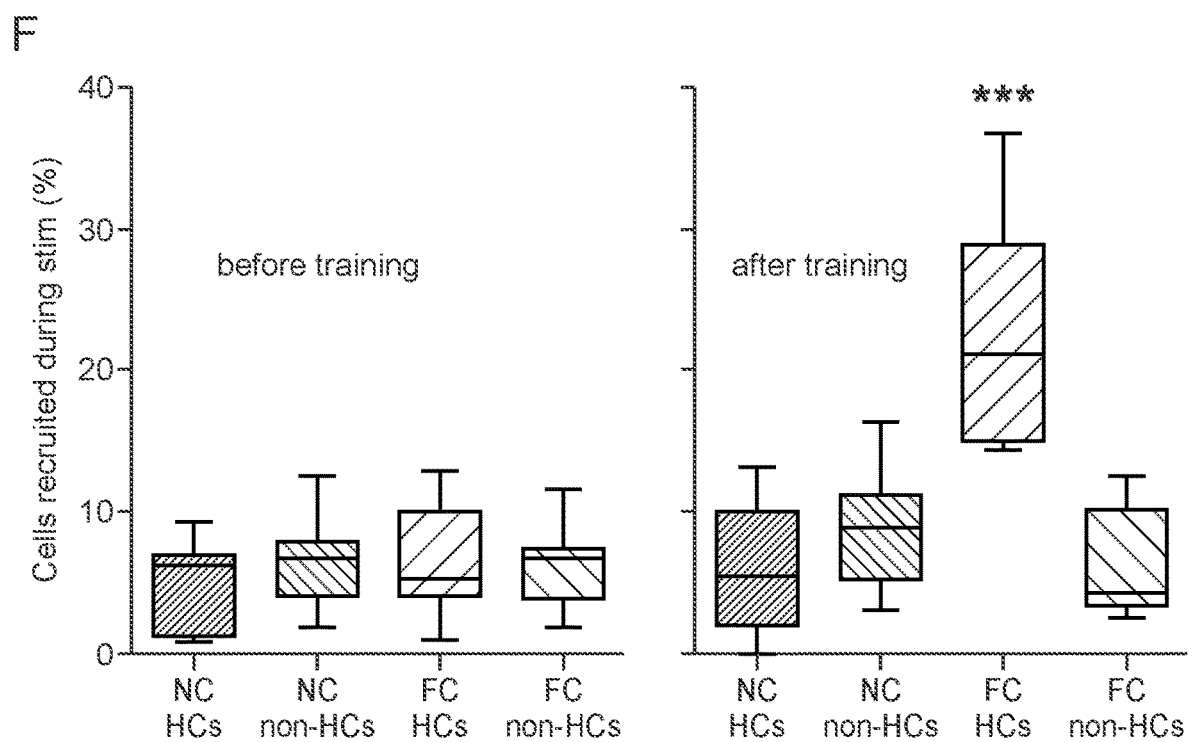

FIG. 18
A
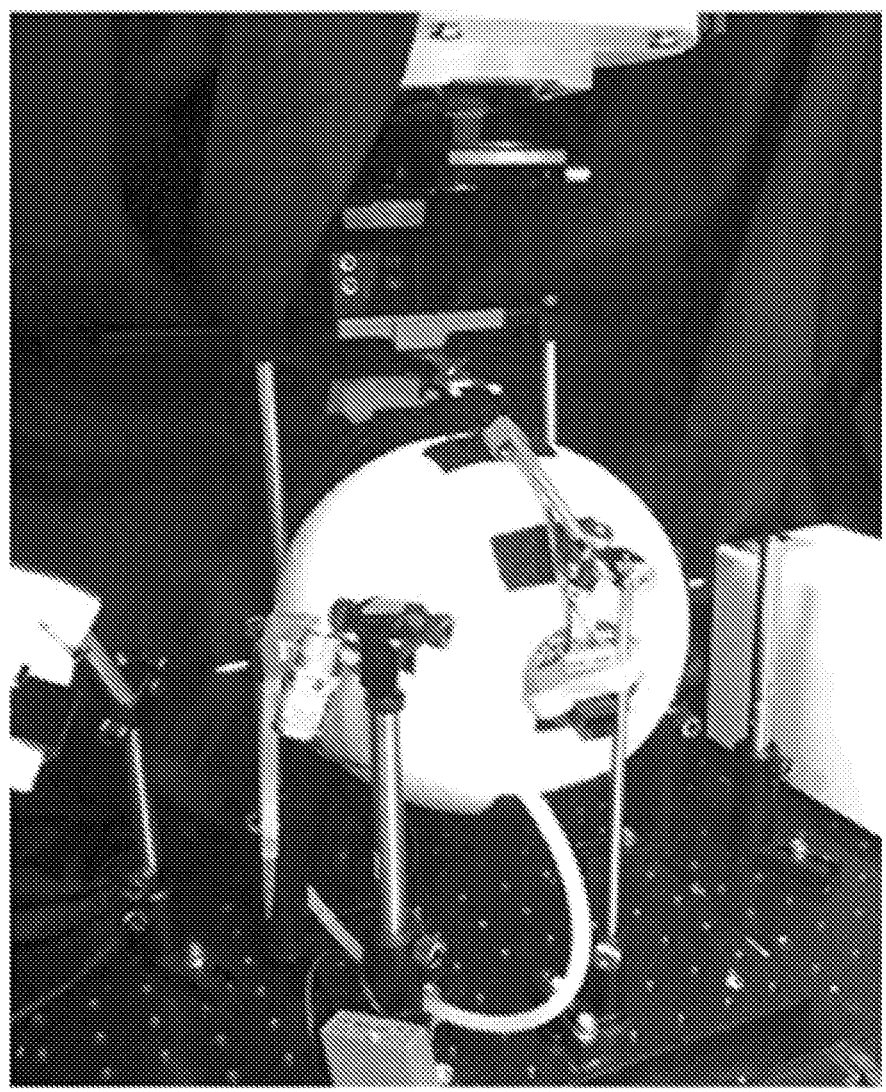
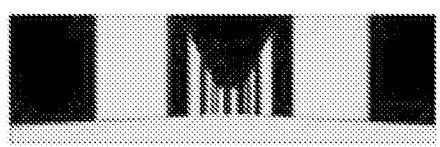
Context 1
Rough Velcro
70% Ethanol
3 KHz steady tone
Context 2
Smooth Velcro
1% Acetic Acid
8 KHz phasic tone

B

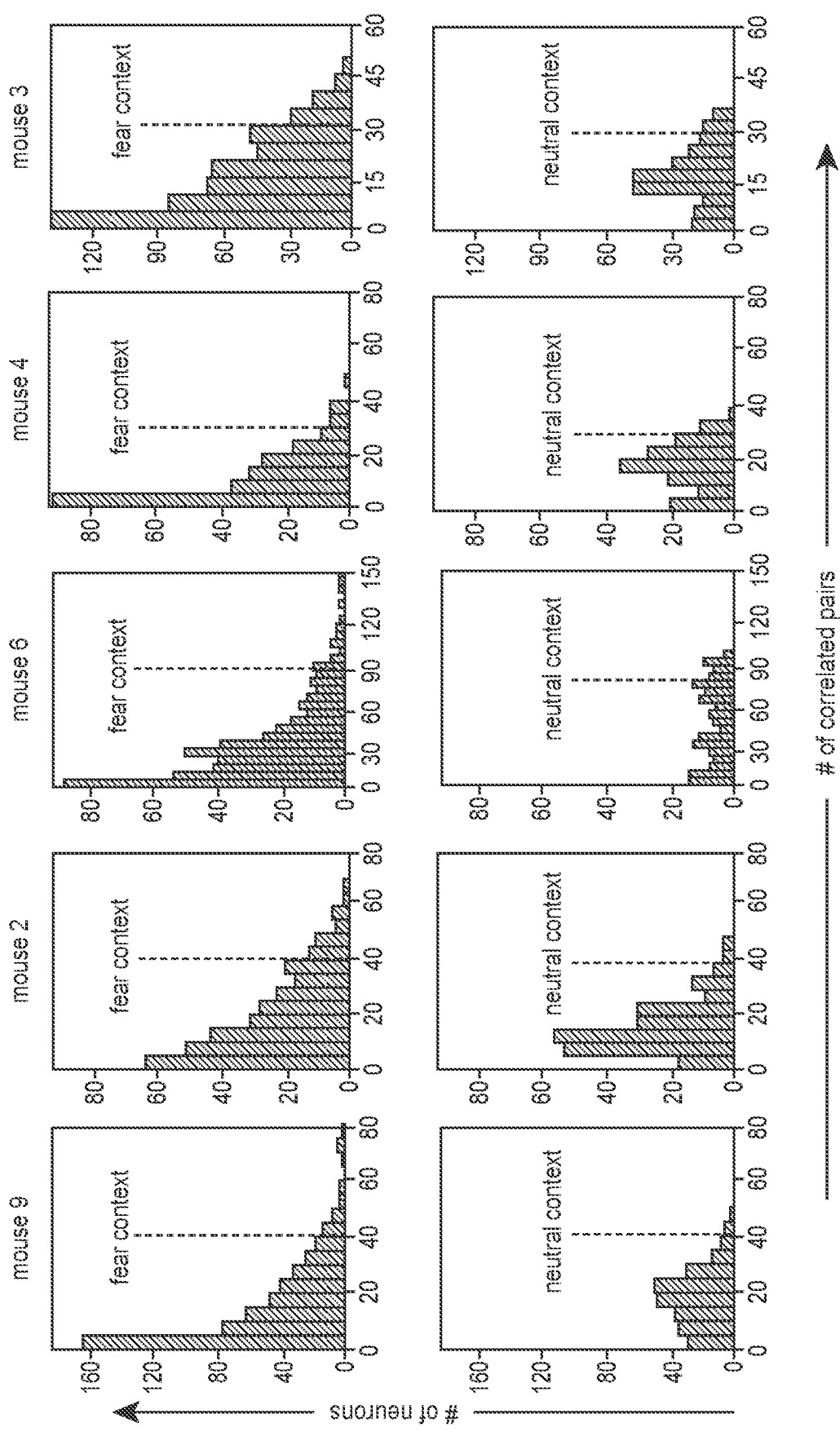

FIG. 19 (Cont.)
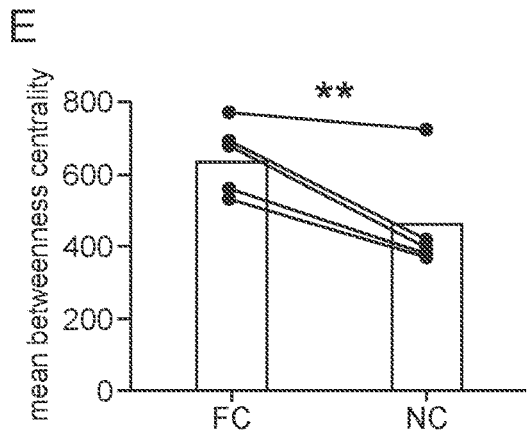
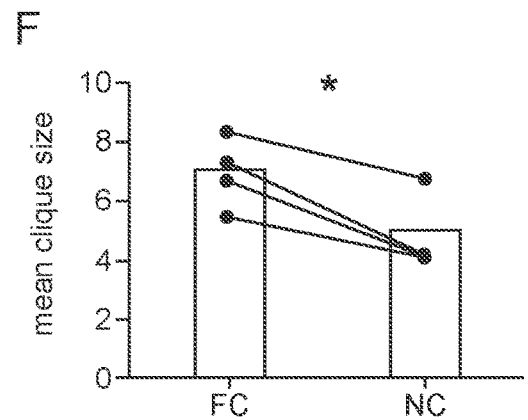
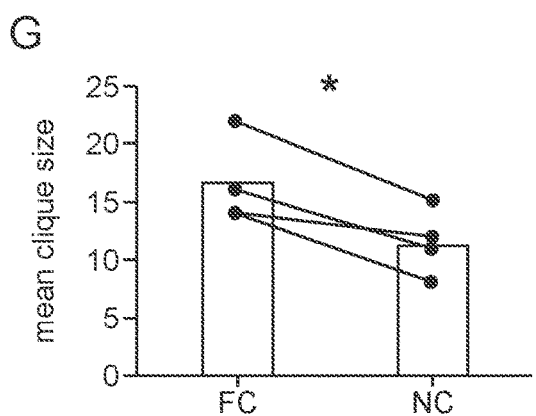
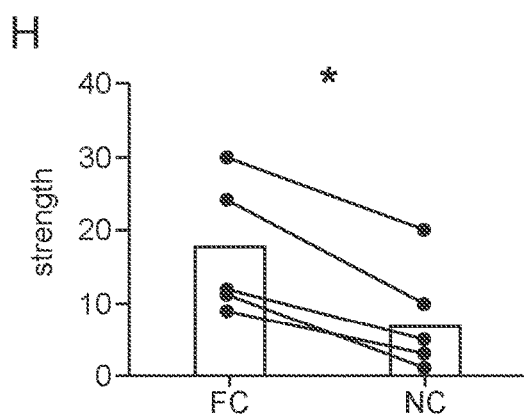
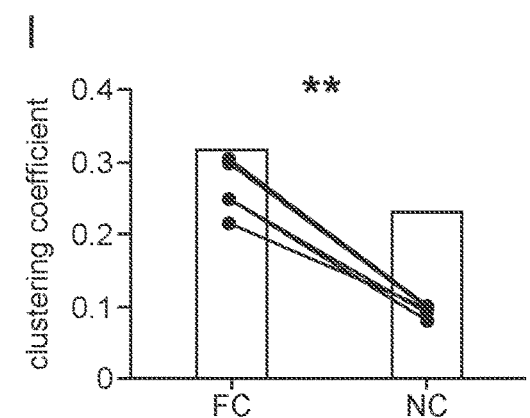
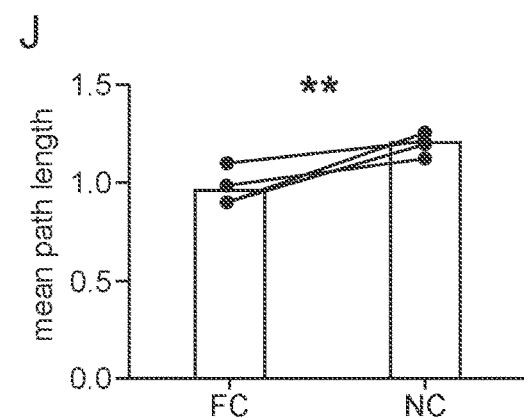

FIG. 20
A
mouse 3
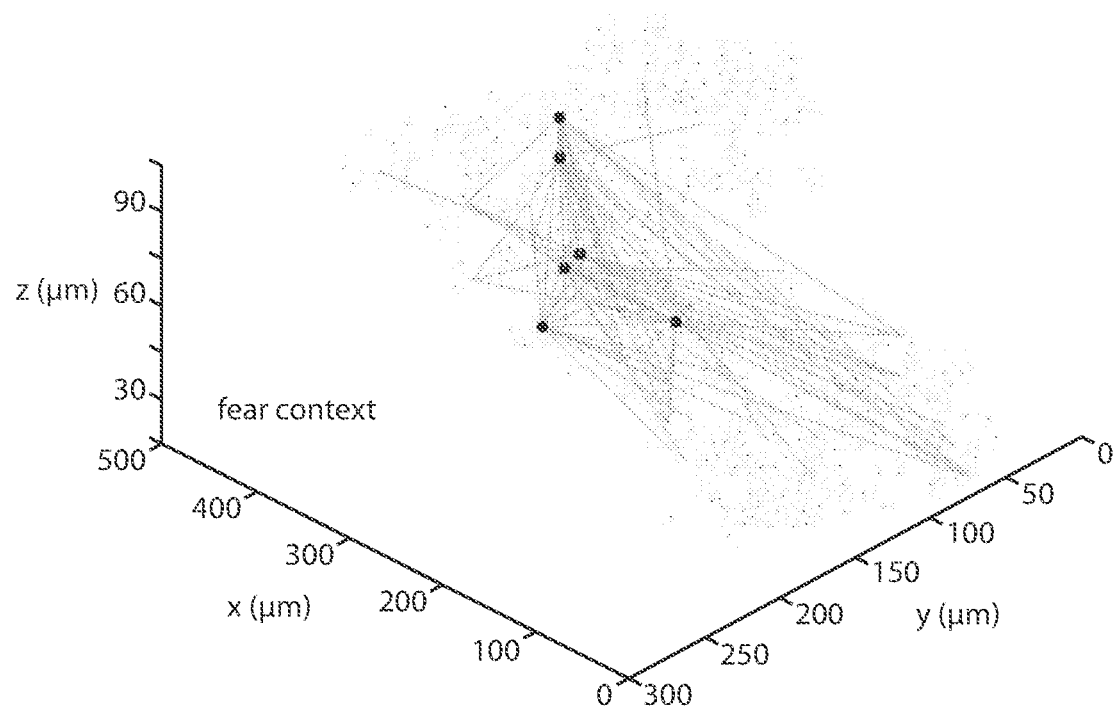
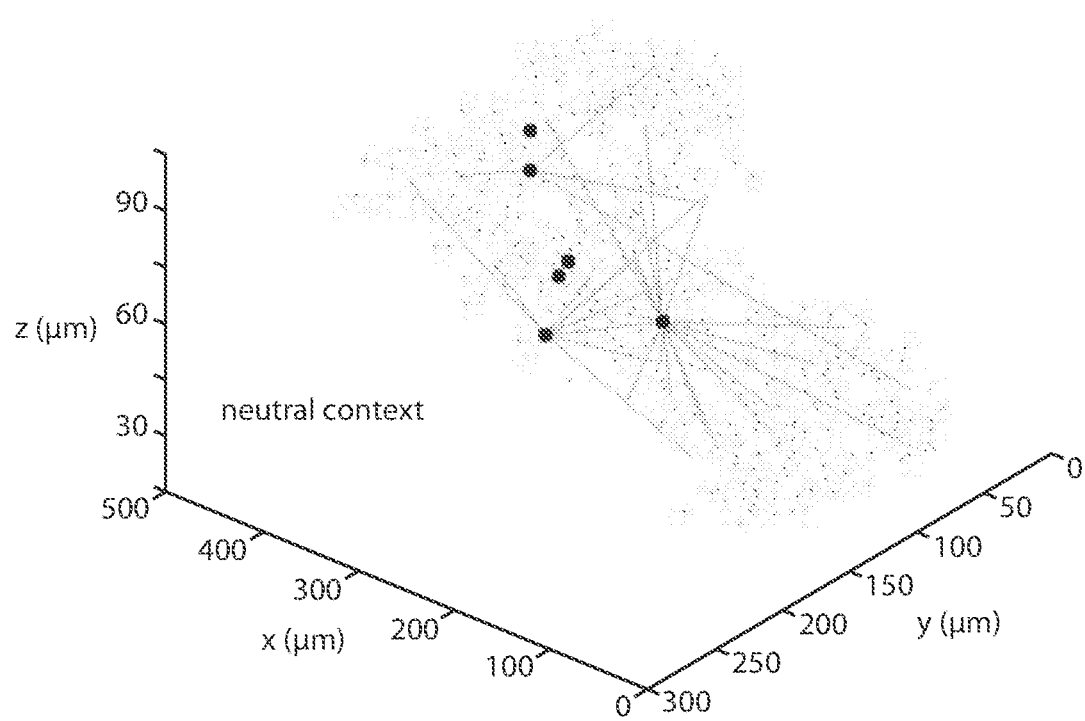

FIG. 20 (Cont.)
B
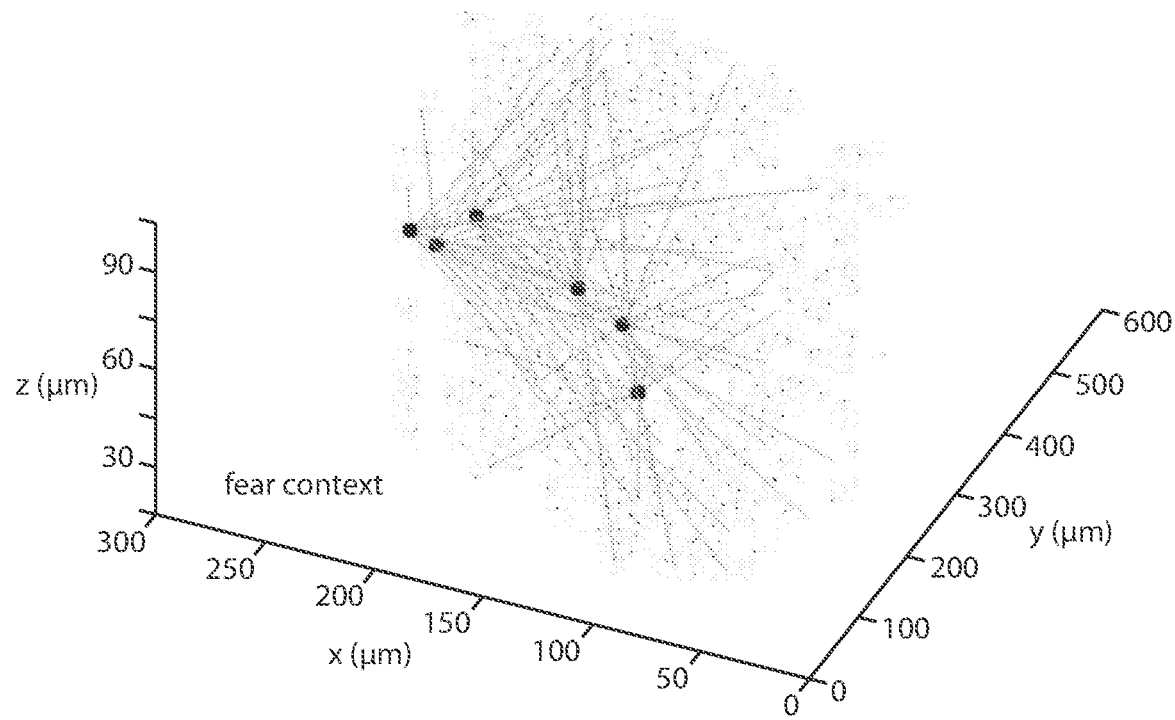
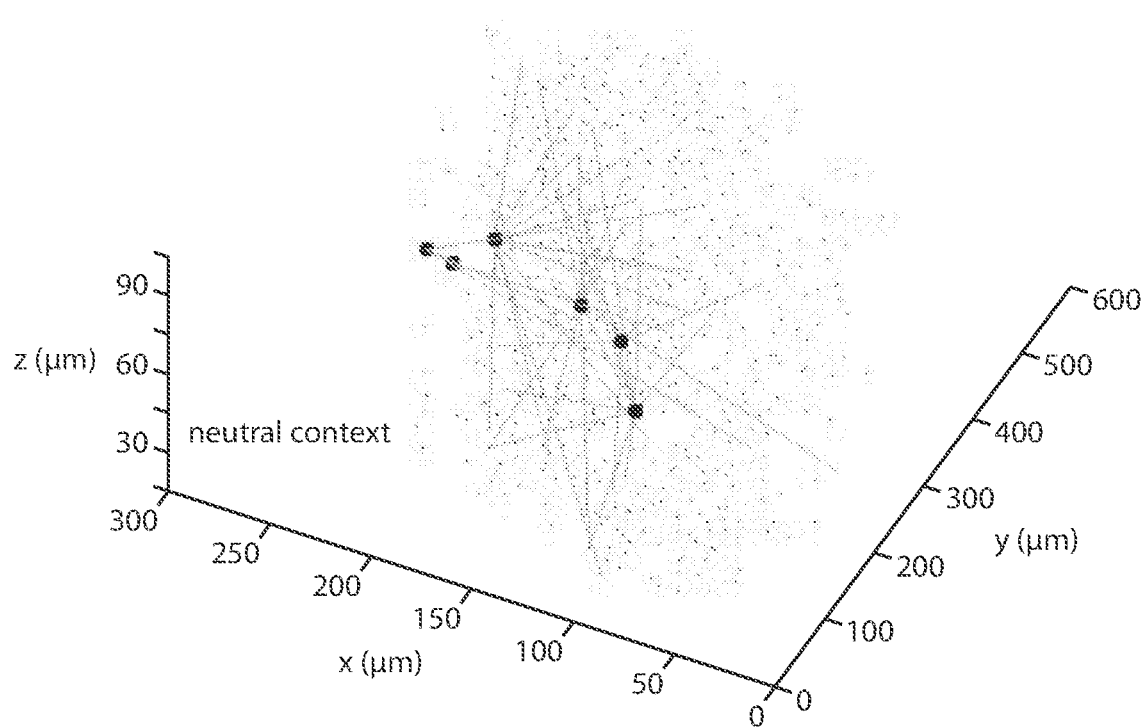

FIG. 20 (Cont.)
C
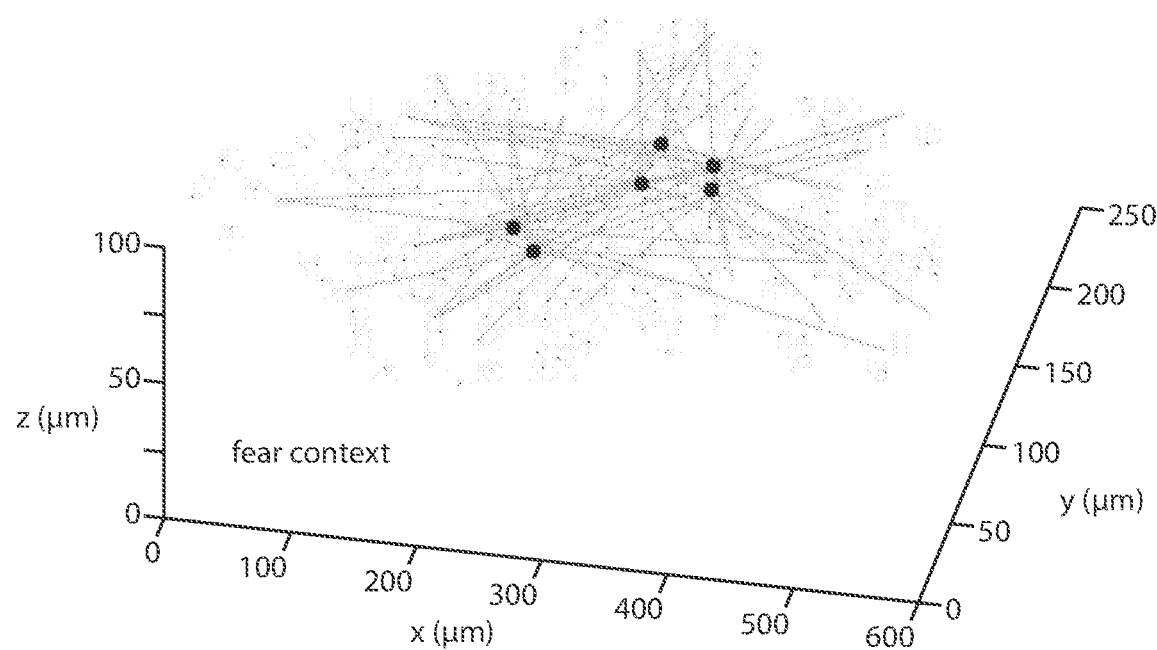
mouse 2
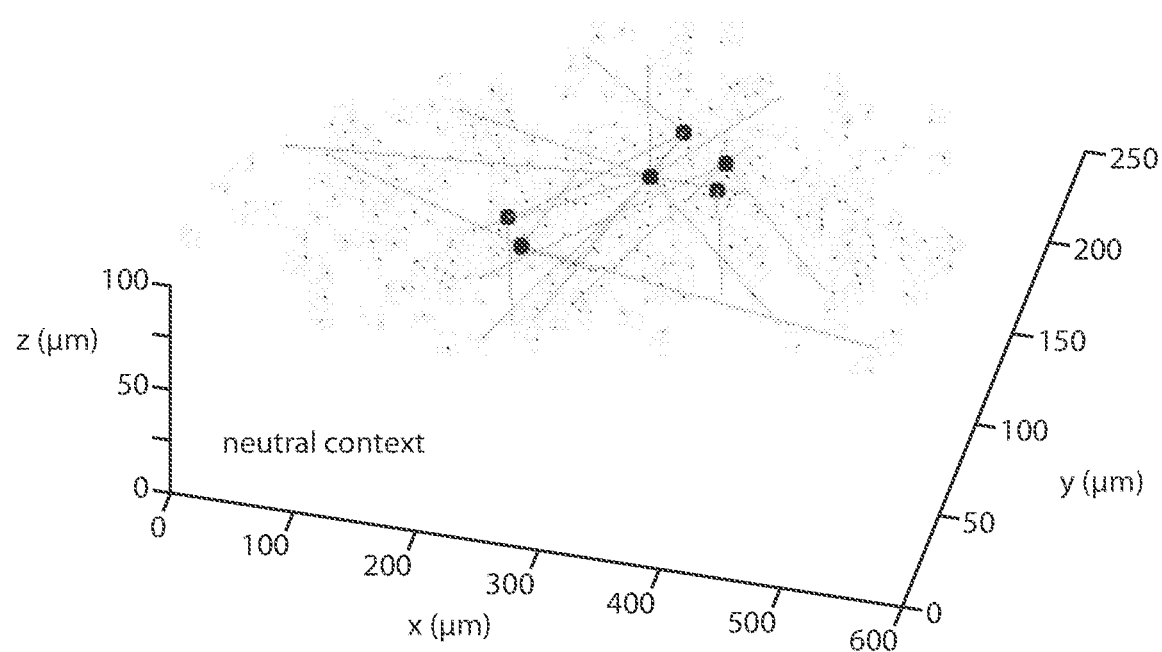

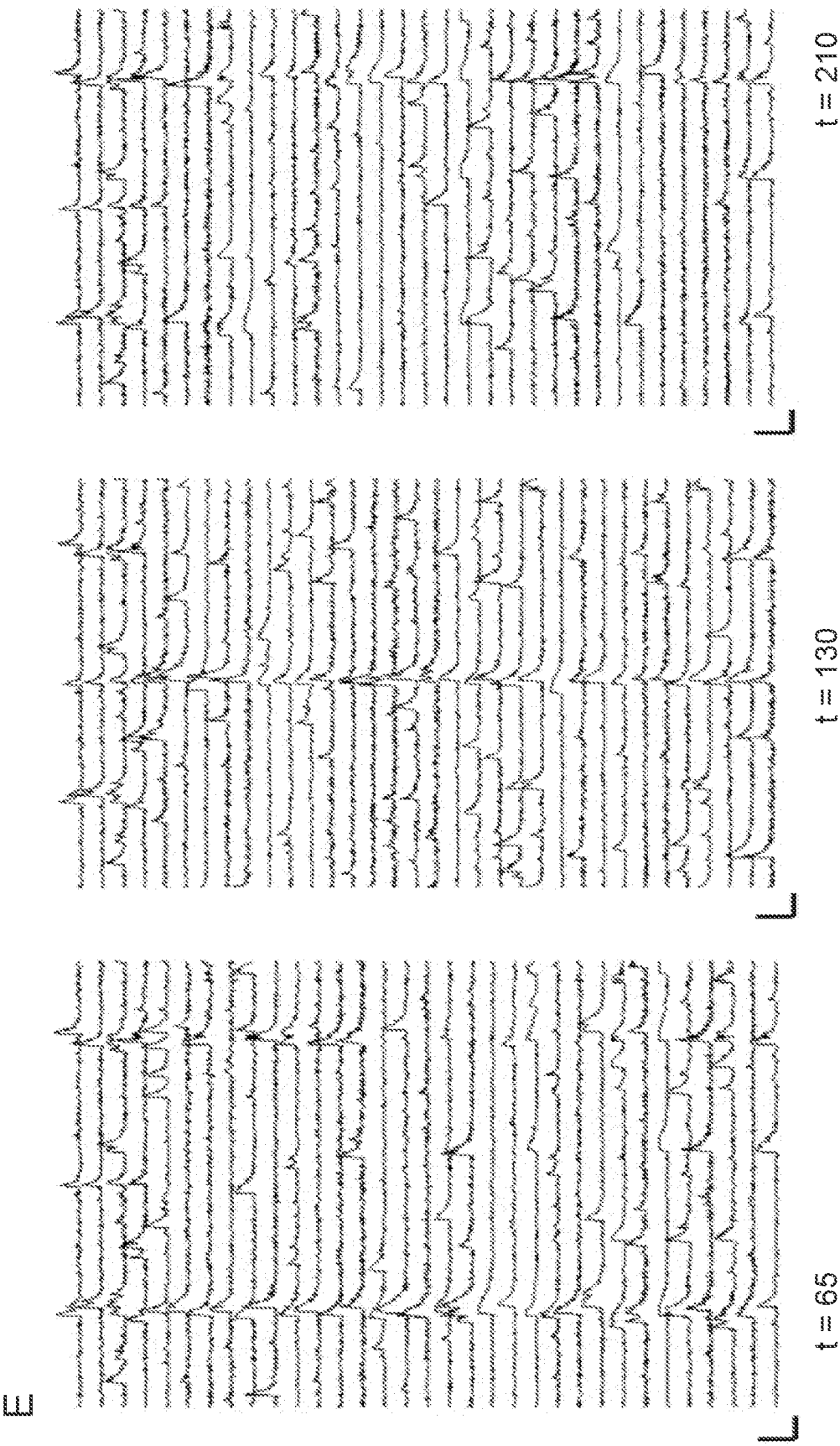

FIG. 24
A
ReaChR
bReaCh-ES
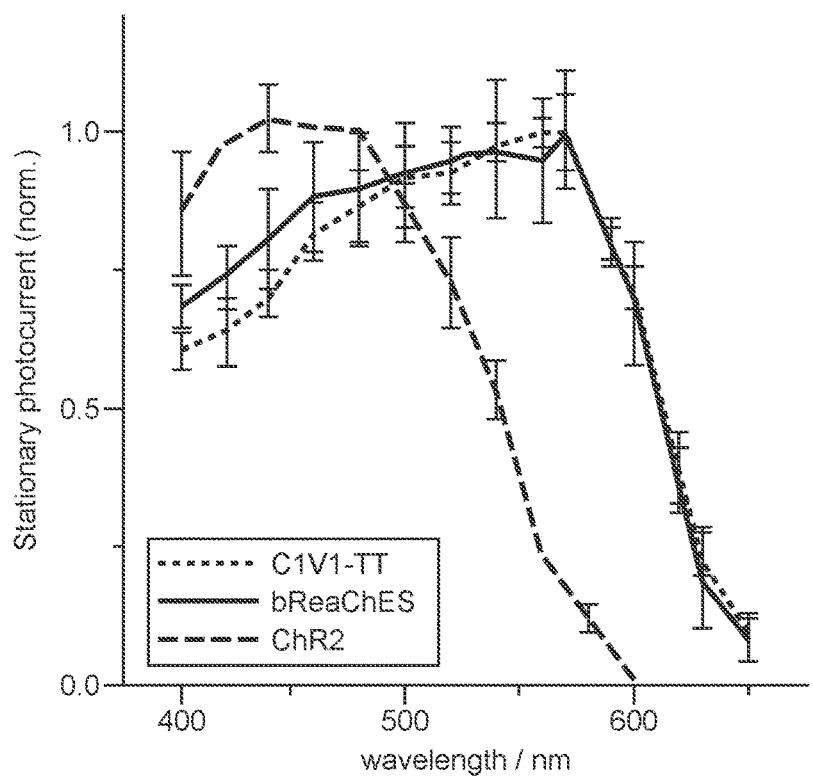

SEQUENCE LISTING

<160> NUMBER OF SEQ ID NOS: 62

<210> SEQ ID NO 1
<211> LENGTH: 350
<212> TYPE: PRT
<213> ORGANISM: Artificial sequence
<220> FEATURE:
<223> OTHER INFORMATION: Synthetic polypeptide sequence

<400> SEQUENCE: 1

```
Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Val Phe Ala Leu Ser Val Ala Cys Leu Gly Trp Tyr Ala Tyr
            100                 105                 110

Gln Ala Trp Arg Ala Thr Cys Gly Trp Glu Val Tyr Val Ala Leu
        115                 120                 125

Ile Glu Met Met Lys Ser Ile Ile Glu Ala Phe His Glu Phe Asp Ser
    130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Glu Asp Lys Tyr Glu Ser Ser
```

340             345             350

<210> SEQ ID NO 2
<211> LENGTH: 350
<212> TYPE: PRT
<213> ORGANISM: Artificial sequence
<220> FEATURE:
<223> OTHER INFORMATION: Synthetic polypeptide sequence

<400> SEQUENCE: 2

Met Val Ser Arg Arg Pro Trp Leu Leu Ala Leu Ala Leu Ala Val Ala
1               5                   10                  15

Leu Ala Ala Gly Ser Ala Gly Ala Ser Thr Gly Ser Asp Ala Thr Val
            20                  25                  30

Pro Val Ala Thr Gln Asp Gly Pro Asp Tyr Val Phe His Arg Ala His
        35                  40                  45

Glu Arg Met Leu Phe Gln Thr Ser Tyr Thr Leu Glu Asn Asn Gly Ser
    50                  55                  60

Val Ile Cys Ile Pro Asn Asn Gly Gln Cys Phe Cys Leu Ala Trp Leu
65                  70                  75                  80

Lys Ser Asn Gly Thr Asn Ala Glu Lys Leu Ala Ala Asn Ile Leu Gln
                85                  90                  95

Trp Val Val Phe Ala Leu Ser Val Ala Cys Leu Gly Trp Tyr Ala Tyr
            100                 105                 110

Gln Ala Trp Arg Ala Thr Cys Gly Trp Glu Val Tyr Val Ala Leu
        115                 120                 125

Ile Glu Met Met Lys Ser Ile Ile Glu Ala Phe His Glu Phe Asp Ser
130                 135                 140

Pro Ala Thr Leu Trp Leu Ser Ser Gly Asn Gly Val Val Trp Met Arg
145                 150                 155                 160

Tyr Gly Ser Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

```
<210> SEQ ID NO 3
<211> LENGTH: 305
<212> TYPE: PRT
<213> ORGANISM: Artificial sequence
<220> FEATURE:
<223> OTHER INFORMATION: Synthetic polypeptide sequence

<400> SEQUENCE: 3

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Val Phe Ala Leu Ser Val
    50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Glu Met Met Lys Ser Ile Ile
                85                  90                  95

Glu Ala Phe His Glu Phe Asp Ser Pro Ala Thr Leu Trp Leu Ser Ser
            100                 105                 110

Gly Asn Gly Val Val Trp Met Arg Tyr Gly Ser Trp Leu Leu Thr Cys
        115                 120                 125

Pro Val Ile Leu Ile His Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Gly Pro Glu Gly Phe Gly His Ile
225                 230                 235                 240

Ser Pro Tyr Gly Ser Ala Ile Gly His Ser Ile Leu Asp Leu Ile Ala
                245                 250                 255

Lys Asn Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 4
<211> LENGTH: 335
<212> TYPE: PRT
<213> ORGANISM: Artificial sequence
<220> FEATURE:
<223> OTHER INFORMATION: Synthetic polypeptide sequence

<400> SEQUENCE: 4
```

```
Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
            20                  25                  30

Gln Cys Phe Cys Leu Ala Trp Leu Lys Ser Asn Gly Thr Asn Ala Glu
        35                  40                  45

Lys Leu Ala Ala Asn Ile Leu Gln Trp Val Val Phe Ala Leu Ser Val
50                  55                  60

Ala Cys Leu Gly Trp Tyr Ala Tyr Gln Ala Trp Arg Ala Thr Cys Gly
65                  70                  75                  80

Trp Glu Glu Val Tyr Val Ala Leu Ile Glu Met Met Lys Ser Ile Ile
                85                  90                  95

Glu Ala Phe His Glu Phe Asp Ser Pro Ala Thr Leu Trp Leu Ser Ser
            100                 105                 110

Gly Asn Gly Val Val Trp Met Arg Tyr Gly Ser Trp Leu Leu Thr Cys
        115                 120                 125

Pro Val Ile Leu Ile His Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
    210                 215                 220

Met Phe Pro Val Leu Phe Leu Leu Gly Pro Glu Gly Phe Gly His Ile
225                 230                 235                 240

Ser Pro Tyr Gly Ser Ala Ile Gly His Ser Ile Leu Asp Leu Ile Ala
                245                 250                 255

Lys Asn Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp Ala Ala Ala Lys Ser Arg Ile Thr Ser Glu Gly Glu Tyr Ile Pro
305                 310                 315                 320

Leu Asp Gln Ile Asp Ile Asn Val Phe Cys Tyr Glu Asn Glu Val
                325                 330                 335

<210> SEQ ID NO 5
<211> LENGTH: 294
<212> TYPE: PRT
<213> ORGANISM: Artificial sequence
<220> FEATURE:
<223> OTHER INFORMATION: Synthetic polypeptide sequence

<400> SEQUENCE: 5

Leu Phe Gln Thr Ser Tyr Thr Leu Glu Asn Asn Gly Ser Val Ile Cys
1               5                   10                  15

Ile Pro Asn Asn Gly Gln Cys Phe Cys Leu Ala Trp Leu Lys Ser Asn
            20                  25                  30
```

```
Gly Thr Asn Ala Glu Lys Leu Ala Ala Asn Ile Leu Gln Trp Val Val
             35                  40                  45

Phe Ala Leu Ser Val Ala Cys Leu Gly Trp Tyr Ala Tyr Gln Ala Trp
 50                  55                  60

Arg Ala Thr Cys Gly Trp Glu Glu Val Tyr Val Ala Leu Ile Glu Met
 65                  70                  75                  80

Met Lys Ser Ile Ile Glu Ala Phe His Glu Phe Asp Ser Pro Ala Thr
                 85                  90                  95

Leu Trp Leu Ser Ser Gly Asn Gly Val Val Trp Met Arg Tyr Gly Ser
            100                 105                 110

Trp Leu Leu Thr Cys Pro Val Ile Leu Ile His Leu Ser Asn Leu Thr
            115                 120                 125

Gly Leu Lys Asp Asp Tyr Ser Lys Arg Thr Met Gly Leu Leu Val Ser
130                 135                 140

Asp Val Gly Cys Ile Val Trp Gly Ala Thr Ser Ala Met Cys Thr Gly
145                 150                 155                 160

Trp Thr Lys Ile Leu Phe Phe Leu Ile Ser Leu Ser Tyr Gly Met Tyr
                165                 170                 175

Thr Tyr Phe His Ala Ala Lys Val Tyr Ile Glu Ala Phe His Thr Val
            180                 185                 190

Pro Lys Gly Leu Cys Arg Gln Leu Val Arg Ala Met Ala Trp Leu Phe
            195                 200                 205

Phe Val Ser Trp Gly Met Phe Pro Val Leu Phe Leu Leu Gly Pro Glu
210                 215                 220

Gly Phe Gly His Ile Ser Pro Tyr Gly Ser Ala Ile Gly His Ser Ile
225                 230                 235                 240

Leu Asp Leu Ile Ala Lys Asn Met Trp Gly Val Leu Gly Asn Tyr Leu
                245                 250                 255

Arg Val Lys Ile His Glu His Ile Leu Leu Tyr Gly Asp Ile Arg Lys
            260                 265                 270

Lys Gln Lys Ile Thr Ile Ala Gly Gln Glu Met Glu Val Glu Thr Leu
            275                 280                 285

Val Ala Glu Glu Glu Asp
    290

<210> SEQ ID NO 6
<211> LENGTH: 324
<212> TYPE: PRT
<213> ORGANISM: Artificial sequence
<220> FEATURE:
<223> OTHER INFORMATION: Synthetic polypeptide sequence

<400> SEQUENCE: 6

Leu Phe Gln Thr Ser Tyr Thr Leu Glu Asn Asn Gly Ser Val Ile Cys
 1               5                  10                  15

Ile Pro Asn Asn Gly Gln Cys Phe Cys Leu Ala Trp Leu Lys Ser Asn
             20                  25                  30

Gly Thr Asn Ala Glu Lys Leu Ala Ala Asn Ile Leu Gln Trp Val Val
             35                  40                  45

Phe Ala Leu Ser Val Ala Cys Leu Gly Trp Tyr Ala Tyr Gln Ala Trp
 50                  55                  60

Arg Ala Thr Cys Gly Trp Glu Glu Val Tyr Val Ala Leu Ile Glu Met
 65                  70                  75                  80

Met Lys Ser Ile Ile Glu Ala Phe His Glu Phe Asp Ser Pro Ala Thr
                 85                  90                  95
```

Leu Trp Leu Ser Ser Gly Asn Gly Val Val Trp Met Arg Tyr Gly Ser
                100                 105                 110

Trp Leu Leu Thr Cys Pro Val Ile Leu Ile His Leu Ser Asn Leu Thr
            115                 120                 125

Gly Leu Lys Asp Asp Tyr Ser Lys Arg Thr Met Gly Leu Leu Val Ser
        130                 135                 140

Asp Val Gly Cys Ile Val Trp Gly Ala Thr Ser Ala Met Cys Thr Gly
145                 150                 155                 160

Trp Thr Lys Ile Leu Phe Phe Leu Ile Ser Leu Ser Tyr Gly Met Tyr
                165                 170                 175

Thr Tyr Phe His Ala Ala Lys Val Tyr Ile Glu Ala Phe His Thr Val
            180                 185                 190

Pro Lys Gly Leu Cys Arg Gln Leu Val Arg Ala Met Ala Trp Leu Phe
        195                 200                 205

Phe Val Ser Trp Gly Met Phe Pro Val Leu Phe Leu Leu Gly Pro Glu
210                 215                 220

Gly Phe Gly His Ile Ser Pro Tyr Gly Ser Ala Ile Gly His Ser Ile
225                 230                 235                 240

Leu Asp Leu Ile Ala Lys Asn Met Trp Gly Val Leu Gly Asn Tyr Leu
                245                 250                 255

Arg Val Lys Ile His Glu His Ile Leu Leu Tyr Gly Asp Ile Arg Lys
            260                 265                 270

Lys Gln Lys Ile Thr Ile Ala Gly Gln Glu Met Glu Val Glu Thr Leu
        275                 280                 285

Val Ala Glu Glu Glu Asp Ala Ala Ala Lys Ser Arg Ile Thr Ser Glu
290                 295                 300

Gly Glu Tyr Ile Pro Leu Asp Gln Ile Asp Ile Asn Val Phe Cys Tyr
305                 310                 315                 320

Glu Asn Glu Val

<210> SEQ ID NO 7
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 7

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly

```
            130                 135                 140
Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
                195                 200                 205

Lys Leu Pro Val Pro Trp Pro Thr Leu Val Thr Thr Leu Thr Tyr Gly
        210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
                275                 280                 285

Glu Asp Gly Asn Ile Leu Gly His Lys Leu Glu Tyr Asn Thr Arg Asp
        290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350

Met Ile Asn Glu Val Asp Ala Asp Gly Asp Gly Thr Ile Asp Phe Pro
                355                 360                 365

Glu Phe Leu Thr Met Met Ala Arg Lys Met Lys Tyr Thr Asp Ser Glu
        370                 375                 380

Glu Glu Ile Gly Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
                435                 440                 445

Ala Lys
    450

<210> SEQ ID NO 8
<211> LENGTH: 451
<212> TYPE: PRT
<213> ORGANISM: Artificial sequence
<220> FEATURE:
<223> OTHER INFORMATION: Synthetic polypeptide sequence

<400> SEQUENCE: 8

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Leu Ala Thr Met Val Asp Ser Ser Arg Arg Lys Trp Asn Lys Thr Gly
```

```
            35                  40                  45
His Ala Val Arg Ala Ile Gly Arg Leu Ser Ser Leu Glu Asn Val Tyr
 50                  55                  60
Ile Met Ala Asp Lys Gln Lys Asn Gly Ile Lys Ala Asn Phe Lys Ile
 65                  70                  75                  80
Arg His Asn Ile Glu Asp Gly Gly Val Gln Leu Ala Tyr His Tyr Gln
                     85                  90                  95
Gln Asn Thr Pro Ile Gly Asp Gly Pro Val Leu Leu Pro Asp Asn His
                    100                 105                 110
Tyr Leu Ser Thr Gln Ser Lys Leu Ser Lys Asp Pro Asn Glu Lys Arg
                    115                 120                 125
Asp His Met Val Leu Leu Glu Phe Val Thr Ala Ala Gly Ile Thr Leu
                    130                 135                 140
Gly Met Asp Glu Leu Tyr Lys Gly Gly Thr Gly Gly Ser Met Val Ser
145                 150                 155                 160
Lys Gly Glu Glu Leu Phe Thr Gly Val Val Pro Ile Leu Val Glu Leu
                    165                 170                 175
Asp Gly Asp Val Asn Gly His Lys Phe Ser Val Ser Gly Glu Gly Glu
                    180                 185                 190
Gly Asp Ala Thr Tyr Gly Lys Leu Thr Leu Lys Phe Ile Cys Thr Thr
                    195                 200                 205
Gly Lys Leu Pro Val Pro Trp Pro Thr Leu Val Thr Thr Leu Thr Tyr
210                 215                 220
Gly Val Gln Cys Phe Ser Arg Tyr Pro Asp His Met Lys Gln His Asp
225                 230                 235                 240
Phe Phe Lys Ser Ala Met Pro Glu Gly Tyr Ile Gln Glu Arg Thr Ile
                    245                 250                 255
Phe Phe Lys Asp Asp Gly Asn Tyr Lys Thr Arg Ala Glu Val Lys Phe
                    260                 265                 270
Glu Gly Asp Thr Leu Val Asn Arg Ile Glu Leu Lys Gly Ile Asp Phe
                    275                 280                 285
Lys Glu Asp Gly Asn Ile Leu Gly His Lys Leu Glu Tyr Asn Thr Arg
                    290                 295                 300
Asp Gln Leu Thr Glu Glu Gln Ile Ala Glu Phe Lys Glu Ala Phe Ser
305                 310                 315                 320
Leu Phe Asp Lys Asp Gly Asp Gly Thr Ile Thr Thr Lys Glu Leu Gly
                    325                 330                 335
Thr Val Met Arg Ser Leu Gly Gln Asn Pro Thr Glu Ala Glu Leu Gln
                    340                 345                 350
Asp Met Ile Asn Glu Val Asp Ala Asp Gly Asn Gly Thr Ile Asp Phe
                    355                 360                 365
Pro Glu Phe Leu Thr Met Met Ala Arg Lys Met Lys Asp Thr Asp Ser
                    370                 375                 380
Glu Glu Glu Ile Arg Glu Ala Phe Arg Val Phe Asp Lys Asp Gly Asn
385                 390                 395                 400
Gly Tyr Ile Ser Ala Ala Glu Leu Arg His Val Met Thr Asn Leu Gly
                    405                 410                 415
Glu Lys Leu Thr Asp Glu Glu Val Asp Glu Met Ile Arg Glu Ala Asp
                    420                 425                 430
Ile Asp Gly Asp Gly Gln Val Asn Tyr Glu Glu Phe Val Gln Met Met
                    435                 440                 445
Thr Ala Lys
450
```

<210> SEQ ID NO 9
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 9

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Thr Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365
```

```
Glu Phe Leu Thr Met Met Ala Arg Lys Met Lys Asp Thr Asp Ser Glu
        370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
            435                 440                 445

Ala Lys
    450

<210> SEQ ID NO 10
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 10

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
                35                  40                  45

Ala Val Arg Ala Ile Gly Arg Leu Ser Ser Leu Glu Asn Val Tyr Ile
            50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270
```

```
Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
                340                 345                 350

Met Ile Asn Glu Val Asp Ala Asp Gly Asn Gly Thr Ile Asp Phe Pro
                355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
                420                 425                 430

Asp Gly Asp Gly Gln Val Asn Tyr Glu Glu Phe Val Gln Met Met Thr
                435                 440                 445

Ala Lys
    450

<210> SEQ ID NO 11
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 11

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Thr Gln Cys Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175
```

```
Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
            355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450

<210> SEQ ID NO 12
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 12

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80
```

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asn Gly Thr Ile Asp Phe Pro
        355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 13
<211> LENGTH: 450
<212> TYPE: PRT
<213> ORGANISM: Artificial sequence
<220> FEATURE:

<223> OTHER INFORMATION: Synthetic polypeptide sequence

<400> SEQUENCE: 13

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Met Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Asp Thr Asp Ser Glu
    370                 375                 380

Glu Glu Ile Arg Glu Ala Phe Arg Val Phe Asp Lys Asp Gly Asn Gly
385                 390                 395                 400
```

-continued

```
Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 14
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 14

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300
```

```
Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
            325                 330                 335

Val Met Arg Ser Leu Gly Gln Asn Pro Thr Glu Ala Glu Leu Gln Asp
        340                 345                 350

Met Ile Asn Glu Val Asp Ala Asp Gly Asp Gly Thr Ile Asp Phe Pro
    355                 360                 365

Glu Phe Leu Thr Met Met Ala Arg Lys Met Lys Asp Thr Asp Ser Glu
370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
        420                 425                 430

Asp Gly Asp Gly Gln Val Asn Tyr Glu Glu Phe Val Gln Met Met Thr
    435                 440                 445

Ala Lys
    450

<210> SEQ ID NO 15
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 15

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205
```

Lys Leu Pro Val Pro Trp Pro Thr Leu Val Thr Thr Leu Thr Tyr Gly
    210             215                 220

Val Gln Cys Phe Ser Arg Tyr Pro Asp His Met Lys Gln His Asp Phe
225             230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Leu Pro Asp
290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Thr Asp Ser Glu
370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
    450

<210> SEQ ID NO 16
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 16

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
        50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
            115                 120                 125

His Met Val Leu Glu Phe Val Thr Ala Ala Gly Ile Thr Leu Gly
        130                 135                 140

Met Asp Glu Leu Tyr Lys Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Gly Ser Tyr Arg Asp Thr Glu
    370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 17
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 17

Met Gly Ser His His His His His Gly Met Ala Ser Met Thr Gly
1               5                   10                  15

```
Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
 50                  55                  60

Lys Ala Asp Lys Gln Lys Asn Gly Ile Lys Ala Asn Phe His Ile Arg
 65                  70                  75                  80

His Asn Ile Glu Asp Gly Gly Val Gln Leu Ala Tyr His Tyr Gln Gln
            85                  90                  95

Asn Thr Pro Ile Gly Asp Gly Pro Val Leu Leu Pro Asp Asn His Tyr
        100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Arg Asp Thr Glu
    370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
```

```
                435                 440                 445
Ala Lys
    450

<210> SEQ ID NO 18
<211> LENGTH: 450
<212> TYPE: PRT
<213> ORGANISM: Artificial sequence
<220> FEATURE:
<223> OTHER INFORMATION: Synthetic polypeptide sequence

<400> SEQUENCE: 18

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
                35                  40                  45

Ala Val Arg Ala Ile Gly Arg Leu Ser Ser Leu Glu Asn Val Tyr Ile
50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
                115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
                195                 200                 205

Lys Leu Pro Val Pro Trp Pro Thr Leu Val Thr Thr Leu Thr Tyr Gly
                210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
                260                 265                 270

Gly Asp Thr Leu Val Asn Arg Ile Glu Leu Lys Gly Ile Asp Phe Lys
                275                 280                 285

Glu Asp Gly Asn Ile Leu Gly His Lys Leu Glu Tyr Asn Leu Pro Asp
                290                 295                 300

Gln Leu Thr Glu Glu Gln Ile Ala Glu Phe Lys Glu Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
```

```
            340                 345                 350
Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Arg Asp Thr Glu
    370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 19
<211> LENGTH: 415
<212> TYPE: PRT
<213> ORGANISM: Artificial sequence
<220> FEATURE:
<223> OTHER INFORMATION: Synthetic polypeptide sequence

<400> SEQUENCE: 19

Met Val Asp Ser Ser Arg Arg Lys Trp Asn Lys Thr Gly His Ala Val
1               5                   10                  15

Arg Ala Ile Gly Arg Leu Ser Ser Pro Glu Asn Val Tyr Ile Lys Ala
            20                  25                  30

Asp Glu Gln Lys Asn Gly Ile Lys Ala Tyr Phe Lys Ile Arg His Asn
        35                  40                  45

Ile Glu Gly Gly Gly Val Gln Leu Ala Tyr His Tyr Gln Gln Ile Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Ser Gly Gly Met Val Ser Lys Gly Glu Glu
        115                 120                 125

Leu Phe Thr Gly Val Val Pro Ile Gln Val Glu Leu Asp Gly Asp Val
    130                 135                 140

Asn Gly His Lys Phe Ser Val Ser Gly Glu Gly Glu Gly Asp Ala Thr
145                 150                 155                 160

Tyr Gly Lys Leu Thr Leu Lys Phe Ile Cys Thr Thr Gly Lys Leu Pro
                165                 170                 175

Val Pro Trp Pro Thr Leu Val Thr Thr Leu Ser Tyr Gly Val Gln Cys
            180                 185                 190

Phe Ser Arg Tyr Pro Asp His Met Lys Gln His Asp Phe Phe Lys Ser
        195                 200                 205

Ala Met Pro Glu Gly Tyr Ile Gln Glu Arg Thr Ile Phe Phe Lys Asp
    210                 215                 220

Asp Gly Asn Tyr Lys Thr Arg Ala Glu Val Lys Phe Glu Gly Asp Thr
225                 230                 235                 240

Leu Val Asn Arg Ile Glu Leu Lys Gly Ile Asp Phe Lys Glu Asp Gly
```

```
                        245                 250                 255
Asn Ile Leu Gly His Lys Leu Glu Tyr Ser Thr Arg Asp Gln Leu Thr
                260                 265                 270
Glu Glu Gln Ile Ala Glu Phe Lys Glu Ala Phe Ser Leu Phe Asp Lys
            275                 280                 285
Asp Gly Asp Gly Thr Ile Thr Thr Lys Glu Leu Gly Thr Val Met Arg
        290                 295                 300
Ser Leu Gly Gln Asn Pro Thr Glu Ala Glu Leu Gln Asp Met Ile Asn
305                 310                 315                 320
Glu Val Asp Ala Asp Gly Asp Gly Thr Ile Asp Phe Pro Glu Phe Leu
                325                 330                 335
Thr Met Met Ala Pro Lys Met Gln Asp Thr Asp Ser Glu Glu Glu Ile
                340                 345                 350
Arg Glu Ala Phe Arg Val Phe Asp Lys Asp Gly Asn Gly Tyr Ile Gly
            355                 360                 365
Ala Ala Glu Leu Arg His Val Met Thr Asn Leu Gly Glu Lys Leu Thr
        370                 375                 380
Asp Glu Glu Val Asp Glu Met Ile Arg Val Ala Asp Ile Asp Gly Asp
385                 390                 395                 400
Gly Gln Val Asn Tyr Glu Glu Phe Val Gln Met Met Thr Ala Lys
                405                 410                 415

<210> SEQ ID NO 20
<211> LENGTH: 416
<212> TYPE: PRT
<213> ORGANISM: Artificial sequence
<220> FEATURE:
<223> OTHER INFORMATION: Synthetic polypeptide sequence

<400> SEQUENCE: 20

Met Val Asp Ser Ser Arg Arg Lys Trp Asn Lys Thr Gly His Ala Val
1               5                   10                  15
Arg Ala Ile Gly Arg Leu Ser Ser Leu Glu Asn Val Tyr Ile Lys Ala
                20                  25                  30
Asp Glu Gln Lys Asn Gly Ile Lys Ala Asn Phe Lys Ile Arg His Asn
            35                  40                  45
Ile Glu Asp Gly Gly Val Gln Leu Ala Tyr His Tyr Gln Gln Asn Thr
        50                  55                  60
Pro Ile Gly Asp Gly Pro Val Leu Leu Pro Asp Asn His Tyr Leu Ser
65                  70                  75                  80
Val Gln Ser Ile Leu Ser Lys Asp Pro Asn Glu Lys Arg Asp His Met
                85                  90                  95
Val Leu Leu Glu Phe Val Thr Ala Ala Gly Ile Thr Leu Gly Met Asp
            100                 105                 110
Glu Leu Tyr Lys Gly Gly Thr Gly Gly Ser Met Val Ser Lys Gly Glu
        115                 120                 125
Glu Leu Phe Thr Gly Val Val Pro Ile Gln Val Glu Leu Asp Gly Asp
    130                 135                 140
Val Asn Gly His Lys Phe Ser Val Ser Gly Glu Gly Glu Gly Asp Ala
145                 150                 155                 160
Thr Tyr Gly Lys Leu Thr Leu Lys Phe Ile Cys Thr Thr Gly Lys Leu
                165                 170                 175
Pro Val Pro Trp Pro Thr Leu Val Thr Thr Leu Ser Tyr Gly Val Gln
            180                 185                 190
Cys Phe Ser Arg Tyr Pro Asp His Met Lys Gln His Asp Phe Phe Lys
```

```
                195                 200                 205
Ser Ala Met Pro Glu Gly Tyr Ile Gln Glu Arg Thr Ile Phe Phe Lys
210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
                260                 265                 270

Thr Glu Glu Gln Ile Ala Glu Leu Lys Glu Ala Phe Ser Leu Phe Asp
                275                 280                 285

Lys Asp Gly Asp Gly Thr Ile Thr Thr Lys Glu Leu Gly Thr Val Met
290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Leu Pro Glu Phe
                325                 330                 335

Gln Thr Met Met Ala Arg Lys Met Asn Asp Thr Asp Ser Glu Glu Glu
                340                 345                 350

Ile Arg Glu Ala Phe Arg Val Phe Asp Lys Asp Gly Asn Gly Tyr Ile
                355                 360                 365

Gly Ala Ala Glu Leu Arg His Val Met Thr Asn Leu Gly Glu Lys Leu
                370                 375                 380

Thr Asp Glu Glu Val Asp Glu Met Ile Arg Val Ala Asp Ile Asp Gly
385                 390                 395                 400

Asp Gly Gln Val Asn Tyr Glu Phe Val Gln Met Met Thr Ala Lys
                405                 410                 415
```

<210> SEQ ID NO 21
<211> LENGTH: 417
<212> TYPE: PRT
<213> ORGANISM: Artificial sequence
<220> FEATURE:
<223> OTHER INFORMATION: Synthetic polypeptide sequence

<400> SEQUENCE: 21

```
Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
                20                  25                  30

Pro Glu Asp Gly Ala Leu Lys Ser Glu Ile Lys Lys Gly Leu Arg Leu
            35                  40                  45

Lys Asp Gly Gly His Tyr Ala Ala Glu Val Lys Thr Thr Tyr Lys Ala
        50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
                100                 105                 110

Gly Gly Thr Gly Gly Ser Leu Val Ser Lys Gly Glu Glu Asp Asn Met
            115                 120                 125

Ala Ile Ile Lys Glu Phe Met Arg Phe Lys Val His Met Glu Gly Ser
        130                 135                 140

Val Asn Gly His Glu Phe Glu Ile Glu Gly Glu Gly Glu Gly Arg Pro
```

```
                145                 150                 155                 160
Tyr Glu Ala Phe Gln Thr Ala Lys Leu Lys Val Thr Lys Gly Gly Pro
                165                 170                 175

Leu Pro Phe Ala Trp Asp Ile Leu Ser Pro Gln Phe Met Tyr Gly Ser
                180                 185                 190

Lys Ala Tyr Ile Lys His Pro Ala Asp Ile Pro Asp Tyr Phe Lys Leu
                195                 200                 205

Ser Phe Pro Glu Gly Phe Arg Trp Glu Arg Val Met Asn Phe Glu Asp
210                 215                 220

Gly Gly Ile Ile His Val Asn Gln Asp Ser Ser Leu Gln Asp Gly Val
225                 230                 235                 240

Phe Ile Tyr Lys Val Lys Leu Arg Gly Thr Asn Phe Pro Pro Asp Gly
                245                 250                 255

Pro Val Met Gln Lys Lys Thr Met Gly Trp Glu Ala Thr Arg Asp Gln
                260                 265                 270

Leu Thr Glu Glu Gln Ile Ala Glu Phe Lys Glu Ala Phe Ser Leu Phe
                275                 280                 285

Asp Lys Asp Gly Asp Gly Thr Ile Thr Thr Lys Glu Leu Gly Thr Val
                290                 295                 300

Met Arg Ser Leu Gly Gln Asn Pro Thr Glu Ala Glu Leu Gln Asp Met
305                 310                 315                 320

Ile Asn Glu Val Asp Ala Asp Gly Asp Gly Thr Phe Asp Phe Pro Glu
                325                 330                 335

Phe Leu Thr Met Met Ala Arg Lys Met Asn Asp Thr Asp Ser Glu Glu
                340                 345                 350

Glu Ile Arg Glu Ala Phe Arg Val Phe Asp Lys Asp Gly Asn Gly Tyr
                355                 360                 365

Ile Gly Ala Ala Glu Leu Arg His Val Met Thr Asp Leu Gly Glu Lys
                370                 375                 380

Leu Thr Asp Glu Glu Val Asp Glu Met Ile Arg Val Ala Asp Ile Asp
385                 390                 395                 400

Gly Asp Gly Gln Val Asn Tyr Glu Glu Phe Val Gln Met Met Thr Ala
                405                 410                 415

Lys

<210> SEQ ID NO 22
<211> LENGTH: 418
<212> TYPE: PRT
<213> ORGANISM: Artificial sequence
<220> FEATURE:
<223> OTHER INFORMATION: Synthetic polypeptide sequence

<400> SEQUENCE: 22

Met Val Asp Ser Pro Arg Arg Lys Trp Asn Lys Thr Gly His Ala Val
1               5                   10                  15

Arg Ala Ile Gly Arg Leu Ser Ser Pro Glu Asn Val Tyr Ile Lys Ala
                20                  25                  30

Asp Lys Gln Lys Asn Gly Ile Lys Ala Asn Phe Lys Ile Arg His Asn
                35                  40                  45

Ile Glu Gly Gly Gly Val Gln Leu Ala Tyr His Tyr Gln Gln Asn Thr
                50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95
```

```
Val Leu Leu Glu Phe Val Thr Ala Ala Gly Ile Thr Leu Gly Met Asp
            100                 105                 110

Glu Leu Tyr Lys Gly Gly Thr Gly Ser Glu Ser Met Val Ser Lys
            115                 120                 125

Gly Glu Glu Leu Phe Thr Gly Val Val Pro Ile Gln Val Glu Leu Asp
130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
            165                 170                 175

Lys Leu Pro Val Pro Trp Pro Thr Leu Val Thr Thr Leu Ser His Gly
            180                 185                 190

Val Gln Cys Phe Ser Arg Tyr Pro Asp His Met Lys Gln His Asp Phe
            195                 200                 205

Phe Lys Ser Ala Met Pro Gly Gly Tyr Ile Gln Glu Arg Thr Ile Phe
            210                 215                 220

Phe Lys Asp Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
            245                 250                 255

Glu Asp Gly Asn Ile Leu Gly His Lys Leu Glu Tyr Asn Thr Arg Gly
            260                 265                 270

Gln Leu Thr Glu Glu Gln Ile Ala Glu Phe Lys Glu Ala Phe Ser Leu
            275                 280                 285

Phe Asp Lys Asp Gly Asp Gly Thr Ile Thr Thr Lys Glu Leu Gly Thr
            290                 295                 300

Val Met Arg Ser Leu Gly Gln Asn Pro Thr Glu Ala Glu Leu Gln Asp
305                 310                 315                 320

Met Ile Asn Glu Val Asp Ala Asp Gly Asp Gly Thr Ile Asp Phe Pro
            325                 330                 335

Glu Phe Leu Thr Met Met Ala Pro Lys Met Gln Asp Thr Asp Ser Glu
            340                 345                 350

Glu Glu Ile Arg Glu Ala Phe Arg Val Phe Asp Lys Asp Gly Asn Gly
            355                 360                 365

Tyr Ile Gly Ala Ala Glu Leu Arg His Val Met Thr Asn Leu Gly Glu
            370                 375                 380

Lys Leu Thr Asp Glu Glu Val Asp Glu Met Ile Arg Glu Ala Asp Ile
385                 390                 395                 400

Asp Gly Asp Gly Gln Val Asn Tyr Glu Glu Phe Val Gln Met Met Thr
            405                 410                 415

Ala Lys

<210> SEQ ID NO 23
<211> LENGTH: 416
<212> TYPE: PRT
<213> ORGANISM: Artificial sequence
<220> FEATURE:
<223> OTHER INFORMATION: Synthetic polypeptide sequence

<400> SEQUENCE: 23

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30
```

-continued

Asp Lys Gln Lys Asn Gly Ile Lys Ala Asn Phe Lys Ile Arg His Asn
             35                  40                  45

Ile Glu Asp Gly Gly Val Gln Leu Ala Tyr His Tyr Gln Gln Asn Thr
 50                  55                  60

Pro Ile Gly Asp Gly Pro Val Leu Leu Pro Asp Asn His Tyr Leu Ser
 65                  70                  75                  80

Val Gln Ser Ile Leu Ser Lys Asp Pro Asn Glu Lys Arg Asp His Met
                 85                  90                  95

Val Leu Leu Glu Phe Val Thr Ala Ala Gly Ile Thr Leu Gly Met Asp
                100                 105                 110

Glu Leu Tyr Lys Gly Gly Thr Gly Gly Ser Met Val Ser Lys Gly Glu
            115                 120                 125

Glu Leu Phe Thr Gly Val Val Pro Ile Gln Val Glu Leu Asp Gly Asp
130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Thr Tyr Gly Val Gln
            180                 185                 190

Cys Phe Ser Arg Tyr Pro Asp His Met Lys Gln His Asp Phe Phe Lys
        195                 200                 205

Ser Ala Met Pro Glu Gly Tyr Ile Gln Glu Arg Thr Ile Phe Phe Lys
    210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
            260                 265                 270

Thr Glu Glu Gln Ile Ala Glu Phe Lys Glu Ala Phe Ser Leu Phe Asp
        275                 280                 285

Lys Asp Gly Asp Gly Thr Ile Thr Thr Lys Glu Leu Gly Thr Val Met
290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Phe Pro Glu Phe
                325                 330                 335

Leu Thr Met Met Ala Arg Lys Met Lys Asp Thr Asp Ser Glu Glu Glu
            340                 345                 350

Ile Arg Glu Ala Phe Arg Val Phe Asp Lys Asp Gly Asn Gly Tyr Ile
        355                 360                 365

Gly Ala Ala Glu Leu Arg His Val Met Thr Asn Leu Gly Glu Lys Leu
370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys
                405                 410                 415

<210> SEQ ID NO 24
<211> LENGTH: 416
<212> TYPE: PRT
<213> ORGANISM: Artificial sequence
<220> FEATURE:
<223> OTHER INFORMATION: Synthetic polypeptide sequence

<400> SEQUENCE: 24

```
Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Glu Gln Lys Asn Gly Ile Lys Ala Tyr Phe Lys Ile Arg His Asn
        35                  40                  45

Ile Glu Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65                  70                  75                  80

Val Gln Ser Ile Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Met Val Ser Lys Gly Glu
        115                 120                 125

Glu Leu Phe Thr Gly Val Val Pro Ile Gln Val Glu Leu Asp Gly Asp
    130                 135                 140

Val Asn Gly His Lys Phe Ser Val Ser Gly Glu Gly Glu Gly Asp Ala
145                 150                 155                 160

Thr Tyr Gly Lys Leu Thr Leu Lys Phe Ile Cys Thr Thr Gly Lys Leu
                165                 170                 175

Pro Val Pro Trp Pro Thr Leu Val Thr Thr Leu Thr Tyr Gly Val Gln
            180                 185                 190

Cys Phe Ser Arg Tyr Pro Asp His Met Lys Gln His Asp Phe Phe Lys
        195                 200                 205

Ser Ala Met Pro Glu Gly Tyr Ile Gln Glu Arg Thr Ile Phe Phe Lys
    210                 215                 220

Asp Asp Gly Asn Tyr Lys Thr Arg Ala Glu Val Lys Phe Glu Gly Asp
225                 230                 235                 240

Thr Leu Val Asn Arg Ile Glu Leu Lys Gly Ile Asp Phe Lys Glu Asp
                245                 250                 255

Gly Asn Ile Leu Gly His Lys Leu Glu Tyr Asn Thr Arg Asp Gln Leu
            260                 265                 270

Thr Glu Glu Gln Ile Ala Glu Phe Lys Glu Ala Phe Ser Leu Phe Asp
        275                 280                 285

Lys Asp Gly Asp Gly Thr Ile Thr Thr Lys Glu Leu Gly Thr Val Met
    290                 295                 300

Arg Ser Leu Gly Gln Asn Pro Thr Glu Ala Glu Leu Gln Asp Met Ile
305                 310                 315                 320

Asn Glu Val Asp Ala Asp Gly Asp Gly Thr Ile Asp Phe Pro Glu Phe
                325                 330                 335

Leu Thr Met Met Ala Arg Lys Met Asn Asp Thr Asp Ser Glu Glu Glu
            340                 345                 350

Ile Arg Glu Ala Phe Arg Val Phe Asp Lys Asp Gly Asn Gly Tyr Ile
        355                 360                 365

Gly Ala Ala Glu Leu Arg His Val Met Thr Asn Leu Gly Glu Lys Leu
    370                 375                 380

Thr Asp Glu Glu Val Asp Glu Met Ile Arg Val Ala Asp Ile Asp Gly
385                 390                 395                 400

Asp Gly Gln Val Asn Tyr Glu Glu Phe Val Gln Met Met Thr Ala Lys
```

<210> SEQ ID NO 25
<211> LENGTH: 418
<212> TYPE: PRT
<213> ORGANISM: Artificial sequence
<220> FEATURE:
<223> OTHER INFORMATION: Synthetic polypeptide sequence

<400> SEQUENCE: 25

Met Val Asp Ser Ser Arg Arg Lys Trp Asn Lys Thr Gly His Ala Val
1               5                   10                  15

Arg Ala Ile Gly Arg Leu Ser Ser Leu Glu Asn Val Tyr Ile Lys Ala
            20                  25                  30

Asp Glu Gln Lys Asn Gly Ile Lys Ala Tyr Phe Lys Ile Arg His Asn
        35                  40                  45

Ile Glu Gly Gly Gly Val Gln Leu Ala Tyr His Tyr Gln Gln Asn Thr
    50                  55                  60

Pro Ile Gly Asp Gly Pro Val Leu Leu Pro Asp Asn His Tyr Leu Ser
65                  70                  75                  80

Val Gln Ser Met Leu Ser Lys Asp Pro Asn Glu Lys Arg Asp His Met
                85                  90                  95

Val Leu Leu Glu Phe Val Thr Ala Ala Gly Ile Thr Leu Gly Met Asp
            100                 105                 110

Glu Leu Tyr Lys Gly Gly Thr Gly Gly Ser Glu Ser Met Val Ser Lys
        115                 120                 125

Gly Glu Glu Leu Phe Thr Gly Val Val Pro Ile Gln Val Glu Leu Asp
130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
                165                 170                 175

Lys Leu Pro Val Pro Trp Pro Thr Leu Val Thr Thr Leu Thr Tyr Gly
            180                 185                 190

Val Gln Cys Phe Ser Arg Tyr Pro Asp His Met Lys Gln His Asp Phe
        195                 200                 205

Phe Lys Ser Ala Met Pro Glu Gly Tyr Ile Gln Glu Arg Thr Ile Phe
    210                 215                 220

Phe Lys Gly Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Thr Arg Asp
            260                 265                 270

Gln Leu Thr Glu Glu Gln Ile Ala Glu Phe Lys Glu Ala Phe Ser Leu
        275                 280                 285

Phe Asp Lys Asp Gly Asp Gly Thr Ile Thr Thr Lys Glu Leu Gly Thr
    290                 295                 300

Val Met Arg Ser Leu Gly Gln Asn Pro Thr Glu Ala Glu Leu Gln Asp
305                 310                 315                 320

Met Ile Asn Glu Val Asp Ala Asp Gly Asp Gly Thr Ile Asp Phe Pro
                325                 330                 335

Glu Phe Leu Thr Met Met Ala Arg Lys Met Lys Asp Thr Asp Ser Glu
            340                 345                 350

Glu Glu Ile Arg Glu Ala Phe Arg Val Phe Asp Lys Asp Gly Asn Gly

```
                355                 360                 365
Tyr Ile Gly Ala Ala Glu Leu Arg His Val Met Thr Asn Leu Gly Glu
            370                 375                 380

Lys Leu Thr Asp Glu Glu Val Asp Glu Met Ile Arg Val Ala Asp Ile
385                 390                 395                 400

Asp Gly Asp Gly Gln Val Asn Tyr Glu Glu Phe Val Gln Met Met Thr
                405                 410                 415

Ala Lys

<210> SEQ ID NO 26
<211> LENGTH: 619
<212> TYPE: PRT
<213> ORGANISM: Artificial sequence
<220> FEATURE:
<223> OTHER INFORMATION: Synthetic polypeptide sequence

<400> SEQUENCE: 26

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Arg Met Leu Ser Glu Glu Leu Ala Asn Cys Phe
225                 230                 235                 240

Arg Ile Phe Asp Lys Asp Ala Asn Gly Phe Ile Asp Ile Glu Glu Leu
                245                 250                 255

Gly Glu Ile Leu Arg Ala Thr Gly Glu His Val Thr Glu Glu Asp Ile
            260                 265                 270

Glu Asp Leu Met Lys Asp Ser Asp Lys Asn Asn Asp Gly Arg Ile Asp
        275                 280                 285

Phe Asp Glu Phe Leu Lys Met Met Glu Gly Val Gln Gly Thr Ser Glu
    290                 295                 300
```

Glu Leu Ala Asn Cys Phe Arg Ile Phe Asp Lys Asp Ala Asn Gly
305                 310                 315                 320

Phe Ile Asp Ile Glu Glu Leu Gly Glu Ile Leu Arg Ala Thr Gly Glu
            325                 330                 335

His Val Thr Glu Glu Asp Ile Glu Asp Leu Met Lys Asp Ser Asp Lys
        340                 345                 350

Asn Asn Asp Gly Arg Ile Asp Phe Asp Glu Phe Leu Lys Met Met Glu
            355                 360                 365

Gly Val Gln Glu Leu Met Gly Gly Val Gln Leu Ala Asp His Tyr Gln
370                 375                 380

Gln Asn Thr Pro Ile Gly Asp Gly Pro Val Leu Leu Pro Asp Asn His
385                 390                 395                 400

Tyr Leu Ser Tyr Gln Ser Lys Leu Ser Lys Asp Pro Asn Glu Lys Arg
                405                 410                 415

Asp His Met Val Leu Leu Glu Phe Val Thr Ala Ala Gly Ile Thr Leu
            420                 425                 430

Gly Met Asp Glu Leu Tyr Lys Gly Gly Thr Gly Gly Ser Met Val Ser
            435                 440                 445

Lys Gly Glu Glu Leu Phe Thr Gly Val Val Pro Ile Leu Val Glu Leu
450                 455                 460

Asp Gly Asp Val Asn Gly His Lys Phe Ser Val Arg Gly Glu Gly Glu
465                 470                 475                 480

Gly Asp Ala Thr Asn Gly Lys Leu Thr Leu Lys Phe Ile Cys Thr Thr
                485                 490                 495

Gly Lys Leu Pro Val Pro Trp Pro Thr Leu Val Thr Thr Leu Gly Tyr
            500                 505                 510

Gly Leu Met Cys Phe Ala Arg Tyr Pro Asp His Met Lys Gln His Asp
            515                 520                 525

Phe Phe Lys Ser Ala Met Pro Glu Gly Tyr Val Gln Glu Arg Thr Ile
    530                 535                 540

Phe Phe Lys Asp Asp Gly Asn Tyr Lys Thr Arg Ala Glu Val Lys Phe
545                 550                 555                 560

Glu Gly Asp Thr Leu Val Asn Arg Ile Glu Leu Lys Gly Ile Asp Phe
                565                 570                 575

Lys Glu Asp Gly Asn Ile Leu Gly His Lys Leu Glu Tyr Asn Tyr Asn
            580                 585                 590

Ser His Asn Val Tyr Ile Met Ala Asp Lys Gln Lys Asn Gly Ile Lys
        595                 600                 605

Ala Asn Phe Lys Ile Arg His Asn Ile Glu Asp
    610                 615

<210> SEQ ID NO 27
<211> LENGTH: 673
<212> TYPE: PRT
<213> ORGANISM: Artificial sequence
<220> FEATURE:
<223> OTHER INFORMATION: Synthetic polypeptide sequence

<400> SEQUENCE: 27

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

-continued

```
Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
210                 215                 220

Val Thr Ala Ala Arg Met His Asp Gln Leu Thr Glu Glu Gln Ile Ala
225                 230                 235                 240

Glu Phe Lys Glu Ala Phe Ser Leu Phe Asp Lys Asp Gly Asp Gly Thr
                245                 250                 255

Ile Thr Thr Lys Glu Leu Gly Thr Val Met Arg Ser Leu Gly Gln Asn
                260                 265                 270

Pro Thr Glu Ala Glu Leu Gln Asp Met Ile Asn Glu Val Asp Ala Asp
                275                 280                 285

Gly Asn Gly Thr Ile Tyr Phe Pro Glu Phe Leu Thr Met Met Ala Arg
290                 295                 300

Lys Met Lys Asp Thr Asp Ser Glu Glu Glu Ile Arg Glu Ala Phe Arg
305                 310                 315                 320

Val Phe Asp Lys Asp Gly Asn Gly Tyr Ile Ser Ala Ala Gln Leu Arg
                325                 330                 335

His Val Met Thr Asn Leu Gly Glu Lys Leu Thr Asp Glu Glu Val Asp
                340                 345                 350

Glu Met Ile Arg Glu Ala Asp Ile Asp Gly Asp Gly Gln Val Asn Tyr
                355                 360                 365

Glu Glu Phe Val Gln Met Met Thr Ala Lys Gly Gly Lys Arg Arg Trp
                370                 375                 380

Lys Lys Asn Phe Ile Ala Val Ser Ala Ala Asn Arg Phe Lys Lys Ile
385                 390                 395                 400

Ser Ser Ser Gly Ala Leu Glu Leu Met Asp Gly Val Gln Leu Ala
                405                 410                 415

Asp His Tyr Gln Gln Asn Thr Pro Ile Gly Asp Gly Pro Val Leu Leu
                420                 425                 430

Pro Asp Asn His Tyr Leu Ser Tyr Gln Ser Ala Leu Ser Lys Asp Pro
                435                 440                 445

Asn Glu Lys Arg Asp His Met Val Leu Leu Glu Phe Val Thr Ala Ala
450                 455                 460
```

```
Gly Ile Thr Leu Gly Met Asp Glu Leu Tyr Lys Gly Gly Ser Gly Gly
465                 470                 475                 480

Met Val Ser Lys Gly Glu Glu Leu Phe Thr Gly Val Val Pro Ile Leu
                485                 490                 495

Val Glu Leu Asp Gly Asp Val Asn Gly His Lys Phe Ser Val Ser Gly
            500                 505                 510

Glu Gly Glu Gly Asp Ala Thr Tyr Gly Lys Leu Thr Leu Lys Leu Ile
        515                 520                 525

Cys Thr Thr Gly Lys Leu Pro Val Pro Trp Pro Thr Leu Val Thr Thr
    530                 535                 540

Leu Gly Tyr Gly Leu Gln Cys Phe Ala Arg Tyr Pro Asp His Met Lys
545                 550                 555                 560

Gln His Asp Phe Phe Lys Ser Ala Met Pro Glu Gly Tyr Val Gln Glu
                565                 570                 575

Arg Thr Ile Phe Phe Lys Asp Asp Gly Asn Tyr Lys Thr Arg Ala Glu
            580                 585                 590

Val Lys Phe Glu Gly Asp Thr Leu Val Asn Arg Ile Glu Leu Lys Gly
        595                 600                 605

Ile Asp Phe Lys Glu Asp Gly Asn Ile Leu Gly His Lys Leu Glu Tyr
    610                 615                 620

Asn Tyr Asn Ser His Asn Val Tyr Ile Thr Ala Asp Lys Gln Lys Asn
625                 630                 635                 640

Gly Ile Lys Ala Asn Phe Lys Ile Arg His Asn Ile Glu Leu Ser Arg
                645                 650                 655

Gly Pro Gly Thr Ser Ala Glu Ile Tyr Ala Cys Arg Leu Glu Ile Ser
            660                 665                 670

Asn

<210> SEQ ID NO 28
<211> LENGTH: 653
<212> TYPE: PRT
<213> ORGANISM: Artificial sequence
<220> FEATURE:
<223> OTHER INFORMATION: Synthetic polypeptide sequence

<400> SEQUENCE: 28

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
```

-continued

```
                145                 150                 155                 160
            Gly Ile Lys Ala His Phe Lys Ile Arg His Asn Ile Glu Asp Gly Ser
                            165                 170                 175
            Val Gln Leu Ala Asp His Tyr Gln Gln Asn Thr Pro Ile Gly Asp Gly
                            180                 185                 190
            Pro Val Leu Leu Pro Asp Asn His Tyr Leu Ser Thr Gln Ser Ala Leu
                            195                 200                 205
            Ser Lys Asp Pro Asn Glu Lys Arg Asp His Met Val Leu Leu Glu Phe
                210                 215                 220
            Val Thr Ala Ala Arg Met His Asp Gln Leu Thr Glu Glu Gln Ile Ala
            225                 230                 235                 240
            Glu Phe Lys Glu Ala Phe Ser Leu Leu Asp Lys Asp Gly Asp Gly Thr
                            245                 250                 255
            Ile Thr Thr Lys Glu Leu Gly Thr Ala Leu Arg Ser Leu Gly Gln Asn
                            260                 265                 270
            Pro Thr Glu Ala Glu Leu Gln Asp Met Ile Asn Glu Val Asp Ala Asp
                            275                 280                 285
            Gly Asn Gly Thr Ile Tyr Phe Pro Glu Phe Leu Thr Met Met Ala Arg
                290                 295                 300
            Lys Met Lys Asp Thr Asp Ser Glu Glu Glu Ile Arg Glu Ala Phe Arg
            305                 310                 315                 320
            Val Phe Asp Lys Asp Gly Asn Gly Tyr Ile Ser Ala Ala Glu Leu Arg
                            325                 330                 335
            His Val Met Thr Asn Leu Gly Glu Lys Leu Thr Asp Glu Glu Val Asp
                            340                 345                 350
            Glu Met Ile Arg Glu Ala Asp Ile Asp Gly Asp Gly Gln Val Asn Tyr
                            355                 360                 365
            Glu Glu Phe Val Gln Met Met Thr Ala Lys Gly Lys Arg Arg Trp
                370                 375                 380
            Gln Lys Thr Gly His Ala Val Arg Ala Phe Gly Arg Leu Lys Lys Ile
            385                 390                 395                 400
            Ser Ser Ser Gly Ala Leu Glu Leu Met Asp Gly Gly Val Gln Leu Ala
                            405                 410                 415
            Asp His Tyr Gln Gln Asn Thr Pro Ile Gly Asp Gly Pro Val Leu Leu
                            420                 425                 430
            Pro Asp Asn His Tyr Leu Ser Tyr Gln Ser Ala Leu Ser Lys Asp Pro
                            435                 440                 445
            Asn Glu Lys Arg Asp His Met Val Leu Leu Glu Phe Val Thr Ala Ala
                450                 455                 460
            Gly Ile Thr Leu Gly Met Asp Glu Leu Tyr Lys Gly Gly Ser Gly Gly
            465                 470                 475                 480
            Met Val Ser Lys Gly Glu Glu Leu Phe Thr Gly Val Val Pro Ile Leu
                            485                 490                 495
            Val Glu Leu Asp Gly Asp Val Asn Gly His Lys Phe Ser Val Ser Gly
                            500                 505                 510
            Glu Gly Glu Gly Asp Ala Thr Tyr Gly Lys Leu Thr Leu Lys Leu Ile
                            515                 520                 525
            Cys Thr Thr Gly Lys Leu Pro Val Pro Trp Pro Thr Leu Val Thr Thr
                530                 535                 540
            Leu Gly Tyr Gly Leu Gln Cys Phe Ala Arg Tyr Pro Asp His Met Lys
            545                 550                 555                 560
            Gln His Asp Phe Phe Lys Ser Ala Met Pro Glu Gly Tyr Val Gln Glu
                            565                 570                 575
```

```
Arg Thr Ile Phe Phe Lys Asp Asp Gly Asn Tyr Lys Thr Arg Ala Glu
            580                 585                 590

Val Lys Phe Glu Gly Asp Thr Leu Val Asn Arg Ile Glu Leu Lys Gly
        595                 600                 605

Ile Asp Phe Lys Glu Asp Gly Asn Ile Leu Gly His Lys Leu Glu Tyr
    610                 615                 620

Asn Tyr Asn Ser His Asn Val Tyr Ile Thr Ala Asp Lys Gln Lys Asn
625                 630                 635                 640

Gly Ile Lys Ala Asn Phe Lys Ile Arg His Asn Ile Glu
                645                 650

<210> SEQ ID NO 29
<211> LENGTH: 344
<212> TYPE: PRT
<213> ORGANISM: Artificial sequence
<220> FEATURE:
<223> OTHER INFORMATION: Synthetic polypeptide sequence

<400> SEQUENCE: 29

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285
```

```
Ala Ile Leu Asp Leu Ala Ser Lys Asn Ala Trp Ser Met Met Gly His
            290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp
            340

<210> SEQ ID NO 30
<211> LENGTH: 310
<212> TYPE: PRT
<213> ORGANISM: Artificial sequence
<220> FEATURE:
<223> OTHER INFORMATION: Synthetic polypeptide sequence

<400> SEQUENCE: 30

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300
```

```
Glu Ala Gly Ala Val Pro
305                 310

<210> SEQ ID NO 31
<211> LENGTH: 310
<212> TYPE: PRT
<213> ORGANISM: Artificial sequence
<220> FEATURE:
<223> OTHER INFORMATION: Synthetic polypeptide sequence

<400> SEQUENCE: 31

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 32
<211> LENGTH: 310
<212> TYPE: PRT
<213> ORGANISM: Artificial sequence
```

<220> FEATURE:
<223> OTHER INFORMATION: Synthetic polypeptide sequence

<400> SEQUENCE: 32

```
Met Asp Tyr Gly Gly Ala Leu Ser Ala Val Gly Arg Glu Leu Leu Phe
1               5                   10                  15
Val Thr Asn Pro Val Val Asn Gly Ser Val Leu Val Pro Glu Asp
            20                  25                  30
Gln Cys Tyr Cys Ala Gly Trp Ile Glu Ser Arg Gly Thr Asn Gly Ala
            35                  40                  45
Gln Thr Ala Ser Asn Val Leu Gln Trp Leu Ala Gly Phe Ser Ile
        50                  55                  60
Leu Leu Leu Met Phe Tyr Ala Tyr Gln Thr Trp Lys Ser Thr Cys Gly
65                  70                  75                  80
Trp Glu Glu Ile Tyr Val Cys Ala Ile Glu Met Val Lys Val Ile Leu
                85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Glu Trp Leu Leu Thr Ser
            115                 120                 125
Pro Val Ile Leu Ile His Leu Ser Asn Leu Thr Gly Leu Ser Asn Asp
        130                 135                 140
Tyr Ser Arg Arg Thr Met Gly Leu Leu Val Ser Ala Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
            195                 200                 205
Arg Gln Val Val Thr Gly Met Ala Trp Leu Phe Phe Val Ser Trp Gly
        210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ala
        290                 295                 300
Glu Ala Gly Ala Val Pro
305                 310
```

<210> SEQ ID NO 33
<211> LENGTH: 300
<212> TYPE: PRT
<213> ORGANISM: Artificial sequence
<220> FEATURE:
<223> OTHER INFORMATION: Synthetic polypeptide sequence

<400> SEQUENCE: 33

```
Met Asp Tyr Pro Val Ala Arg Ser Leu Ile Val Arg Tyr Pro Thr Asp
1               5                   10                  15
Leu Gly Asn Gly Thr Val Cys Met Pro Arg Gly Gln Cys Tyr Cys Glu
```

```
                     20                  25                  30
Gly Trp Leu Arg Ser Arg Gly Thr Ser Ile Glu Lys Thr Ile Ala Ile
             35                  40                  45
Thr Leu Gln Trp Val Val Phe Ala Leu Ser Val Ala Cys Leu Gly Trp
         50                  55                  60
Tyr Ala Tyr Gln Ala Trp Arg Ala Thr Cys Gly Trp Glu Glu Val Tyr
 65                  70                  75                  80
Val Ala Leu Ile Glu Met Met Lys Ser Ile Ile Glu Ala Phe His Glu
                 85                  90                  95
Phe Asp Ser Pro Ala Thr Leu Trp Leu Ser Ser Gly Asn Gly Val Val
            100                 105                 110
Trp Met Arg Tyr Gly Glu Trp Leu Leu Thr Cys Pro Val Leu Leu Ile
            115                 120                 125
His Leu Ser Asn Leu Thr Gly Leu Lys Asp Asp Tyr Ser Lys Arg Thr
        130                 135                 140
Met Gly Leu Leu Val Ser Asp Val Gly Cys Ile Val Trp Gly Ala Thr
145                 150                 155                 160
Ser Ala Met Cys Thr Gly Trp Thr Lys Ile Leu Phe Phe Leu Ile Ser
                165                 170                 175
Leu Ser Tyr Gly Met Tyr Thr Tyr Phe His Ala Ala Lys Val Tyr Ile
            180                 185                 190
Glu Ala Phe His Thr Val Pro Lys Gly Ile Cys Arg Glu Leu Val Arg
        195                 200                 205
Val Met Ala Trp Thr Phe Phe Val Ala Trp Gly Met Phe Pro Val Leu
    210                 215                 220
Phe Leu Leu Gly Thr Glu Gly Phe Gly His Ile Ser Pro Tyr Gly Ser
225                 230                 235                 240
Ala Ile Gly His Ser Ile Leu Asp Leu Ile Ala Lys Asn Met Trp Gly
                245                 250                 255
Val Leu Gly Asn Tyr Leu Arg Val Lys Ile His Glu His Ile Leu Leu
            260                 265                 270
Tyr Gly Asp Ile Arg Lys Lys Gln Lys Ile Thr Ile Ala Gly Gln Glu
        275                 280                 285
Met Glu Val Glu Thr Leu Val Ala Glu Glu Asp
    290                 295                 300

<210> SEQ ID NO 34
<211> LENGTH: 300
<212> TYPE: PRT
<213> ORGANISM: Artificial sequence
<220> FEATURE:
<223> OTHER INFORMATION: Synthetic polypeptide sequence

<400> SEQUENCE: 34

Met Asp Tyr Pro Val Ala Arg Ser Leu Ile Val Arg Tyr Pro Thr Asp
 1                   5                  10                  15
Leu Gly Asn Gly Thr Val Cys Met Pro Arg Gly Gln Cys Tyr Cys Glu
             20                  25                  30
Gly Trp Leu Arg Ser Arg Gly Thr Ser Ile Glu Lys Thr Ile Ala Ile
         35                  40                  45
Thr Leu Gln Trp Val Val Phe Ala Leu Ser Val Ala Cys Leu Gly Trp
     50                  55                  60
Tyr Ala Tyr Gln Ala Trp Arg Ala Thr Cys Gly Trp Glu Glu Val Tyr
 65                  70                  75                  80
Val Ala Leu Ile Glu Met Met Lys Ser Ile Ile Glu Ala Phe His Glu
```

```
                    85                  90                  95
Phe Asp Ser Pro Ala Thr Leu Trp Leu Ser Ser Gly Asn Gly Val Val
                100                 105                 110

Trp Met Arg Tyr Gly Glu Trp Leu Leu Thr Ser Pro Val Leu Leu Ile
            115                 120                 125

His Leu Ser Asn Leu Thr Gly Leu Lys Asp Asp Tyr Ser Lys Arg Thr
        130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
        210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
                260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Asp
        290                 295                 300

<210> SEQ ID NO 35
<211> LENGTH: 300
<212> TYPE: PRT
<213> ORGANISM: Artificial sequence
<220> FEATURE:
<223> OTHER INFORMATION: Synthetic polypeptide sequence

<400> SEQUENCE: 35

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
        130                 135                 140

Met Gly Leu Leu Val Ser Ala Val Gly Cys Ile Val Trp Gly Ala Thr
```

```
               145                 150                 155                 160
Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
                195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
                260                 265                 270

Tyr Gly Asp Ile Arg Lys Lys Gln Lys Ile Thr Ile Ala Gly Gln Glu
                275                 280                 285

Met Glu Val Glu Thr Leu Val Ala Glu Glu Asp
    290                 295                 300

<210> SEQ ID NO 36
<211> LENGTH: 344
<212> TYPE: PRT
<213> ORGANISM: Artificial sequence
<220> FEATURE:
<223> OTHER INFORMATION: Synthetic polypeptide sequence

<400> SEQUENCE: 36

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
                115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
```

```
                210                 215                 220
Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340
```

<210> SEQ ID NO 37
<211> LENGTH: 348
<212> TYPE: PRT
<213> ORGANISM: Artificial sequence
<220> FEATURE:
<223> OTHER INFORMATION: Synthetic polypeptide sequence

<400> SEQUENCE: 37

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
```

```
                225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Val Tyr Gly Ser Thr Val Gly His
                275                 280                 285

Thr Ile Ile Asp Leu Met Ser Lys Asn Cys Trp Gly Leu Leu Gly His
                290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
                340                 345

<210> SEQ ID NO 38
<211> LENGTH: 316
<212> TYPE: PRT
<213> ORGANISM: Artificial sequence
<220> FEATURE:
<223> OTHER INFORMATION: Synthetic polypeptide sequence

<400> SEQUENCE: 38

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
                20                  25                  30

Asn Pro Pro Tyr His Pro Val His Gly Tyr Glu Glu Gln Cys Ser Ser
                35                  40                  45

Ile Tyr Ile Tyr Tyr Gly Ala Leu Trp Glu Gln Glu Thr Ala Arg Gly
                50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
                100                 105                 110

Thr Ser Pro Ala Met Leu Phe Leu Tyr Gly Gly Asn Ile Thr Pro Trp
                115                 120                 125

Leu Arg Tyr Ala Glu Trp Leu Leu Thr Cys Pro Val Ile Leu Ile His
                130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
                180                 185                 190

Val Tyr Gly Thr Gln Thr Phe Tyr Asn Ala Gly Ile Ile Tyr Val Glu
                195                 200                 205

Ser Tyr Tyr Ile Met Pro Ala Gly Gly Cys Lys Lys Leu Val Leu Ala
                210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
```

```
                        245                 250                 255
Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
            275                 280                 285

Gly Asp Ile Arg Arg Pro Val Ser Ser Gln Phe Leu Gly Arg Lys Val
            290                 295                 300

Asp Val Leu Ala Phe Val Thr Glu Glu Asp Lys Val
305                 310                 315

<210> SEQ ID NO 39
<211> LENGTH: 349
<212> TYPE: PRT
<213> ORGANISM: Artificial sequence
<220> FEATURE:
<223> OTHER INFORMATION: Synthetic polypeptide sequence

<400> SEQUENCE: 39

Met Glu Pro Val Leu Gly Leu Ala Ser Thr Ala Val Arg Glu Leu Thr
1               5                   10                  15

Ala Gly Gly Ser Gly Asn Pro Tyr Glu Ser Tyr Lys Pro Pro Glu Asp
            20                  25                  30

Pro Cys Ala Leu Thr Pro Phe Gly Cys Leu Thr Asn Phe Trp Cys Asp
            35                  40                  45

Pro Gln Phe Gly Leu Ala Asp Ala Lys Tyr Asp Tyr Cys Tyr Val Lys
            50                  55                  60

Ala Ala Tyr Gly Glu Leu Ala Ile Val Glu Thr Ser Arg Leu Pro Trp
65                  70                  75                  80

Leu Tyr Ser His Gly Ser Asp Ala Glu His Gln Gly Ala Leu Ala Met
                85                  90                  95

Gln Trp Met Ala Phe Ala Leu Cys Ile Ile Cys Leu Val Phe Tyr Ala
            100                 105                 110

Tyr His Ser Trp Lys Ala Thr Thr Gly Trp Glu Glu Val Tyr Val Cys
            115                 120                 125

Val Val Glu Leu Val Lys Val Leu Leu Glu Ile Tyr Lys Glu Phe Glu
130                 135                 140

Ser Pro Ala Ser Ile Tyr Leu Pro Thr Ala Asn Ala Ala Leu Trp Leu
145                 150                 155                 160

Arg Tyr Gly Glu Trp Leu Leu Thr Cys Pro Val Ile Leu Ile His Leu
                165                 170                 175

Ser Asn Ile Thr Gly Leu Lys Asp Asp Tyr Asn Lys Arg Thr Met Gln
            180                 185                 190

Leu Leu Val Ser Asp Ile Gly Cys Val Val Trp Gly Ile Thr Ala Ala
            195                 200                 205

Phe Ser Val Gly Trp Leu Lys Trp Val Phe Phe Val Leu Gly Leu Leu
210                 215                 220

Tyr Gly Ser Asn Thr Tyr Phe His Ala Ala Lys Val Tyr Ile Glu Ser
225                 230                 235                 240

Tyr His Thr Val Pro Lys Gly His Cys Arg Leu Ile Val Arg Leu Met
                245                 250                 255

Ala Tyr Cys Phe Tyr Val Ala Trp Thr Met Tyr Pro Ile Leu Phe Ile
            260                 265                 270

Leu Gly Pro Glu Gly Leu Gly His Met Ser Ala Tyr Met Ser Thr Ala
            275                 280                 285

Leu His Gly Val Ala Asp Met Leu Ser Lys Gln Ile Trp Gly Leu Leu
```

```
              290                 295                 300
Gly His His Leu Arg Val Lys Ile Phe Glu His Ile Leu Ile His Gly
305                 310                 315                 320

Asp Ile Arg Lys Thr Thr Thr Met Gln Val Gly Gly Gln Met Val Gln
                325                 330                 335

Val Glu Glu Met Val Asp Glu Glu Asp Glu Asp Thr Ile
            340                 345

<210> SEQ ID NO 40
<211> LENGTH: 345
<212> TYPE: PRT
<213> ORGANISM: Artificial sequence
<220> FEATURE:
<223> OTHER INFORMATION: Synthetic polypeptide sequence

<400> SEQUENCE: 40

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
                20                  25                  30

Thr Asp Gly Thr Ala Ala Ala Val Ser His Tyr Ala Met Asn Gly
            35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
                100                 105                 110

Lys Ala Thr Cys Gly Trp Glu Glu Val Tyr Val Cys Cys Val Glu Val
            115                 120                 125

Leu Phe Val Thr Leu Glu Ile Phe Lys Glu Phe Ser Ser Pro Ala Thr
    130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
        195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
        275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
```

```
                305                 310                 315                 320
Thr Thr Lys Met Glu Ile Gly Gly Glu Val Glu Val Glu Phe
                    325                 330                 335
Val Glu Glu Glu Asp Glu Asp Thr Val
        340                 345

<210> SEQ ID NO 41
<211> LENGTH: 325
<212> TYPE: PRT
<213> ORGANISM: Artificial sequence
<220> FEATURE:
<223> OTHER INFORMATION: Synthetic polypeptide sequence

<400> SEQUENCE: 41

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Val Val
            20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
                325
```

-continued

```
                          325

<210> SEQ ID NO 42
<211> LENGTH: 258
<212> TYPE: PRT
<213> ORGANISM: Artificial sequence
<220> FEATURE:
<223> OTHER INFORMATION: Synthetic polypeptide sequence

<400> SEQUENCE: 42

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 43
<211> LENGTH: 248
<212> TYPE: PRT
<213> ORGANISM: Artificial sequence
<220> FEATURE:
<223> OTHER INFORMATION: Synthetic polypeptide sequence

<400> SEQUENCE: 43

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
```

```
            35                  40                  45
Ala Arg Glu Tyr Tyr Ser Ile Thr Ile Leu Val Pro Gly Ile Ala Ser
 50                  55                  60

Ala Ala Tyr Leu Ser Met Phe Phe Gly Ile Gly Leu Thr Glu Val Thr
 65                  70                  75                  80

Val Ala Gly Glu Val Leu Asp Ile Tyr Tyr Ala Arg Tyr Ala Asp Trp
                 85                  90                  95

Leu Phe Thr Thr Pro Leu Leu Leu Asp Leu Ala Leu Leu Ala Lys
                100                 105                 110

Val Asp Arg Val Ser Ile Gly Thr Leu Val Gly Val Asp Ala Leu Met
                115                 120                 125

Ile Val Thr Gly Leu Ile Gly Ala Leu Ser His Thr Pro Leu Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
                210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245

<210> SEQ ID NO 44
<211> LENGTH: 223
<212> TYPE: PRT
<213> ORGANISM: Artificial sequence
<220> FEATURE:
<223> OTHER INFORMATION: Synthetic polypeptide sequence

<400> SEQUENCE: 44

Ala Ser Ser Phe Gly Lys Ala Leu Leu Glu Phe Val Phe Ile Val Phe
 1               5                  10                  15

Ala Cys Ile Thr Leu Leu Leu Gly Ile Asn Ala Ala Lys Ser Lys Ala
                 20                  25                  30

Ala Ser Arg Val Leu Phe Pro Ala Thr Phe Val Thr Gly Ile Ala Ser
                 35                  40                  45

Ile Ala Tyr Phe Ser Met Ala Ser Gly Gly Trp Val Ile Ala Pro
 50                  55                  60

Asp Cys Arg Gln Leu Phe Val Ala Arg Tyr Leu Asp Trp Leu Ile Thr
 65                  70                  75                  80

Thr Pro Leu Leu Leu Ile Asp Leu Gly Leu Val Ala Gly Val Ser Arg
                 85                  90                  95

Trp Asp Ile Met Ala Leu Cys Leu Ser Asp Val Leu Met Ile Ala Thr
                100                 105                 110

Gly Ala Phe Gly Ser Leu Thr Val Gly Asn Val Lys Trp Val Trp Trp
                115                 120                 125

Phe Phe Gly Met Cys Trp Phe Leu His Ile Ile Phe Ala Leu Gly Lys
130                 135                 140

Ser Trp Ala Glu Ala Ala Lys Ala Lys Gly Gly Asp Ser Ala Ser Val
```

```
            145                 150                 155                 160
Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
                180                 185                 190

Glu Val Leu Ile Tyr Gly Val Leu Asp Val Ile Ser Lys Ala Val Phe
                195                 200                 205

Gly Leu Ile Leu Met Ser Gly Ala Ala Thr Gly Tyr Glu Ser Ile
                210                 215                 220

<210> SEQ ID NO 45
<211> LENGTH: 262
<212> TYPE: PRT
<213> ORGANISM: Artificial sequence
<220> FEATURE:
<223> OTHER INFORMATION: Synthetic polypeptide sequence

<400> SEQUENCE: 45

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
                20                  25                  30

Phe Phe Trp Leu Gln Leu Pro Asn Val Thr Lys Asn Tyr Arg Thr Ala
                35                  40                  45

Leu Thr Ile Thr Gly Ile Val Thr Leu Ile Ala Thr Tyr His Tyr Phe
            50                  55                  60

Arg Ile Phe Asn Ser Trp Val Ala Ala Phe Asn Val Gly Leu Gly Val
65              70                  75                  80

Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
                100                 105                 110

Leu Ile Leu Val Met Lys Leu Pro Ala Lys Glu Thr Val Cys Leu Ala
                115                 120                 125

Trp Thr Leu Gly Ile Ala Ser Ala Val Met Val Ala Leu Gly Tyr Pro
            130                 135                 140

Gly Glu Ile Gln Asp Asp Leu Ser Val Arg Trp Phe Trp Ala Cys
145                 150                 155                 160

Ala Met Val Pro Phe Val Tyr Val Val Gly Thr Leu Val Val Gly Leu
                165                 170                 175

Gly Ala Ala Thr Ala Lys Gln Pro Glu Gly Val Val Asp Leu Val Ser
                180                 185                 190

Ala Ala Arg Tyr Leu Thr Val Val Ser Trp Leu Thr Tyr Pro Phe Val
                195                 200                 205

Tyr Ile Val Lys Asn Ile Gly Leu Ala Gly Ser Thr Ala Thr Met Tyr
                210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala
                260

<210> SEQ ID NO 46
<211> LENGTH: 313
<212> TYPE: PRT
```

<213> ORGANISM: Artificial sequence
<220> FEATURE:
<223> OTHER INFORMATION: Synthetic polypeptide sequence

<400> SEQUENCE: 46

```
Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310
```

<210> SEQ ID NO 47
<211> LENGTH: 273
<212> TYPE: PRT
<213> ORGANISM: Artificial sequence
<220> FEATURE:
<223> OTHER INFORMATION: Synthetic polypeptide sequence

<400> SEQUENCE: 47

```
Val Thr Gln Arg Glu Leu Phe Glu Phe Val Leu Asn Asp Pro Leu Leu
1               5                   10                  15
```

Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
        35                  40                  45

Ile Ala Val Ser Thr Ile Leu Val Pro Val Val Ser Ile Ala Ser Tyr
50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
            85                  90                  95

Asp Gly Val Val Thr Met Trp Gly Arg Tyr Leu Thr Trp Ala Leu Ser
        100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
        195                 200                 205

Ile Val Trp Ala Leu Gly Val Glu Gly Ile Ala Val Leu Pro Val Gly
210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
            260                 265                 270

Asp

<210> SEQ ID NO 48
<211> LENGTH: 365
<212> TYPE: PRT
<213> ORGANISM: Artificial sequence
<220> FEATURE:
<223> OTHER INFORMATION: Synthetic polypeptide sequence

<400> SEQUENCE: 48

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr

```
            100                 105                 110
Ile Val Phe Ala Ile Cys Ile Val Gln Leu Val Tyr Phe Met Phe Ala
        115                 120                 125

Ala Trp Lys Ala Thr Val Gly Trp Glu Glu Val Tyr Val Asn Ile Ile
130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
            165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
            195                 200                 205

Val Ser Asp Ile Gly Thr Ile Val Phe Gly Thr Ser Ala Ala Leu Ala
        210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
            245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
            275                 280                 285

Gly Arg Glu Gly Phe Gly His Ile Thr Tyr Phe Gly Ser Ser Ile Gly
        290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
            325                 330                 335

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val
            355                 360                 365

<210> SEQ ID NO 49
<211> LENGTH: 1084
<212> TYPE: PRT
<213> ORGANISM: Artificial sequence
<220> FEATURE:
<223> OTHER INFORMATION: Synthetic polypeptide sequence

<400> SEQUENCE: 49

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
```

```
                100                 105                 110
Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
            165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
            210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
            245                 250                 255

Ala Asp Lys Ser Arg Ile Thr Ser Glu Gly Glu Tyr Ile Pro Leu Asp
            260                 265                 270

Gln Ile Asp Ile Asn Val Gly Ala Pro Gly Ser Gly Ala Thr Asn Phe
            275                 280                 285

Ser Leu Leu Lys Gln Ala Gly Asp Val Glu Glu Asn Pro Gly Pro Met
            290                 295                 300

Asp Leu Lys Glu Ser Pro Ser Glu Gly Ser Leu Gln Pro Ser Ser Ile
305                 310                 315                 320

Gln Ile Phe Ala Asn Thr Ser Thr Leu His Gly Ile Arg His Ile Phe
            325                 330                 335

Val Tyr Gly Pro Leu Thr Ile Arg Arg Val Leu Trp Ala Val Ala Phe
            340                 345                 350

Val Gly Ser Leu Gly Leu Leu Leu Val Glu Ser Ser Glu Arg Val Ser
            355                 360                 365

Tyr Tyr Phe Ser Tyr Gln His Val Thr Lys Val Asp Glu Val Val Ala
            370                 375                 380

Gln Ser Leu Val Phe Pro Ala Val Thr Leu Cys Asn Leu Asn Ser Gly
385                 390                 395                 400

Phe Arg Phe Ser Arg Leu Thr Thr Asn Asp Leu Tyr His Ala Gly Glu
            405                 410                 415

Leu Leu Ala Leu Leu Asp Val Asn Leu Gln Ile Pro Asp Pro His Leu
            420                 425                 430

Ala Asp Pro Thr Val Leu Glu Ala Leu Arg Gln Lys Ala Asn Phe Lys
            435                 440                 445

His Tyr Lys Pro Lys Gln Phe Ser Met Leu Glu Phe Leu His Arg Val
            450                 455                 460

Gly His Asp Leu Lys Asp Met Met Leu Tyr Cys Lys Phe Lys Gly Gln
465                 470                 475                 480

Glu Cys Gly His Gln Asp Phe Thr Val Phe Thr Lys Tyr Gly Lys
            485                 490                 495

Cys Tyr Met Phe Asn Ser Gly Glu Asp Gly Lys Pro Leu Leu Thr Thr
            500                 505                 510

Val Lys Gly Gly Thr Gly Asn Gly Leu Glu Ile Met Leu Asp Ile Gln
            515                 520                 525
```

```
Gln Asp Glu Tyr Leu Pro Ile Trp Gly Glu Thr Glu Thr Thr Phe
    530                 535                 540

Glu Ala Gly Val Lys Val Gln Ile His Ser Gln Ser Glu Pro Pro Phe
545                 550                 555                 560

Ile Gln Glu Leu Gly Phe Gly Val Ala Pro Gly Phe Gln Thr Phe Val
                565                 570                 575

Ala Thr Gln Glu Gln Arg Leu Thr Tyr Leu Pro Pro Trp Gly Glu
            580                 585                 590

Cys Arg Ser Ser Glu Met Gly Leu Asp Phe Phe Pro Val Tyr Ser Ile
        595                 600                 605

Thr Ala Cys Arg Ile Asp Cys Glu Thr Arg Tyr Ile Val Glu Asn Cys
610                 615                 620

Asn Cys Arg Met Val His Met Pro Gly Asp Ala Pro Phe Cys Thr Pro
625                 630                 635                 640

Glu Gln His Lys Glu Cys Ala Glu Pro Ala Leu Gly Leu Leu Ala Glu
            645                 650                 655

Lys Asp Ser Asn Tyr Cys Leu Cys Arg Thr Pro Cys Asn Leu Thr Arg
            660                 665                 670

Tyr Asn Lys Glu Leu Ser Met Val Lys Ile Pro Ser Lys Thr Ser Ala
            675                 680                 685

Lys Tyr Leu Glu Lys Lys Phe Asn Lys Ser Glu Lys Tyr Ile Ser Glu
690                 695                 700

Asn Ile Leu Val Leu Asp Ile Phe Phe Glu Ala Leu Asn Tyr Glu Thr
705                 710                 715                 720

Ile Glu Gln Lys Lys Ala Tyr Glu Val Ala Ala Leu Leu Gly Asp Ile
                725                 730                 735

Gly Gly Gln Met Gly Leu Phe Ile Gly Ala Ser Leu Leu Thr Ile Leu
            740                 745                 750

Glu Leu Phe Asp Tyr Ile Tyr Glu Leu Ile Lys Glu Lys Leu Leu Asp
            755                 760                 765

Leu Leu Gly Lys Glu Glu Glu Gly Ser His Asp Glu Asn Met Ser
770                 775                 780

Thr Cys Asp Thr Met Pro Asn His Ser Glu Thr Ile Ser His Thr Val
785                 790                 795                 800

Asn Val Pro Leu Gln Thr Ala Leu Gly Thr Leu Glu Glu Ile Ala Cys
                805                 810                 815

Ala Ala Ala Lys Ser Arg Ile Thr Ser Glu Gly Glu Tyr Ile Pro Leu
            820                 825                 830

Asp Gln Ile Asp Ile Asn Val Val Ser Lys Gly Glu Glu Leu Phe Thr
            835                 840                 845

Gly Val Val Pro Ile Leu Val Glu Leu Asp Gly Asp Val Asn Gly His
850                 855                 860

Lys Phe Ser Val Ser Gly Glu Gly Glu Gly Asp Ala Thr Tyr Gly Lys
865                 870                 875                 880

Leu Thr Leu Lys Phe Ile Cys Thr Thr Gly Lys Leu Pro Val Pro Trp
                885                 890                 895

Pro Thr Leu Val Thr Thr Phe Gly Tyr Gly Leu Gln Cys Phe Ala Arg
            900                 905                 910

Tyr Pro Asp His Met Lys Gln His Asp Phe Phe Lys Ser Ala Met Pro
            915                 920                 925

Glu Gly Tyr Val Gln Glu Arg Thr Ile Phe Phe Lys Asp Asp Gly Asn
930                 935                 940
```

```
Tyr Lys Thr Arg Ala Glu Val Lys Phe Glu Gly Asp Thr Leu Val Asn
945                 950                 955                 960
Arg Ile Glu Leu Lys Gly Ile Asp Phe Arg Glu Asp Gly Asn Ile Leu
                965                 970                 975
Gly His Lys Leu Glu Tyr Asn Tyr Asn Ser His Asn Val Tyr Ile Met
            980                 985                 990
Ala Asp Lys Gln Lys Asn Gly Ile  Lys Val Asn Phe Lys  Ile Arg His
        995                 1000                 1005
Asn Ile  Glu Asp Gly Ser Val  Gln Leu Ala Asp His  Tyr Gln Gln
    1010                 1015                 1020
Asn Thr  Pro Ile Gly Asp Gly  Pro Val Leu Leu Pro  Asp Asn His
    1025                 1030                 1035
Tyr Leu  Ser Tyr Gln Ser Ala  Leu Ser Lys Asp Pro  Asn Glu Lys
    1040                 1045                 1050
Arg Asp  His Met Val Leu Leu  Glu Phe Val Thr Ala  Ala Gly Ile
    1055                 1060                 1065
Thr Leu  Gly Met Asp Glu Leu  Tyr Lys Phe Cys Tyr  Glu Asn Glu
    1070                 1075                 1080
Val

<210> SEQ ID NO 50
<211> LENGTH: 50
<212> TYPE: PRT
<213> ORGANISM: Artificial sequence
<220> FEATURE:
<223> OTHER INFORMATION: Synthetic polypeptide sequence

<400> SEQUENCE: 50

Met Val Ser Arg Arg Pro Trp Leu Leu Ala Leu Ala Leu Ala Val Ala
1               5                   10                  15
Leu Ala Ala Gly Ser Ala Gly Ala Ser Thr Gly Ser Asp Ala Thr Val
                20                  25                  30
Pro Val Ala Thr Gln Asp Gly Pro Asp Tyr Val Phe His Arg Ala His
            35                  40                  45
Glu Arg
    50

<210> SEQ ID NO 51
<211> LENGTH: 11
<212> TYPE: PRT
<213> ORGANISM: Artificial sequence
<220> FEATURE:
<223> OTHER INFORMATION: Synthetic polypeptide sequence

<400> SEQUENCE: 51

Met Asp Tyr Gly Gly Ala Leu Ser Ala Val Gly
1               5                   10

<210> SEQ ID NO 52
<211> LENGTH: 20
<212> TYPE: PRT
<213> ORGANISM: Artificial sequence
<220> FEATURE:
<223> OTHER INFORMATION: Synthetic polypeptide sequence

<400> SEQUENCE: 52

Lys Ser Arg Ile Thr Ser Glu Gly Glu Tyr Ile Pro Leu Asp Gln Ile
1               5                   10                  15
Asp Ile Asn Val
            20
```

```
<210> SEQ ID NO 53
<211> LENGTH: 26
<212> TYPE: PRT
<213> ORGANISM: Artificial sequence
<220> FEATURE:
<223> OTHER INFORMATION: Synthetic polypeptide sequence

<400> SEQUENCE: 53

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 54
<211> LENGTH: 27
<212> TYPE: PRT
<213> ORGANISM: Artificial sequence
<220> FEATURE:
<223> OTHER INFORMATION: Synthetic polypeptide sequence

<400> SEQUENCE: 54

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 55
<211> LENGTH: 23
<212> TYPE: PRT
<213> ORGANISM: Artificial sequence
<220> FEATURE:
<223> OTHER INFORMATION: Synthetic polypeptide sequence

<400> SEQUENCE: 55

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 56
<211> LENGTH: 18
<212> TYPE: PRT
<213> ORGANISM: Artificial sequence
<220> FEATURE:
<223> OTHER INFORMATION: Synthetic polypeptide sequence

<400> SEQUENCE: 56

Met Arg Gly Thr Pro Leu Leu Leu Val Val Ser Leu Phe Ser Leu Leu
1               5                   10                  15

Gln Asp

<210> SEQ ID NO 57
<211> LENGTH: 5
<212> TYPE: PRT
<213> ORGANISM: Artificial sequence
<220> FEATURE:
<223> OTHER INFORMATION: Synthetic polypeptide sequence

<400> SEQUENCE: 57

Val Lys Glu Ser Leu
1               5

<210> SEQ ID NO 58
```

-continued

```
<211> LENGTH: 5
<212> TYPE: PRT
<213> ORGANISM: Artificial sequence
<220> FEATURE:
<223> OTHER INFORMATION: Synthetic polypeptide sequence

<400> SEQUENCE: 58

Val Leu Gly Ser Leu
1               5

<210> SEQ ID NO 59
<211> LENGTH: 16
<212> TYPE: PRT
<213> ORGANISM: Artificial sequence
<220> FEATURE:
<223> OTHER INFORMATION: Synthetic polypeptide sequence

<400> SEQUENCE: 59

Asn Ala Asn Ser Phe Cys Tyr Glu Asn Glu Val Ala Leu Thr Ser Lys
1               5                   10                  15

<210> SEQ ID NO 60
<211> LENGTH: 6
<212> TYPE: PRT
<213> ORGANISM: Artificial sequence
<220> FEATURE:
<223> OTHER INFORMATION: Synthetic polypeptide sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 60

Phe Xaa Tyr Glu Asn Glu
1               5

<210> SEQ ID NO 61
<211> LENGTH: 7
<212> TYPE: PRT
<213> ORGANISM: Artificial sequence
<220> FEATURE:
<223> OTHER INFORMATION: Synthetic polypeptide sequence

<400> SEQUENCE: 61

Phe Cys Tyr Glu Asn Glu Val
1               5

<210> SEQ ID NO 62
<211> LENGTH: 19
<212> TYPE: PRT
<213> ORGANISM: Artificial sequence
<220> FEATURE:
<223> OTHER INFORMATION: Synthetic polypeptide sequence

<400> SEQUENCE: 62

Lys Ser Arg Ile Thr Ser Glu Gly Glu Tyr Ile Pro Leu Asp Gln Ile
1               5                   10                  15

Asp Ile Asn
```

LIGHT-RESPONSIVE POLYPEPTIDES AND METHODS OF USE THEREOF

CROSS-REFERENCE

This application is a national stage filing under 35 U.S.C. § 371 of PCT/US2016/051684, filed Sep. 14, 2016, which claims the benefit of U.S. Provisional Patent Application No. 62/218,971, filed Sep. 15, 2015, each of which applications is incorporated herein by reference in its entirety.

INCORPORATION BY REFERENCE OF SEQUENCE LISTING PROVIDED AS A TEXT FILE

A Sequence Listing is provided herewith as a text file, "STAN-1250PRV_SeqList_ST25.txt" created on Sep. 14, 2015 and having a size of 172 KB. The contents of the text file are incorporated by reference herein in their entirety.

INTRODUCTION

Optogenetics involves the use of light-activated proteins to change the membrane voltage potentials of excitable cells, such as neurons, upon exposure to light of various wavelengths. In neurons, membrane depolarization leads to the activation of transient electrical signals (also called action potentials or "spikes"), which are the basis of neuronal communication. Conversely, membrane hyperpolarization leads to the inhibition of such signals. By expressing, in a neuron or other excitable cell, a light-activated protein that changes the membrane potential, light can be utilized as a triggering means to induce inhibition or excitation.

SUMMARY

The present disclosure provides variant light-responsive polypeptides, and nucleic acids comprising nucleotide sequences encoding the light-responsive polypeptides. The present disclosure provides methods, devices, and systems for controlling the activity of a cell expressing a variant light-responsive polypeptide of the present disclosure.

The present disclosure provides a variant light-activated polypeptide that comprises an amino acid sequence having at least about 85%, at least 90%, at least 95%, at least 98% or at least 99%, amino acid sequence identity to the amino acid sequence set forth in SEQ ID NO:1, wherein the amino acid sequence comprises an E163S substitution relative to the amino acid sequence set forth in SEQ ID NO:1, and wherein the variant light-activated polypeptide exhibits at least 5-fold increased kinetics compared to the light-activated polypeptide of SEQ ID NO:1. The present disclosure provides a variant light-activated polypeptide that comprises an amino acid sequence having at least about 85%, at least 90%, at least 95%, at least 98%, at least 99%, or 100%, amino acid sequence identity to the amino acid sequence set forth in SEQ ID NO:5. In some cases, a variant light-responsive polypeptide of the present disclosure comprises a heterologous membrane trafficking signal. In some cases, the heterologous membrane trafficking signal comprises the amino acid sequence KSRITSEGEYIPLDQIDIN (SEQ ID NO:62). In some cases, a variant light-responsive polypeptide of the present disclosure comprises an endoplasmic reticulum (ER) export signal. In some cases, the ER export signal comprises the amino acid sequence FCYENEV (SEQ ID NO:61). In some cases, a variant light-responsive polypeptide of the present disclosure comprises a membrane trafficking signal and an ER export signal. In some cases, a variant light-responsive polypeptide of the present disclosure comprises, in order from N-terminus to C-terminus: a) a variant light-responsive polypeptide comprising an amino acid sequence having at least 85%, at least 90%, at least 95%, at least 98%, at least 99%, or 100%, amino acid sequence identity to the amino acid sequence set forth in SEQ ID NO:5; b) a membrane trafficking signal; and c) an ER export signal. In some cases, a variant light-activated polypeptide of the present disclosure comprises an amino acid sequence having at least 85%, at least 90%, at least 95%, at least 98%, at least 99%, or 100%, amino acid sequence identity to the amino acid sequence set forth in SEQ ID NO:3. In some cases, a variant light-activated polypeptide of the present disclosure comprises an amino acid sequence having at least 85%, at least 90%, at least 95%, at least 98%, at least 99%, or 100%, amino acid sequence identity to the amino acid sequence set forth in SEQ ID NO:4 or SEQ ID NO:6. In some cases, a variant light-activated polypeptide of the present disclosure evokes action potentials at frequencies of from 5 Hz to 20 Hz when present in a eukaryotic cell and when activated by light of a wavelength of from 600 nm to 700 nm. In some cases, a variant light-activated polypeptide of the present disclosure exhibits at least 10-fold increased kinetics compared to the light-activated polypeptide of SEQ ID NO:1.

The present disclosure provides a nucleic acid (e.g., an isolated nucleic acid) comprising a nucleotide sequence encoding a variant light-activated polypeptide as described above or elsewhere herein. In some cases, the nucleotide sequence is operably linked to a transcriptional control element that is functional in a eukaryotic cell. In some cases, the transcriptional control element is a constitutive promoter. In some cases, the transcriptional control element is an inducible promoter. In some cases, the transcriptional control element is a neuron-specific promoter.

The present disclosure provides a recombinant expression vector comprising a nucleic acid as described above or elsewhere herein, where the recombinant expression vector comprises a nucleotide sequence encoding a variant light-responsive polypeptide of the present disclosure. In some cases, the expression vector is a retroviral vector, a lentiviral vector, or an adeno-associated virus vector.

The present disclosure provides a mammalian cell comprising a variant light-activated polypeptide, as described above or elsewhere herein, where the variant light-activated polypeptide is present in the cell membrane, where the variant light-activated polypeptide is responsive to light, and where the variant light-activated polypeptide is capable of mediating a depolarizing current in the cell when the cell is illuminated with red light (e.g., light of a wavelength of from about 600 nm to about 700 nm). In some cases, the cell is a neuronal cell.

The present disclosure provides a method of modulating the voltage potential of a mammalian cell in response to a light stimulus, the method comprising exposing a mammalian cell that comprises a variant light-activated polypeptide, as described above or elsewhere herein, in the plasma membrane of the cell, wherein in response to exposure to a light stimulus, the voltage potential of the cell is modulated. In some cases, the cell is a neuronal cell. In some cases, the cell is a cardiac cell. In some cases, the cell is a stem cell. In some cases, the cell is in vitro. In some cases, the cell is in vivo. In some cases, the light has a wavelength of from 600 nm to 700 nm.

The present disclosure provides a method of modulating activity of a mammalian cell that comprises the variant light-activated polypeptide, as described above or elsewhere herein, the method comprising activating the variant light-activated polypeptide with light (e.g., red light). In some cases, the light has a wavelength of from 600 nm to 700 nm. In some cases, the cell is a neuronal cell, a cardiac cell, or a stem cell. In some cases, the cell is in vivo. In some cases, the cell expresses a genetically encoded calcium indicator (GECI). In some cases, the GECI comprises an amino acid sequence having at least 85%, at least 90%, at least 95%, at least 98%, at least 99%, or at least 100%, amino acid sequence identity to the amino acid sequence set forth in any one of SEQ ID NOs: 7-28. In some cases, the cell further comprises a hyperpolarizing light-responsive polypeptide. In some cases, the hyperpolarizing light-responsive polypeptide comprises an amino acid sequence having at least 85% amino acid sequence identity to the amino acid sequence set forth in any one of SEQ ID NOs:42-48.

The present disclosure provides a device comprising: a) a container comprising a variant light-responsive polypeptide as described above or elsewhere herein, a nucleic acid comprising a nucleotide sequence encoding the variant light-responsive polypeptide, or a recombinant vector comprising a nucleotide sequence encoding the variant light-responsive polypeptide; and b) a light source. In some cases, the device is implantable. In some cases, the light source is an optical fiber.

The present disclosure provides a system comprising: a) a container comprising a variant light-responsive polypeptide as described above or elsewhere herein, a nucleic acid comprising a nucleotide sequence encoding the variant light-responsive polypeptide, or a recombinant vector comprising a nucleotide sequence encoding the variant light-responsive polypeptide; b) an implantable optical applicator configured to deliver light to a targeted tissue after implantation in a location adjacent to the targeted tissue structure; c) a light source operatively coupled to the implantable optical applicator; d) a controller; e) a power supply; and f) an implantable illuminance sensor, wherein the controller causes the power supply to allow current to flow to the light source to cause an emission of photons to the implantable light actuator based at least in part upon an output signal from the implantable illuminance sensor, wherein the implantable illuminance sensor is configures such that it can be positioned to capture at least a portion of the photons directed toward the targeted tissue by the implantable light applicator. In some cases, the implantable illuminance sensor is selected from the group consisting of: a photovoltaic cell, a photodiode, a pyroelectric sensor, a photoresistor, a photoconductor, a phototransistor, and a photogalvanic sensor. In some cases, the implantable input sensor is selected from the group consisting of: a photovoltaic cell, a photodiode, a pyroelectric sensor, a photoresistor, a photoconductor, a phototransistor, and a photogalvanic sensor. In some cases, the system comprises a physiologic sensor configured to produce an output signal that is correlated with a physiologic parameter believed be variable at least in part in response to the input of light to the targeted tissue structure. In some cases, the physiologic sensor is selected from the group consisting of: an electromyogram sensor, an electroneurogram sensor, electroencephalogram sensor, an electrocardiogram sensor, a pressure sensor, a temperature sensor, a chemometric sensor, a motion sensor, an accelerometer, a gyro, a strain sensor, an impedance sensor, and a capacitance sensor.

The present disclosure provides a treatment method comprising delivering light of an activating wavelength to a target cell or tissue in an individual in need thereof, wherein the target cell or tissue comprises a variant light-responsive polypeptide, as described above or elsewhere herein, in the plasma membrane of the target cell or of a cell in the target tissue, wherein said delivering activates the variant light-activated polypeptide and depolarizes the target cell or cell in the target tissue. In some cases, said depolarizing treats a neurological disease or disorder in the individual.

The present disclosure provides a method for illuminating a target tissue of an individual, where the targeted tissue structure comprises a variant light-responsive polypeptide, as described above or elsewhere herein, in the plasma membrane of a cell in the targeted tissue, the method comprising: a) providing an implantable optical applicator configured to deliver light to the target tissue after implantation in a location adjacent to the target tissue; and b) operatively coupling the implantable optical applicator to a light source, a controller, a power supply, and an implantable illuminance sensor such that the controller causes the power supply to allow current to flow to the light source to cause an emission of photons to the implantable light actuator based at least in part upon an output signal from the implantable illuminance sensor, wherein the implantable illuminance sensor is positioned such that it captures at least a portion of the photons directed toward the target tissue by the implantable light applicator. In some cases, the method further comprises providing an implantable input sensor configured to produce an output signal that is correlated to the illuminance of the implantable optical applicator at a position of photon emission before intersection of such photons with the targeted tissue. In some cases, the method further comprises operatively coupling the controller to the implantable input sensor, such that it may compare the output signal from both the implantable input sensor and the implantable illuminance sensor to determine whether unexpected losses are being experienced. In some cases, the implantable illuminance sensor is selected from the group consisting of: a photovoltaic cell, a photodiode, a pyroelectric sensor, a photoresistor, a photoconductor, a phototransistor, and a photogalvanic sensor. In some cases, the implantable input sensor is selected from the group consisting of: a photovoltaic cell, a photodiode, a pyroelectric sensor, a photoresistor, a photoconductor, a phototransistor, and a photogalvanic sensor.

The present disclosure provides a method of inducing contextual memory retrieval in a mammalian subject, the method comprising delivering light having a wavelength of from 600 nm to 700 nm to a monosynaptic prefrontal to hippocampus projection of a neuron in the mammalian subject, wherein the projection comprises a variant light-responsive polypeptide as described above or elsewhere herein, wherein delivering light to the projection depolarizes the projection and induces contextual memory retrieval. In some cases, the prefrontal to hippocampus projection is a prefrontal to hippocampus projection. In some cases, the prefrontal to hippocampus projection is an anterior cingulate to hippocampus projection. In some cases, the projection is to pyramidal CA3/CA1 cells the hippocampus. In some cases, neurons of the anterior cingulate comprise the variant light-responsive polypeptide. The present disclosure provides a method of modulating contextual memory retrieval, the method comprising delivering light to a monosynaptic prefrontal to hippocampus projection of a neuron in the mammalian subject, wherein the projection comprises: i) a variant light-responsive polypeptide as described above or elsewhere herein, wherein delivering light of a first activating wavelength (e.g., red light) to the projection depolarizes the projection and induces contextual memory retrieval; and ii) a hyperpolarizing opsin, wherein delivering light of a second activating wavelength hyperpolarizes the projection, wherein hyperpolarizing the projection reduces (e.g., suppresses) contextual memory retrieval.

BRIEF DESCRIPTION OF THE DRAWINGS

FIG. 1A-1E depict design and characterization of bReaChE-S.

FIG. 2A-2B depict confocal images of opsin expression in cell bodies near the injection site in medial prefrontal cortex, and in downstream axonal fibers in the amygdala.

FIG. 4A-4F provide amino acid sequences of ReaChR and variant light-responsive polypeptides (e.g., bReachES).

FIG. 5A-5S provide amino acid sequences of single-fluorescent protein genetically encoded calcium indicators.

FIG. 6A-6C provide amino acid sequences of multi-fluorescent protein genetically encoded calcium indicators.

FIG. 7A-7U provide amino acid sequences of various light-responsive polypeptides.

FIG. 20A-20C depict the functional relationships of fear context-defined HC neurons as appearing in fear vs. neutral context.

DEFINITIONS

Figure 3:
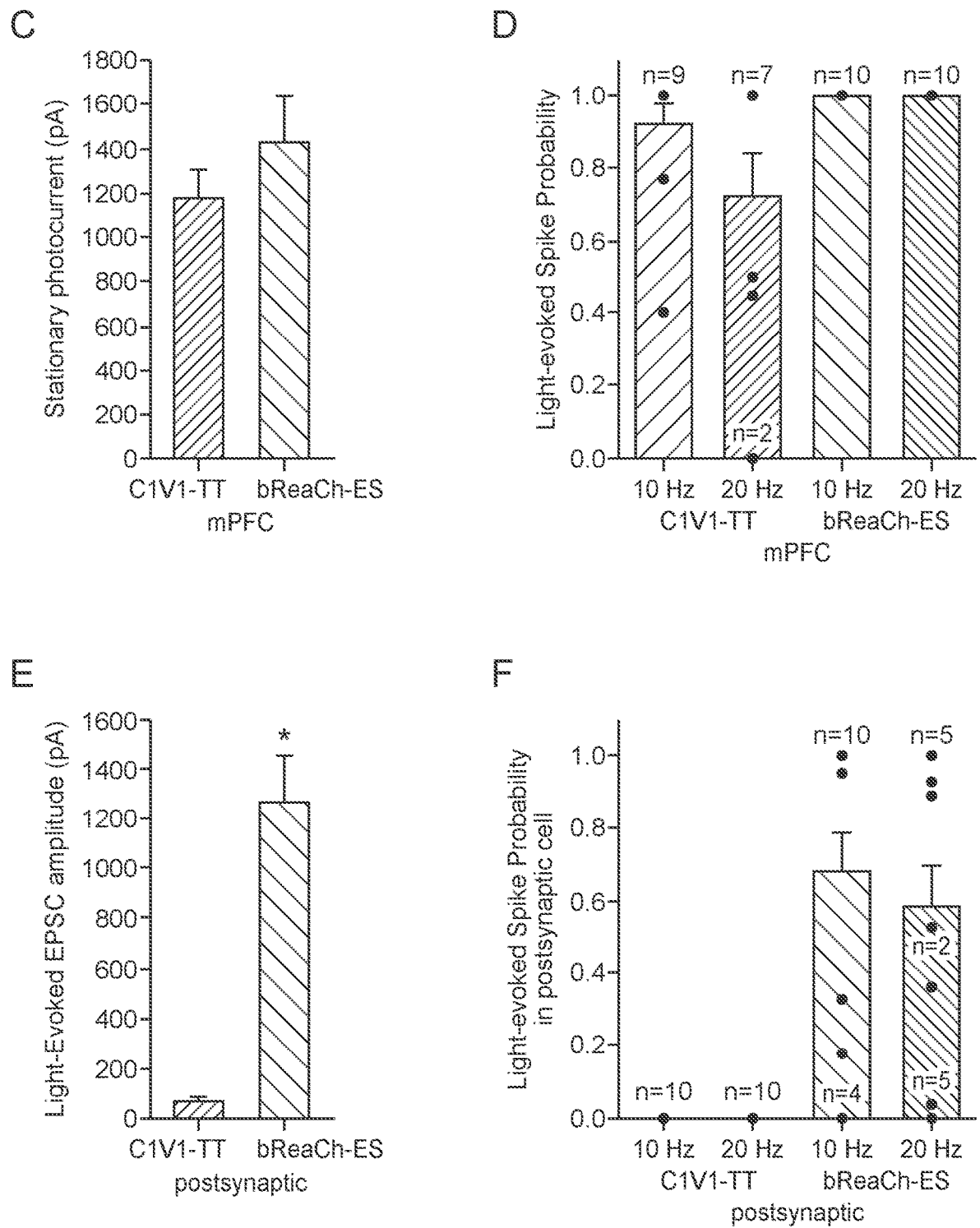
FIG. 3A-3F depict whole-cell recording analysis of bReachES.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Any suitable means for making this adjustment may be used. This may involve scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences.

The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Any suitable methods of alignment of sequences for comparison may be employed. Thus, the determination of percent identity between any two sequences can be accomplished using a mathematical algorithm. Examples of such mathematical algorithms are the algorithm of Myers and Miller, CABIOS, 4:11 (1988), which is hereby incorporated by reference in its entirety; the local homology algorithm of Smith et al, Adv. Appl. Math., 2:482 (1981), which is hereby incorporated by reference in its entirety; the homology alignment algorithm of Needleman and Wunsch, J. Mol. Biol. 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karhn and Altschul, Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST programs of Altschul et al., JMB, 215:403 (1990); Nucl. Acids Res., 25:3389 (1990), which are hereby incorporated by reference in their entirety, are based on the algorithm of Karlin and Altschul supra.

Software for performing BLAST analyses is publicly available through the National Center for Biotechnology Information (NCBI; worldwideweb.ncbi.nlm.nih.gov).

Amino acid substitutions in an amino acid sequence, relative to a reference amino acid sequence, may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard (coded) twenty amino acids divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

The term "genetic modification" refers to a permanent or transient genetic change induced in a cell following introduction into the cell of a heterologous nucleic acid (e.g., a nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The term "promoter" as used herein refers to a sequence of DNA that directs the expression (transcription) of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "operably-linked" refers to a functional linkage between a regulatory sequence and a coding sequence. The components so described are thus in a relationship permitting them to function in their intended manner. For example, placing a coding sequence under regulatory control of a promoter means positioning the coding sequence such that the expression of the coding sequence is controlled by the promoter.

As used herein, an "individual," "subject," or "patient" can be a mammal, including a human. Mammals include, but are not limited to, ungulates, canines, felines, bovines, ovines, non-human primates, lagomorphs, and rodents (e.g., mice and rats). In one aspect, an individual is a human. In another aspect, an individual is a non-human mammal.

As used herein, "treatment" or "treating" refers to obtaining beneficial or desired results, including clinical results. For purposes of this disclosure, beneficial or desired clinical results include, but are not limited to, one or more of the following: decreasing symptoms (ameliorating adverse symptoms) resulting from a disease, increasing the quality of life of those suffering from a disease, decreasing the dose of other medications required to treat a disease, delaying the progression of a disease, and/or prolonging survival of individuals having a disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a light-activated polypeptide" includes a plurality of such polypeptides and reference to "the GECI" includes reference to one or more GECIs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant light-responsive polypeptides, and nucleic acids comprising nucleotide sequences encoding the light-responsive polypeptides. The present disclosure provides methods, devices, and systems for controlling the activity of a cell expressing a variant light-responsive polypeptide of the present disclosure.
Variant Light-Activated Polypeptides The present disclosure provides variant light-responsive polypeptides. A variant light-responsive polypeptide of the present disclosure is also referred to as a "variant light-activated polypeptide." A variant light-responsive polypeptide of the present disclosure, when expressed in a eukaryotic cell (e.g., a mammalian cell; e.g., an excitable cell such as a neuronal cell) and when exposed to light of an activating wavelength, induces depolarization of the cell membrane.

A variant light-responsive polypeptide of the present disclosure exhibits at least 5-fold increased kinetics compared to the light-activated polypeptide of SEQ ID NO:1. The light-activated polypeptide of SEQ ID NO:1 (and depicted in FIG. 1A) is referred to as "ReaChR." The channel closure of ReaChR has a tau value of the mono exponential kinetics of 682 milliseconds (ms), as measured in cultured rat hippocampal neurons. In contrast, a variant light-responsive polypeptide of the present disclosure exhibits channel closure having a tau value of less than 300 ms, less than 200 ms, or less than 100 ms, when measured in cultured rat hippocampal neurons. A variant light-responsive polypeptide of the present disclosure exhibits channel closure having kinetics of channel closure that are at least 2-fold, at least 2.5-fold, at least 3-fold, at least 5-fold, at least 7-fold, at least 10-fold, at least 13-fold, or at least 15-fold, faster than the kinetics of channel closure of ReaChR.

For example, in some cases, a variant light-responsive polypeptide of the present disclosure exhibits channel closure having a tau value of from about 25 ms to about 50 ms, from about 50 ms to about 75 ms, from about 75 ms to about 100 ms, from about 100 ms to about 125 ms, from about 125 ms to about 150 ms, from about 150 ms to about 200 ms, from about 150 ms to about 200 ms, from about 200 ms to about 250 ms, or from about 250 ms to about 300 ms, when measured in cultured rat hippocampal neurons. In some cases, a variant light-responsive polypeptide of the present disclosure exhibits channel closure having a tau value of from about 25 ms to about 50 ms, from about 50 ms to about 75 ms, or from about 75 ms to about 100 ms, when measured in cultured rat hippocampal neurons. In some cases, a variant light-responsive polypeptide of the present disclosure exhibits channel closure having a tau value of from about 40 ms to about 60 ms, when measured in cultured rat hippocampal neurons.

A variant light-responsive polypeptide of the present disclosure can, when exposed to light of an activating wavelength, evoke action potentials at a higher frequency than the frequency of action potentials evoked by ReaChR, e.g., when expressed in a mammalian neuron. ReaChR induces neuronal firing (evokes action potentials) in in vitro cultured rat hippocampal neurons at a frequency of 1-2 Hertz (Hz). A variant light-responsive polypeptide of the present disclosure can, when exposed to light of an activating wavelength, evoke action potentials at a frequency of greater than 2 Hz, greater than 5 Hz, greater than 10 Hz, greater than 15 Hz, or greater than 20 Hz, in a cell expressing the variant light-responsive polypeptide. For example, a variant light-responsive polypeptide of the present disclosure can, when exposed to light of an activating wavelength, evoke action potentials at a frequency of from 3 Hz to 5 Hz, from 5 Hz to 7 Hz, from 7 Hz to 10 Hz, from 10 Hz to 12 Hz, from 12 Hz to 15 Hz, from 15 Hz to 17 Hz, from 17 Hz to 20 Hz, or more than 20 Hz. In some cases, a variant light-responsive polypeptide of the present disclosure can, when exposed to light of an activating wavelength, evoke action potentials at a frequency of from 15 Hz to 20 Hz.

A variant light-responsive polypeptide of the present disclosure is activated by light of an activating wavelength, e.g., light having a wavelength of from 600 nm to 700 nm, e.g., from 600 nm to 625 nm, from 625 nm to 650 nm, from 650 nm to 675 nm, or from 675 nm to 700 nm. In some cases, a variant light-responsive polypeptide of the present disclosure is activated by light having a wavelength of from 625 nm to 650 nm. In some cases, a variant light-responsive polypeptide of the present disclosure is activated by light having a wavelength of 630 nm.

A variant light-responsive polypeptide of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:1, and comprises a glutamic acid to serine substitution at position 163 based on the numbering of the amino acid sequence set forth in SEQ ID NO:1.

In some cases, a variant light-responsive polypeptide of the present disclosure comprises an amino acid sequence having at least 75%, at least 80%, at least 85%, at least 90%, at least 95%, at least 98%, or at least 99%, amino acid sequence identity to amino acids 52 to 345 of the amino acid sequence set forth in SEQ ID NO:1, and comprises a glutamic acid to serine substitution at position 163 based on the numbering of the amino acid sequence set forth in SEQ ID NO:1.

In some cases, a variant light-responsive polypeptide of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:2, and comprises a serine at position 163 based on the numbering of the amino acid sequence set forth in SEQ ID NO:2, and depicted in FIG. 4B.

In some cases, the signal sequence of a variant light-responsive polypeptide of the present disclosure is modified relative to the signal sequence of the amino acid sequence set forth in SEQ ID NO:1. For example, the signal sequence of the amino acid sequence set forth in SEQ ID NO:1 is MVSRRPWLLALALAVALAAGSAGASTGSDATVP-VATQDGPDYVFHRAHER (SEQ ID NO:50). In some cases, the signal sequence is replaced with a different signal sequence. For example, the signal sequence can be MDYG-GALSAVG (SEQ ID NO:51). Thus, for example, in some cases, a variant light-responsive polypeptide of the present disclosure comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:3 and depicted in FIG. 4C, and has a serine at position 123 based on the numbering of the amino acid sequence set forth in SEQ ID NO:3.

In some cases, a variant light-responsive polypeptide of the present disclosure comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:5 and depicted in FIG. 4E, and has a serine at position 112 based on the numbering of the amino acid sequence set forth in SEQ ID NO:5. In some cases, a variant light-responsive polypeptide of the present disclosure comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:5, and has a serine at position 112 based on the numbering of the amino acid sequence set forth in SEQ ID NO:5, and includes 1, 2, 3, 4, 5, 6, 7, or all of: a) a Val at amino acid 48 based on the numbering of the amino acid sequence set forth in SEQ ID NO:5; b) a Glu at amino acid 79 based on the numbering of the amino acid sequence set forth in SEQ ID NO:5; c) a Glu at amino acid 90 based on the numbering of the amino acid sequence set forth in SEQ ID NO:5; d) a Val at amino acid 106 based on the numbering of the amino acid sequence set forth in SEQ ID NO:5; e) a His at amino acid 123 based on the numbering of the amino acid sequence set forth in SEQ ID NO:5; f) a Pro at amino acid 231 based on the numbering of the amino acid sequence set forth in SEQ ID NO:5; g) an Ala at amino acid 235 based on the numbering of the amino acid sequence set forth in SEQ ID NO:5; and h) an Asn at amino acid 247 based on the numbering of the amino acid sequence set forth in SEQ ID NO:5. In some cases, a variant light-responsive polypeptide of the present disclosure comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:5, and has a serine at position 112 based on the numbering of the amino acid sequence set forth in SEQ ID NO:5, and includes: a) a Val at amino acid 48 based on the numbering of the amino acid sequence set forth in SEQ ID NO:5; b) a Glu at amino acid 79 based on the numbering of the amino acid sequence set forth in SEQ ID NO:5; c) a Glu at amino acid 90 based on the numbering of the amino acid sequence set forth in SEQ ID NO:5; d) a Val at amino acid 106 based on the numbering of the amino acid sequence set forth in SEQ ID NO:5; e) a His at amino acid 123 based on the numbering of the amino acid sequence set forth in SEQ ID NO:5; f) a Pro at amino acid 231 based on the numbering of the amino acid sequence set forth in SEQ ID NO:5; g) an Ala at amino acid 235 based on the numbering of the amino acid sequence set forth in SEQ ID NO:5; and h) an Asn at amino acid 247 based on the numbering of the amino acid sequence set forth in SEQ ID NO:5. In some cases, the variant light-responsive polypeptide includes a signal sequence (e.g., MDYGGAL-SAVG (SEQ ID NO:51) or other suitable signal sequence). In some cases, the variant light-responsive polypeptide includes an ER export signal. In some cases, the variant light-responsive polypeptide includes an ER export signal and a membrane trafficking signal.

In some cases, a variant light-responsive polypeptide of the present disclosure comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:6 and depicted in FIG. 4F, and has a serine at position 112 based on the numbering of the amino acid sequence set forth in SEQ ID NO:6. In some cases, a variant light-responsive polypeptide of the present disclosure comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:6, and has a serine at position 112 based on the numbering of the amino acid sequence set forth in SEQ ID NO:6; and includes 1, 2, 3, 4, 5, 6, 7, or all of: a) a Val at amino acid 48 based on the numbering of the amino acid sequence set forth in SEQ ID NO:6; b) a Glu at amino acid 79 based on the numbering of the amino acid sequence set forth in SEQ ID NO:6; c) a Glu at amino acid 90 based on the numbering of the amino acid sequence set forth in SEQ ID NO:6; d) a Val at amino acid 106 based on the numbering of the amino acid sequence set forth in SEQ ID NO:6; e) a His at amino acid 123 based on the numbering of the amino acid sequence set forth in SEQ ID NO:6; f) a Pro at amino acid 231 based on the numbering of the amino acid sequence set forth in SEQ ID NO:6; g) an Ala at amino acid 235 based on the numbering of the amino acid sequence set forth in SEQ ID NO:6; and h) an Asn at amino acid 247 based on the numbering of the amino acid sequence set forth in SEQ ID NO:6. In some cases, a variant light-responsive polypeptide of the present disclosure comprises an amino acid sequence having at least 75%, at least 80%, at least 85%, at least 90%, at least 95%, at least 98%, at least 99%, or 100%, amino acid sequence identity to the amino acid sequence set forth in SEQ ID NO:6, and has a serine at position 112 based on the numbering of the amino acid sequence set forth in SEQ ID NO:6; and includes: a) a Val at amino acid 48 based on the numbering of the amino acid sequence set forth in SEQ ID NO:6; b) a Glu at amino acid 79 based on the numbering of the amino acid sequence set forth in SEQ ID NO:6; c) a Glu at amino acid 90 based on the numbering of the amino acid sequence set forth in SEQ ID NO:6; d) a Val at amino acid 106 based on the numbering of the amino acid sequence set forth in SEQ ID NO:6; e) a His at amino acid 123 based on the numbering of the amino acid sequence set forth in SEQ ID NO:6; f) a Pro at amino acid 231 based on the numbering of the amino acid sequence set forth in SEQ ID NO:6; g) an Ala at amino acid 235 based on the numbering of the amino acid sequence set forth in SEQ ID NO:6; and h) an Asn at amino acid 247 based on the numbering of the amino acid sequence set forth in SEQ ID NO:6.

In some cases, a variant light-responsive polypeptide of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:1, and comprises a glutamic acid to serine substitution at position 163 based on the numbering of the amino acid sequence set forth in SEQ ID NO:1. In some cases, a variant light-responsive polypeptide of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:1, and comprises a glutamic acid to serine substitution at position 163 based on the numbering of the amino acid sequence set forth in SEQ ID NO:1, and includes 1, 2, 3, 4, 5, 6, 7, or all of: a) a Val at amino acid 99 based on the numbering of the amino acid sequence set forth in SEQ ID NO:1; b) a Glu at amino acid 130 based on the numbering of the amino acid sequence set forth in SEQ ID NO:1; c) a Glu at amino acid 141 based on the numbering of the amino acid sequence set forth in SEQ ID NO:1; d) a Val at amino acid 157 based on the numbering of the amino acid sequence set forth in SEQ ID NO:1; e) a His at amino acid 174 based on the numbering of the amino acid sequence set forth in SEQ ID NO:1; f) a Pro at amino acid 282 based on the numbering of the amino acid sequence set forth in SEQ ID NO:1; g) an Ala at amino acid 286 based on the numbering of the amino acid sequence set forth in SEQ ID NO:1; and h) an Asn at amino acid 298 based on the numbering of the amino acid sequence set forth in SEQ ID NO:1. In some cases, a variant light-responsive polypeptide of the present disclosure comprises an amino acid sequence having at least 75%, at least 80%, at least 85%, at least 90%, at least 95%, at least 98%, or at least 99%, amino acid sequence identity to the amino acid sequence set forth in SEQ ID NO:1, and comprises a glutamic acid to serine substitution at position 163 based on the numbering of the amino acid sequence set forth in SEQ ID NO:1, and includes a Val at amino acid 99 based on the numbering of the amino acid sequence set forth in SEQ ID NO:1, a Glu at amino acid 130 based on the numbering of the amino acid sequence set forth in SEQ ID NO:1, a Glu at amino acid 141 based on the numbering of the amino acid sequence set forth in SEQ ID NO:1, a Val at amino acid 157 based on the numbering of the amino acid sequence set forth in SEQ ID NO:1, a His at amino acid 174 based on the numbering of the amino acid sequence set forth in SEQ ID NO:1, a Pro at amino acid 282 based on the numbering of the amino acid sequence set forth in SEQ ID NO:1, an Ala at amino acid 286 based on the numbering of the amino acid sequence set forth in SEQ ID NO:1, and an Asn at amino acid 298 based on the numbering of the amino acid sequence set forth in SEQ ID NO:1.

A variant light-responsive polypeptide of the present disclosure can be fused to one or more amino acid sequence motifs selected from the group consisting of a signal peptide, an endoplasmic reticulum (ER) export signal, a membrane trafficking signal, and an N-terminal Golgi export signal. The one or more amino acid sequence motifs that enhance protein transport to the plasma membranes of mammalian cells can be fused to the N-terminus, the C-terminus, or to both the N- and C-termini of a protein in order to facilitate optimal expression and/or localization of the protein in the plasma membrane of a cell. Optionally, a variant light-responsive polypeptide of the present disclosure and the one or more amino acid sequence motifs may be separated by a linker. In some embodiments, a variant light-responsive polypeptide of the present disclosure can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:52). In some embodiments, the heterologous membrane trafficking signal can comprise the amino acid sequence KSRITSEGEYIPLDQIDIN (SEQ ID NO:62).

Trafficking sequences that are suitable for use can comprise an amino acid sequence having 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:52)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having 90%, 91%, 92%, 93%, 94%, 95%, 96%, 97%, 98%, 99%, or 100%, amino acid sequence identity to an amino acid sequence such as one of the following:

```
1) the signal peptide of hChR2 (e.g.,
MDYGGALSAVGRELLFVTNPVVVNGS (SEQ ID NO: 53))

2) the β2 subunit signal peptide of the
neuronal nicotinic acetylcholine receptor (e.g.,
MAGHSNSMALFSFSLLWLCSGVLGTEF (SEQ ID NO: 54));

3) a nicotinic acetylcholine receptor
signal sequence (e.g.,
MGLRALMLWLLAAAGLVRESLQG (SEQ ID NO: 55));
and
```

-continued
4) a nicotinic acetylcholine receptor
signal sequence (e.g.,
MRGTPLLLVVSLFSLLQD (SEQ ID NO: 56)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use with a variant light-responsive polypeptide of the present disclosure include, e.g., VXXSL (where X is any amino acid) (e.g., VKESL (SEQ ID NO:57); VLGSL (SEQ ID NO:58); etc.); NANSFCYENEVALTSK (SEQ ID NO:59); FXYENE (SEQ ID NO:60) (where X is any amino acid), e.g., FCYENEV (SEQ ID NO:61); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

A variant light-responsive polypeptide of the present disclosure can further include one or more additional polypeptides. For example, a variant light-responsive polypeptide of the present disclosure can include a linker; an epitope tag; a fluorescent protein; a peptide that provides for ease of purification; a cleavable linker peptide; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) Nature Biotechnol. 17:969-973, is suitable for use.

Nucleic Acids, Expression Vectors, and Host Cells

The present disclosure provides nucleic acids that comprise a nucleotide sequence that encodes one or more of the subject proteins described herein (e.g., one or more variant light-responsive polypeptides, as described above). The present disclosure also provides recombinant expression vectors comprising a nucleic acid that comprises a variant light-responsive polypeptide of the present disclosure. The present disclosure also provides host cells genetically modified to include a nucleic acid of the present disclosure or a recombinant expression vector of the present disclosure.

Nucleic Acids and Recombinant Expression Vectors

The present disclosure provides nucleic acids that comprise a nucleotide sequence that encodes one or more of the subject proteins described herein (e.g., one or more variant light-responsive polypeptides, as described above). In some embodiments, a subject polynucleotide comprises an expression cassette, wherein the expression cassette contains a plurality of components (e.g., a plurality of coding sequences) that are utilized to express one or more proteins encoded by the polynucleotide in a target cell.

In some cases, a nucleotide sequence encoding a variant light-responsive polypeptide of the present disclosure is operably linked to a transcriptional control element, e.g., a promoter. Any suitable promoter that functions in a target cell is suitable for use. In certain embodiments, a promoter can be a promoter that is specific to a particular target cell type or to a particular tissue type, such as a particular neuron or a pan-neuronal promoter. Initiation control regions of promoters, which are useful to drive expression of polynucleotides in a specific animal cell, are numerous and familiar to those skilled in the art. Virtually any promoter capable of driving expression of the subject polynucleotides can be used. In some embodiments, the promoter used to drive expression of a variant light-responsive polypeptide of the present disclosure can be a Thy1 promoter (See, e.g., Llewellyn, et al., 2010, Nat. Med., 16(10):1161-1166). In some embodiments, the promoter used to drive expression of a variant light-responsive polypeptide of the present disclosure is a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, a vesicular γ-amino butyric acid (VGAT) promoter, a glial fibrillary acidic protein (GFAP) promoter, a Pea promoter, a neuropeptide Y (NPY) promoter, a somatostatin (SST) promoter, an arginine vasopressin (AVP) promoter, a hypocretin (Hcrt) promoter, or any other promoter capable of driving expression of a nucleotide sequence encoding a variant light-responsive polypeptide of the present disclosure in a target cell.

In some cases, a suitable promoter is an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

In some cases, a suitable promoter is a constitutive promoter. Such constitutive promoters are active in all circumstances, and are not regulated.

In some embodiments, a subject polynucleotide may comprise a ribosomal skip sequence that can be used to generate two separate proteins from the same transcript. In such cases, a subject polynucleotide will typically include a coding sequence that encodes a light-activated protein as well as a response protein. In these embodiments, a ribosomal skip sequence may be placed between the two coding sequences to produce two distinct proteins (namely, the light-activated protein and the response protein) from the same transcript.

Also provided herein are recombinant expression vectors comprising the subject polynucleotides (comprising a nucleotide sequence encoding a variant light-responsive polypeptide of the present disclosure) or any variant thereof as described herein. Vectors according to the present disclosure also include vectors comprising a nucleotide sequence that encodes an RNA (e.g., an mRNA) that when transcribed from the polynucleotides of the vector will result in the accumulation of a variant light-responsive polypeptide of the present disclosure on the plasma membranes of target cells. Vectors which may be used include, without limitation, lentiviral, retroviral, herpes simplex virus (HSV), adenoviral, and adeno-associated viral (AAV) vectors. Lentivirus vectors include, but are not limited to vectors based on human immunodeficiency virus (e.g., HIV-1, HIV-2), simian immunodeficiency virus (SIV), feline immunodeficiency virus (FIV), and equine infectious anemia virus (EIAV). Lentiviruses may be pseudotyped with the envelope proteins of other viruses, including, but not limited to vesicular stomatitis virus (VSV), rabies virus, Moloney-murine leukemia virus (Mo-MLV), baculovirus, and Ebola virus. Such vectors may be prepared using standard methods in the art. Retroviruses include, but are not limited to Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus, and the like.

In some cases, a suitable vector is a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (JR Kerr, S F Cotmore. M E Bloom, R M Linden, C R Parrish, Eds.) p 5-14, Hudder Arnold, London, U K (2006); and D E Bowles, J E Rabinowitz, R J Samulski "The Genus Dependovirus" (JR Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

In some cases, a nucleotide sequence encoding a variant light-responsive polypeptide of the present disclosure can be operably linked to various promoters for targeting specific neuronal populations in mammalian brains. Non-limiting examples of suitable recombinant expression constructs include, e.g.: AAV-CamKII-bReaCh-ES, AAV-hSyn-bReaCh-ES, AAV-mThy1-bReaCh-ES, AAV-hThy1-bReaCh-ES, AAV-GFAP-bReaCh-ES, AAV-VGAT-bReaCh-ES, AAV-PET1-bReaCh-ES, AAV-NPY-bReaCh-ES, AAV-SST-bReaCh-ES, AAV-AVP5.5-bReaCh-ES, AAV-Ef1a-bReaCh-ES, AAV-FLEX-rev-bReaCh-ES, AAV-CAG-bReaCh-ES, AAV-CAG-FLEX-bReaCh-ES, where "bReaCh-ES" is a nucleotide sequence encoding a variant light-responsive polypeptide of the present disclosure, where "CamKII" is a CamKII promoter, where "hSyn" is a human synapsin promoter, where "mThy1" is a mouse Thy1 promoter, where "hThy1" is a human Thy1 promoter, "GFAP" is a glial fibrillary acid protein (GFAP) promoter (see, e.g., Lee et al. (2008) Glia 56:481), where "VGAT" is a vesicular gamma amino butyric acid transporter (VGAT) promoter, where "PET1" is a PET1 promoter (see, e.g., Liu et al. (2010) Nat. Neurosci. 13:1190), where "NPY" is a neuropeptide Y (NPY) promoter, where "SST" is a somatostatin (SST) promoter, where "AVP5.5" is an arginine vasopressin promoter (see, e.g., Pak et al. (2007) 148:3371), where "Ef1a" is an Ef1a promoter, where "CAG" is a cytomegalovirus early enhancer/chicken β actin (CAG) promoter (see, e.g., Alexopoulou et al. (2008) MBC Cell Biol. 9:2), where "FLEX-for" is a FLEX-for switch and where "FLEX-rev" is a FLEX-rev switch. For flip-excision (FLEX) switches, see, e.g., Atasoy et al. (2008) J Neurosci. 28:7025. A recombinant expression vector comprising a nucleotide sequence encoding a variant light-responsive polypeptide of the present disclosure can also comprises a nucleotide sequence encoding a fluorescent protein (XFP). For example, the following adeno associated vectors (AAVs) and components thereof may be used without limitation: AAV-CamKII-bReaCh-ES-XFP, AAV-hSyn-bReaCh-ES-XFP, AAV-mThy1-bReaCh-ES-XFP, AAV-hThy1-bReaCh-ES-XFP, AAV-GFAP-bReaCh-ES-XFP, AAV-VGAT-bReaCh-ES-XFP, AAV-PET1-bReaCh-ES-XFP, AAV-NPY-bReaCh-ES-XFP, AAV-SST-bReaCh-ES-XFP, AAV-AVP5.5-bReaCh-ES-XFP, AAV-Ef1a-bReaCh-ES-XFP, AAV-FLEX-rev-bReaCh-ES-XFP, AAV-CAG-bReaCh-ES-XFP, AAV-CAG-FLEX-bReaCh-ES-XFP, where "bReaCh-ES" is a nucleotide sequence encoding a variant light-responsive polypeptide of the present disclosure, where "CamKII" is a CamKII promoter, where "hSyn" is a human synapsin promoter, where "mThy1" is a mouse Thy1 promoter, where "hThy1" is a human Thy1 promoter, "GFAP" is a GFAP promoter, where "VGAT" is a VGAT promoter, where "PET1" is a PET1 promoter, where "NPY" is a NPY promoter, where "SST" is a SST promoter, where "AVP5.5" is an AVP5.5 promoter, where "Ef1a" is an Ef1a promoter, where "CAG" is a CAG promoter, where "FLEX" is a FLEX-for switch and where "FLEX-rev" is a FLEX-rev switch. Other AAV vectors that may be used in association with the polynucleotides include those with double floxed inverted reading frames (DIO) which allow expression of proteins under the control of recombinases such as as Cre and Flp: AAV-Ef1a-DIO(Cre)-bReaCh-ES (Cre-dependent expression), AAV-Ef1a-DIO(Flp)-bReaCh-ES (Flp-dependent expression), AAV-Ef1a-DIO(Cre)-DIO(Flp)-bReaCh-ES (Cre and Flp dependent expression), optionally, in operable linkage with a nucleotide sequence encoding a fluorescent protein (XFP), e.g., AAV-Ef1a-DIO(Cre)-bReaCh-ES-XFP (Cre-dependent expression), AAV-Ef1a-DIO(Flp)-bReaCh-ES-XFP (Flp-dependent expression), AAV-Ef1a-DIO(Cre)-DIO(Flp)-bReaCh-ES-XFP (Cre and Flp dependent expression), where "bReaCh-ES" is a nucleotide sequence encoding a variant light-responsive polypeptide of the present disclosure.

Another major viral transduction system utilizes lentivirus including the following potential expression vectors. In some cases, a nucleotide sequence encoding a variant light-responsive polypeptide of the present disclosure can be operably linked to various lentivirus expression promoters. Non-limiting examples of suitable lentivirus expression promoters include, e.g.: pLenti-CamKII-bReaCh-ES, pLenti-Ef1a-bReaCh-ES, pLenti-mThy1-bReaCh-ES, pLenti-hThy1-bReaCh-ES, pLenti-hSyn-bReaCh-ES, pLenti-VGAT-bReaCh-ES, pLenti-Hcrt-bReaCh-ES, where "bReaCh-ES" is a nucleotide sequence encoding a variant light-responsive polypeptide of the present disclosure, where "CamKII" is a CamKII promoter, where "hSyn" is a human synapsin promoter, where "mThy1" is a mouse Thy1 promoter, where "hThy1" is a human Thy1 promoter, where "VGAT" is a VGAT promoter, where "Ef1a" is an Ef1a promoter, where "Hcrt" is a hypocretin neuropeptide (Hcrt) promoter. A nucleotide sequence encoding a variant light-responsive polypeptide of the present disclosure operably linked to various lentivirus expression promoters can further comprise a nucleotide sequence encoding a fluorescent protein (XFP), e.g.: pLenti-CamKII-bReaCh-ES-XFP, pLenti-Ef1a-bReaCh-ES-XFP, pLenti-mThy1-bReaCh-ES-XFP, pLenti-hThy1-bReaCh-ES-XFP, pLenti-hSyn-bReaCh-ES-XFP, pLenti-VGAT-bReaCh-ES-XFP, pLenti-Hcrt-bReaCh-ES-XFP, where "CamKII" is a CamKII promoter, where "hSyn" is a human synapsin promoter, where "mThy1" is a mouse Thy1 promoter, where "hThy1" is a human Thy1 promoter, where "VGAT" is a VGAT promoter, where "Ef1a" is an Ef1a promoter, where "Hcrt" is a Hcrt promoter. Herpes simplex virus (HSV) can be utilized to transport proteins of interest over synapses (anterograde) which includes the following expression vectors: HSV-EF1a-bReaCh-ES and HSV-EF1α-DIO-bReaCh-ES, optionally, in operable linkage with a nucleotide sequence encoding a fluorescent protein (XFP), e.g., HSV-EF1a-bReaCh-ES-XFP and HSV-EF1α-DIO-bReaCh-ES-XFP, where "EF1α" is a EF1α promoter and "DIO" means that the vector comprises polynucleotides with double floxed inverted reading frames. Rabies and pseudorabies virus can be utilized for retrograde transports over synapses using the following expression vector: SAD(delta)G-bReaCh-ES-XFP and SAD(delta)G-DIO-bReaCh-ES-XFP, where "SAD (delta)G" is a G gene-deficient recombinant rabies virus (see, e.g., Etessami et al. (2000) J. Gen. Virol. 81:2147-2153) and "DIO" means the vector comprises polynucleotides with double floxed inverted reading frames. Other mammalian expression vectors include: pcDNA3.1-CMV-bReaCh-ES and pCAGGS-bReaCh-ES, optionally, in operable linkage with a nucleotide sequence encoding a fluorescent protein (XFP), e.g., pcDNA3.1-CMV-bReaCh-ES-XFP and pCAGGS-bReaCh-ES-XFP, where "CMV" is a CMV promoter.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); an alpha subunit of $Ca^{(2+)}$-calmodulin-dependent protein kinase II (CaMKIIα) promoter (see, e.g., Mayford et al. (1996) Proc. Natl. Acad. Sci. USA 93:13250); a methyl-CpG-binding protein-2 (MeCP2); a Pax6 promoter; an Nkx6.1 promoter; a latency-associated promoter 2 (LAP2) promoter; a ETS domain transcription factor PET1 promoter (see, e.g., Liu et al. (2011) Nat. Neurosci. 13(10): 1190-1198); a glial fibrillary acidic protein (GFAP) promoter (see, e.g., Brenner et al. (1994) J. Neurosci. 14:1030-1037); a vesicular GABA transporter (VGAT) promoter (see, e.g., Ebihara et al. (2003) Brain Res. Mol. Brain Res. 110:126-139); a neuropeptide tyrosine (NPY) promoter (see, e.g., Andersson et al. (1994) Cell Growth Differ. 5:27-36); a somatostatin (SST) promoter (see, e.g., Grosser et al. (2014) Neurosci. Lett. 566:241-246); an arginine vasopressin (AVP) promoter (e.g., AVP5.5 promoter; see, e.g., Pak et al. (2007) Endocrinology. 148:3371-3382); an elongation factor 1a (EF1a) promoter (see, e.g., Zhu et al. (2001) Biochim. Biophys. Acta. 1521:19-29); a hypocretin neuropeptide precursor (HCRT) promoter (see, e.g., Dong et al. (2013) Sleep Med. 14:482-487); and the like.

In some cases, a recombinant expression vector of the present disclosure can comprise a control element such as a Cre-dependent genetic switch (FLEX switch) which in the presence of Cre turns the expression of an operably linked gene "on" or "off" depending on the orientation of the gene (see, e.g., Atasoy et al. (2008) J. Neurosci. 28:7025-7030). In some cases, in the presence of Cre, a FLEX switch of the present disclosure will turn "on" the expression of an operably linked gene that is of forward orientation (e.g., a FLEX-for switch). In other cases, in the presence of Cre, a FLEX switch of the present disclosure will turn "off" the expression of an operably linked gene that is of reverse orientation (e.g., a FLEX-rev switch).

In some cases, a recombinant expression vector of the present disclosure can comprise a nucleotide sequence encoding a variant light-responsive polypeptide of the present disclosure, and a nucleotide sequence encoding a calcium indicator, e.g., a genetically encoded calcium indicator (GECI). In some cases, a variant light-responsive polypeptide of the present disclosure and a GECI are encoded on two separate expression vectors.

Variant light-responsive polypeptides of the present disclosure can be used as tools for the effective mapping of functional connection between brain regions. In some embodiments, the effective mapping of functional connections is achieved in combination with a GECI. In general, GECIs are fluorescent molecules that can respond to the intracellular level of calcium ions, and as such, have a wide range of use in the study of calcium signaling in a variety of cell types (e.g., neuronal activity). GECIs can be easily targeted to specific cell types or sub-cellular compartments, and when expressed together with variant light-responsive polypeptides, can provide long-term repeated in vivo measurements of cell activity. A GECI comprises a fluorescent protein, a calcium-binding domain (e.g., calmodulin, troponin C, and the like), and a domain that binds the calcium-binding domain (e.g., the M13 domain of the myosin light chain kinase, which binds calmodulin). Examples of GECI include Pericams, Cameleons, GCaMP, TN-XXL, and Twitch.

Fluorescent polypeptides that are suitable for use in a GECI include, but are not limited to, green fluorescent protein (GFP), blue fluorescent variant of GFP (BFP), cyan fluorescent variant of GFP(CFP), yellow fluorescent variant of GFP (YFP), enhanced GFP (EGFP), enhanced CFP (ECFP), enhanced YFP (EYFP), Venus, GFPS65T, Emerald, Topaz, GFPuv, destabilized EGFP (dEGFP), destabilized ECFP (dECFP), destabilized EYFP (dEYFP), HcRed, t-HcRed, DsRed, DsRed2, mCherry, t-dimer2, t-dimer2(12), mRFP1, mEos, pocilloporin, Renilla GFP, Monster GFP, paGFP, Kaede protein or a Phycobiliprotein, or a biologically active variant or fragment of any one thereof.

GECIs comprise a calcium-binding domain such as calmodulin or troponin C, fused to one or more (e.g., one, two, three, four, or more) fluorescent proteins (FPs). In single-FP GECIs, upon calcium binding, the fluorescence intensity of a circularly permutated FP (cpFP) may be modulated by calcium binding-dependent changes in the chromophore environment. In multiple-FP GECIs (e.g., two-FP GECIs, three-FP GECIs, four-FP GECIs), calcium binding modulates Förster resonance energy transfer (FRET) between FPs.

For example, in some cases, single-FP GECIs may find use in combination with variant light-responsive polypeptides as tools for the effective mapping of functional connection between brain regions. Single-FP GECIs that find use in the present disclosure may be a fusion product of a fluorescent protein, calmodulin and an M13 peptide sequence (e.g., GFP calmodulin-M13 GECI (GCaMP)), including, but are not limited to, GCaMPK (SEQ ID NO:7), GCaMP2 (SEQ ID NO:8), GCaMP2.1 (SEQ ID NO:9), GCaMP2.2a (SEQ ID NO:10), GCaMP2.2b (SEQ ID NO:11), GCaMP2.3 (SEQ ID NO:12), GCaMP2.4 (SEQ ID NO:13), GCaMP3 (SEQ ID NO:14), GCaMP5g (SEQ ID NO:15), GCaMP6m (SEQ ID NO:16), GCaMP6s (SEQ ID NO:17), GCaMP6f (SEQ ID NO:18), and the like. Other single-FP GECIs that find use in the present disclosure include genetically encoded calcium indicators for optical imaging (GECOs) such as, the green fluorescing indicators G-GECO1 (SEQ ID NO:23), G-GECO1.1 (SEQ ID NO:24) and G-GECO1.2 (SEQ ID NO:25), the red fluorescing indicator R-GECO1 (SEQ ID NO:21), the blue fluorescing indicator B-GECO1 (SEQ ID NO:22), the emission ratiometric indicator GEM-GECO1 (SEQ ID NO:19), and the excitation ratiometric GEX-GECO1 (SEQ ID NO:20), and the like.

Single-FP GECIs that are suitable for use include, but are not limited to those that comprise an amino acid sequence having at least 75%, at least 80%, at least 85%, at least 90%, at least 95%, at least 98%, or at least 99%, amino acid sequence identity to the amino acid sequences depicted in FIG. 5A-FIG. 5S (SEQ ID NOs:7-25).

For example, in some cases, multi-FP GECIs (e.g., two-FP GECIs, three-FP GECIs, four-FP GECIs) may find use in combination with variant light-responsive polypeptides as tools for the effective mapping of functional connection between brain regions. Multi-FP GECIs that find use in the present disclosure include, but are not limited to, TN-XXL (SEQ ID NO:26), Yellow Cameleons (e.g., YC3.6 (SEQ ID NO:27)), D3CPVenus (SEQ ID NO:28), and the like.

Multi-FP GECIs that are suitable for use comprise an amino acid sequence having at least 75%, at least 80%, at least 85%, at least 90%, at least 95%, at least 98%, or at least 99%, amino acid sequence identity to the amino acid sequences depicted in FIG. 6 (SEQ ID NOs:26-28).

Host Cells

The present disclosure provides genetically modified host cells (e.g., isolated genetically modified host cells; in vitro genetically modified host cells; in vivo genetically modified host cells) that are genetically modified with a nucleic acid of the present disclosure or a recombinant expression vector of the present disclosure. In some cases, a subject isolated genetically modified host cell can produce a variant light-responsive polypeptide of the present disclosure. In some cases, a genetically modified host cell of the present disclosure produces a variant light-responsive polypeptide of the present disclosure, such that the variant light-responsive polypeptide is present in the cell membrane.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. In some cases, the mammalian cell is a neuron, e.g., a non-immortalized (primary) neuron. In other cases, the mammalian cell is an immortalized cell line. In some cases, the cell is a human primary cell. In some cases, the cell is a human neuron. In some cases, the cell is a cardiac cell. In some cases, the cell is a stem cell (e.g., a neural stem cell; a hematopoietic stem cell; a pluripotent stem cell; an embryonic stem cell).

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

Suitable yeast cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like. Yeast cells can be used to produce a variant light-responsive polypeptide of the present disclosure.

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella* disenteriae. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. Prokaryotic cells can be used to propagate a nucleic acid of the present disclosure.

In some cases, a genetically modified mammalian host cell of the present disclosure is genetically modified with a nucleic acid (or recombinant expression vector) comprising a nucleotide sequence encoding a variant light-responsive polypeptide of the present disclosure; and is also genetically modified with a nucleic acid (or recombinant expression vector) comprising a nucleotide sequence encoding a GECI, where suitable GECIs are described above.

In some cases, a genetically modified mammalian host cell of the present disclosure is genetically modified with a nucleic acid (or recombinant expression vector) comprising a nucleotide sequence encoding a variant light-responsive polypeptide of the present disclosure; and is also genetically modified with a nucleic acid (or recombinant expression vector) comprising a nucleotide sequence encoding a second light-responsive polypeptide. In some cases, the second light-responsive polypeptide is a depolarizing light-responsive polypeptide. In some cases, the second light-responsive polypeptide is a depolarizing light-responsive polypeptide that is activated in response to light of a wavelength that is different from the wavelength of light that activates a variant light-responsive polypeptide of the present disclosure. In some cases, the second light-responsive polypeptide is a hyperpolarizing light-responsive polypeptide. Suitable second light-responsive polypeptides are described hereinbelow.

Methods of Modulating the Activity of a Cell

The present disclosure provides methods for optogenetic modulation of action potentials in target cells. The subject methods generally involve introducing a variant light-responsive polypeptide of the present disclosure into a target cell and illuminating the target cell with light of an activating wavelength. Illumination of the target cell with light of an activating wavelength causes the light-activated channel protein to allow one or more cations to pass through the plasma membrane of the target cell. The passage of the cations through the plasma membrane of the target cell has a desired effect, such as, e.g., modulating the membrane potential of the plasma membrane. In some cases, the passage of the cations species through the plasma membrane may be used to modulate one or more neurological responses or processes in a patient, and may therefore by used to treat a disease or condition in the patient. In some cases, the subject methods involve treating a patient for a condition, such as a neurological condition, using the systems and devices provided herein. The subject methods are now described in greater detail below.

In some cases, a method of the present disclosure for modulating the activity of a target cell comprises introducing into the target cell a variant light-responsive polypeptide of the present disclosure, or introducing into a target cell a nucleic acid (or recombinant expression vector) comprising a nucleotide sequence encoding a variant light-responsive polypeptide of the present disclosure, thereby generating a modified target cell that comprises the variant light-responsive polypeptide in its plasma membrane; and exposing the modified target cell to light of a wavelength (e.g., red light) that activates the variant light-responsive polypeptide. The modified target cell is exposed to light having a wavelength in a range of from 600 nm to 700 nm, e.g., from 600 nm to 625 nm, from 625 nm to 650 nm, from 650 nm to 675 nm, or from 675 nm to 700 nm. In some cases, the modified target cell is exposed to light having a wavelength of from 625 nm to 650 nm. In some cases, the modified target cell is exposed to light having a wavelength of 630 nm.

In some cases, a method of the present disclosure for modulating the activity of a target cell comprises introducing into the target cell a variant light-responsive polypeptide of the present disclosure, thereby generating a modified target cell that comprises the variant light-responsive polypeptide in its plasma membrane; and exposing the modified target cell to light of a wavelength (e.g., light having a wavelength in a range of from 600 nm to 700 nm; e.g., light having a wavelength of from 625 nm to 650 nm) that activates the variant light-responsive polypeptide.

In some cases, a method of the present disclosure for modulating the activity of a target cell comprises introducing into a target cell a nucleic acid comprising a nucleotide sequence encoding a variant light-responsive polypeptide of the present disclosure, thereby generating a modified target cell that comprises the variant light-responsive polypeptide in its plasma membrane; and exposing the modified target cell to light of a wavelength (e.g., light having a wavelength in a range of from 600 nm to 700 nm; e.g., light having a wavelength of from 625 nm to 650 nm) that activates the variant light-responsive polypeptide. In some cases, the target cell is a neuron, and the nucleotide sequence is operably linked to a neuron-specific promoter.

In some cases, a method of the present disclosure for modulating the activity of a target cell comprises introducing into a target cell a recombinant expression vector comprising a nucleotide sequence encoding a variant light-responsive polypeptide of the present disclosure, thereby generating a modified target cell that comprises the variant light-responsive polypeptide in its plasma membrane; and exposing the modified target cell to light of a wavelength (e.g., light having a wavelength in a range of from 600 nm to 700 nm; e.g., light having a wavelength of from 625 nm to 650 nm) that activates the variant light-responsive polypeptide. In some cases, the target cell is a neuron, and the nucleotide sequence is operably linked to a neuron-specific promoter.

In some cases, a target cell is an in vivo cell, e.g., a cell present in a multicellular organism, e.g., a mammal. Mammals include, e.g., humans; non-human primates; rodents, e.g., rats, mice; lagomorphs, e.g., rabbits; ungulates, e.g., caprines, equines, ovines, bovines, etc.; cats; dogs; etc. In some cases, the mammal is a human. In some cases, the mammal is a non-human primate. In some cases, the mammal is a rodent.

Where the target cell is an in vivo cell, e.g., a cell present in an individual, e.g., a mammal, a recombinant expression vector (e.g., recombinant viral vector) comprising a nucleotide sequence encoding a variant light-responsive polypeptide of the present disclosure can be delivered by administering the recombinant expression vector to the individual. Administering the recombinant expression vector can be carried out by injecting a composition comprising the recombinant expression vector into the individual. For example, the recombinant expression vector can be injected at or near (e.g., within about 5 cm, within about 4 cm, within about 3 cm, within about 2 cm, within about 1 cm, or within about 0.5 cm) of the target cell or a target tissue comprising the target cell. In some cases, administering the recombinant expression vector can be carried out using a device or system, as described below, comprising a container that includes a composition comprising the recombinant expression vector. The container can be a syringe. The container can be totally or partially implanted within the individual. The targeted tissue structure may be genetically modified with a nucleic acid comprising a nucleotide sequence encoding a variant light-responsive polypeptide of the present disclosure such as by such as by viral mediated gene delivery, electroporation, ultrasound, hydrodynamic delivery, or introduction of naked DNA by direct injection or as complemented by additional facilitators such as cationic lipids or polymers.

In some cases, a nucleic acid comprising a nucleotide sequence encoding a variant light-responsive polypeptide of the present disclosure is introduced into the genome of a target cell. For example, in some cases, a nucleic acid comprising a nucleotide sequence encoding a variant light-responsive polypeptide of the present disclosure is introduced into the genome of a target cell using a CRISPR/Cas9 system. For example, a donor polynucleotide comprising a nucleotide sequence encoding a variant light-responsive polypeptide of the present disclosure is used in combination with a Cas9 polypeptide and a guide RNA to effect introduction of the nucleotide sequence encoding the variant light-responsive polypeptide into the genome of a target cell. The donor polynucleotide could include, e.g., an open reading frame (ORF) of a target gene in the target cell and a nucleotide sequence encoding a variant light-responsive polypeptide of the present disclosure, where the ORF and the nucleotide sequence encoding the variant light-responsive polypeptide are separated by an internal ribosome entry site or a nucleotide sequence encoding a 2A peptide; and the guide RNA could include, e.g., a nucleotide sequence that hybridizes to the 3' end of a promoter sequence that is operably linked to the ORF in the genome of the target cell. In some cases, the donor polynucleotide could include, e.g., sequence homologous to a non-coding region in a genome of a target cell, such a nucleic acid comprising a nucleotide sequence encoding a variant light-responsive polypeptide of the present disclosure in operable linkage with a neuron-specific promoter is introduced into a target cell (e.g., neuron) without affecting any endogenous gene expression.

Target cells are generally cells that carry or transmit electrical impulses, such as nerve cells. Target cells include neurons, cardiac cells, and stem cells. In some case, a target cell is a neuron. In some case, a target cell is a sensory neuron, a motor neuron, or an interneuron. Target cells can include cells of the central nervous system and/or cells of the peripheral nervous system. Target cells can be present in a target tissue. In some cases, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord. In some cases, a target tissue may be a portion of an individual cell, such as specific axon of a nerve cell.

Modulating Membrane Potentials in Target Cells

The present disclosure provides a method for modulating the activity of a target cell (e.g., a target mammalian cell), e.g., by modulating the membrane potential in the target cell. In some cases, a nucleic acid encoding a variant light-responsive polypeptide of the present disclosure is introduced into a target cell such that the target cell expresses the variant light-responsive polypeptide, e.g., where the variant light-responsive polypeptide is expressed and is present in the plasma membrane of the target cell. The target cell is then illuminated with light of an activating wavelength using a light-generating device. Illumination of the variant light-responsive polypeptide results in the movement of one or more cations through the plasma membrane of the cell in response to light. In some cases, light activation of a variant light-responsive polypeptide of the present disclosure results in depolarization of a cell expressing the variant light-responsive polypeptide. In certain embodiments, the activation of a variant light-responsive polypeptide results in depolarization of a nerve cell membrane and triggering of action potentials. In some cases, light activation of a variant light-responsive polypeptide of the present disclosure results in activation of an endogenous voltage-gated transporter such as a sodium channel or a calcium channel, where activation of the endogenous voltage-gated transporter evokes an action potential(s). In some cases, light activation of a variant light-responsive polypeptide of the present disclosure results in activation of an endogenous voltage-gated sodium channel, where activation of the endogenous voltage-gated sodium channel evokes an action potential(s). In some cases, light activation of a variant light-responsive polypeptide of the present disclosure results in activation of an endogenous voltage-gated calcium channel, where activation of the endogenous voltage-gated calcium channel evokes an action potential(s). In some embodiments, a method of the present disclosure for modulating the activity of a target cell involves use of a system or device of the present disclosure.

Specific Increase of Activity Along an Axonal Projection

In some embodiments, the subject methods involve activating and/or increasing activity along a portion of a nerve cell (e.g., along an axon of a nerve cell, or at the termination of an axonal projection of a nerve cell). In some embodiments, the subject methods involve activating and/or increasing activity along a portion of a nerve cell (e.g., along an axon of a nerve cell, or at the termination of an axonal projection of a nerve cell) using the subject systems and devices. In some case, a method of the present disclosure involves introducing into a nerve cell a variant light-activated polypeptide of the present disclosure. A nucleic acid (or recombinant expression vector) encoding a variant light-activated polypeptide of the present disclosure is introduced into a the nerve cell, and the variant light-activated polypeptide is expressed by the nerve cell and inserted into the plasma membrane of the nerve cell.

Next, a light-generating device is positioned such that a target portion of the nerve cell (e.g., the axon, or a portion of the axon of the nerve cell) is illuminated with light of an activating wavelength when the light-generating device is activated. Next, the light-generating device is activated to deliver light to the desired nerve cell or portion thereof to cause the light-activated polypeptide to allow cations to flow through the plasma membrane of the nerve cell.

Depolarization of the plasma membrane of the nerve cell triggers action potentials. Accordingly, the subject methods may be used to trigger and/or increase action potentials in a particular nerve cell or in a portion thereof (e.g., an axon or a portion thereof) by delivering light of an activating wavelength to the nerve cell or to a specific portion of the nerve cell. Importantly, action potentials may still propagate and behave as normal through other portions of the nerve cell or axon that are not illuminated with light of a wavelength that activates the variant light-activated polypeptide of the present disclosure. In this way, specificity is achieved in target cells or specific portions thereof.

Target Cells and Tissues

As summarized above, aspects of the present disclosure include delivering a nucleic acid or a recombinant expression vector comprising a nucleotide sequence encoding a variant light-activated polypeptide of the present disclosure to a target cell. Target cells are generally cells that carry or transmit electrical impulses, such as nerve cells. In some case, a target cell is a sensory neuron, a motor neuron, or an interneuron. Target cells can include cells of the central nervous system and/or cells of the peripheral nervous system. Target cells can be present in a target tissue. In some cases, a target tissue may include a plurality of nerve fibers, a nerve, a nerve cell ganglion, a neuromuscular junction, a tissue that is innervated by nerves, including but not limited to muscle, skin, or endocrine tissue, or an anatomical region, such as a portion or sub-portion of the brain or spinal cord.

In some cases, a target tissue may be a portion of an individual cell, such as specific axon of a nerve cell.

Once the subject polynucleotides have been delivered to a target cell or tissue, the polynucleotides enter the target cells and are expressed. In some embodiments, the subject polynucleotides may contain tissue-specific promoters so that expression only occurs in target cells wherein the tissue-specific promoter is active. In this way, if a subject polynucleotide is delivered to cells other than a target cell, the polynucleotide will not be expressed in the non-target cells because the tissue-specific promoter will be inactive in those cells. In some embodiments, a subject polynucleotide may contain an inducible promoter, such that expression of the polynucleotide only takes place when an exogenously administered drug is present is a sufficient concentration within the cell to activate the promoter.

Additional Polypeptides

In some cases, a method of the present disclosure for modulating the activity of a target cell comprises introducing into a target cell a variant light-responsive polypeptide of the present disclosure, or introducing into a target cell a nucleic acid (or recombinant expression vector) comprising a nucleotide sequence encoding a variant light-responsive polypeptide of the present disclosure, thereby generating a modified target cell that expresses the variant light-responsive polypeptide in its cell membrane; and exposing the modified target cell to light of a wavelength (e.g., light having a wavelength in a range of from 600 nm to 700 nm; e.g., light having a wavelength of from 625 nm to 650 nm) that activates the variant light-responsive polypeptide, where the modified target cell expresses an additional heterologous polypeptide, such as a GECI, a second light-responsive polypeptide, and the like.

GECI

In some cases, a method of the present disclosure for modulating the activity of a target cell comprises introducing into a target cell a variant light-responsive polypeptide of the present disclosure, or introducing into a target cell a nucleic acid (or recombinant expression vector) comprising a nucleotide sequence encoding a variant light-responsive polypeptide of the present disclosure, thereby generating a modified target cell that expresses the variant light-responsive polypeptide in its cell membrane; and exposing the modified target cell to light of a wavelength (e.g., light having a wavelength in a range of from 600 nm to 700 nm; e.g., light having a wavelength of from 625 nm to 650 nm) that activates the variant light-responsive polypeptide, where the modified target cell expresses a GECI. Where the modified target cell expresses a GECI, the method can comprise detecting the level of intracellular calcium in the modified target cell after light activation of the light-responsive polypeptide present in the cell membrane of the modified target cell.

A GECI comprises a fluorescent protein, a calcium-binding domain (e.g., calmodulin, troponin C, and the like), and a domain that binds the calcium-binding domain (e.g., the M13 domain of the myosin light chain kinase, which binds calmodulin). Examples of GECI include Pericams, Cameleons, GCaMP, TN-XXL, and Twitch.

Fluorescent polypeptides that are suitable for use in a GECI include, but are not limited to, green fluorescent protein (GFP), blue fluorescent variant of GFP (BFP), cyan fluorescent variant of GFP(CFP), yellow fluorescent variant of GFP (YFP), enhanced GFP (EGFP), enhanced CFP (ECFP), enhanced YFP (EYFP), Venus, GFPS65T, Emerald, Topaz, GFPuv, destabilized EGFP (dEGFP), destabilized ECFP (dECFP), destabilized EYFP (dEYFP), HcRed, t-HcRed, DsRed, DsRed2, mCherry, t-dimer2, t-dimer2(12), mRFP1, mEos, pocilloporin, Renilla GFP, Monster GFP, paGFP, Kaede protein or a Phycobiliprotein, or a biologically active variant or fragment of any one thereof.

GECIs comprise a calcium-binding domain such as calmodulin or troponin C, fused to one or more (e.g., one, two, three, four, or more) fluorescent proteins (FPs). In single-FP GECIs, upon calcium binding, the fluorescence intensity of a circularly permutated FP (cpFP) may be modulated by calcium binding-dependent changes in the chromophore environment. In multiple-FP GECIs (e.g., two-FP GECIs, three-FP GECIs, four-FP GECIs), calcium binding modulates Forster resonance energy transfer (FRET) between FPs.

For example, in some cases, single-FP GECIs may find use in combination with variant light-responsive polypeptides as tools for the effective mapping of functional connection between brain regions. Single-FP GECIs that find use in the present disclosure may be a fusion product of a fluorescent protein, calmodulin and an M13 peptide sequence (e.g., GFP calmodulin-M13 GECI (GCaMP)), including, but are not limited to, GCaMPK (SEQ ID NO:7), GCaMP2 (SEQ ID NO:8), GCaMP2.1 (SEQ ID NO:9), GCaMP2.2a (SEQ ID NO:10), GCaMP2.2b (SEQ ID NO:11), GCaMP2.3 (SEQ ID NO:12), GCaMP2.4 (SEQ ID NO:13), GCaMP3 (SEQ ID NO:14), GCaMP5g (SEQ ID NO:15), GCaMP6m (SEQ ID NO:16), GCaMP6s (SEQ ID NO:17), GCaMP6f (SEQ ID NO:18), and the like. Other single-FP GECIs that find use in the present disclosure include genetically encoded calcium indicators for optical imaging (GECOs) such as, the green fluorescing indicators G-GECO1 (SEQ ID NO:23), G-GECO1.1 (SEQ ID NO:24) and G-GECO1.2 (SEQ ID NO:25), the red fluorescing indicator R-GECO1 (SEQ ID NO:21), the blue fluorescing indicator B-GECO1 (SEQ ID NO:22), the emission ratiometric indicator GEM-GECO1 (SEQ ID NO:19), and the excitation ratiometric GEX-GECO1 (SEQ ID NO:20), and the like.

Single-FP GECIs that are suitable for use include, but are not limited to those that comprise an amino acid sequence having at least 75%, at least 80%, at least 85%, at least 90%, at least 95%, at least 98%, or at least 99%, amino acid sequence identity to the amino acid sequences depicted in FIG. 5A-FIG. 5S (SEQ ID NOs:7-25).

For example, in some cases, multi-FP GECIs (e.g., two-FP GECIs, three-FP GECIs, four-FP GECIs) may find use in combination with variant light-responsive polypeptides as tools for the effective mapping of functional connection between brain regions. Multi-FP GECIs that find use in the present disclosure include, but are not limited to, TN-XXL (SEQ ID NO:26), Yellow Cameleons (e.g., YC3.6 (SEQ ID NO:27)), D3CPVenus (SEQ ID NO:28), and the like.

Multi-FP GECIs that are suitable for use comprise an amino acid sequence having at least 75%, at least 80%, at least 85%, at least 90%, at least 95%, at least 98%, or at least 99%, amino acid sequence identity to the amino acid sequences depicted in FIG. 6 (SEQ ID NOs:26-28).

Light-Responsive Polypeptides

In some cases, a method of the present disclosure for modulating the activity of a target cell comprises introducing into a target cell a variant light-responsive polypeptide of the present disclosure, or introducing into a target cell a nucleic acid (or recombinant expression vector) comprising a nucleotide sequence encoding a variant light-responsive polypeptide of the present disclosure, thereby generating a modified target cell that expresses the variant light-responsive polypeptide in its cell membrane; and exposing the modified target cell to light of a wavelength (e.g., light having a wavelength in a range of from 600 nm to 700 nm; e.g., light having a wavelength of from 625 nm to 650 nm) that activates the variant light-responsive polypeptide, where the modified target cell is also genetically modified to express a second light-responsive polypeptide. In some cases, the second light-responsive polypeptide is a depolarizing light-responsive polypeptide. In some cases, the second light-responsive polypeptide is a depolarizing light-responsive polypeptide that is activated by light of a wavelength that is different from the wavelength of light used to activate the variant light-responsive polypeptide of the present disclosure, e.g., where the second light-responsive polypeptide is a depolarizing light-responsive polypeptide that is activated by blue light, by yellow light, by green light, by orange light, etc. In some cases, the second light-responsive polypeptide is a hyperpolarizing light-responsive polypeptide. In some cases, the second light-responsive polypeptide is a hyperpolarizing light-responsive polypeptide that is activated by light of a wavelength that is different from the wavelength of light used to activate the variant light-responsive polypeptide of the present disclosure, e.g., where the second light-responsive polypeptide is a hyperpolarizing light-responsive polypeptide that is activated by blue light, by yellow light, by green light, by orange light, etc.

In some embodiments, a depolarizing light-responsive polypeptide is a channelrhodopsin (ChR1-NCBI Gene ID: 5724518, ChR2-NCBI Gene ID: 5727376) derived from *Chlamydomonas reinhardtii*, wherein the polypeptide is capable of transporting cations across a cell membrane when the cell is illuminated with light. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some embodiments, activation of the light-responsive cation channel derived from *Chlamydomonas reinhardtii* with light pulses having a temporal frequency of about 100 Hz can cause depolarization of the excitable cells, e.g., neurons, expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can comprise one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane. In some cases, a suitable channelrhodopsin is a ChR1 polypeptide that comprises an amino acid sequence having at least 75%, at least 80%, at least 85%, at least 90%, at least 95%, at least 98%, or at least 99%, or 100%, amino acid sequence identity to the amino acid sequence depicted in FIG. 7A (SEQ ID NO:29). In some cases, a suitable channelrhodopsin is a ChR2 polypeptide that comprises an amino acid sequence having at least 75%, at least 80%, at least 85%, at least 90%, or 100%, at least 95%, at least 98%, or at least 99%, amino acid sequence identity to the amino acid sequence depicted in FIG. 7B (SEQ ID NO:30).

In other embodiments, the light-responsive polypeptide is a step function opsin (SFO) protein or a stabilized step function opsin (SSFO) protein that can have specific amino acid substitutions at key positions in the retinal binding pocket of the amino acid sequence of ChR2. Further disclosure related to SFO or SSFO proteins can be found in International Patent Application Publication No. WO 2010/056970, the disclosure of which is hereby incorporated by reference in its entirety. In some cases, a suitable ChR2 SFO comprises an amino acid sequence having at least 75%, at least 80%, at least 85%, at least 90%, at least 95%, at least 98%, or at least 99%, or 100%, amino acid sequence identity to the amino acid sequence depicted in FIG. 7C (SEQ ID NO:31). In some cases, a suitable ChR2 SSFO comprises an amino acid sequence having at least 75%, at least 80%, at least 85%, at least 90%, at least 95%, at least 98%, or at least 99%, or 100%, amino acid sequence identity to the amino acid sequence depicted in FIG. 7D (SEQ ID NO:32).

In some embodiments, a suitable light-responsive polypeptide is a cation channel derived from *Volvox carteri* (VChR1-NCBI Gene ID: 9619570) and is activated by illumination with light of a wavelength of from about 500 nm to about 600 nm, e.g., from about 525 nm to about 550 nm, e.g., 545 nm. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can comprise one or more conservative amino acid substitutions and/or one or more non-conservative amino acid substitutions. The light-responsive ion channel protein containing substitutions, deletions, and/or insertions introduced into the native amino acid sequence suitably retains the ability to transport ions across the plasma membrane of a excitable cell in response to light. In some cases, a suitable cation channel derived from *Volvox carteri* is a VChR1 polypeptide that comprises an amino acid sequence having at least 75%, at least 80%, at least 85%, at least 90%, at least 95%, at least 98%, or at least 99%, or 100%, amino acid sequence identity to the amino acid sequence depicted in FIG. 7E (SEQ ID NO:33).

In other embodiments, the light-responsive polypeptide is a SFO or an SSFO based on VChR1. In some embodiments an SFO or SSFO protein is capable of mediating a depolarizing current in the cell when the cell is illuminated with blue light. In some embodiments, the light has a wavelength of about 560 nm. Additionally, in some embodiments the light is delivered as a single pulse of light or as spaced pulses of light due to the prolonged stability of SFO and SSFO photocurrents. In some embodiments, activation of the SFO or SSFO protein with single pulses or spaced pulses of light can cause depolarization of an excitable cell, e.g., neuron, expressing the SFO or SSFO protein. In some embodiments, each of the disclosed step function opsin and stabilized step function opsin proteins can have specific properties and characteristics for use in depolarizing the membrane of an excitable cell in response to light. In some cases, a suitable VChR1 SFO comprises an amino acid sequence having at least 75%, at least 80%, at least 85%, at least 90%, at least 95%, at least 98%, or at least 99%, or 100%, amino acid sequence identity to the amino acid sequence depicted in FIG. 7F (SEQ ID NO:34). In some cases, a suitable VChR1 SSFO comprises an amino acid sequence having at least 75%, at least 80%, at least 85%, at least 90%, at least 95%, at least 98%, or at least 99%, or 100%, amino acid sequence identity to the amino acid sequence depicted in FIG. 7G (SEQ ID NO:35).

In other embodiments, the light-responsive cation channel protein is a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein further comprises a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein further comprises a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1.

In some embodiments, the C1V1 protein mediates a depolarizing current in the cell when the cell is illuminated with green light. In some embodiments, the light has a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some aspects, a suitable light-responsive polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, suitable light-responsive proteins include C1V1 chimeric light-responsive proteins that can have specific amino acid substitutions at key positions throughout the retinal binding pocket of the VChR1 portion of the chimeric polypeptide. In some cases, a suitable C1V1 chimeric light-responsive protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7H (SEQ ID NO:36).

In other embodiments, the light-responsive cation channel protein is a C1C2 chimeric protein derived from the ChR1 and the ChR2 proteins from *Chlamydomonas reinhardti*, wherein the protein is responsive to light and is capable of mediating a depolarizing current in the cell when the cell is illuminated with light. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein comprises one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane. In some cases, a suitable C1C2 chimeric light-responsive protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7I (SEQ ID NO:37).

In some aspects, a depolarizing light-responsive polypeptide is a SdChR polypeptide (Genbank Accession No.: AHH02138) derived from *Scherffelia dubia*, wherein the SdChR polypeptide is capable of transporting cations across a cell membrane when the cell is illuminated with light. The light used to activate the SdChR polypeptide can have a wavelength between about 440 and about 490 nm or can have a wavelength of about 460 nm. The SdChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the SdChR protein to regulate the polarization state of the plasma membrane of the cell. In some instances, the SdChR protein comprises one or more conservative amino acid substitutions and/or one or more non-conservative amino acid substitutions. The SdChR protein containing substitutions, deletions, and/or insertions introduced into the native amino acid sequence suitably retains the ability to transport cations across a cell membrane. In some cases, a suitable SdChR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7J (SEQ ID NO:38).

In some aspects, a depolarizing light-responsive polypeptide can be, e.g. CnChR2 (Genbank Accession No.: AHH02139), derived from *Chlamydomonas noctigama*, wherein the CnChR2 polypeptide is capable of transporting cations across a cell membrane when the cell is illuminated with light. The light used to activate the CnChR2 polypeptide can have a wavelength between about 560 and about 630 nm or can have a wavelength of about 600 nm. The CnChR2 protein can additionally comprise substitutions, deletions, and/or insertions introduced into a native amino acid sequence to increase or decrease sensitivity to light, increase or decrease sensitivity to particular wavelengths of light, and/or increase or decrease the ability of the CnChR2 protein to regulate the polarization state of the plasma membrane of the cell. In some cases, the CnChR2 protein comprises one or more conservative amino acid substitutions and/or one or more non-conservative amino acid substitutions. The CnChR2 protein containing substitutions, deletions, and/or insertions introduced into the native amino acid sequence suitably retains the ability to transport cations across a cell membrane. In some cases, a suitable CnChR2 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7K (SEQ ID NO:39).

In other embodiments, the light-responsive cation channel protein is a CsChrimson chimeric protein derived from a CsChR (Genbank Accession No.: AHI-I02144) protein of Chloromonas subdivisa and CnChR1 protein from *Chlamydomonas noctigama*, wherein the N terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. The CsChrimson protein can additionally comprise substitutions, deletions, and/or insertions introduced into a native amino acid sequence to increase or decrease sensitivity to light, increase or decrease sensitivity to particular wavelengths of light, and/or increase or decrease the ability of the CsChrimson protein to regulate the polarization state of the plasma membrane of the cell. Additionally, the CsChrimson protein can comprise one or more conservative amino acid substitutions and/or one or more non-conservative amino acid substitutions. A CsChrimson protein containing substitutions, deletions, and/or insertions introduced into the native amino acid sequence suitably retains the ability to transport cations across a cell membrane. In some cases, a suitable CsChrimson protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7L (SEQ ID NO:40).

In some aspects, a depolarizing light-responsive polypeptide can be, e.g. ShChR1 (Genbank Accession No.: AHH02106), derived from *Stigeoclonium helveticum*, wherein the ShChR1 polypeptide is capable of transporting cations across a cell membrane when the cell is illuminated with light. The light used to activate the ShChR1 protein derived from *Stigeoclonium helveticum* can have a wavelength between about 480 and about 510 nm or can have a wavelength of about 500 nm. The ShChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the ShChR1 protein to regulate the polarization state of the plasma membrane of the cell. Additionally, the ShChR1 protein can comprise one or more conservative amino acid substitutions and/or one or more non-conservative amino acid substitutions. A ShChR1 protein containing substitutions, deletions, and/or insertions introduced into the native amino acid sequence suitably retains the ability to transport cations across a cell membrane. In some cases, a suitable ShChR1 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7M (SEQ ID NO:41).

In some embodiments, a suitable hyperpolarizing light-responsive polypeptide is an Archaerhodopsin (Arch—Genbank Accession No.: ADB03111) proton pump (e.g., a proton pump derived from *Halorubrum sodomense*) that can transport one or more protons across the plasma membrane of a cell when the cell is illuminated with light. The Arch protein can additionally have substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can comprise one or more conservative amino acid substitutions and/or one or more non-conservative amino acid substitutions. An Arch protein containing substitutions, deletions, and/or insertions introduced into the native amino acid sequence suitably retains the ability to transport ions across the plasma membrane of a target cell in response to light. In some cases, a suitable Arch protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7N (SEQ ID NO:42).

In some embodiments, a suitable light-activated protein is an Archaerhodopsin (ArchT-Genbank Accession No.: ABT17417) proton pump (e.g., a proton pump derived from *Halorubrum* sp. TP009) that can transport one or more protons across the plasma membrane of a cell when the cell is illuminated with light. The light can have a wavelength between about 530 and about 595 nm or can have a wavelength of about 560 nm. The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a target cell. Additionally, the ArchT protein can comprise one or more conservative amino acid substitutions and/or one or more non-conservative amino acid substitutions. The ArchT protein containing substitutions, deletions, and/or insertions introduced into the native amino acid sequence suitably retains the ability to transport ions across the plasma membrane of a target cell in response to light. In some cases, a suitable ArchT protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7O (SEQ ID NO:43).

In some embodiments, the light-responsive polypeptide is responsive to blue light and is a proton pump protein derived from *Guillardia theta*, wherein the proton pump protein is capable of mediating a hyperpolarizing current in the cell when the cell is illuminated with blue light; such a protein is referred to herein as a "GtR3 protein" or a "GtR3 polypeptide". The GtR3 (NCBI Gene ID: 17301498) protein can additionally comprise substitutions, deletions, and/or insertions introduced into a native amino acid sequence to increase or decrease sensitivity to light, increase or decrease sensitivity to particular wavelengths of light, and/or increase or decrease the ability of the GtR3 protein to regulate the polarization state of the plasma membrane of the cell. Additionally, the GtR3 protein can comprise one or more conservative amino acid substitutions and/or one or more non-conservative amino acid substitutions. The GtR3 protein containing substitutions, deletions, and/or insertions introduced into the native amino acid sequence suitably retains the ability to hyperpolarize the plasma membrane of an excitable cell, e.g., neuron, in response to light. In some cases, a suitable GtR3 protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7P (SEQ ID NO:44).

In some embodiments, a light-activated protein is an *Oxyrrhis marina* (Oxy—Genbank Accession No.: ADY17806) proton pump that can transport one or more protons across the plasma membrane of a cell when the cell is illuminated with light. The light can have a wavelength between about 500 and about 560 nm or can have a wavelength of about 530 nm. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can comprise one or more conservative amino acid substitutions and/or one or more non-conservative amino acid substitutions. The Oxy protein containing substitutions, deletions, and/or insertions introduced into the native amino acid sequence suitably retains the ability to transport ions across the plasma membrane of a target cell in response to light. In some cases, a suitable Oxy protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7Q (SEQ ID NO:45).

In some embodiments, the light-responsive proton pump protein (referred to herein as "Mac protein"—NCBI Gene ID: 13287905) is responsive to light and is derived from *Leptosphaeria maculans*, wherein the Mac proton pump protein is capable of pumping protons across the membrane of a cell when the cell is illuminated with 520 nm to 560 nm light. The Mac protein can additionally comprise substitutions, deletions, and/or insertions introduced into a native amino acid sequence to increase or decrease sensitivity to light, increase or decrease sensitivity to particular wavelengths of light, and/or increase or decrease the ability of the Mac protein to regulate the polarization state of the plasma membrane of the cell. Additionally, the Mac protein can comprise one or more conservative amino acid substitutions and/or one or more non-conservative amino acid substitutions. A Mac protein containing substitutions, deletions, and/or insertions introduced into the native amino acid sequence suitably retains the ability to pump protons across the plasma membrane of an excitable cell, e.g., neuron, in response to light. In some cases, a suitable Mac protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7R (SEQ ID NO:46).

In some cases, a suitable light-responsive chloride pump protein is derived from *Natronomonas pharaonis*; such a protein is referred to herein as an "NpHR protein" or an "NpHR polypeptide." In some embodiments, the NpHR (NCBI Gene ID: 3702828) protein can be responsive to amber light as well as red light and can mediate a hyperpolarizing current in the excitable cell, e.g., the neuron, when the NpHR protein is illuminated with amber or red light. The wavelength of light that can activate the NpHR protein can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the NpHR protein can hyperpolarize a neural membrane for at least about 90 minutes when exposed to a continuous pulse of light. Additionally, the NpHR protein can comprise substitutions, deletions, and/or insertions introduced into a native amino acid sequence to increase or decrease sensitivity to light, increase or decrease sensitivity to particular wavelengths of light, and/or increase or decrease the ability of the NpHR protein to regulate the polarization state of the plasma membrane of the cell. In some embodiments, the NpHR protein comprises one or more conservative amino acid substitutions. In some embodiments, the NpHR protein comprises one or more non-conservative amino acid substitutions. A NpHR protein containing substitutions, deletions, and/or insertions introduced into the native amino acid sequence suitably retains the ability to hyperpolarize the plasma membrane of an excitable cell in response to light. In some cases, a suitable NpHR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7S (SEQ ID NO:47).

Further disclosure related to light-responsive chloride pump proteins can be found in U.S. Patent Application Publication Nos: 2009/0093403 and 2010/0145418 as well as in International Patent Application NO: PCT/US2011/028893, the disclosures of each of which are hereby incorporated by reference in their entireties.

In some embodiments, a suitable light-responsive ion channel protein is, e.g., a DsChR protein (Genbank Accession No.: AEY68833) derived from *Dunaliella salina*, wherein the ion channel protein is capable of mediating a hyperpolarizing current in the cell when the cell is illuminated with light. The light can have a wavelength between about 470 nm and about 510 nm or can have a wavelength of about 490 nm. The DsChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the DsChR protein to regulate the polarization state of the plasma membrane of the cell. Additionally, the DsChR protein can comprise one or more conservative amino acid substitutions and/or one or more non-conservative amino acid substitutions. A DsChR protein containing substitutions, deletions, and/or insertions introduced into the native amino acid sequence suitably retains the ability to transport ions across the plasma membrane of an excitable cell, e.g., a neuron, in response to light. In some cases, a suitable DsChR protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7T (SEQ ID NO:48).

In some embodiments, the light-responsive protein is a chimeric protein comprising Arch-TS-p2A-ASIC 2a-TS-EYFP-ER-2 (Champ). A Champ protein of the present disclosure comprises an Arch domain and an Acid-sensing ion channel (ASIC)-2a domain. Light activation of Champ activates a proton pump (Arch domain) that activates the ASIC-2a proton-activated cation channel (ASIC-2a domain). In some cases, a suitable Champ protein comprises an amino acid sequence having at least 75%, at least 80%, at least 85%, at least 90%, at least 95%, at least 98%, or at least 99%, or 100%, amino acid sequence identity to the amino acid sequence depicted in FIG. 7U (SEQ ID NO:49).

In some embodiments, a hyperpolarizing light-responsive ion channel is based on a depolarizing light-responsive ion channel, as described in, e.g., PCT App. No. PCT/US2015/23087, which is incorporated herein by reference. In some embodiments, a light-responsive anion channel polypeptide is based on a C1C2 protein (Genbank Accession No.: AHA49646). In some embodiments, a suitable hyperpolarizing light-responsive polypeptide is based on the amino acid sequence of the protein ChR2 (Genbank Accession No.: AER29835). In some embodiments, a suitable hyperpolarizing light-responsive polypeptide is based on the amino acid sequence of the protein C1V1 (Genbank Accession No.: AEL28924).

Use of Indicator Dyes

In some cases, a target cell is modified such that it expresses in its cell membrane a variant light-responsive polypeptide of the present disclosure; where the modified target cell includes an indicator dye. The indicator dye can provide for detection of a change in the intracellular calcium ion concentration, a change in the intracellular sodium ion concentration, etc.

In some cases, the indicator dye is a fluorescent dye. In such cases, fluorescent dyes of interest include fluorescein, fluorescein isothiocyanate (FITC), rhodamine, tetramethylenerhodamine isothiocyanate (TRITC), sulforhodamine 101 acid chloride (Texas Red®), phycoerythrin (PE), allophycocyanin, phycoerythrin-Texas Red® (PETR), 4-methylumbelliferone, etc.

In some cases, the indicator dye is a calcium indicator dye. Suitable calcium indicator dyes include, e.g., Indo-1, Fura-2, and Fluo-3, Calcium Green®, Fluo-4, etc.

In some cases, the indicator dye is a sodium indicator dye. Suitable sodium indicator dyes include, e.g., sodium-binding benzofuran isophthalate (SBFI), Sodium Green™, CoroNa™ Green, CoroNa™ Red, etc.); and proton indicator dyes (2',7'-bis-(carboxyethyl)-5-(and-6)-carboxyfluorescein (BCECF), etc.

Methods of Inducing Memory Retrieval

The present disclosure provides a method of inducing contextual memory retrieval in a mammalian subject, the method comprising delivering light having a wavelength of from 600 nm to 700 nm to a monosynaptic prefrontal to hippocampus projection of a neuron in the mammalian subject, where the projection comprises a variant light-responsive polypeptide of the present disclosure, and where delivering light to the projection depolarizes the projection and induces contextual memory retrieval. In some cases, the prefrontal to hippocampus projection is a prefrontal to hippocampus projection. In some cases, the prefrontal to hippocampus projection is an anterior cingulate to hippocampus projection. In some cases, the projection is to pyramidal CA3/CA1 cells the hippocampus. In some cases, neurons of the anterior cingulate comprise the variant light-responsive polypeptide.

Devices

The present disclosure provides systems and devices that can be used to carry out aspects of the subject methods (methods of modulating the activity of a target cell; treatment methods). In some cases, a system of the present disclosure includes a variant light-activated polypeptide of the present disclosure, as described above, and one or more devices for delivering light of an activating wavelength to a target tissue or cell. Devices that find use in carrying out a method of the present disclosure include delivery devices that can be used to deliver a nucleic acid (or recombinant expression vector) comprising a nucleotide sequence encoding a variant light-activated polypeptide of the present disclosure to target cells and tissues; delivery devices that can be used to deliver a variant light-activated polypeptide of the present disclosure to target cells and tissues; light-generating devices that can be used to illuminate target cells that express a variant light-activated polypeptide of the present disclosure; and control devices that can be used to control the delivery of light to specific target cells or tissues. Each of these components is further described below.

Delivery Devices

Aspects of the present disclosure include delivery devices that can be used to deliver a variant light-activated polypeptide of the present disclosure, or a nucleic acid (or recombinant expression vector) comprising a nucleotide sequence encoding a variant light-activated polypeptide of the present disclosure, to a target cell. A delivery device of the present disclosure may provide regular, irregular, programmed, or clinician- or patient-activated doses of the variant light-activated polypeptide of the present disclosure, or the nucleic acid (or recombinant expression vector) comprising a nucleotide sequence encoding a variant light-activated polypeptide of the present disclosure, to one or more target cells to ensure that the target cells continue to express the variant light-activated polypeptide for a desired period of time.

The subject delivery devices may generally include various components, such as reservoirs, pumps, actuators, tubing components, needles, catheters, and any other suitable components for delivering the subject pharmaceutical compositions to a target cell or tissue of a patient. Delivery devices may also include components that facilitate computerized operation, such as a power source, a processor comprising a memory, a user input device, and/or a graphical user interface. In some embodiments, a delivery device may be completely or partially implantable within a patient. In some embodiments, a delivery device may be operated by a caregiver, wherein the device is introduced into a portion of the patient's body, e.g., into the patient's brain, and a subject pharmaceutical composition is delivered to a target tissue, e.g., a portion of the patient's brain. In some embodiments, following delivery of the pharmaceutical composition, the device may be removed. In other embodiments, the device may be kept in place for later delivery of additional pharmaceutical compositions.

Light-Generating Devices

Aspects of the present disclosure include light-generating devices that can be used to deliver light to target cells that express a variant light-activated polypeptide of the present disclosure. The terms "light-generating device", "optical applicator" and "light applicator" are used interchangeably herein. Light-generating devices in accordance with embodiments of the present disclosure can generally produce light of a variety of different wavelengths from one or more light sources on the device. In some embodiments, a light-generating device may include a light cuff or sleeve that can be placed around or near target cells expressing a variant light-activated polypeptide of the present disclosure. In some cases, a portion of the light source or the entire light source is implantable. The subject light-generating devices may be of any useful configuration for stimulating the light-activated proteins disclosed herein. In some embodiments, for example, a light-generating device (i.e., optical applicator) may comprise components that facilitate exclusive illumination of a target cell or tissue. For example, in some embodiments, a light-generating device may exclusively direct light to a target cell, a portion of a target cell, e.g., a particular axon of a nerve cell, or a specific anatomical structure, such as, e.g. a bundle of nerve fibers, a target tissue, or a portion of the spinal cord. By "exclusively direct light" is meant that the light-generating device only delivers light to the specific target structure, and does not illuminate other structures. For example, in some embodiments, a light-generating device may be configured to illuminate an axon of a nerve cell, but not to illuminate any other portion of the nerve cell. In this way, the light from the light-generating device only affects light-activated proteins in the specific target structure that is illuminated.

Aspects of the disclosure include light delivery devices (i.e., optical applicators) that include one or more optical sources that are configured to deliver light in one or more 2-dimensional and/or 3-dimensional patterns to one or more target locations, including but not limited to one or more portions (e.g., multiple layers) of a target tissue and/or anatomical structure. In certain embodiments, a light delivery device may include a plurality of light sources (e.g., a plurality of laser light sources, light-emitting diodes (LEDs), and the like), as well as any suitable number of light guides that are configured to bend or shape light in a desired manner. Examples of light delivery devices are provided in U.S. Pat. No. 8,545,543, the disclosure of which is hereby incorporated by reference in its entirety.

In some embodiments, a light-generating device (i.e., optical applicator) may not completely surround the region containing a target cell expressing a light-activated protein, but, rather, can have a U-shape. In some cases, a light-generating device can have an attachment arm that can be used to guide the light-generating device to a specific region or target structure, e.g., a specific neuronal region. The attachment arm can be removed following implantation of the light-generating device or can be left in place to fix the position of the light-generating device in proximity to the target cells of interest.

In some cases, the subject light-generating devices may comprise an inner body, the inner body having at least one means for generating light which is connected to a power source. In some embodiments, the power source can be an internal battery for powering the light-generating device. In some embodiments, an implantable light-generating device may comprise an external antenna for receiving wirelessly transmitted electromagnetic energy from an external source for powering the device. The wirelessly transmitted electromagnetic energy can be a radio wave, a microwave, or any other electromagnetic energy source that can be transmitted from an external source to power the light-generating device. In some embodiments, the light-generating device is controlled by, e.g., an integrated circuit produced using semiconductor or other processes known in the art.

In some cases, the light-generating device comprises a light emitting diode (LED). In some embodiments, the LED can generate blue and/or green light. In other embodiments, the LED can generate amber and/or yellow light. In some cases, several micro LEDs are embedded into the inner body of the light-generating device. In other cases, the light-generating device is a solid state laser diode or any other means capable of generating light. The light-generating device can generate light having a wavelength and intensity sufficient to activate a variant light-activated polypeptide of the present disclosure. In some cases, a light-generating device produces light having an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers. In some embodiments, the light-generating device produces light at a frequency of at least about 5 Hz, such as up to about 20 Hz, at least about 10 Hz, such as up to about 25 Hz, such as up to about 50 Hz, such as up to about 75 Hz, such as up to about 100 Hz.

The subject light-generating devices are generally capable of generating light having a wavelength ranging from about 350 nm, up to about 360 nm, up to about 370 nm, up to about 380 nm, up to about 390 nm, up to about 400 nm, up to about 410 nm, up to about 420 nm, up to about 430 nm, up to about 440 nm, up to about 450 nm, up to about 460 nm, up to about 470 nm, up to about 475 nm, up to about 480 nm, up to about 490 nm, up to about 500 nm, up to about 510 nm, up to about 520 nm, up to about 530 nm, up to about 540 nm, up to about 550 nm, up to about 560 nm, up to about 570 nm, up to about 580 nm, up to about 590 nm, up to about 600 nm, up to about 610 nm, up to about 620 nm, up to about 630 nm, up to about 635 nm, up to about 640 nm, up to about 650 nm, up to about 660 nm, up to about 670 nm, up to about 680 nm, up to about 690 nm, up to about 700 nm, up to about 710 nm, up to about 720 nm, up to about 730 nm, up to about 740 nm, and/or up to about 750 nm. Subject light-generating devices of the present disclosure are capable of generating light having a wavelength sufficient to activate a subject light-activated protein. Such light-generating devices are capable of generating light having a wavelength ranging from about 550 nm to about 650 nm, from about 600 nm to about 700 nm, from about 650 nm to about 750 nm.

In some embodiments, a light generating device may generate red light having a wavelength ranging from about 600 nm to about 775 nm. For example, a light generating device may generate red light having a wavelength ranging from about 600 nm to about 650 nm, from about 625 nm to about 675 nm, from about 650 nm to about 700 nm, from about 675 nm to about 725 nm, from about 700 nm to about 750 nm, from about 725 nm to about 775 nm, from about 600 nm to about 700 nm.

In some embodiments, a suitable light-generating device may include one or more optical fibers that can transmit light from a light source and deliver the light to a target structure. The optical fibers may comprise plastic or glass materials, and in some embodiments may be suitably flexible to facilitate placement of the light-generating device in locations that could not be accommodated by rigid structures. For example, in some embodiments, a light-generating device may comprise a light source that generates light, as well as one or more optical fibers that can be placed in various locations on or in the patient's body. Light from the light source can pass through the optical fiber, passing around corners and bends in the optical fiber, and emerge at the end of the optical fiber to deliver light to a target structure.

In some embodiments, the subject light-generating devices may comprise a plurality of light sources that can be used to illuminate a target tissue with different wavelengths of light. For example, in some embodiments, a light-generating device may comprise a first light source that generates light of a first wavelength, e.g., red light, and a second light source that generates light of a second wavelength, e.g., blue light. Such light-generating devices may be used to simultaneously illuminate the same target tissue with light of both wavelengths, or may alternately illuminate the target tissue with light of the first wavelength and light of the second wavelength. In some embodiments, such light generating devices may be used to deliver light from the same light source to different target tissues. For example, in some embodiments a light-generating device may deliver light of a first wavelength to a first target tissue, and may deliver light of a second wavelength to a different target tissue.

Suitable light-generating devices can comprise an implantable optical applicator which is configured to deliver light to a target area, and an operatively coupled light source which is configured to generate light of certain intensities and wavelengths.

Control Devices

Aspects of the disclosure include a controller, processor (e.g., a computer) and computer readable medium that are configured or adapted to control or operate one or more components of the subject systems. In some embodiments, a system includes a controller that is in communication with one or more components of the systems, as described herein, and is configured to control aspects of the systems and/or execute one or more operations or functions of the subject systems. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein.

In some embodiments, a system includes a user interface, such as a graphical user interface (GUI), that is adapted or configured to receive input from a user, and to execute one or more of the methods as described herein. In some embodiments, a GUI is configured to display data or information to a user.

Aspects of the present disclosure include control devices that can control, or modulate, the amount of light that is emitted from the subject light-generating devices. In some embodiments, a control device may be configured to modulate the wavelength and/or the intensity of light that is delivered to a target tissue from a light-generating device. In some embodiments, a control device may be configured to modulate the frequency and/or duration of light that is delivered to a target tissue from a light-generating device. For example, in some embodiments, a control device may be configured to deliver pulses of light from the light-generating device to a target tissue. The control device can modulate the frequency and/or duration of the light pulses such that the target tissue is illuminated with light from the light-generating device, e.g., at a regular or irregular rate, according to a user input, etc. In some embodiments, a control device can produce pulses of light from the light-generating device that have a duration ranging from about 1 millisecond or less, up to about 1 second, up to about 10 seconds, up to about 20 seconds, up to about 30 seconds, up to about 40 seconds, up to about 50 seconds, up to about 60 seconds or more. In some embodiments, a control device can produce pulses of light from the light-generating device that have a frequency of 1 pulse per millisecond, up to about 1 pulse per second, up to about 1 pulse per minute, up to about 1 pulse per 10 minutes, up to about 1 pulse per 20 minutes, up to about 1 pulse per 30 minutes.

In some embodiments, a subject control device may comprise a power source that can be mounted to a transmitting coil. In some embodiments, a battery can be connected to the power source for providing power thereto. A switch can be connected to the power source, allowing an operator (e.g., a patient or caregiver) to manually activate or deactivate the power source. In some embodiments, upon activation of the switch, the power source can provide power to the light-generating device through electromagnetic coupling between the transmitting coil on the control device and an external antenna of an implantable light-generating device (such as a light cuff or sleeve). The transmitting coil can establish an electromagnetic coupling with the external antenna of the implantable light-generating device when in proximity thereof, for supplying power to the light-generating device and for transmitting one or more control signals to the light-generating device. In some embodiments, the electromagnetic coupling between the transmitting coil of the control device and the external antenna of the implantable light-generating device can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). However, other coupling techniques may be used, such as an optical receiver, infrared, or a biomedical telemetry system (See, e.g., Kiourti, "Biomedical Telemetry: Communication between Implanted Devices and the External World, Opticon1826, (8): Spring, 2010).

Systems

A system of the present disclosure is an optical stimulation system comprising a delivery device, a light-generating device, a control device. In some cases, a subject system comprises a container comprising a nucleic acid or recombinant expression vector of the present disclosure (where the nucleic acid or recombinant expression vector comprises a nucleotide sequence encoding a variant light-responsive polypeptide of the present disclosure), an implantable optical applicator, a light source operatively coupled to the implantable optical applicator, a controller (i.e., control device), a power supply and an implantable illuminance sensor. In some cases, a subject system comprises a container comprising a variant light-responsive polypeptide of the present disclosure, an implantable optical applicator, a light source operatively coupled to the implantable optical applicator, a controller (i.e., control device), a power supply and an implantable illuminance sensor. In some cases, the implantable optical applicator is configured to deliver light to a targeted tissue structure after implantation in a location adjacent to the targeted tissue structure. The controller of a subject system causes the power supply to allow current to flow to the light source to cause an emission of photons to the implantable light actuator based at least in part upon an output signal from the implantable illuminance sensor.

In some embodiments, a system of the present disclosure comprises an implantable illuminance sensor that is positioned such that it captures at least a portion of the photons directed toward the targeted tissue structure by the implantable light applicator. The system further may comprise an implantable input sensor configured to produce an output signal that is correlated to the illuminance of the implantable optical applicator at a position of photon emission before intersection of such photons with the targeted tissue structure. The controller (i.e., control device) may be operatively coupled to the implantable input sensor, such that it may compare the output signal from both the implantable input sensor and the implantable illuminance sensor to determine whether unexpected losses are being experienced. The controller may be configured to react to a loss level that is past a predetermined threshold loss level. The controller may be configured to react by flagging the event on the loss level being past the predetermined level in a software log file maintained by the controller. The controller may be configured to stop causing the power supply to allow current to flow to the light source.

The implantable illuminance sensor and input sensor of a system of the present disclosure can be a photovoltaic cell, a photodiode, a pyroelectric sensor, a photoresistor, a photoconductor, a phototransistor, or a photogalvanic sensor.

The system may further comprise a physiologic sensor configured to produce an output signal that is correlated with a physiologic parameter believed to be variable at least in part in response to the input of light to the target tissue structure. The physiologic sensor can be, e.g., an electromyogram sensor, an electroneurogram sensor, an electroencephalogram sensor, an electrocardiogram sensor, a pressure sensor, a temperature sensor, a chemometric sensor, a motion sensor, an accelerometer, a gyro, a strain sensor, an impedance sensor, or a capacitance sensor.

The controller of a system of the present disclosure may be configured to react to an output of the physiologic sensor being past a certain predetermined threshold. The controller may be configured to react by flagging the event on the loss level being past the predetermined level in a software log file maintained by the controller. The controller may be configured to stop causing the power supply to allow current to flow to the light source.

Figure 8:
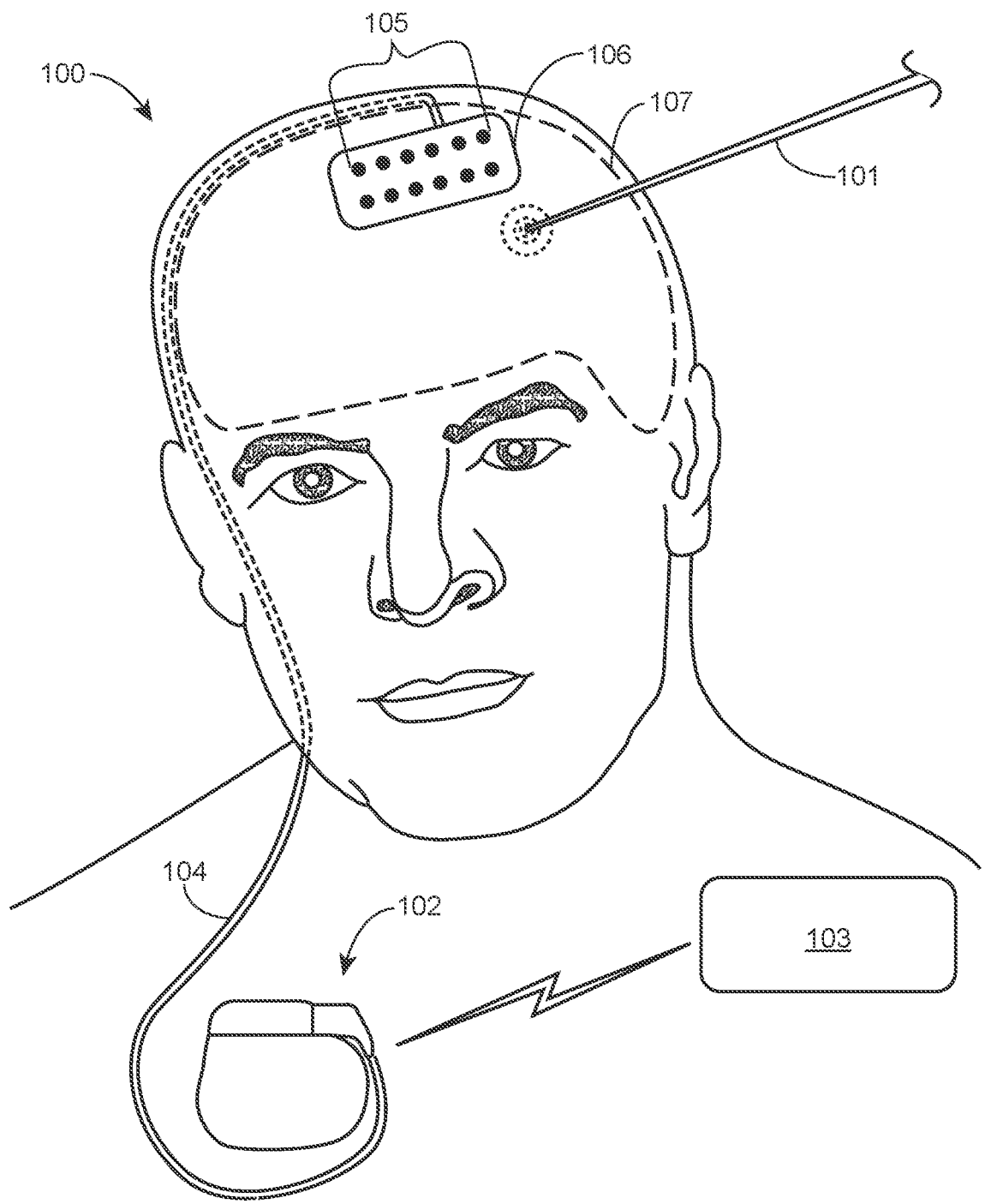
FIG. 8 provides a first example of an optical stimulation system.

Turning now to FIG. 8, a first example of an optical stimulation system 100 is depicted. The optical stimulation system 100 comprises a delivery device 101 for delivering a variant light-responsive polypeptide of the present disclosure, or a nucleic acid or recombinant expression vector comprising a nucleotide sequence encoding a variant light-responsive polypeptide of the present disclosure, to a target tissue, e.g., brain tissue 107 of a patient. Also provided are a light-generating device 102, a control device 103, and optical fibers 104 for conveying light generated by the light-generating device 102 to a light array 105 positioned on a light cuff 106.

Figure 9:
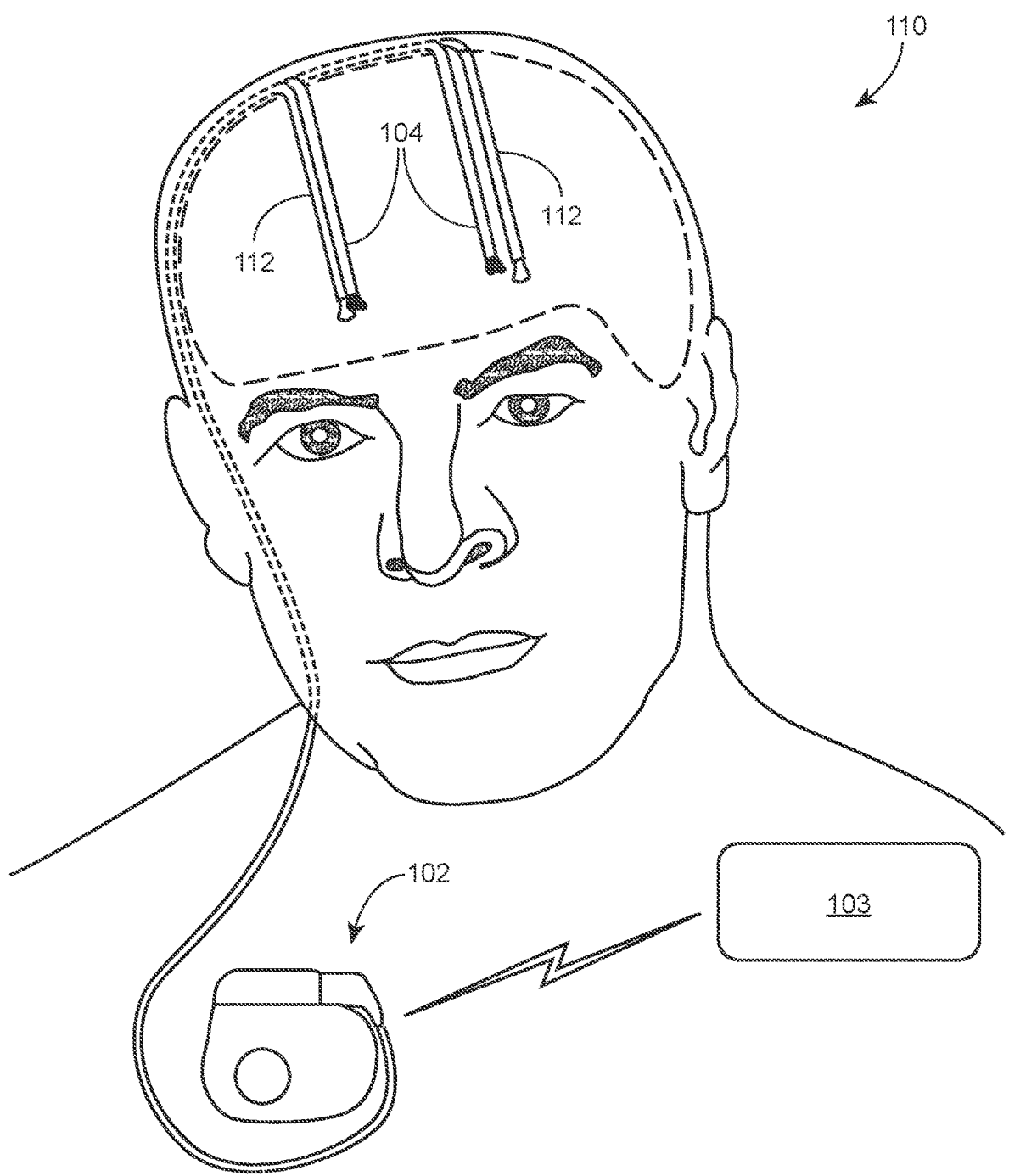
FIG. 9 provides a second example of an optical stimulation system.

Turning now to FIG. 9, a second example of an optical stimulation system 110 is depicted. The optical stimulation system 110 comprises a catheter 112 for delivering a variant light-responsive polypeptide of the present disclosure, or a nucleic acid or recombinant expression vector comprising a nucleotide sequence encoding a variant light-responsive polypeptide of the present disclosure, to a target tissue, e.g., brain tissue 107 of a patient. Also provided are a light-generating device 102, a control device 103, and optical fibers 104 for conveying light generated by the light-generating device 102 to the end of the optical fibers 104.

Figure 10:
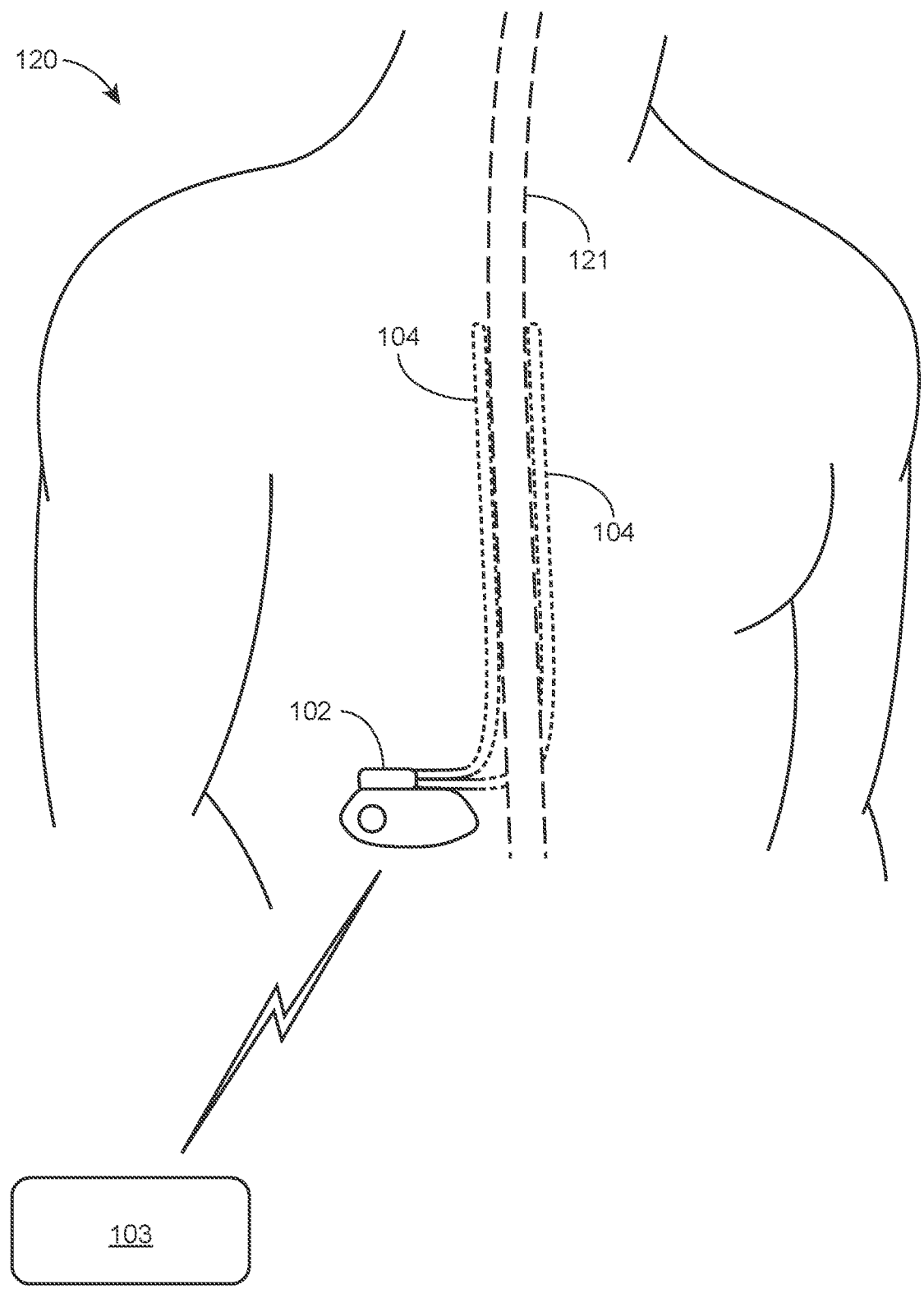
FIG. 10 provides a third example of an optical stimulation system.

Turning now to FIG. 10, a third example of an optical stimulation system 120 is depicted. The optical stimulation system 120 comprises a light-generating device 102, a control device 103, and optical fibers 104 for conveying light generated by the light generating device 102 to various positions along the spinal cord 121 of the patient.

Utility

A method of the present disclosure for modulating the activity of a target cell is useful in a variety of research, diagnostic, imaging, and treatment applications. The subject methods generally involve introducing a variant light-activated polypeptide of the present disclosure, or a nucleic acid (or recombinant expression vector) comprising a nucleotide sequence encoding a variant light-activated polypeptide of the present disclosure, into a target cell, such that the target cell expresses a light-activated cation channel protein and inserts it into the membrane; and illuminating the target cell with light of an activating wavelength. Illumination of the target cell with light of an activating wavelength causes the light-activated cation channel protein to allow one or more cations to pass through the plasma membrane of the target cell. The passage of the cations through the plasma membrane of the target cell has a desired effect, such as, e.g., modulating the membrane potential of the plasma membrane. In some embodiments, the passage of the cation species through the plasma membrane may be used to modulate one or more neurological responses or processes in a patient, and may therefore by used to treat a disease or condition in the patient. As such, in some embodiments, the subject methods involve treating a patient for a condition, such as a neurological condition. In some embodiments, the subject methods involve treating a patient for a condition, such as a neurological condition, using the systems and devices provided herein.

Using the subject methods, the ordinarily skilled artisan will be able to perform in vivo recording and imaging of the activity of excitable cells, such as neurons. In some embodiments, in vivo calcium imaging may be performed substantially simultaneously on 100 or more neurons at 30 Hz or more for each neuron.

The subject methods also find use in analyzing or mapping the connectivity of neurons in target tissues, such as the brain. For example, the subject methods may be used to measure the individual activity of a plurality of neurons in a target tissue volume in response to a stimulus, either to one or more neurons in the local area of the target tissue that is being analyzed, or to sites distal to the measurement site. The stimulus may be a sensory stimulation, an electrical stimulation through an electrode, or an optical stimulation. By observing the pattern of activity of the measured neurons in response to various stimuli and other manipulations, one may deduce the connectivity of the neurons in the observed area of the target tissue.

In some embodiments, the neuronal regions targeted for measurement or stimulation by the subject methods include any neocortical region. With proper tissue exposure, suitable target neural regions include: the hypothalamus, entorhinal and hippocampal formation cortex, mammillary bodies, septum, bed nucleus of stria terminalis, dorsal and ventral striatum, thalamus, amygdala, accumbens, brainstem, and subcortical structures in general. The target location may include: a cell, a portion of a cell, a plurality of cells, a bundle of nerve fibers, a neuromuscular junction, a central nervous system (CNS) tissue, a peripheral nervous system (PNS) tissue, muscle or cardiac tissue, or an anatomical region.

Modeling of Diseases or Conditions Involving Action Potentials

In some embodiments, the subject methods can be used for studying and/or modeling certain diseases or conditions in a subject, such as conditions that involve or result from increased formation of action potentials and/or an improper promotion of action potential formation within a cell. For example, the subject methods may be used to specifically increase the formation of action potentials in target cells, such as specific target nerve cells, to study the effects of promoting action potential formation in those cells. In some embodiments, the subject methods may be used to selectively increase the formation of action potentials in certain portions of a target cell, such as an axon of a target nerve cell, to study the effects of promoting action potential formation in the selected portion of the target cell. Such methods may be used as models of diseases or conditions in which action potentials fire at abnormally high rates in a target cell or a portion thereof, or wherein action potentials are erroneously formed in a target cell or a portion thereof.

In some embodiments, the subject methods may be used in animal models (including but not limited to transgenic animal models) of diseases of conditions associated with abnormal formation of action potentials within target cells, or portions thereof, or associated with the increased formation of action potentials within target cells, or portions thereof. For example, in some embodiments, a target cell of an animal (such as a nerve cell, e.g., a brain cell of a rodent) may be contacted with a nucleic acid encoding a subject engineered light-activated cation channel protein so that the cation channel protein is expressed by the target cell. Next, the target cell is illuminated with light of an activating wavelength to promote the formation of action potentials in the target cell. The effect of the promotion of action potential formation within the target cell, or a portion thereof, on the animal can then be examined. The use of transgenic animals that overexpress one or more gene products, or the use of "knock-out" transgenic animals that fail to express one or more gene products, may be used to investigate the role of specific gene products in the formation of action potentials in target cells.

Methods of Screening

In some embodiments, the subject methods may be used, e.g., for screening compounds that may be effective in treating diseases or conditions involving the formation of action potentials in target cells, or the increased formation of action potentials in target cells. In some embodiments, the screening methods involve culturing cells in vitro, where the cultured cells comprise a variant light-activated polypeptide of the present disclosure. The cultured cell expressing the variant light-activated polypeptide of the present disclosure is contacted with a test compound; and the cell is then exposed to light of an activating wavelength to promote the formation of action potentials within the cell or a portion thereof. The ability of the test compound to elicit a desired effect or response from the cell while action potential formation is promoted may be useful in the treatment of a particular disease or condition.

In some embodiments, the subject methods find use in screening, in an in vivo non-human animal model, for neuronal circuit elements diagnostic of or causative for neuropsychiatric disease. For example, the non-human animal can be modified to express a variant light-responsive polypeptide of the present disclosure in one or more neuron cells, in a particular neuronal tissue, etc. Neuropsychiatric disease of interest may include disorders of mood and affect, anxiety, psychosis, personality, etc. The animal model may be any suitable model, including, but not limited to, rodents, cats, dogs, monkeys, and non-human primates. Perturbations used to model a neuropsychiatric disease include genetic models of neurological or psychiatric disease, such as autism; chronically induced models as with kainate or pilocarpine-induced epilepsy or chronic stress-induced depression; and acutely induced models as with hallucinogens or psychotogenic agents such as ketamine or phencyclidine (PCP). By comparing the difference in activity pattern between neurons in normal target tissue and neurons in abnormal target tissue, neural correlates of the neuropsychiatric disorder may be identified. Optical control of neurons in the target tissue may then allow identification of causative neuronal activity patterns for a particular neuropsychiatric disorder. These manipulations may potentially provide novel treatment targets.

In some embodiments, the subject methods find use in methods for identifying a treatment, e.g., a therapeutic treatment, with a desired activity on a group of neurons. If the desired outcome is known, then the present system and method may be used to screen for treatments, including, but not limited to, pharmacological agents, nonchemical based therapeutic treatment; behavioral treatment; electrical, magnetic, or optical based neural-modulation treatment; etc., that will bring about the desired neuronal activity pattern. The screening may be performed in any suitable animal model, either normal, or a model for a neurological disorder, such as Alzheimer's and Parkinson's disease, mild cognitive impairment, other dementias, and Down's Syndrome, as well as schizophrenia, autism, mood, affective, anxiety, and personality/developmental disorders.

Methods of Treatment

In some cases, a subject method involves modulating the activity of a target cell in vivo. In some cases, a nucleic acid (or recombinant expression vector) comprising a nucleotide sequence encoding a variant light-responsive polypeptide of the present disclosure is introduced into a target cell, where the encoded variant light-responsive polypeptide is produced in the target cell; and the variant light-responsive polypeptide is activated by exposure to light of an activating wavelength. In some cases, a nucleic acid (or recombinant expression vector) comprising a nucleotide sequence encoding a variant light-responsive polypeptide of the present disclosure is administered to an individual in need thereof, such that the variant light-responsive polypeptide is produced in a target cell (e.g., such that the variant light-responsive polypeptide is present on the plasma membrane of a target cell), thereby allowing the activity of the target cell to be modulated by light of an activating wavelength. In some cases, a variant light-responsive polypeptide of the present disclosure is administered to an individual in need thereof, such that the variant light-responsive polypeptide is introduced into a target cell (e.g., such that the variant light-responsive polypeptide is present on the plasma membrane of a target cell), thereby allowing the activity of the target cell to be modulated by light of an activating wavelength. Once a variant light-responsive polypeptide of the present disclosure is present in the plasma membrane of a target cell(s) in an individual, the target cell(s) is exposed to light of an activating wavelength, thereby depolarizing the target cell(s).

In some embodiments, the subject methods are used to treat a patient for a condition or disorder, such as a neurological condition or disorder, by optogenetically modulating the action potentials of target cells within the patient. In some embodiments, the subject methods involve introducing a variant light-responsive polypeptide of the present disclosure into a target tissue within the patient. In some embodiments, introduction of a variant light-responsive polypeptide of the present disclosure into the target tissue is accomplished using a subject delivery device. A polynucleotide (e.g., a recombinant expression vector) encoding a variant light-responsive polypeptide of the present disclosure is introduced into the target tissue, and the variant light-responsive polypeptide is expressed by target cells (e.g., nerve cells) in the target tissue and inserted into the plasma membrane of the target cells.

Next, a light-generating device is positioned to illuminate the target tissue with light of an activating wavelength when the light-generating device is activated. The light-generating device is activated (either by the patient, or by a caregiver (e.g., medical personnel)) to deliver light to the target tissue to cause the variant light-responsive polypeptide of the present disclosure to allow cations (e.g., sodium cations) to pass through the plasma membrane and depolarize the plasma membrane, thus promoting the formation of action potentials within the cell(s) of the target tissue.

As such, the formation of action potentials within the cell is increased for the duration of the effect of the light pulse and the resulting depolarization of the plasma membrane. Accordingly, the subject methods may be used to promote the formation of an action potential in a nerve cell by introducing variant light-responsive polypeptide of the present disclosure into the nerve cell and illuminating the nerve cell with light of an activating wavelength from a light-generating device. As the duration of the action potential increase can be tailored to outlast the duration of a light pulse, increase of action potential formation may be achieved using pulsed light delivery, rather than continuous light delivery.

In some case, a method of the present disclosure involves treating a subject for a disorder by promoting the formation of action potentials in a target tissue. Accordingly, in some cases, the subject methods involve treating a subject by introducing into a target cell a variant light-responsive polypeptide of the present disclosure. Polynucleotides encoding these proteins are introduced into the target cell, and the proteins are expressed by the target cell and inserted into the plasma membrane of the target cell. Next, the target cell is illuminated with light of an activating wavelength from a light-generating device to cause the light-activated cation channel protein to allow cations (e.g., sodium cations) to flow through the plasma membrane from outside of the cell to the inside of the cell.

Once inside the cell, the cations depolarize the membrane to promote the formation of an action potential. The depolarization of the membrane promotes the formation of an action potential and therefore allows the cell to, e.g., generate action potentials in surrounding cells, e.g., neighboring nerve cells; mediate the release of neurotransmitters, modulators, or hormones; mediate muscle contraction; and the like until the effect of the membrane depolarization dissipates. Accordingly, the subject methods may be used to treat a subject for a disorder by promoting the formation of action potentials within a target cell. Since the duration of the membrane depolarization can be tailored to outlast the duration of the light pulse, promotion of action potential formation may be achieved using pulsed light delivery, rather than continuous light delivery.

A treatment method of the present disclosure may be used to treat any disease or condition in promoting or increasing the formation of an action potential a target cell, or along a particular portion of a target cell, would have a therapeutic effect for the patient. Examples of therapeutic applications of the subject methods include, without limitation, neurological disorders, such as Alzheimer's and Parkinson's disease, mild cognitive impairment, other dementias, and Down's Syndrome, as well as schizophrenia, autism, mood disorders, affective disorders, anxiety disorders, and personality/developmental disorders, and the like. Specificity can be achieved as above by promoting action potential formation in specific subdomains or portions of the axonal arborization or cell.

In some embodiments, the subject methods find use in the treatment of a condition or disorder, such as a neurological or psychiatric condition using optogenetic control (closed loop control). As real time activity of neurons is monitored using the subject methods, a controller may be configured to modulate the activity of neurons in response to the imaged activity signals in such a way as to treat or reduce symptoms of the condition or disorder, at the behavioral and/or physiological levels.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Characterization of bReach-ES

FIG. 1A-1K depict the properties of ReaChR and bReach-ES. FIG. 1A shows the schematic design of ReaChR and bReach-ES. Both constructs are hybrids of channelrhodopsin 1 (ChR1), Volvox channelrhodopsin 1 and 2 (VChR1, VChR2). Arrows depict the underlying channelrhodopsin in each segment with numbering of the last amino acid (aa) respectively. ReaChR contains the additional mutation Leu171Ile. In bReach-ES, the first 51 n-terminal residues of ReachR were replaced by the first 11 n-terminal residues from channelrhodopsin-2 (ChR2) and the last 5 c-terminal residues were completely truncated. Additionally, bReach-ES contains the mutations Glu123Ser and Leu171Ile. FIG. 1B shows the spectra of C1V1-TT, bReach-ES and ChR2 measured at wavelength between 400 and 650 nm at 0.65 mW/mm2 in cultured neurons from rat hippocampus (n=6 each). FIG. 1C shows stationary photocurrents at 575 nm (left: C1V1-TT=630 pA, s.e.m.=109, ReaChR=963 pA, s.e.m.=113, bReaChR=1365 pA, s.e.m.=128) and 632 nm (right: C1V1-TT=315 pA, s.e.m.=111, ReaChR=1003 pA, s.e.m.=95, bReaChR=841 pA, s.e.m.=102). Current amplitudes were measured in cultured neurons from rat hippocampus at −80 mV and 5 mW/mm$^2$ light intensity respectively. FIG. 1D shows the speed of the channel closure depicted as tau value of the mono-exponential off-kinetics (C1V1-TT=79 ms, s.e.m.=3.7, ReaChR=682 ms, s.e.m.=86, bReaChR=49 ms, s.e.m.=4.4). p<0.0005. Error bars represent standard error of the mean (s.e.m.). C1V1-TT: n=26, ReaChR: n=6, bReaCh-ES: n=25. FIG. 1E shows representative voltage traces of ReaChR and bReaCh-ES expressing cultured neurons excited with 633 nm light pulses (5 ms, 5 mW/mm$^2$). The ReaChR kinetics were so slow that reliable action potential generation was only possible at low frequencies. The accelerated channel closure of bReaChR-ES allowed reliable spike generation up to 20 Hz.

Example 2

FIG. 2A shows confocal images of opsin expression in cell bodies near the injection site in medial prefrontal cortex, and in downstream axonal fibers in the amygdala. Scale bar: 100 μm. FIG. 2B shows representative voltage and current clamp traces of postsynaptic cells in response to light pulse stimulation (bars) of C1V1-TT-expressing presynaptic terminals. Pulse length was 5 ms. Light wavelength was set at 575/25 nm and light power density was 5 mW/mm2.

Example 3

FIG. 3A depicts a schematic diagram of the whole-cell recording paradigm. FIG. 3B shows representative voltage and current clamp traces of postsynaptic cells in response to light pulse stimulation (bars) of bReaCh-ES-expressing presynaptic terminals. Pulse length was 5 ms. FIG. 3C shows a summary bar graph of stationary photocurrent in opsin-expressing mPFC cells (C1V1-TT: n=11, bReaCh-ES: n=10). FIG. 3D shows a summary bar graph of light-evoked spike probability in opsin-expressing mPFC cells (C1V1-TT: n=11, bReaCh-ES: n=10). FIG. 3E shows a summary bar graph of light-evoked EPSC amplitude (C1V1-TT: n=10, bReaCh-ES: n=18). FIG. 3F shows a summary bar graph of light-evoked spike probability in postsynaptic cells (C1V1-TT: n=10, bReaCh-ES: n=17). Light wavelength was set at 575/25 nm and light power density was 5 mW/mm$^2$. Data are presented as mean±s.e.m, p<0.05.

Example 4: Projections from the Neocortex Mediate Top-Down Control of Memory Retrieval The data presented below indicate that a monosynaptic prefrontal (predominantly anterior cingulate) to hippocampus (CA3/CA1) projection exists in mice, and that optogenetic manipulation of this projection (here termed AC-CA) is capable of eliciting contextual memory retrieval.
Materials and Methods
Animals Wild-type C57Bl6/J male mice were group housed three to five to a cage and kept on a reverse 12 hour light/dark cycle with ad libitum food and water (except in virtual reality behavior experiments where water restricted; details below). Experimental protocols were approved by Stanford University IACUC and meet guidelines of the National Institutes of Health guide for the Care and Use of Laboratory Animals. The target number of subjects used in each experiment was determined based on numbers reported in published studies. No statistical methods were used to predetermine sample size.
Anatomical Tracing & Histology Viral injections were carried out under protocols approved by Stanford University IACUC and were performed in mice anesthetized with 1-2% isoflurane using a stereotaxic apparatus (Kopf Instruments). For retrograde tracing, 4-5 week old wild-type male mice were injected slowly (50 nl/min) with small amounts (200 nl) of highly concentrated glycoprotein-deleted rabies virus (RV) tagged with tdTomato (RV-tdTomato)[22] in dorsal hippocampus (A/P: −1.5 mm; M/L: +1.75 mm; D/V: −1.8 mm) with a 1 ul Hamilton syringe and a 35 gauge beveled needle (World Precision Instruments) under the control of a UMP3 syringe pump (WPI). Following injections, the incisions were closed using Vetbond tissue adhesive (Fischer), and mice were allowed to recover and were housed for 5 days to allow for expression before their brains were collected for histological analysis. In the case of anterograde tracing, 4-5 week old wild type male mice were injected (150 nl/min) with 500 nl of AAV5-CaMKIIα::EYFP (titer: $2 \times 10^{12}$ vg/ml) in dorsal anterior cingulate (A/P: +1; M/L: −0.35; D/V: +1.2) and were housed for 30 days to allow for expression in terminals prior to collection of brains for histological analysis.

For histological analysis, injected mice were transcardially perfused with ice-cold 1×PBS, immediately followed by perfusion of 4% paraformaldehyde (PFA). Brains were fixed overnight in PFA, then transferred to a 30% sucrose/phosphate buffered saline (PBS) solution. Coronal sections of either 40 μm (for retrograde tracing with RV) prepared using a freezing microtome (Leica) or 300 μm (for anterograde tracing with AAV5) prepared using a vibratome (Leica) were collected and stored in a cryoprotectant solution (25% glycerol, 30% ethylene glycol, in PBS) until further processing. For 4',6-diamidino-2-phenylindole (DAPI) staining, slices were washed in PBS, incubated for 20 minutes with DAPI at 1:50,000, washed again in PBS, then mounted with PVA-DABCO (Sigma). A scanning confocal microscope (TCS SP5, Leica) and LAS AF software (Leica) was used to obtain and analyze images.

Acute Slice Electrophysiology for PFC-to-Hippocampus Synapse Characterization

Acute brain slices were prepared from mice 6-8 weeks following viral injection with AAV5-CaMKIIα::ChR2 (H134R)-EYFP, to allow sufficient time for channelrhodopsin to express in axon terminals. After lethal anesthesia, mice were transcardially perfused with cold sucrose slicing solution (see below) prior to decapitation, following which the brain was rapidly extracted and submerged in ice-cold sucrose-based slicing solution (234 mM sucrose, 26 mM $NaHCO_3$, 11 mM glucose, 10 mM $MgSO_4 \cdot 7H_2O$, 2.5 KCl, 1.25 mM $NaH_2PO_4 \cdot H_2O$, 0.5 mM $CaCl_2 \cdot 2H_2O$). Coronal hippocampal slices (300 μm thick) were cut on a Leica vibratome (Leica VT1000S) in sucrose solution and then submerged in a hypertonic recovery solution (artificial cerebrospinal fluid (ACSF) at an 8% increased osmolarity) at 33° C. for 15 min before being transferred to standard ACSF (123 mM NaCl, 26 mM $NaHCO_3$, 11 mM glucose, 3 mM KCl, 2 mM $CaCl_2 \cdot 2H_2O$, 1.25 mM $NaH_2PO_4 \cdot H_2O$, 1 mM $MgCl_2 \cdot 6H_2O$) for a further 45 mins at 33° C., at which point they were transferred to room temperature.

Whole cell patch clamp recordings from CA3/CA1 hippocampal neurons were performed on an upright Leica DM-LFSA microscope. Borosilicate glass (Sutter Instruments) pipette resistances were pulled to 3-6 MCI and filled with potassium gluconate intracellular solution (130 mM KGluconate, 10 mM KCl, 10 mM HEPES, 10 mM EGTA, 2 mM $MgCl_2$, pH adjusted with KOH to 7.3). Voltage and current clamp recordings were performed using pClamp (Axon Instruments). Cells with leak current greater than −200 pA or series resistance greater than 35 MS2 were excluded. Light stimulation was performed using a 300 W DG-4 lamp (Sutter Instruments, Novato, Calif., USA) with an external filter for blue light (wavelength in nm/bandwidth in nm: 470/20). Light pulses (2-5 ms pulse width) were delivered through a 40×, 0.8 NA water-immersion objective at 4-10 $mW/mm^2$ light power density. Latencies measured as light pulse start to EPSC initiation.

Optogenetics & Behavior

After injection with the indicated virus (e.g. CAV or RV, expressing ChR2, eNpHR3.0, or EYFP) at the appropriate location (e.g. cingulate, hippocampus, or medial septum), as described in FIG. 14 and FIG. 13, 4-5 week old wild type male mice were implanted with IFLs (implantable fiberoptic lightguides) consisting of a 2.5 mm diameter metal ferrule with 0.22 NA and a 200 μm thick protruding cleaved bare optic fiber cut to the desired length (Thorlabs) as previously described[36], either at the injection site (typically ~0.2 mm dorsal to the injection site) or at the terminals for stimulation experiments as indicated. For inhibition experiments, dual fiberoptic cannulas of 200 μm thickness and 0.22 NA spaced 0.7 mm apart were used to target anterior cingulate bilaterally, and two-ferrule cannulas spaced 3 mm apart were used to target hippocampus bilaterally. Mice were typically allowed to recover and housed for 1 month to allow for adequate expression prior to behavioral testing. All animals undergoing behavioral experiments were acclimated to a 12-hour reverse light/dark cycle, handled for several days, and prior to behavioral testing, were acclimated to the room in which experiments were to be conducted for at least 30 minutes.

The fear conditioning apparatus consisted of a square conditioning cage (18×18×30 cm) with a grid floor wired to a shock generator and a scrambler, surrounded by an acoustic chamber (Coulburn instruments, PA, USA). The apparatus was modified to enable light delivery during retrieval testing. Contextual fear conditioning was performed by placing mice in the conditioning cage (visual cues: bare walls, tactile cues: grid floor, odor cues: 70% ethanol) for 6 min, while receiving four 2 s shock pulses of 7 mA each at 1 minute intervals with the first shock presented 2 min after placing the mouse in the conditioning context. A fraction of animals of the same cohort were not fear conditioned, and instead served as a control group that were just exposed to the conditioning context for the same amount of time (6 min) but did not receive any associated shocks. The following day, all mice were tested in a different "neutral" cage (visual cues: colored shapes, tactile cues: smooth paper towel covered plexiglass floor, odor cues: 1% acetic acid) for light-mediated fear retrieval.

For stimulation experiments, optical stimulation through the fiberoptic connector was administered by delivering light through a patch-cord connected to a 473 nm laser in 30 s light-on/1 min light-off sessions. During light-on sessions, stimulation was delivered at 20 Hz, 15 ms pulses, with 8-10 mW power at the fiber tip. On the third day, all mice were then returned to the original conditioning context for 2.5 minutes to assess intact natural fear memory retrieval. In some cases, subsequent extinction of fear memory was performed by placing mice in the original conditioning chamber for three consecutive days, for five minutes each, without shock. Light-induced fear retrieval was then tested in the neutral context 24 h following the last extinction training session. Subsequent re-instatement was performed by again placing the animals back in the conditioning context for one 6-minute interval and providing four 2 s shock pulses of 7 mA each at 1-minute intervals. A final light-induced fear retrieval testing was performed 24 h later as described above.

For loss of function experiments, optical inhibition through a fiberoptic connector was administered by delivering light through a dual patch-cord connected to a 589 nm laser. Constant light at 8-10 mW was used at the fiber tip to deliver inhibition either at cell bodies or terminals. On the first day, both eNpHR3.0 and eYFP control groups were trained to contextual fear conditioning as described above, and on the second day, mice were allowed to perform retrieval as usual during light off for the first two minutes, to assess baseline freezing in each animal. Then light was turned on for the next 30 s (not longer, as the potential for extinction related un-freezing could confound light-related un-freezing at time points succeeding the typical 2-3-min retrieval protocol). Freezing scores during the 30 s light sessions were compared with the percent freezing during 30 s of the immediately preceding light-off sessions. On the third day, all mice underwent retrieval in the conditioning context for 2 min with light-off to test for reversal of light-induced behavior. After context conditioning and retrieval, all mice subsequently underwent auditory-cued conditioning (cued conditioning was done separately from context conditioning to ensure robust conditioning to both context and cue, since when performed together, mice often develop robust conditioning to tone (the more salient cue) and only weak conditioning to context). To perform auditory-cued FC, mice were placed in a different context (with colored shapes as visual cues and a smooth floor), for 6 min, where after the first two minutes, four 20 s auditory cues consisting of 2.9 kHz tone was played at 1 min intervals, each followed by a 2 s 7 mA shock. Retrieval on the subsequent day was performed by presenting the tone four times (two during light off and two during light on) at 1 min intervals and percent freezing was assessed during the 20 s post-tone compared with the immediately preceding 20 s during tone, for both light off and light on conditions. Latency measures were performed as separate experiments, using the same cohorts; after finishing contextual and cued conditioning, these mice were re-trained (contextually fear conditioned) to the first conditioning context. On the following day, 2-min retrieval was performed in the conditioning context with light-on the entire time to test for latency to freezing, where latency was defined as the first instance in time that the animal was immobile for 5 consecutive seconds. Freezing in all experiments was scored by an experimenter blinded to the treatment group. Randomization of animals to experimental and control groups was performed by an experimenter with no explicit randomization algorithm used. All of the results were analyzed by Student's t-test or two-way ANOVA, followed by post-hoc tests, as applicable.

Hippocampal Cranial Window

C57BL/6J male mice were injected with 500 nL of AAVdj-CaMKIIα::GCaMP6m in CA3 (A/P: −1.7, M/L: +1.9, DN: −1.9) and allowed to recover for at least one week prior to surgical implantation of a cranial window above CA3 for optical access similar to previously described hippocampal preps[24]. Briefly, mice were injected with 80 mg/6 mg/kg of ketamine/xylazine intraperitoneally, and maintained under 1.0-2.0% isoflurane throughout. For optimal window placement to access CA3, the mouse's head was angled during surgery such that the skull location at the CA3 injection site was level and exactly perpendicular to dorsal views of the head. A circular titanium headplate (7 mm in diameter) was centered over CA3 and adhered to the skull with adhesive cement (Metabond; Parkell) and a ~3 mm craniotomy was made in the center using a trephine (Fisher). Parts of cortical region Si and of parietal association cortex were vacuum-aspirated, with care taken to avoid the ventricle, until white matter was visible above the hippocampus. Vacuum aspiration was done with a 27 gauge blunt needle while irrigating with chilled 1×PBS. The top layer of white matter above the hippocampus was further removed by vacuum aspiration with a 31 gauge blunt needle, but care was taken to preserve deep layers of external capsule and the alveus (to preserve afferents and efferents to hippocampus). A forceps was used to manually insert a cylindrical borosilicate glass implant until the floor of the implant rested against the hippocampus. The implant was constructed from a 3.0 mm diameter glass capillary tubes (Friedrich & Dimmock) custom cut to 1.5 mm length, adhered on one end to a 3.0 mm diameter coverslip of #0 thickness (Warner Instruments) using UV-curing optical glue (Norland Products). The top of the implant extruding from the craniotomy was then secured to the skull using Metabond adhesive cement. After surgery, mice were given 5 mg/kg carprofen subcutaneously and allowed to recover for at least one week prior to behavior training.

Figure 16:
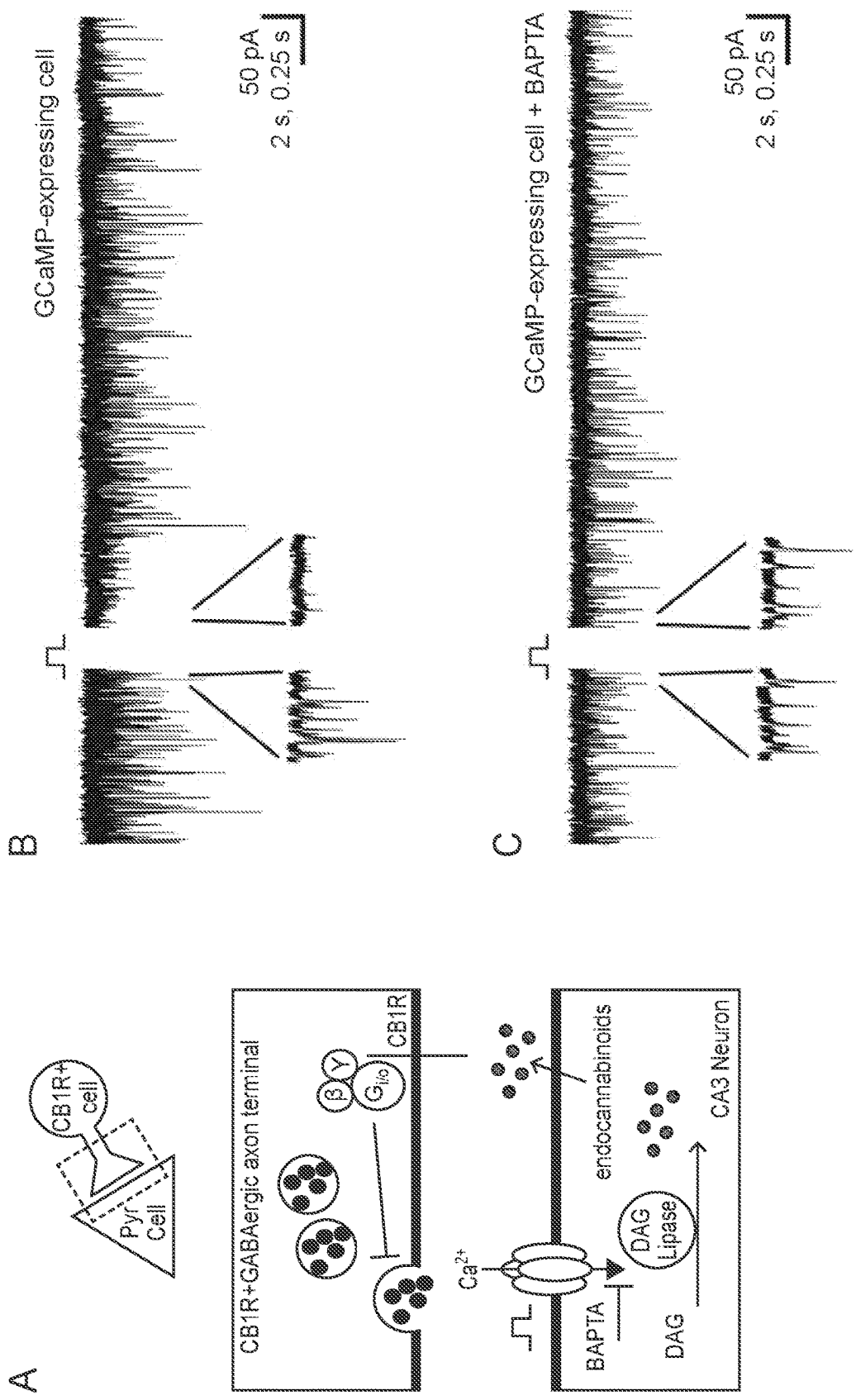
FIG. 16A-16F depict the physiological properties of GCaMP6m-expressing CA3 neurons.

To ensure that the above manipulations (including GCaMP6m virus injection into CA3, GCaMP6m expression, and surgical excavation of certain regions of cortex) did not affect normal physiological properties of the hippocampus, control experiments to assess $Ca^{2+}$ dependent physiology in weakly vs. strongly expressing CA3 neurons in vitro, spontaneous activity in weakly vs. strongly expressing CA3 neurons in vivo, and behavioral measurements before and after placement of the cannula were performed (FIG. 16).

Virtual Reality Behavior

A custom built virtual reality environment, modified from previously reported versions[24,51], was used. A 200 mm diameter styrofoam ball (Graham Sweet Studios) was axially fixed with a 6 mm diameter assembly rod (Thorlabs) passing through the center of the ball and resting on 90° post holders (Thorlabs) at each end, allowing free forward and backward rotation of the ball. Mice were head-fixed in place above the center of the ball using a headplate mount. Virtual environments were designed in game development software Unity3d (unity3d.com). The virtual environment was displayed by back-projection onto projector screen fabric stretched over a clear acrylic hemisphere with a 14-inch diameter placed ~20 cm in front of the center of the mouse. The screen encompasses ~220° of the mouse's field of view. The virtual environment was back-projected onto this screen using two laser-scanning projectors (Microvision), each projector covering one half of the screen. To create a flat image on the 3d screen, the 2d image of the virtual environment was warped using video manipulation software (Madmapper). The game engine allowed scripts written in JavaScript or C# to trigger external events based on the mouse's interactions with the virtual environment by communicating over a TCP socket to custom Python control software. A LabJackU6 (http://labjack.com) was used both to time-lock virtual environment events and imaging frame times, to record mouse licking behavior with incoming TTL pulses from the lickometer (Island Motion), and to send TTL pulses to deliver solenoid-gated water rewards (delivered from a gravity-assisted syringe attached to tubing connected to the lickometer) and aversive air puffs (from a compressed air tank to a tube ending in a pipette tip facing the mouse's snout). Tactile and odor cues were fixed directly to each of two Styrofoam balls representing the two separate contexts. Auditory stimuli were presented through speakers situated behind the animal. The mouse's movements on the ball were recorded using an optical computer mouse (Logitech) that interfaced with the virtual environment software.

For fear conditioning in the virtual environment, mice were water restricted (>80% pre-deprivation weight) and habituated to handling, head-fixation, and the virtual environment for at least 2 weeks, with free access to small water rewards (~0.5 μl/10 licks) while on the ball. By the end of two weeks (one 5-minute session/day), mice appeared comfortable and alert on the ball. After habituation, mice underwent a four-day fear conditioning training and testing protocol. On day 1, mice were exposed to two contexts that differed in visual (blue triangles vs pink vertical stripes), tactile (smooth side of Velcro vs sharp side of Velcro fixed onto running ball), odorant (acetic acid vs ethanol), and auditory cues (8 kHz phasic tone vs 3 kHz pure tone) for five minutes each. On day 2, mice were provided with 8 aversive air puffs to the snout (500 ms, 10 psi) at randomly timed intervals throughout the five minutes while in the fear context, but not while in the neutral context for five minutes. On days 3 and 30, mice were placed back in each of the two contexts for five minutes for retrieval.

Imaging

Five mice were imaged on all days, in 5-minute sessions, during exposure, training, and retrieval. A resonant galvanometer two-photon microscope (Prairie Technologies) was used. The genetically encoded calcium indicator GCaMP6m was used in all experiments (GCaMP 6m was amplified from Addgene plasmid #40754 by polymerase chain reaction (PCR) and subcloned into an AAV backbone under the control of the CaMKIIa promoter.) All experiments were performed using a Coherent Ultra II Ti-Sapphire pulsed laser tuned to 920 nm to excite GCaMP6m through a 20×0.5 LUMPlanFL/N (Olympus) water-immersion objective interfacing with the implanted cannula through a few drops of distilled water. Fluorescence was detected through gallium arsenide phosphide (GaAsP) photomultiplier tubes (PMTs) using the PrairieView acquisition software. High speed z stacks were collected in the green channel (using a 520/44 bandpass filter, Semrock) at 512×512 pixels covering each x-y plane of 500 μm×500 μm over a depth of ~100 μm (3-7 z slices ~10-20 μm apart) by coupling the 30 Hz rapid resonant scanning (x-y) to a Z-piezo to achieve ~6 Hz per volume.

Data Analysis

Below, methods to extract cells (pre-processing), obtain cellular-level activity (dF/F) measures (processing), and evaluate population-level activity measures (post-processing) are provided. In statistical analysis of the post-processed data, both parametric and non-parametric tests were employed as appropriate. In cases where normality could not be assessed (low sample sizes), it was ensured that there were no significant outliers (by Grubbs' test) and that the variance between groups was not significantly different (by Levene's Test).

1. Pre-Processing (Cell Extraction)

Time series datasets were x-y motion corrected with ImageJ plug-in Stack Reg using rigid body transformations. Cell extraction was then performed sequentially, by first computing cell segments automatically followed by manual quality-control for missed cells, non-cells, or conjoined cells. For initial automatic extraction, a metric based on image threshold intensity, variance and skewness was used. Images with high contrast-to-noise ratio, wherein clear thresholds in maximum intensity separated cells and background, were fully segmented with the former. In the remainder of cases, cells were distinguished from background based on standard deviation across time (high for active cells), or skewness (asymmetry) in intensity across time. This resulted in a general mathematical criterion to define cell-masks at each voxel location (i,j,k):

$$M(i,j,k) = \alpha I(F_{max}(i,j,k) > F_c) + \beta I(\sigma_F(i,j,k) > \sigma_o) + \gamma I(s_F(i,j,k) > s_c)$$

where I is the indicator function (=1 if the condition is satisfied); $\sigma_F(i,j,k)$ is the standard deviation of intensity over time defined as $$\sigma_F^2(i,j,k) = E[(F(i,j,k,t) - \bar{F})^2];$$

and skewness is defined as $$S_F(i,j,k) = E\left[\left(\frac{F(i,j,k,t) - \bar{F}}{\sigma_F(i,j,k)}\right)^3\right].$$

E is the expectation operator; $F_c$, $\sigma_c$, and $s_o$ represent cutoffs for image intensity, standard deviation and skewness respectively. Coefficients α, β, and γ are chosen on an image-specific basis; if thresholding is sufficient β and γ are chosen to be zero, otherwise coefficients are iterated to obtain a cell mask containing the largest population of active cells (evaluated by inspection).

Automatic cell extraction was then followed by manual cell-by-cell curation to identify cells that were not extracted using the automated algorithm. This may occur when cell boundaries are not captured due to non-translational motion artifact in the original imaging, and/or lack of clear cut-offs $F_c$, $\sigma_c$, and $s_c$ differentiating cell and background. For these cases, cell detection was performed with a manual editing step involving comparison of the automated cell-mask to the raw image data, and by using a Gaussian filter was applied on the edited image to smooth edges, and edge-detection was used to define cell boundaries. The interior of the resulting cells were filled, and the final cell masks were eroded to minimize contamination from neuropil signal. Each cell was labeled with a unique cell identifier for the next stage; custom-written MATLAB scripts were used for all steps.

2. Processing

Calculation of dF/F:

For each cell identified in step 1, the intensity value F was obtained by averaging over all pixels inside the ROI to compute a space-averaged value for each frame (corresponding to a single time point). These were used to define dF/F in each cell as $$\frac{dF}{F} = \frac{\bar{F} - \overline{F_{baseline}}}{\overline{F_{baseline}}}$$

where $\overline{F_{baseline}}$ is the baseline fluorescence, calculated as the mean of the fluorescence values for a given cell, continuously acquired over a 20 s moving time window to account for slow time-scale changes in fluorescence. Given the sparse firing of neurons in the dataset, the mean served as an accurate estimate of baseline activity (fluorescence). Furthermore, the main results of the study were not influenced by using the median or 8th percentile as the baseline (and correlations were independent of baseline definition).

Statistical Analysis of Neuronal Responses:

An approach similar to that outlined in Dombeck et al. (2007)[24] was used to identify significant transients in each neuron, as well as to estimate and remove effects that may be related to motion artifacts. Briefly, to estimate the occurrence rate of potential motion-related fluorescence changes in the signal, all negative deflections in the dF/F trace were assumed to be due to motion. Because motion-related fluorescence changes should be equally likely to generate positive or negative-going changes, positive and negative deflections in the dF/F curve that are attributable to motion should occur at the same frequency and can be subtracted out of the signal by using the rate of occurrence of the negative-going transients as an estimate of the rate of motion-related positive-going transients.

To determine statistically significant transients, an estimate of the noise for each cell using an iterative approach was first calculated—(i) a cutoff value that separates signal and noise was initialized, (ii) the standard deviation ($\sigma$) of all dF/F values that fall below the cutoff was calculated, and (iii) $3\sigma$ to the cutoff was compared. In this analysis, the goal was to find an estimate of standard deviation ($\sigma$) of the noise, defined for time periods that are unlikely to contain neural events (i.e., using the iterative approach to estimate the $\sigma$ of the noise, rather than calculate standard deviation for the entire time epoch which would contain real events). For each iteration of the analysis, if |cutoff−$3\sigma$|<tolerance, the program terminated (where tolerance=0.02). If cutoff>$3\sigma$, the program increased the cutoff by 10% and goes back to step 1. If cutoff<$3\sigma$, it reduced the cutoff by 10% and go back to step 1. This approach helped ensure that neuronal activity-generated events in dF/F are not included in the estimation of noise and avoided the need for manually selecting epoch intervals in a cell-by-cell basis that did not contain an event in order to estimate noise.

Subsequently, positive- and negative-going transients was analyzed to further determine the false positive rate. Transient onsets are defined as the times when the dF/F exceeds $2\sigma$ and offset is defined as the time at when a given transient falls below $0.5\sigma^3$. A histogram of the number of transients that exist for each $\sigma$ threshold value (i.e >$2\sigma$, >$3\sigma$, >$4\sigma$), for various durations, was extracted, where negative going transients are to the left of the ordinate and plotted in red (FIG. 18C-FIG. 18F). The ratio of the number of negative to positive going transients is calculated for different transient durations across three amplitude levels ($2\sigma$, $3\sigma$, $4\sigma$), and serves as an estimate of false positive rate. Following from the reasoning described above, this ratio will be 50% when the motion-based noise significantly exceeds the signal. The false positive ratio for the different scenarios above was plotted, and the amplitude (in $\sigma$) and duration cutoff (FIG. 18C-FIG. 18F) needed to reduce the false positive rate to below 5% was chosen. As mentioned in Dombeck et al., 2007, it is important to note that this estimate of noise represents an upper bound, and could be influenced by other sources of noise apart from motion (ie photon shot noise).

Calculation of correlation coefficients between neuron pairs:

The Pearson correlation coefficient was calculated between each pair of cells, a and b, as $$\rho_{a,b} = \frac{E((a-\bar{a})(b-\bar{b}))}{\sigma_a \sigma_b}.$$

This metric measures linear dependence between signals in the two cells, and is invariant with respect to scaling or amplitude translation of the cell signals. A matrix of correlation coefficients of size $N_{cells} \times N_{cells}$ wherein each entry corresponds to correlation between the cells identified by the corresponding row and column was defined. To avoid accumulation in correlated signal due to slow drifts (e.g., the long decay curve of GCaMP6m), all dF/F values lying outside the window of a significant transient (as defined above) was set to 0.

3. Post-Processing

Histogram of Cell Activity Correlations:

The property of high correlation (HC) was tested for in each neuron by finding the number of correlated neurons with which the Pearson's correlation coefficient was above 0.3 (a Pearson correlation cutoff of 0.3 was used as a conservative estimate of connectivity since previous studies using in vivo two photon calcium imaging followed by paired whole-cell recordings reported a greater than 50% chance of connectivity when correlations of $Ca^{2+}$ signals exceeded 0.3 in vivo). Histograms were obtained by binning this number across neurons in steps of 5 and calculating the number of neurons that fell into each bin, with the resulting histogram representing the degree distribution of all neurons in the network. HC neurons were defined as those neurons that had more correlated-partners than that of the average neuron in the same volume by >1 standard deviation.

Optimally-Separating Hyper-Plane:

To identify network population activity measures that best distinguished fear and neutral contexts, a space of graph theoretic parameters was used (described below), which together can be used to define an optimally separating hyperplane between the two contexts. Mathematically, this was posed as a constrained optimization problem, with the objective function seeking to maximize the sum of distances of the hyperplane to the nearest data points in each context, and the constraint being that the hyperplane separates the two contexts. This constrained optimization problem was solved using Lagrange multipliers.

Synchrony and Quantification of Lead-Lag:

To analyze the spontaneous activity of the entire network, the onset and duration of each activity transient (where event onsets and offsets are calculated as described above) was computed for each neuron, and then combined transients from all cells into raster plots and collapsed these raster plots into activity histograms, which indicated the percentage of active cells as a function of time.

To identify epochs of synchronous activity that included more active cells than would be expected by chance at each frame, interval reshuffling was used (randomly reordering of intervals between events for each cell), performed 1,000 times for each mouse in each context, such that a surrogate histogram was constructed for each reshuffling. The threshold percentage of active neurons corresponding to a significance level of P<0.05 (appearing only in 5% of histograms) was taken to be the percent of coactive cells required in a single frame to be considered a synchronous event, and this threshold ranged between 2.5% and 5% active neurons per frame across all mice and fields of view. At least three consecutive frames with activity above the significance threshold were required to be considered a synchronous event, and all subsequent contiguous frames above this threshold were grouped together into the same synchronous event. To plot the cumulative distribution function of event onsets for HC and non-HC neurons during synchronous events, all synchronous events across all mice were identified, and the onset times of HC vs non-HC neurons were binned per frame and plotted cumulatively as a function of the percentage of time elapsed during the synchrony window.

To quantify whether the activity of HC neurons was leading or lagging their correlated pairs, the event onset of the HC neurons (defined as the first instance when the signal exceeded 3.5 for 2 consecutive frames) was first fixed at t=0. The event onsets of all correlated pairs were then binned into 0.167 s time windows immediately preceding or succeeding the onset of the hub neuron at t=0.

Principal Component Analysis (PCA):

PCA was used to describe and visualize population activity of all neurons over time in each context. This was done by transforming the $$\frac{dF}{F}$$

of each cell (typically ~500 cells per mouse per context), over all time points in a given context (typically 1800 frames) to a different coordinate system characterized by linearly independent eigenvectors, where each eigenvector represents a weighted combination of the different cells. Eigenvalues were sorted in decreasing order to reveal the most energetic (contributory) eigenvectors as well as the magnitude of their overall contribution. PCA was performed using eigenvalue decomposition of the correlation matrix. The corresponding eigenvalues and eigenvectors were calculated using custom MATLAB scripts.

Estimation of Graph-Theoretic Parameters:

An undirected graph is defined based on the cell correlations in the population. An edge, E, is defined between neurons if they are correlated beyond the threshold described above. The undirected neuronal graph G (V, E) is defined using all the cells, which are denoted by V (vertices), and E (edges). Mean and maximum cell correlations are calculated using aggregate average and the maxima over all of the measured correlations. An exponential distribution was fitted between the number of correlations ($n_{corr}$) and $n_{freq}$ (the degree distribution described above) to quantify how closely the graph mimics small world networks which are characterized by a power law degree distribution $$n_{freq} = a(n_{corr})^{-b}.$$

for which the power law parameters, a and b, are calculated by transforming the above equation into a logarithmic scale and performing a minimum least-squares fit.

A neighborhood is defined for each cell as a sphere of radius 30 micron. The clustering coefficient for a vertex is defined as the ratio of number of edges within its neighborhood to the maximum number of connections possible. If there are k nodes in the neighborhood, k(k−1)/2 is the maximum number of possible connections[9]. The clustering coefficient of the entire network is defined as the mean clustering coefficient across all vertices. The mean path length is defined as average path between any two randomly selected vertices of the graph. The mean path length is calculated by first constructing an adjacency matrix, which is an $n_{cell} \times n_{cell}$ matrix, and all correlated vertex pairs are given a value of one in the corresponding row and column, and zero otherwise. The minimum path from i to j can be recursively calculated using $$mpl_{i,j} = \min(mpl_{i,k} + mpl_{k,j})$$

Small-world networks were characterized by high clustering coefficient and low mean path length, quantified using the ratio of clustering coefficient to mean path length, where each term is normalized to a purely random graph with the same number of vertices. Betweenness centrality is a measure of centrality of nodes in the network, and indicates how central a node is to communication between all pairs of node. Betweenness centrality was computed by calculating all possible paths between two nodes and calculating the number of those that pass through a given node. Strength of a graph quantifies how strongly different sub-component of a graph are connected and is a measure of resistance of the graph to attack on its edges. Let $P=(V_1, V_2, \ldots V_n)$ denote all possible partitions of the graph G into a mutually exclusive set of vertices $V_1, V_2, \ldots V_n$ such that the union of all the vertices is V. Let $E_r$ denote the number of edges that needs to be removed from S to create the partition P. Then the strength is defined as $$s = \min \frac{E_r}{n-1},$$

where the minima are calculated over all possible partitions P. In other words, the strength quantifies how to remove minimal edges to create maximal separation amongst vertices of the graph. The strength was calculated using MATLAB code based on algorithms described previously (Tarjan, R. E. Depth first search and linear graph algorithms. SIAM Journal Computing 1972, 2:146-160; Sedgewick, R. Algorithms in C++, Part 5 Graph Algorithms (Addison-Wesley). 2002).

Fast Non-Negative Deconvolution Algorithm Implementation

Deconvolution algorithms enable the estimation of spike rate trains from fluorescence data. Here, deconvolution was used to estimate activity-event onset, not to detect single spikes, since GCaMP6m is assumed to neither have the linear response kinetics nor the sensitivity needed to detect single spikes from bursting neurons in the hippocampus. This analysis was used to help confirm our main results regarding synchronous events and timing of highly correlated neurons, since these analyses offer an alternative method to identify event onsets, while helping to remove noise (e.g., long $Ca^{2+}$ signal decays) from the analyses.

Many deconvolution algorithms exist. Early methods to de-convolve fluorescence data used either thresholding to infer event onset or optimizations to match a chosen spike profile. More robust algorithms such as the Wiener linear filter are promising (Holekanip et al. Neuron, 2008, 57: 661-672) but with practical value diminished since negative-going spikes are allowed. In 2010, Vogelstein et al provided a fast non-negative deconvolution method that is, in addition to imposing a non-negative constraint on the spike trains, scalable on a large population of neurons[32]. Since the imaging involves hundreds of neurons over multiple contexts and days, the algorithm from Vogelstein et al. was used to deconvolve fluorescence signals.

Figure 22:
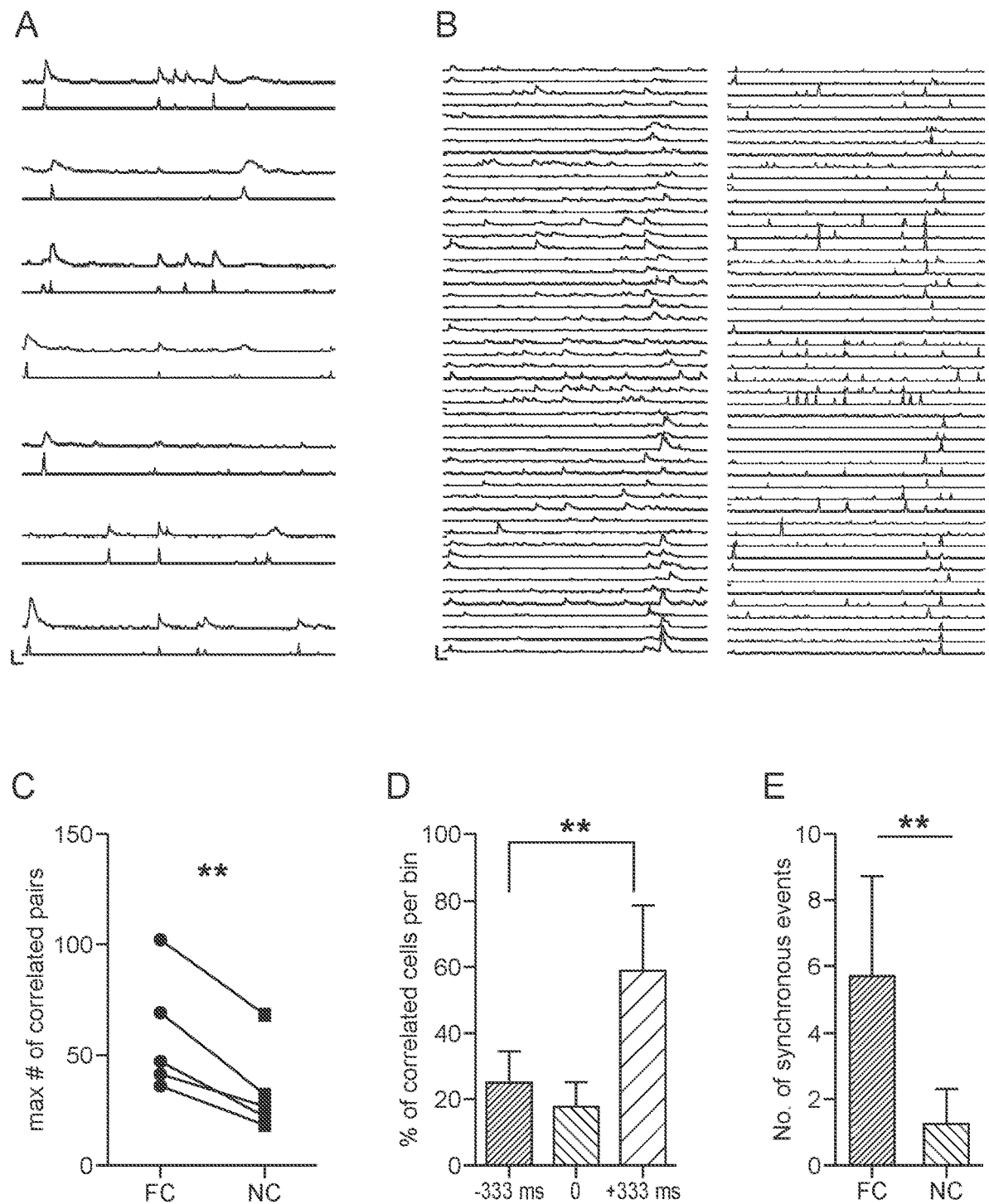
FIG. 22A-22E depict the estimation of event onsets using fast non-negative deconvolution and correlated pair analysis.

Three classes of parameters were optimized in this algorithm to fit data: (a) GCaMP-related parameters, namely sensitivity of fluorescence to elevations in intracellular $Ca^{2+}$ concentration (alpha) and baseline concentration (beta); (b) acquisition parameters, namely the size of the time bin (delta) and the noise (sigma) in the dF/F signals; and (c) system (hippocampus/CA3) related parameters, namely expected spike rate per second (phi) and the time constant (tau), or the length it takes for $Ca^{2+}$ concentrations to decay. For the GCaMP related parameters, beta was set to the baseline of the dF/F traces as described above, and alpha was set to 1 as a default value (since varying alpha broadly around this value did not affect the deconvolution results). Delta was set to ⅓s because image acquisition was at least 3 Hz per optical slice, and sigma was estimated to be 0.16 as explained earlier. The main challenge resided in choosing parameters for phi and tau since 1) the expected spike rate (close to 0.1 Hz on average, but >10 Hz when bursting) is bimodal and insufficiently captured by the Poisson distribution of spikes as assumed by this model, and 2) the time constant expected for $Ca^{2+}$ signals in hippocampus is not fully understood. Therefore, these two parameters was optimized by iterating over multiple combinations of time constants and expected spike rates to yield spike events consistent with good fits to the data (FIG. 22). The final parameters chosen were: alpha=1; beta=baseline; delta=0.33 s; sigma=0.16; phi=5 Hz; tau=2 s. These values were not exactly the same as, but were comparable to, values reported by others in cortical regions. Importantly, varying phi and tau within a fairly broad range (phi-5-10 and tau-0.67-2) did not significantly alter the main conclusions of the subsequent analyses. The dF/F signals for all the mice, context and days were deconvolved. Correlation coefficients were calculated on the deconvolved signals, and metrics that rely on accurate estimate of event onsets were recomputed, such as synchrony, lead-lag, and identification of HC neurons. The only difference from the methods described earlier was that there were no additional noise filters since the noise is filtered in the process of finding the optimal spike rate (here, event rate), and the onset time was characterized by the first instance that the signal became non-zero. Further analysis of the various specific deconvolution parameters would be of interest but likely require combined in vivo imaging and single cell patching experiments, beyond the scope of the current study, and unlikely to significantly affect the specific analyses applied here given the robustness of results to broad ranges of parameters. Furthermore, the above analyses were performed only to help ensure robustness in results obtained from using the raw dF/F for measurements relying on precise timing (correlations, leading vs lagging, and synchrony).

Virtual Reality Behavioral Analysis

Lick rates and movements on the ball were captured in XML log files storing timestamps of behavioral data. These were then parsed with custom Python scripts and imported into MATLAB for synchronizing with microscope imaging frames with kHz precision, and for subsequent analysis. To quantify differences in licking between fear and neutral contexts during retrieval, the number of licks per second (each lick causing a beam-break resulting in TTL pulse output of at least 1V), was integrated over the first two minutes in the context. Total licking amounts were normalized to the highest lick rate, observed from any mouse in any context, and presented as a fraction of this value for each mouse and each context. Lick suppression data were presented as mean values across all mice in each experimental group; significance values of differences between contexts were evaluated by Student's t-test. Lick rates during optogenetic stimulation experiments were scored by quantification during the 15 s of light delivery, which were then normalized to the corresponding value from the 15 s just prior to light delivery. Significant differences in licking for fear vs neutral context, and for neutral/stimulated vs neutral context alone, were evaluated using Student's t-test. Lick rates and velocity on ball during synchronous population activity events were calculated by comparing the amount of licking and distance traveled in the 5 s window beginning at the start of a synchronous event, and then normalizing to the amount of licking and distance traveled in the 5 s window prior to synchronous event. Similar quantitative results were observed with this time window set to 1-10 s after synchrony compared with before, with no significant difference in lick rate and velocity during vs before synchrony.

Simultaneous 1P In Vivo Stimulation and 2P In Vivo Imaging

Figure 17:
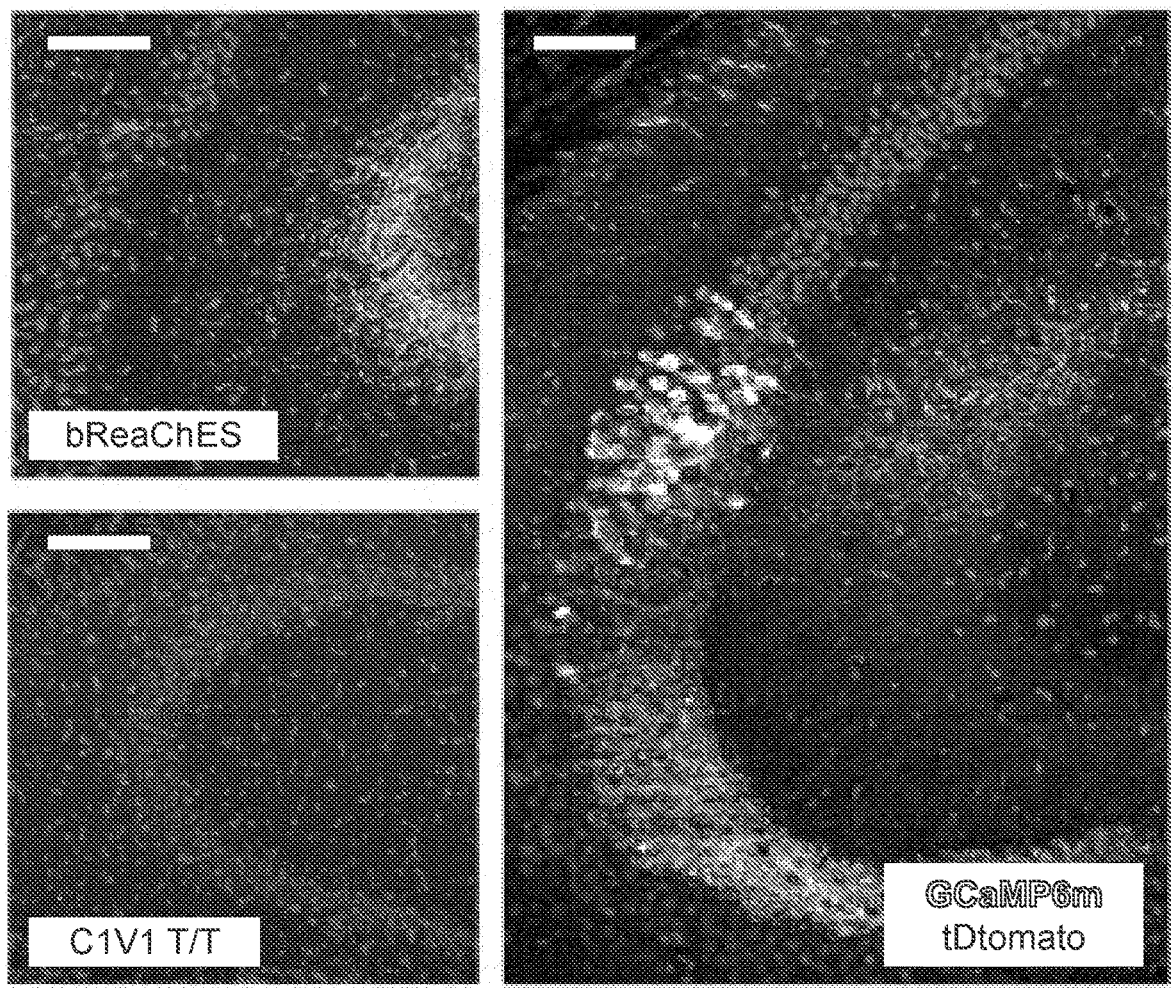
FIG. 17A-17F depict that the AC-CA projection preferentially recruits HC neurons during memory retrieval.
Figure 17:
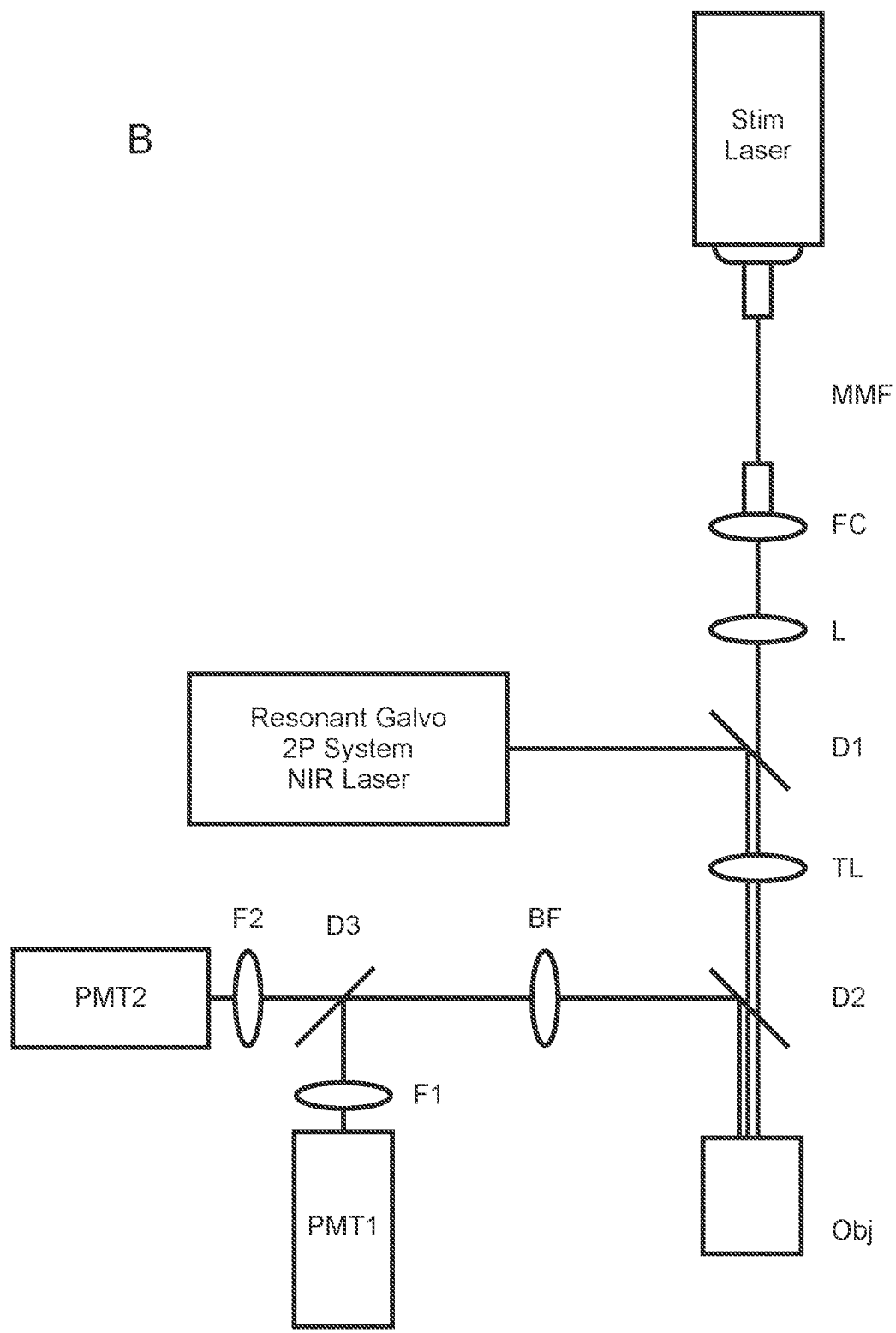

Simultaneous 1-photon (1P) stimulation (594 nm) and 2-photon (2P) imaging (920 nm) was performed by injecting the new red-shifted opsin with improved trafficking and kinetics (bReaChES), via AAV8 in cingulate and GCAMP6m via AAVdj in CA3, and positioning a cranial window above CA2/CA3 for optical access. The two-photon (2P) imaging and full-field optogenetic stimulation setup is shown in FIG. 17B: Green (GCaMP6m signals); Red (stimulation artifact); Multimode fiber (MMF), fiber couple (FC), 25 mm planoconvex lens (L), 680 nm short pass dichroic (D1), tube lens (TL), 594 band/NIR long pass dichroic (D2), objective (Obj), NIR blocking filter (BF), 555 nm long pass dichroic (D3), 520±22 nm filter (F1), 624±20 nm filter (F2), and GaAsP PMTs (PMT1 and PMT2). Briefly, a resonant galvanometer 2P microscope using an NIR pulsed laser set to 920 nm is combined with simultaneous, full field stimulation using a 594 nm continuous wave laser that is coupled into the system with an optical fiber, lenses and dichroic beam splitters. A 2P compatible NIR reflecting dichroic designed with an additional 594 nm band pass filter was used for 1P yellow light stimulation during 2P imaging. GCaMP6m signals (green channel) and stimulation artifact (red channel—used to precisely blank stimulation time points) are recorded using standard 2P resonant scanning imaging. A sub-millisecond PMT shutter was used to prevent collection of stimulation artifact during imaging. In cases where the PMT shutter was not applied, 1P stimulation artifacts were removed offline from the 2P images. Stimulation parameters: 591 nm light, 20 Hz, 15 ms pulses, 15 s, 8-10 mW/mm laser power at sample after the objective. In total, 4 mice (separate cohort from those used in the imaging-only experiments) were used for the combined stimulation & imaging experiments. The same cells and the same FOV are captured for before-training stimulation trials as well as after-training stimulation trials (conducted 5-7 days later). For a neuron to be considered responsive to (recruited by) the stimulus, at least one significant transient as defined above was required to occur during the stimulation window. For latency measurements provided in FIG. 17, event onsets were defined as the first time frame at which the response surpassed 3 standard deviations above noise, and increased for at least 2 consecutive frames; if occurring within the first frame, then only neurons with responses increasing from the previous frame are considered, to exclude responses decaying into the stimulation window. Responding neurons were assigned to latency bins of 333 ms.

DSI Electrophysiology

DSI is dependent on the increase of postsynaptic intracellular $Ca^{2+}$ to suppress GABA release from presynaptic inhibitory neurons expressing cannabinoid receptors. Patch-clamp recordings from CA3 neurons expressing GCaMP6m were performed and spontaneous inhibitory postsynaptic currents (sIPSCs) before and following a depolarizing pulse to induce $Ca^{2+}$ influx were examined. Electrophysiological recordings were performed 4-6 weeks post-injection of AAVdj-CaMKIIα::GCaMP6m into CA3 (in 4-5 week old mice). Coronal slices (300 μm) from injected mice were prepared after intracardial perfusion with ice-cold, sucrose-containing artificial cerebrospinal fluid solution (ACSF; in mM): 85 NaCl, 75 sucrose, 2.5 KCl, 25 glucose, 1.25 $NaH_2PO_4$, 4 $MgCl_2$, 0.5 $CaCl_2$ and 24 $NaHCO_3$. Slices recovered for 1 hour at 32-34° C., and then were transferred to an oxygenated recording ACSF solution (in mM): 123 NaCl, 3 KCl, 26 $NaHCO_3$, 2 $CaCl_2$, 1 $MgCl_2$, 1.25 $NaH_2PO_4$ and 11 glucose, at room temperature. Excitatory synaptic transmission blockers (D-2-amino-5-phosphonovaleric acid (APV; 25 μM) and 2,3-dihydroxy-6-nitro-7-sulfamoyl-benzo[f]quinoxaline-2,3-dione (NBQX; 10 μM) were added to isolate GABAergic postsynaptic currents, and 5 μM carbachol was used to enhance sIPSC frequency to facilitate detection of DSI. Recordings were performed at 32-34° C. under constant perfusion of the oxygenated recording ACSF solution. Slices were visualized with an upright microscope (BX61WI, Olympus) under infrared differential interference contrast (IR-DIC) optics, and a Spectra X Light engine (Lumencor) was used for viewing GCaMP6m expression. Recordings of CA3 neurons were made after identifying GCaMP6m expression, and functional GCaMP6m activity was verifiable (in cells without BAPTA), by observing the increase in GCaMP6m fluorescence during the depolarizing pulse used to induce DSI. The following intracellular solution was used for the patch-clamp electrodes (in mM): 40 CsCl, 90 K-Gluconate, 1.8 NaCl, 1.7 $MgCl_2$, 3.5 KCl, 10 HEPES, 2 MgATP, 0.4 $Na_2GTP$, 10 Phosphocreatine (pH 7.2, 270-290 mOsm). For the BAPTA experiments, 40 mM BAPTA was added to the intracellular solution. Series resistance was monitored for stability, and recordings were discarded if the series resistance changed significantly (by >20%) or reached 20 MΩ. Resting membrane potential was taken at rest, and the reported values incorporate a liquid junction potential of +11.2 mV. Input resistance was calculated from a 100 pA pulse. MiniAnalysis (Synaptosoft) and pClamp10.3 (Molecular Devices) was used to calculate charge transfer (area under sIPSCs) and analyze data. Baseline charge transfer was measured during a 4 s pre-pulse period, DSI was examined during a 4 s period following the depolarizing pulse, and charge transfer after recovery from DSI was measured during a 4 s window. The pulse used to evoke DSI was a 500 ms step to 0 mV from holding potential of −65 mV.

bReaChES Design & Testing
Cloning and Single Mutagenesis of ReaChR and bReaChES
DNA sequences of ReachR and bReaCh were synthesized (GenScript) and cloned into AAV vectors containing the CamKIIα promoter for expression in neurons. All constructs were fused to eYFP DNA (enhanced yellow fluorescent protein) to detect protein expression in neurons by fluorescence microscopy. The Glu123Ser mutation was introduced using QuickChange™ Site-Directed mutagenesis kit (Agilent). Plasmid DNA was purified with QIAprep™ Spin Miniprep Kits (Qiagen) after transformation and amplification in E. coli.

Electrophysiological Recordings in Cultured Hippocampal Neurons
Electrophysiological recordings in neuronal cultures were prepared as described[64]. Patch pipettes (4-6 MS2) were pulled from glass capillaries (Sutter Instruments) with a horizontal puller (P-2000, Sutter Instruments) for whole-cell recordings in voltage and current clamp. Recordings were made using a MultiClamp700B amplifier (Molecular Devices). The external recording solution contained (in mM): 127 NaCl, 10 KCl, 10 HEPES, 2 $CaCl_2$, 2 $MgCl_2$, 30 D-glucose, pH 7.3, including synaptic blockers (25 µM D-APV, 10 µM NBQX). The patch pipette solution contained (in mM): 140 K-gluconate, 10 HEPES, 10 EGTA, 2 $MgCl_2$, pH 7.3. All measurements were corrected for a liquid junction potential of +15 mV. Series resistance was monitored throughout recordings for stability. A Spectra X Light engine (Lumencor) was used to excite eYFP and to apply light for opsin activation. Yellow and red stimulation light was filtered by 575/25 or 632/22 bandpass filters (Chroma) and applied through a 40× objective (Olympus) at 5 $mW/mm^2$ light intensity. Light power density was measured with a power meter (ThorLabs). The functionality of all constructs was determined by comparing stationary photocurrents at −80 mV to 1 s continuous light pulse. Spikes were optically evoked in current clamp mode with light pulses (5 ms) delivered at 633 nm, 5 $mW/mm^2$ and 1-20 Hz.

The activation spectra for C1V1, bReaCH-ES and ChR2 was measured by recording stationary photocurrent in voltage clamp mode at −80 mV and light intensities of 0.65 $mW/mm^2$ at each wavelength. Light was delivered through 20 nm bandbass filters (Thorlabs) at (in nm): 400, 420, 440, 460, 470, 480, 490, 500, 520, 540, 560, 570, 580, 590, 600, 620, 630, 650. Photocurrents were normalized to maximum values respectively: 480 nm for ChR2, 560 nm for C1V1 and 570 nm for bReaCh-ES. Kinetics of channel closure were determined by fitting the decay of photocurrents after light-off, with mono-exponential functions Channel kinetics were quantified by corresponding $tau_{off}$ values respectively. pClamp10.3 (Molecular Devices) and OriginLab8 (OriginLab) software was used to record and analyze data.

Stereotactic Virus Injection of bReaCh-ES
The following adeno-associated viruses (AAV) with serotype DJ were produced at the Stanford Neuroscience Gene Vector and Virus Core:
AAVDJ-CaMKII::bReach-E162S-TS-eYFP
AAVDJ-CaMKII::C1V1(E122T/E162T)-TS-eYFP
4-6 week old mice were injected bilaterally with 1 µl of either virus in the medial prefrontal cortex, at the following coordinates (from bregma): A/P: +1.7 mm; M/L: +0.3 mm; D/V: −2.5 mm. Titer was matched at $1.5 \times 10^{12}$ vg/ml for both viruses.

Slice Electrophysiology for bReaCh-ES Characterization in mPFC and BLA
Electrophysiological recordings were performed 12-14 weeks post-injection for opsin expression at the mPFC terminals. Coronal slices (300 µm) from injected mice were prepared after intracardial perfusion with ice-cold, sucrose-containing artificial cerebrospinal fluid solution (ACSF; in mM): 85 NaCl, 75 sucrose, 2.5 KCl, 25 glucose, 1.25 $NaH_2PO_4$, 4 $MgCl_2$, 0.5 $CaCl_2$ and 24 $NaHCO_3$. Slices recovered for 1 hour at 32-34° C., and then were transferred to an oxygenated recording ACSF solution (in mM): 123 NaCl, 3 KCl, 26 $NaHCO_3$, 2 $CaCl_2$, 1 $MgCl_2$, 1.25 $NaH_2PO_4$ and 11 glucose, at room temperature. Electrophysiological recordings were performed at 32-34° C. under constant perfusion of the oxygenated recording ACSF solution. For mPFC recordings, synaptic transmission blockers (D-2-amino-5-phosphonovaleric acid (APV; 25 µM), 2,3-dihydroxy-6-nitro-7-sulfamoyl-benzo[f]quinoxaline-2,3-dione (NBQX; 10 µM) and gabazine (10 µM)) were added to the recording ACSF solution. Slices were visualized with an upright microscope (BX61WI, Olympus) under infrared differential interference contrast (IR-DIC) optics. A Spectra X Light engine (Lumencor) was used both for viewing fluorescent protein expression and delivering light pulses for opsin activation. Light power density was obtained with a power meter (Thorlabs). Recordings of mPFC neurons were made after first identifying regions of eYFP+ expression, and recordings of postsynaptic basolateral amygdala (BLA) neurons were obtained after confirming eYFP+ expression in both mPFC and the mPFC axonal fibers at the BLA. Whole-cell voltage-clamp recordings were performed at −65 mV, and current-clamp recordings were performed at rest. Patch-clamp pipettes contained the following internal solution (in mM): 125 K-gluconate, 10 KCl, 10 HEPES, 4 $Mg_3$-ATP, 0.3 Na-GTP, 10 phosphocreatine, 1 EGTA. Recordings were conducted using MultiClamp700B amplifier and pClamp10.3 software (Molecular Devices). pClamp10.3, OriginLab8 (OriginLab), and SigmaPlot (SPSS) were used to analyze data. Stationary photocurrent of the opsins was measured at the end of a 1 s light pulse in voltage-clamp mode. Light-evoked spike probability in the mPFC neurons and in the postsynaptic BLA neurons was calculated as the fraction of successful action potentials evoked in the recorded neuron upon various light stimulation frequencies. Light-evoked EPSC amplitude in the postsynaptic BLA neurons was measured at the peak of the evoked response to light stimulation of the opsin-expressing mPFC fibers. Series resistance was monitored for stability, and recordings were discarded if series resistance changed significantly (by >20%) or reached 20 MΩ. Statistical analysis was performed with two-tailed t-test, with significance set at P<0.05 (as indicated by *)

Results

AC-CA: A Direct Top-Down Projection

Figure 11:
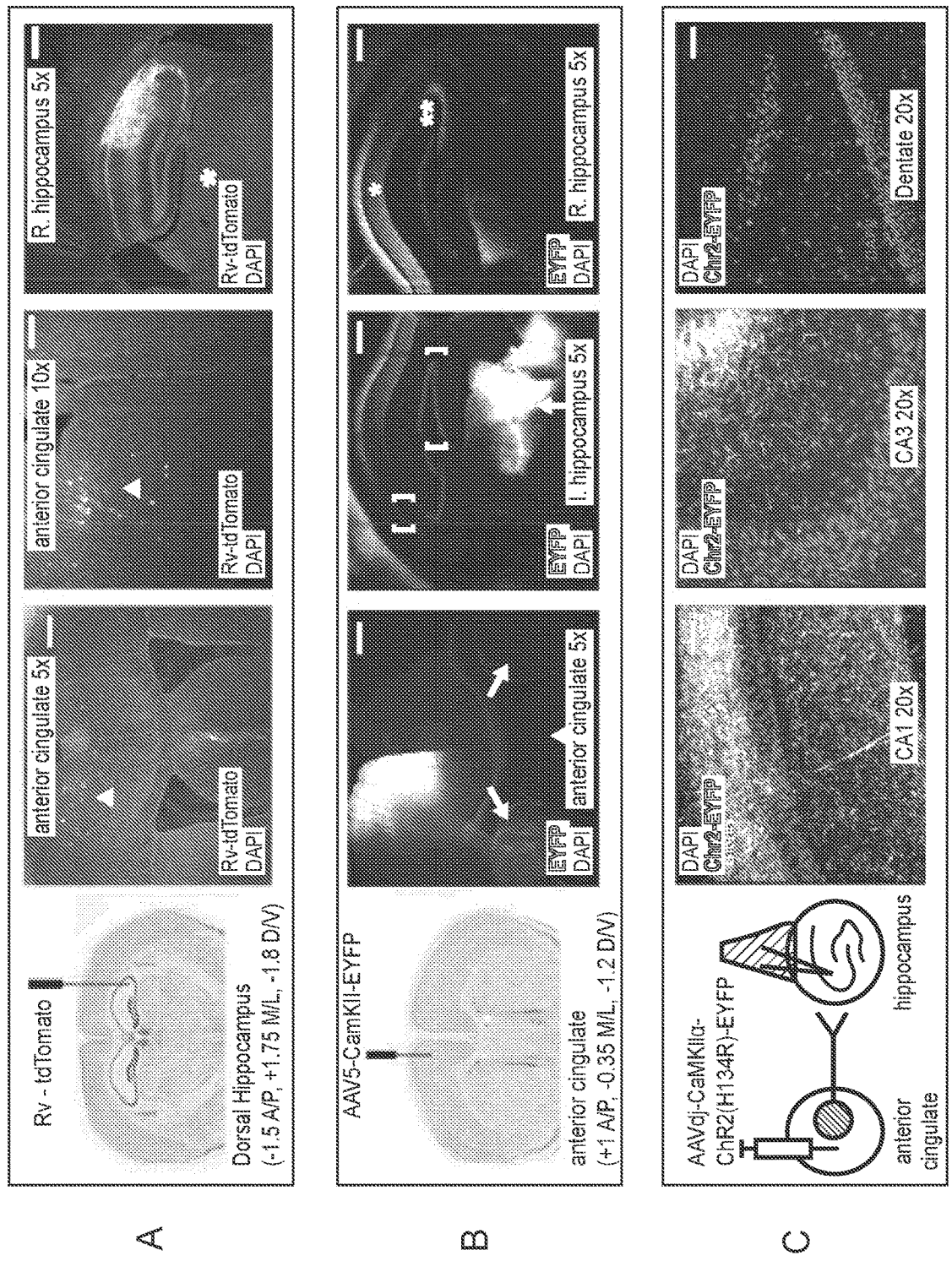
FIG. 11A-11J depict the characterization of the AC-CA monosynaptic projection.
Figure 11:
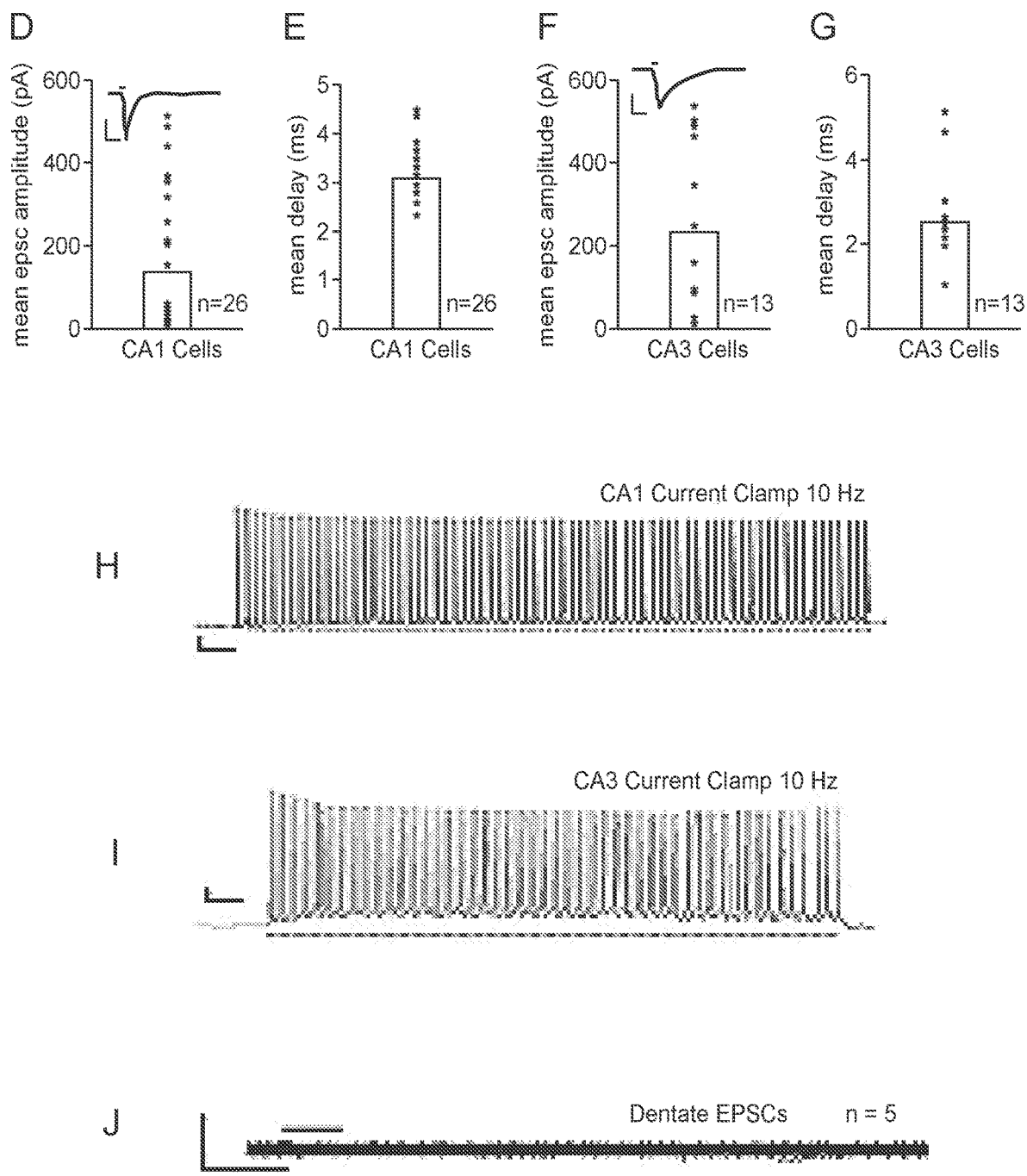
Figure 12:
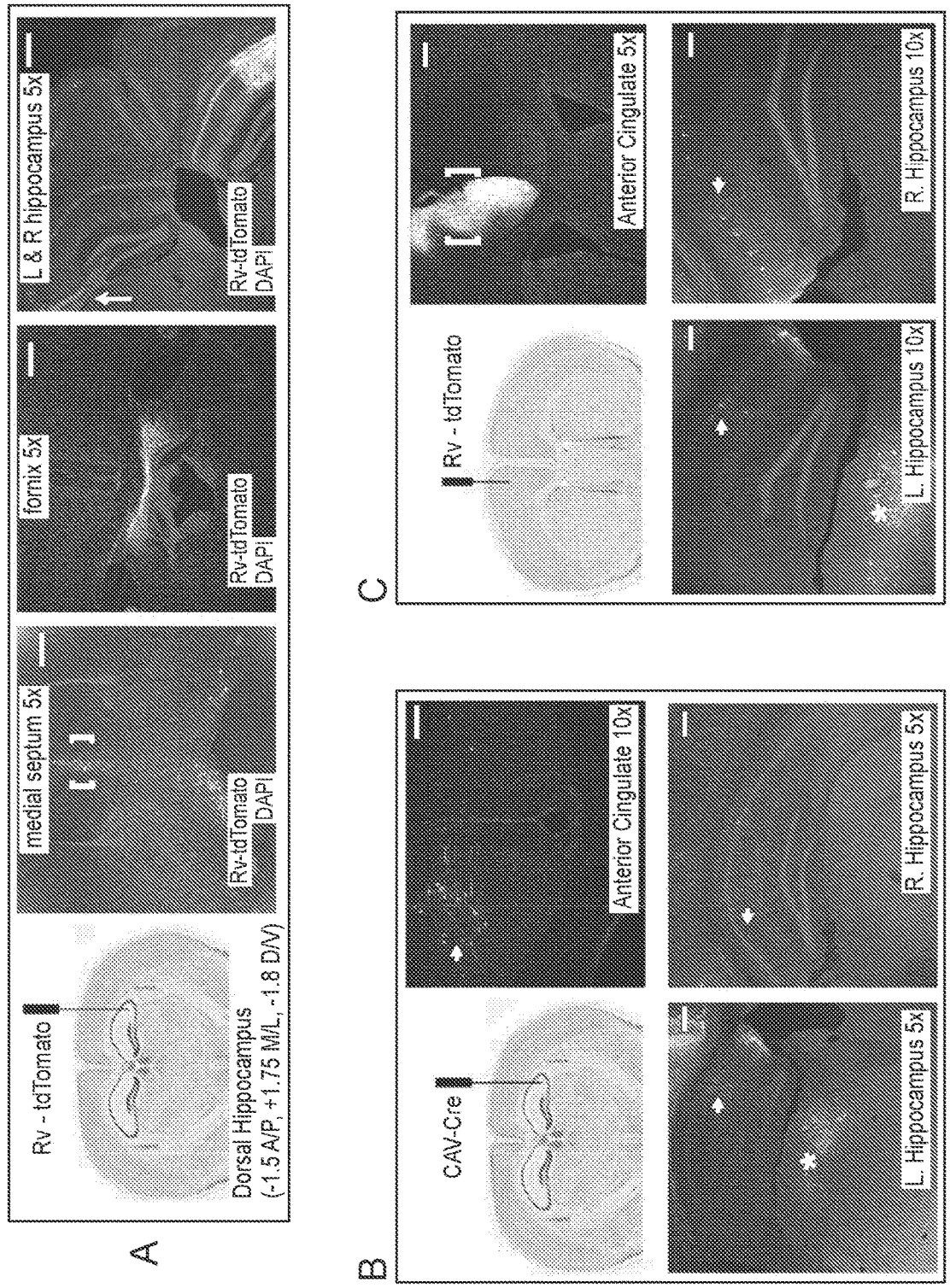
FIG. 12A-12C depict the anatomical characterization of the AC-CA projection.
Figure 13:
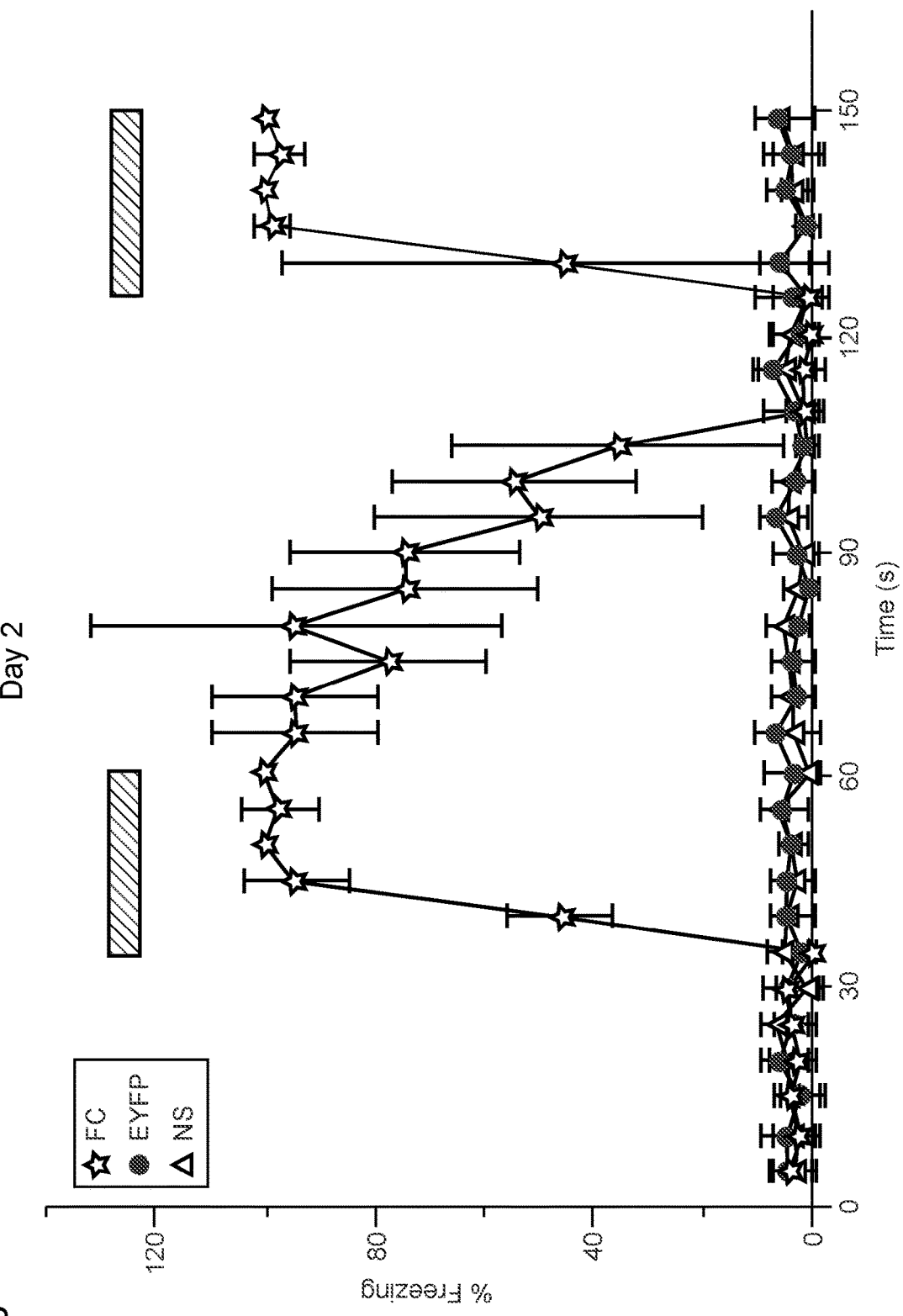
FIG. 13A-13G depict the optogenetic manipulation of the AC-CA projection.
Figure 13:
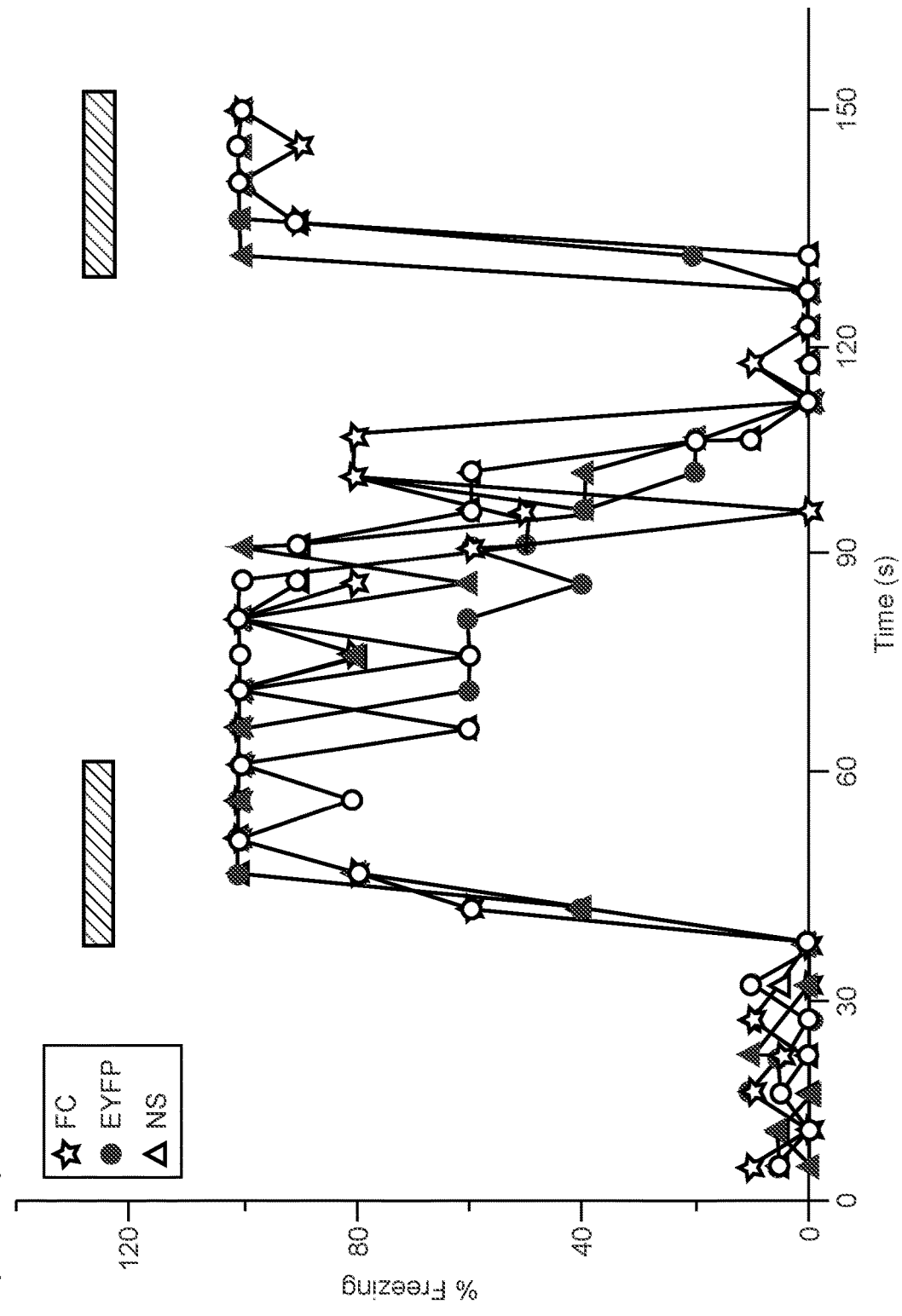
Figure 14:
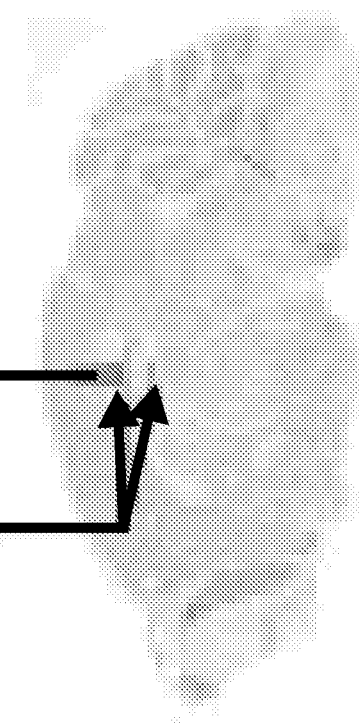
FIG. 14A-14L depict the effect of AC-CA projections on memory retrieval.
Figure 14:
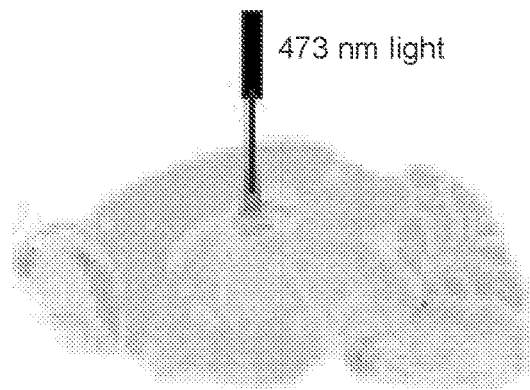

To identify direct top-down inputs to hippocampus, a retrograde tracer capable of labeling afferent neurons with tdTomato (RV-tdT[22]) was injected into the hippocampus. Robust tdT labeling was observed in brain regions with known inputs to hippocampus, including medial septum, contralateral CA3, and entorhinal cortex (FIG. 11A; FIG. 12A). Additionally, a previously-uncharacterized input was identified; the input arose from the dorsal anterior cingulate cortex (AC) and adjacent frontal cortical association cortex (FrC), both of which are reciprocally connected with the mediodorsal thalamic nucleus—a defining feature of the prefrontal cortex (PFC) in rodents (FIG. 11A; also confirmed with another retrograde tracer, canine adenovirus or CAV[23]; FIG. 12B). Injection of RV-tdT in AC also sparsely labeled neurons bilaterally in dorsal hippocampus consistent with potential bidirectional communication between AC and hippocampus (FIG. 12C). To further validate the existence of this novel prefrontal-to-hippocampus projection, an anterograde label (AAV5-EYFP) was injected into dorsal anterior cingulate (FIG. 12B) and fluorescence-filled projection terminals bilaterally in striatum and ipsilaterally in the medial dorsal thalamic nucleus (both areas known to receive projections from PFC), but also bilaterally in the hippocampus was detected.

To determine if these prefrontal projections gave rise to direct monosynaptic drive of hippocampal neurons, anterior cingulate was transduced with AAV encoding a channelrhodopsin, and patch clamp recordings of light-driven excitatory postsynaptic currents (EPSCs) in CA1/CA3 cell bodies (FIG. 11C) were performed. Cells in both CA1 (FIG. 11D) and CA3 (FIG. 11F) reliably responded to light pulse trains, and generated evoked EPSC amplitudes sufficient to drive action potentials (FIG. 11H and FIG. 11I). Responses when present were fast, with mean latency of 3.2 ms in CA1 (n=26, FIG. 11E) and 2.7 ms in CA3 (n=13, FIG. 11G); along with the observation of sustained evoked spikes following 10 Hz stimulation (FIG. 11H and FIG. 11I) this finding was consistent with the presence of a direct and efficacious monosynaptic connection from anterior cingulate onto hippocampal pyramidal cells CA3/CA1, which is accordingly termed the AC-CA projection. No responses were observed in dentate neurons (FIG. 11J).

FIG. 11A-FIG. 11J. Characterization of AC-CA monosynaptic projection. a, 5d after RV-tdT injection in hippocampus (coordinates specified), retrogradely-labeled neurons were detected in AC (arrowhead). Injection did not leak below hippocampus into medial dorsal thalamus (asterisk), a known projection target of PFC. Scale: 5×: 300 µm; 10×: 100 (confocal). b, 5 weeks after AAV5-CaMKIIα::EYFP injection in AC (coordinates specified), projection fibers were visualized in bilateral striatum (arrows), bilateral hippocampus at the stratum oriens and stratum radiatum of CA1 (one asterisk) and CA3 (two asterisks), ipsilateral medial dorsal thalamus (arrowhead), while sparing CA2 and dentate (brackets). Injection did not leak into medial septum, a known input to hippocampus (caret). Scale: 5×: 300 µm; 20×: 60 (100 µm max projections). c, AAVdj-CaMKIIα::ChR2(H134R)-EYFP was injected into dorsal AC; postsynaptic responses recorded from CA1 pyramidals in acute slice. d, CA1 response amplitudes (n=26 neurons, n=6 mice); inset: raw traces. e, CA1 response latency (mean 3.2 ms). f, CA3 response amplitudes (n=13 neurons, n=2 mice); inset raw traces. g, CA3 response latency (mean 2.7 ms). h, CA1 and CA3 (i) current clamp traces illustrating spiking-following reliability at 10 Hz. Scale: 10 mV, 250/500 ms. j, No responses detected in dentate neurons (n=5).

FIG. 12A-FIG. 12C. Anatomical characterization of the AC-CA projection. a, 5d after RV-tdT injection in hippocampus (coordinates specified), retrogradely-labeled neurons were detected in contralateral hippocampus (arrow), medial septum (bracket), and AC (FIG. 11A). Scale bar: 5×: 300 µm; 10×: 100 µm (confocal). b, 8 weeks after injection of CAV-Cre in hippocampus and DIO-EYFP in anterior cingulate (coordinates specified), afferent cell bodies were detected in anterior cingulate (arrow). Confocal image; 10× magnification; scale: 100 µm. c, Retrograde tracing with RV-tdTomato from anterior cingulate to map reciprocal connections from hippocampus. Injection site indicated in brackets, sparse labeling of afferent cell bodies in left and right hippocampus, primarily in the subiculum (arrows), and also in the medial dorsal thalamic nucleus as expected (asterisk). Confocal 5×, Scale: 200 µm; 10× images, Scale: 100 µm.

AC-CA: Causal Role in Contextual Memory

To probe the functional significance of this projection, a series of optogenetic experiments was conducted to manipulate this pathway before and after contextual fear conditioning, and also in the setting of memory extinction and reinstatement. RV-ChR2-EYFP (or RV-EYFP) was injected into dorsal hippocampus, and targeted light-delivery to retrogradely-labeled cell bodies in AC (FIG. 13A). On day 1, ChR2 and EYFP mice underwent contextual fear conditioning in one context, while a ChR2-expressing control group was exposed to context without shock. On day 2, all mice were placed in a different context, in which the ChR2-expressing fear-conditioned group (n=8) showed significant fear behavior (freezing) only during light stimulation, compared with unconditioned ChR2 (no-shock, n=6) or shocked control groups (EYFP, n=6, p<0.001, two-way ANOVA with repeated measures, FIG. 13B). The time-to-freezing and time-to-unfreezing with light on/off switching were largely consistent across animals. On day 3, mice were placed back in the original context, verifying in both ChR2 and EYFP fear-conditioned cohorts strong memory encoding and retrieval, with significantly greater levels of freezing compared to no-shock controls (FIG. 13C, P<0.001, unpaired t-test).

This observation that cells contributing to the AC-CA projection can activate contextually-conditioned fear behavior was replicated and extended using a complementary anterograde projection-targeting strategy. AAVdj-ChR2-EYFP (or AAVdj-EYFP in a parallel cohort) was injected in anterior cingulate, and light stimulation was targeted to terminals in the hippocampus (FIG. 14A). Significant freezing to optical stimulation in neutral context was observed, only in the ChR2 group compared to the no-shock and EYFP controls (FIG. 14B, n=8 for all groups; p<0.001, two-way ANOVA with repeated measures). These animals exhibited the same characteristic latency to freezing during light as in the previous experiment. Whether this consistent behavioral response was indeed due to re-activation of a fear memory, rather than due to direct nonspecific drive of fear behavior, was tested. The same mice corresponding to FIG. 14A and FIG. 14B were subjected to several days of contingency degradation by exposure to context A without shock (Methods), after which stimulation with light failed to produce significant freezing in ChR2 animals, as with no-shock and EYFP controls (FIG. 14C). Fear conditioning was then re-instated in these mice in a new context, after which light stimulation once again reliably produced freezing in ChR2 mice compared with no-shock and EYFP controls (FIG. 14D, n=8 for all groups; p<0.001, two-way ANOVA with repeated measures). Preservation of contextual fear memory on day 3 and successful fear memory extinction on day 14 were confirmed (FIG. 14E). While these data demonstrated that cells contributing to the AC-CA projection can drive fear memory recall, it remained possible that any drive of hippocampus could induce retrieval of a recent strongly-represented memory in hippocampus. However, no evidence for this possibility was found with two additional control experiments, either directly driving a different (septo-hippocampal) projection (FIG. 14F and FIG. 14G) or directly driving hippocampus itself (FIG. 14H and FIG. 14I). Preservation of normal contextual fear memory in these mice was confirmed as before (FIG. 13D and FIG. 13E, n=8, P<0.001, paired t-test).

Extension of findings from effective loss-of-function experiments (FIG. 14A-FIG. 14L) targeting hippocampus-dependent memory formation mediated by cells giving rise to the AC-CA projection: significant effect on speed of onset of memory expression. Experimental design: CAV-Cre was injected in dorsal hippocampus, DIO-eNpHR3.0 (or DIO-eYFP) was injected in AC, and light delivered above cell bodies in AC. All mice were fear conditioned in context A (day 1), tested for latency to contextual retrieval with light on only (day 2), and then for latency to context retrieval in light off only (day 3). Day 2: 66.1±18.1 s for eNpHR3.0 (n=12) vs 43.8±11.1 s for EYFP (n=8) during light on; Day 3: 53.8±13.7 s for eNpHR3.0 vs 48.8±7.7 s for EYFP during light off; P<0.05 two-way ANOVA with repeated measures).

FIG. 13A-FIG. 13G. optogenetic manipulation of the AC-CA projection. a, Experimental design: RV-ChR2-EYFP (or EYFP alone) was injected in dorsal hippocampus and light delivered above cell bodies in anterior cingulate. 5d after injection, ChR2 and EYFP mice were fear conditioned in context A while no-shock controls were only exposed to context A (day 1). All mice were tested with light on and off sessions in context B (day 2), and then tested for contextual memory retrieval in context A (day 3). Optogenetic stimulation was with 473 nm light in a train of 20-Hz, 15 ms pulses, 30 s duration, with 8-10 mW laser power at fiber tip. b, Freezing (no head motion observed) during Day 2 is plotted in 5 s time bins over 150 s in context B (left). ChR2/shock (FC): black; ChR2/no shock (NS): red; EYFP/shock (EYFP): blue. Individuals in FC group (each animal a different color) are shown (middle). Summary (right): % time freezing (mean±s.d.) 20 s before light on (darker shade) vs 20 s after light on (lighter shade); FC: 60.9±7.4% light on vs 6.5±4.4% light off, n=8; NS: 2.7±0.65% light on vs 3.4±0.95% light off, n=6; EYFP: 2.9±0.75% light on vs 3.6±1% light off, n=6; P<0.001, two way ANOVA with repeated measures). c, Preservation of contextual fear memory (% time freezing) on Day 3 in the original context (mean±s.d., P<0.001, unpaired t-test). d, Preservation of contextual memory in medial septum injected mice (FIG. 11F); % time freezing on Day 3 in original context (mean±s.d., P<0.001, comparisons shown, unpaired t-test). e, Preservation of contextual memory in hippocampus injected mice (FIG. h); % time freezing on Day 3 in original context (mean±S.D., n=8 mice, P<0.001, paired t-test). f, The successful loss-of-function experiments targeting hippocampus-dependent memory formation mediated by cells giving rise to the AC-CA projection (reported in FIG. 14A-FIG. 14L) were designed to allow the most robust inhibition of this circuit element. An alternative design (attempting to target the projection field despite the broad and long septotemporal extent of the hippocampal formation) was also explored as shown here but was not effective, as expected; AAV5-eNpHR3.0-EYFP (or AAV5-EYFP in a parallel cohort) bilaterally was injected in anterior cingulate, and targeted light stimulation bilaterally to axon terminals in the hippocampus. 8 wks after injection, all mice were fear conditioned to context (day 1), and tested for context retrieval during light on/off sessions (day 2), and again for context retrieval in light off only (day 3). Optogenetic inhibition was with constant illumination of 589 nm light, 30 s duration, with 8-10 mW laser power at fiber tip. g, a trend toward reduction in freezing due to optical inhibition of the AC-CA projection during memory retrieval was observed. % time freezing in context A during Day 2 before light (darker bar on left) vs after light (lighter bar at right). eNpHR3.0: 73.5±8.5% light off vs. 55.5±11.4% light on, n=10; EYFP: 74±7.4% light off vs. 74±11.3% light on, n=10; % time freezing in context A with light off (dark bars) during Day 3 is shown after dotted line. eNpHR3.0: 67.5±7.2%, n=10; EYFP: 66.5±9.1%, n=10 (P=0.067, two-way ANOVA). As expected, point illumination may be less effective for inhibiting broad axon terminal field volumes.

FIG. 14A-FIG. 14L. AC-CA projections control top-down memory retrieval. a, AAVdj-CaMKIIα::ChR2-EYFP (or EYFP alone) injected in AC, light targeted to dorsal hippocampus 5 weeks post injection. Timelines indicated. b-d, % time freezing, Days 2, 15, 17: 5 s time bins (n=8; P<0.001, two-way ANOVA with repeated measures); Summary bar graphs below are mean±s.d. 20 s before light (dark bar) vs. 20 s after light (lighter bar). e, Preservation of contextual memory (Day 3) and contextual extinction (Day 14), original context A (mean±s.d., n=8, P<0.001, paired t-test). f, AAVdj-CaMKIIα::ChR2-EYFP (or EYFP alone) injected in medial septum; light stimulation targeted to dorsal hippocampus 5 weeks after injection. g, % time freezing during Day 2: 10 s time bins. summary bar graph at right (n.s. unpaired t-test). h, AAVdj-ChR2-EYFP (or EYFP alone) injection and light targeting to dorsal hippocampus 5 weeks after injection. i, % time freezing during Day 2, 5 s time bins. summary bar graph at right (n=8, n.s., paired t-test). j, CAV-Cre injected in dorsal hippocampus, DIO-eNpHR3.0 (or DIO-eYFP) injected in AC, light delivered above cell bodies in AC 8 weeks after injection. k, % time freezing in context A, Day 2 before light (dark bar) vs after light (lighter bar). this effect is reversible on Day 3 (after dotted line). (eNpHR3.0: n=12; EYFP: n=8; P<0.001, two-way ANOVA with repeated measures). 1, Cued conditioning on day 1 followed by retrieval to the tone on day 2 during light on/off sessions.

The above experiments demonstrated that activating AC-CA projecting cells was sufficient to induce contextual memory retrieval; necessity was next tested by targeting the inhibitory opsin eNpHR3.0 to cells giving rise to the projection (FIG. 13F and FIG. 13G), with light targeted focally and bilaterally to AC-CA cell bodies (FIG. 14J). Striking deficits in both the latency and the strength (FIG. 14K, n=12 for eNpHR3.0 group, n=8 for eYFP group, p<0.001, two-way ANOVA with repeated measures) of the fear response in the eNpHR3.0 group compared to EYFP controls were observed. This effect was fully reversible (FIG. 14K). It was found that eNpHR3.0 mice demonstrated intact auditory cued memory recall (FIG. 14L, n=8 for all groups, n.s. with paired t-tests), confirming that the loss-of-function experiments described above represented a hippocampus-specific effect of the AC-CA projecting cells.

Taken together, these anatomical, electrophysiological, and behavioral data reveal the existence of a previously uncharacterized monosynaptic prefrontal-to-hippocampus projection. When this circuit is inhibited, fear-conditioned mice are unable to retrieve the fear memory with the same strength or speed as control counterparts, indicating endogenous importance for memory retrieval. In contrast, activation of this circuit is sufficient for robust fear memory retrieval in recently conditioned mice, but not in naive un-conditioned mice, mice in which the memory had been extinguished, mice not expressing opsin, or mice receiving other types of direct or indirect drive of hippocampus.

Highly-Correlated Neurons Emerge During Learning

Figure 15:
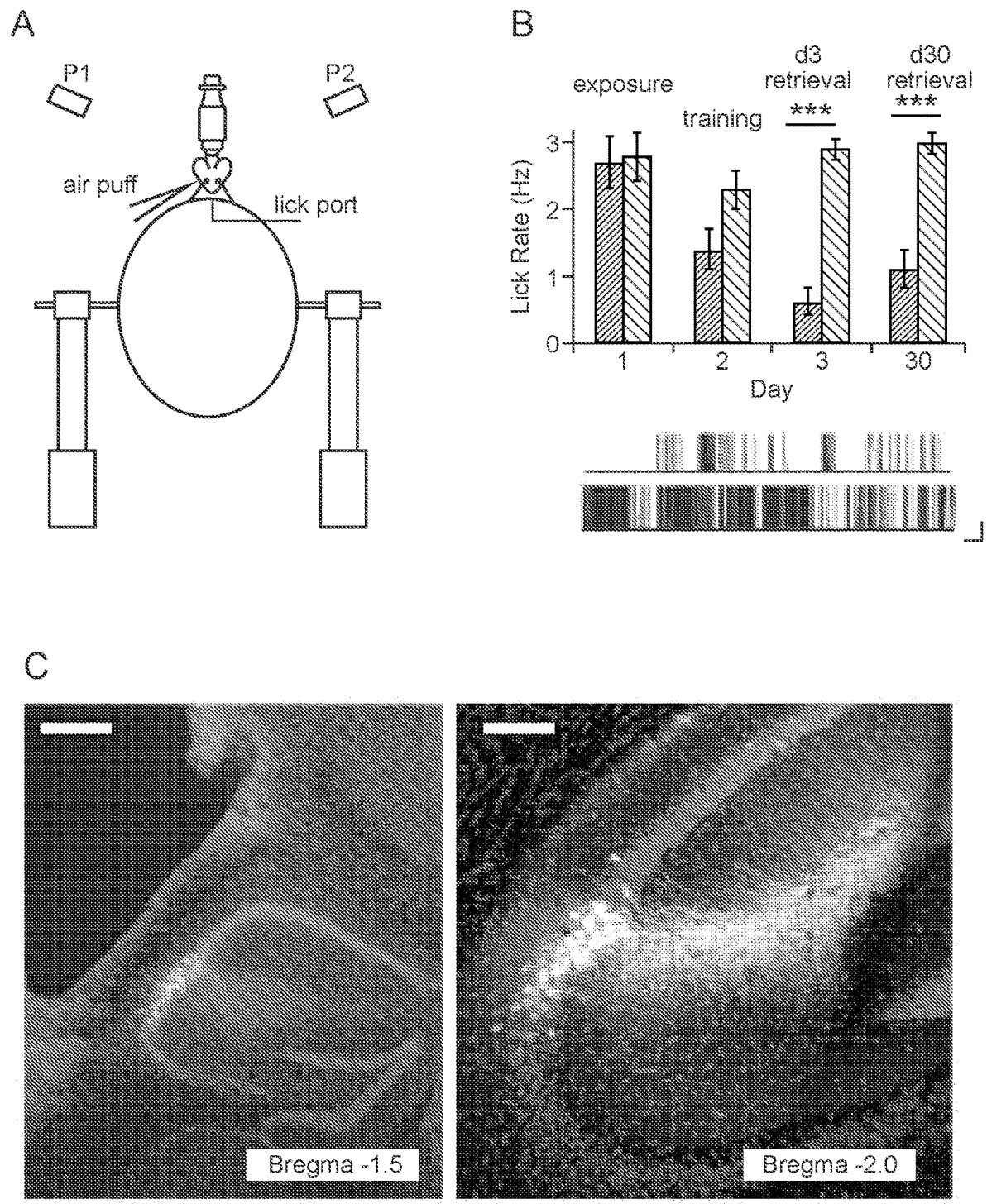
FIG. 15A-15L depict that memory formation generates highly-correlated HC neurons that represent context.
Figure 15:
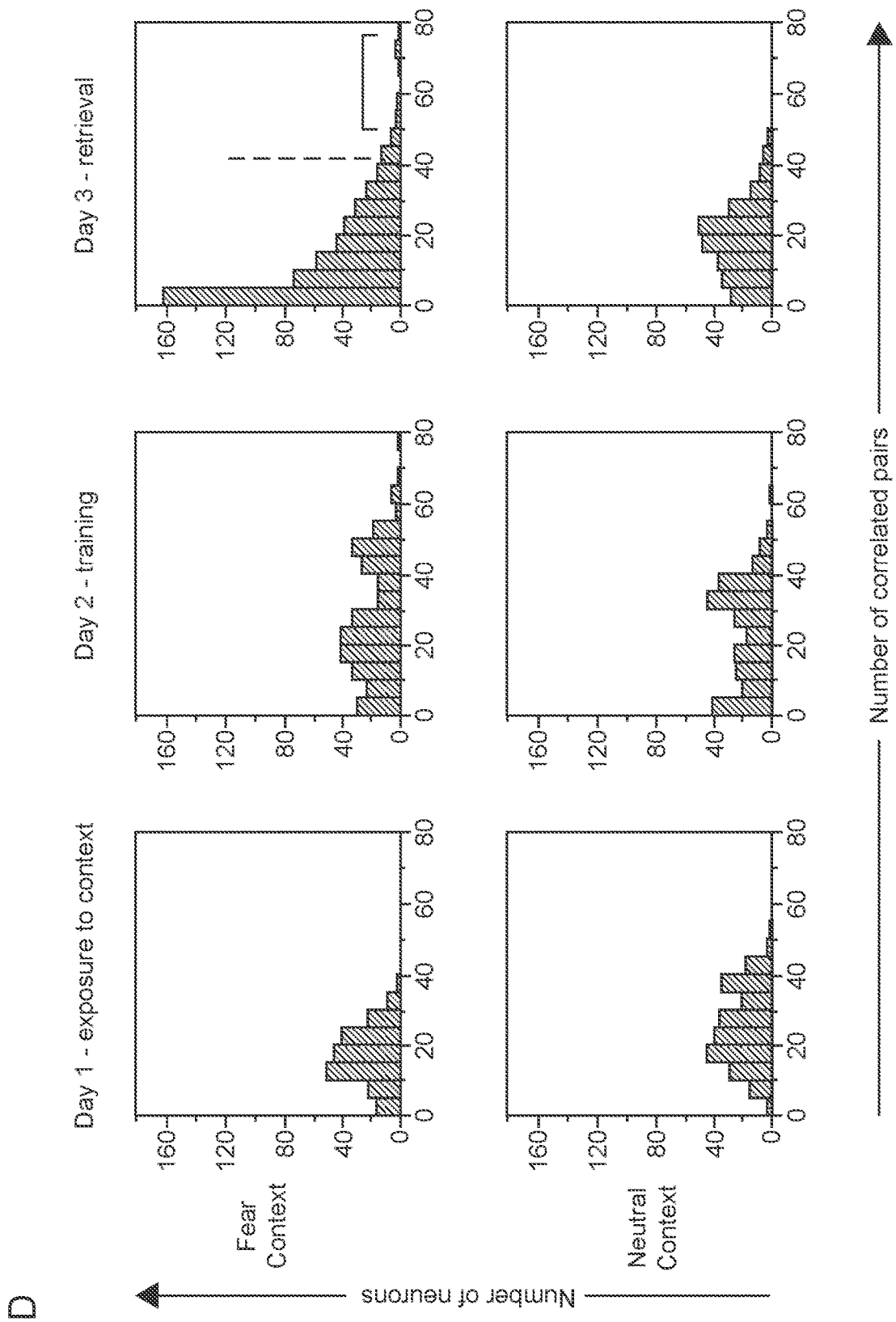
Figure 15:
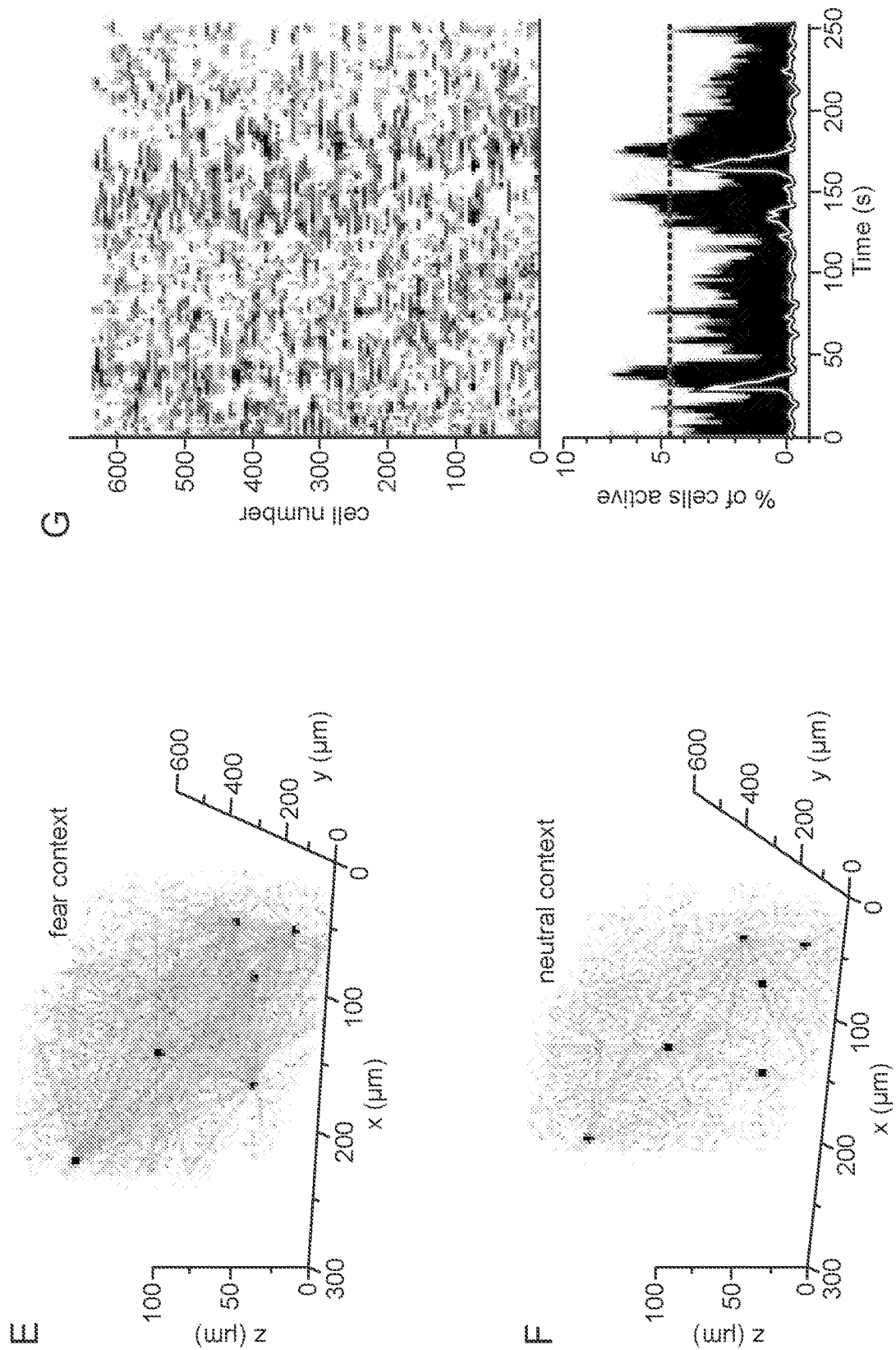
Figure 15:
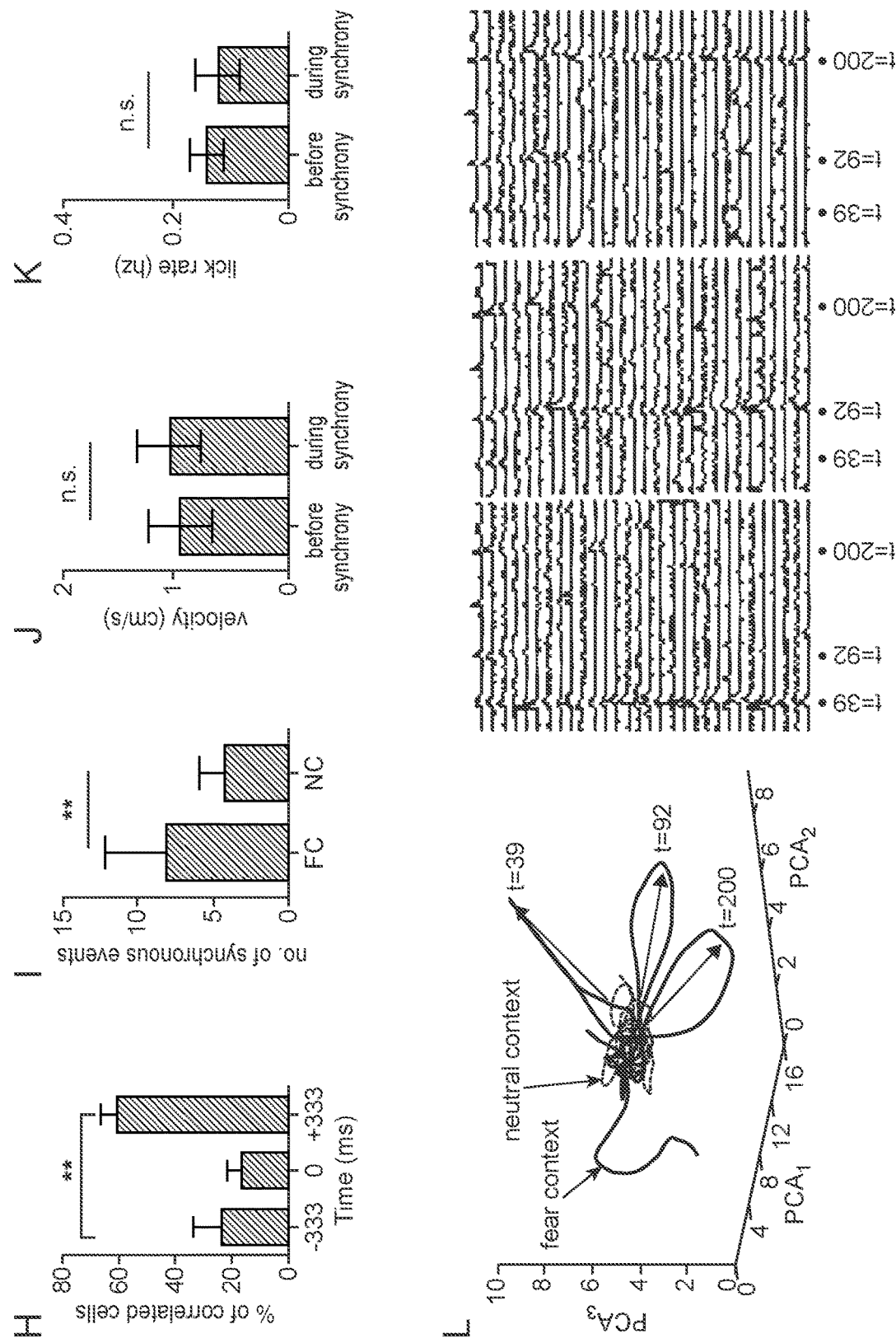
Figure 18:
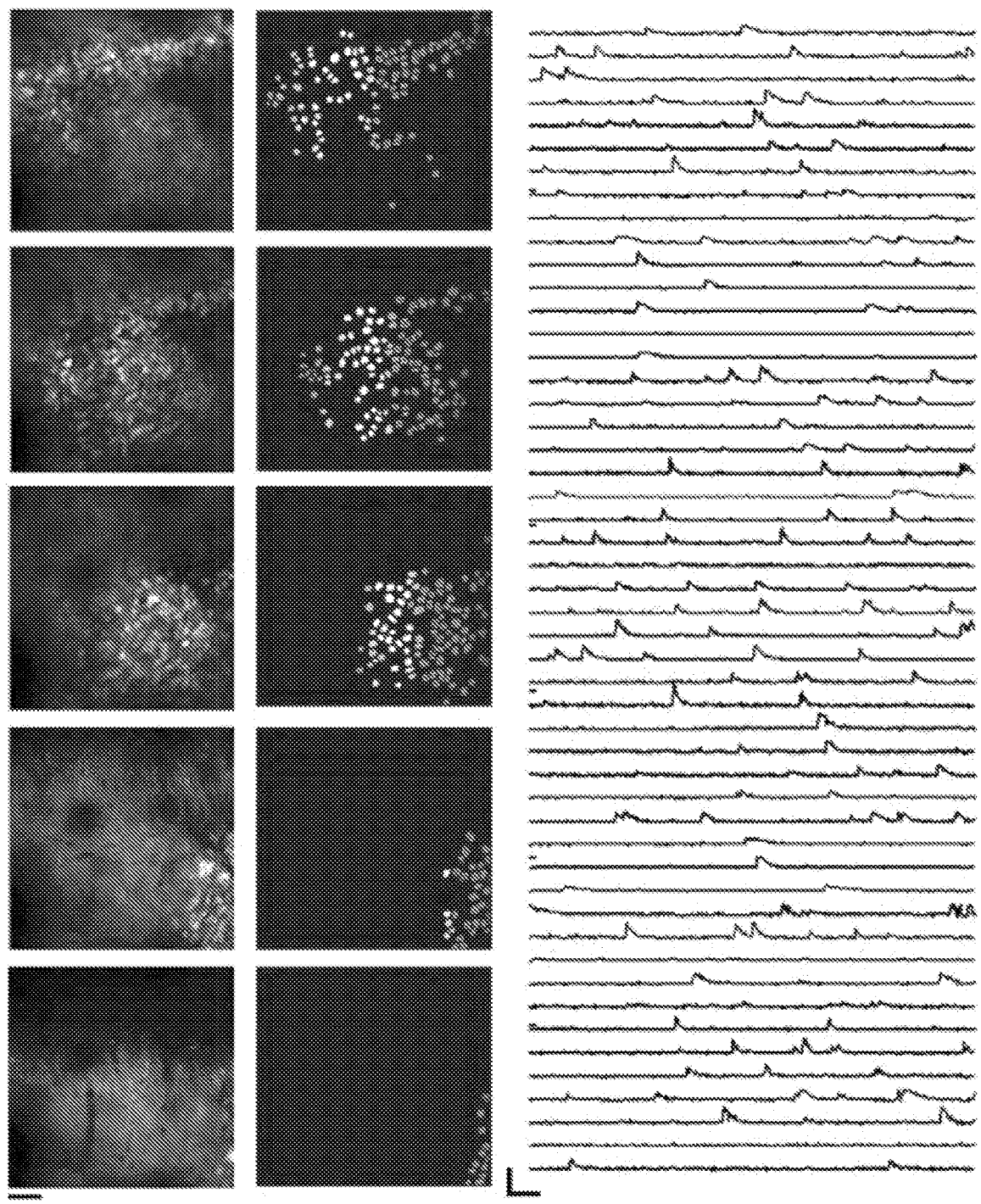
FIG. 18A-18F depict real-time imaging of neural ensembles in 3D hippocampal volumes.
Figure 18:
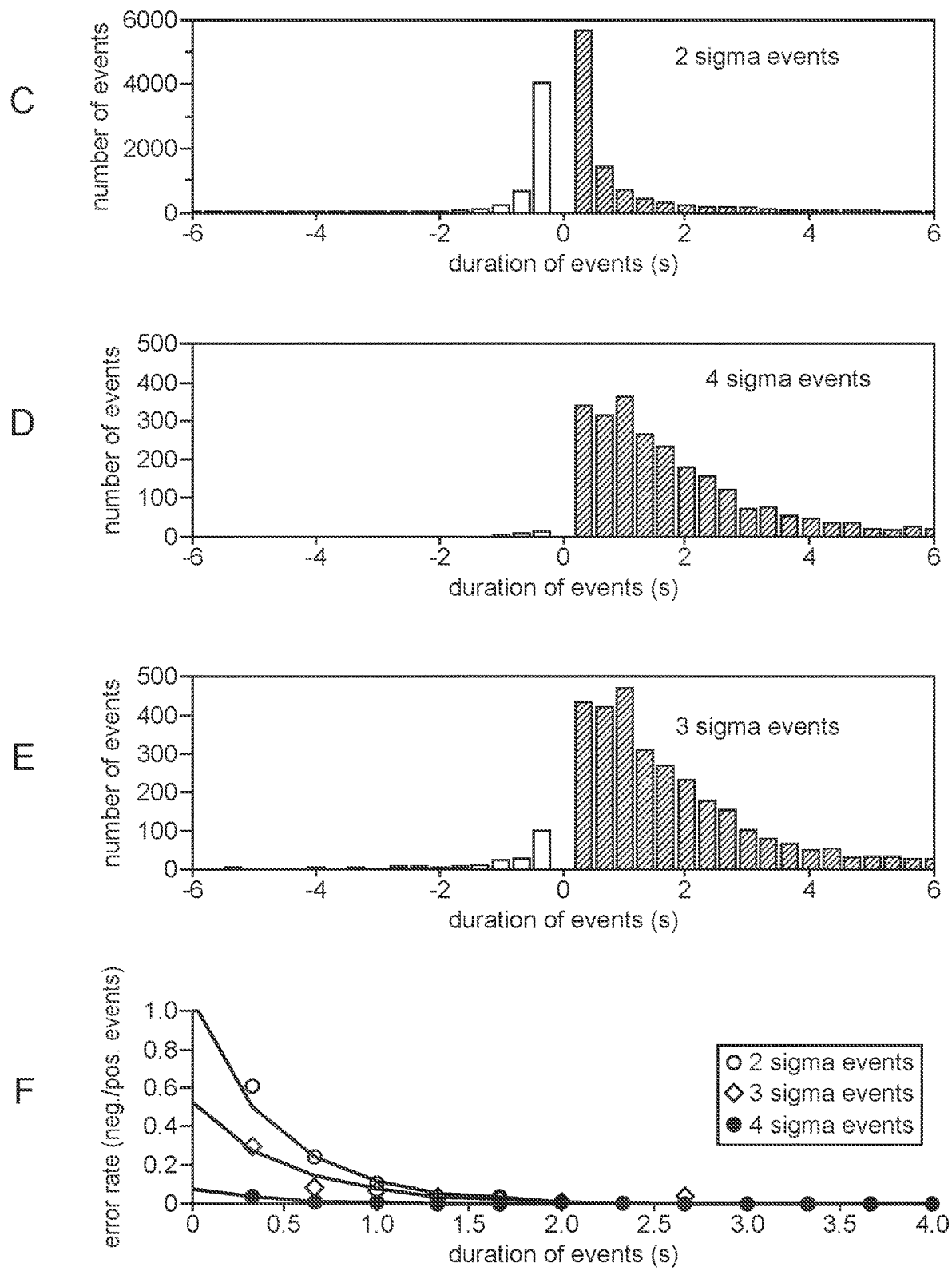

To observe real-time influences of the AC-CA projection on hippocampal network activity, the fear-conditioning paradigm to head-fixed mice navigating in a virtual environment (VE) on an axially-fixed track ball under a two-photon microscope[24] was adapted. Lick-suppression, rather than immobility, was used as a measure of fear behavior[25-27] (FIG. 15A; Methods); mice learned this task and displayed significant lick suppression during retrieval in the fear context indicating successful memory retrieval (FIG. 15B, n=12, P<0.01, paired t-test). For imaging during behavior, mice were injected with the genetically-encoded $Ca^{2+}$ indicator GCaMP6 m[28], implanted with a cranial window above CA3 (FIG. 15C, confirmation of normal hippocampal physiology and behavior in these mice shown in FIG. 16A-FIG. 16F), and imaged daily in both contexts during training and retrieval (FIG. 18A). In all cases, fast volumetric (500×500 μm x/y, 100 μm z) two-photon imaging was performed providing access to >400 neurons (FIG. 18B).

Figure 19:
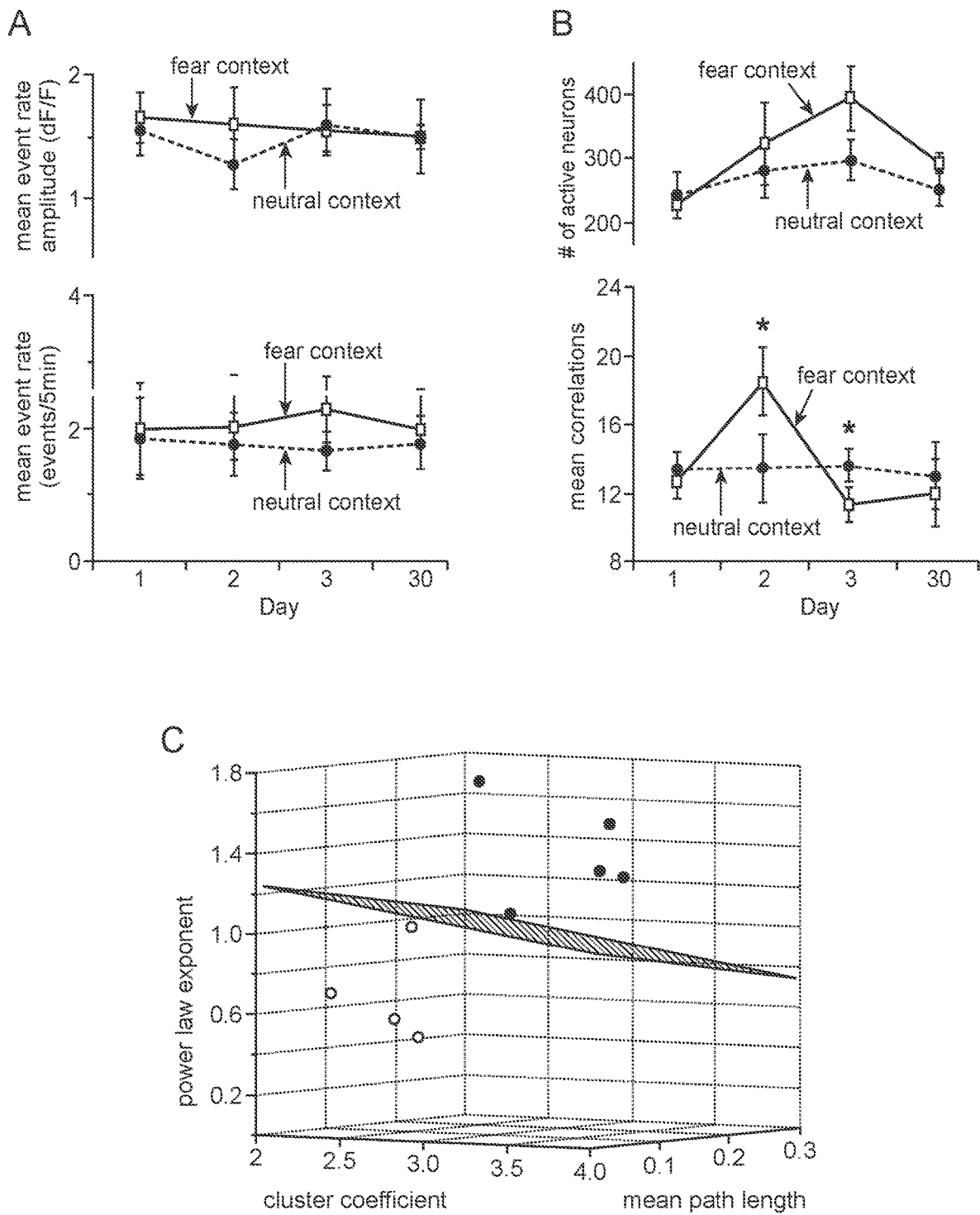
FIG. 19A-19J depict cell populations and graph properties of fear and neutral networks in hippocampus during retrieval.
Figure 23:
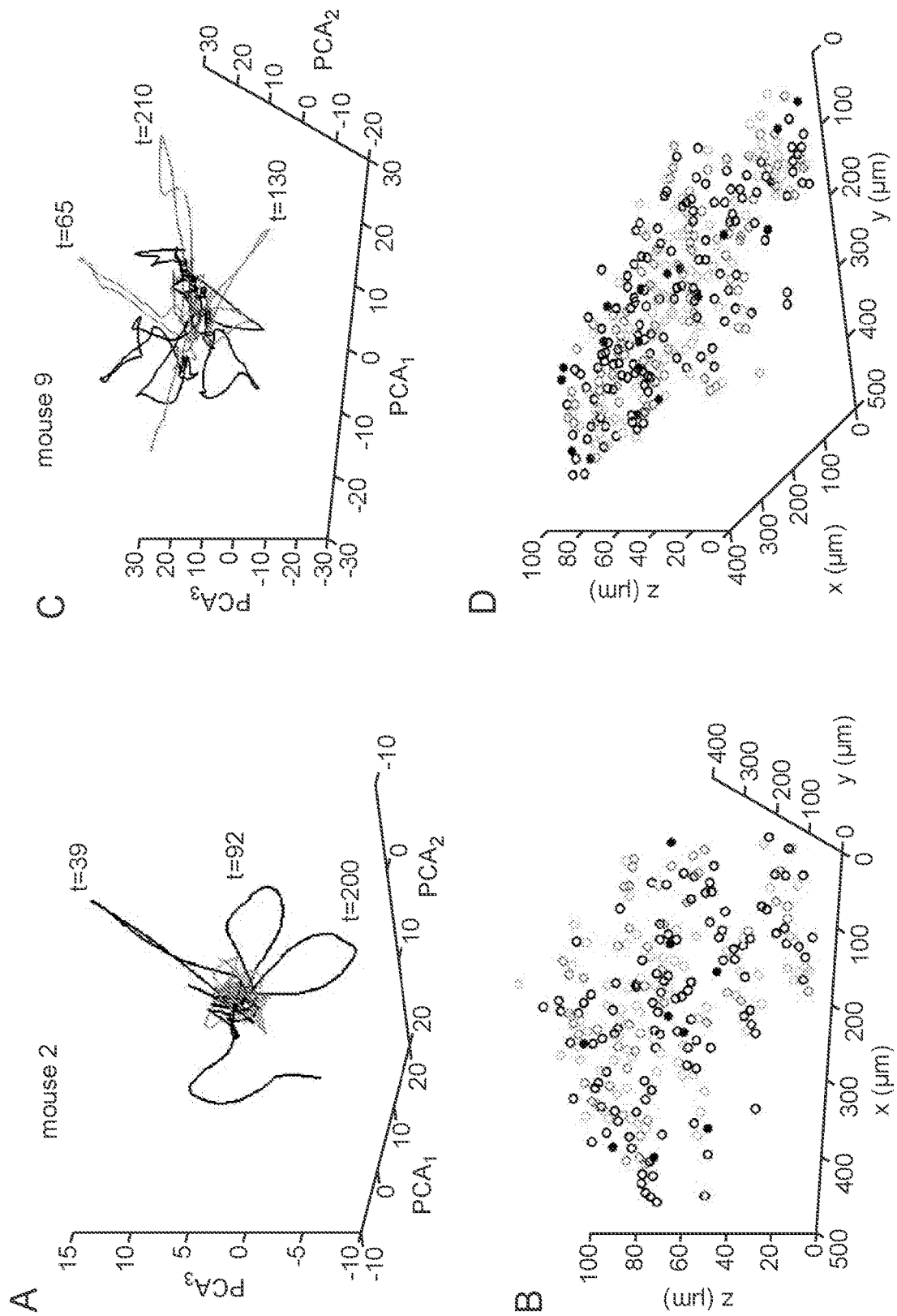
FIG. 23A-23E depict PCA of population trajectories in fear vs. neutral contexts.
Figure 24:
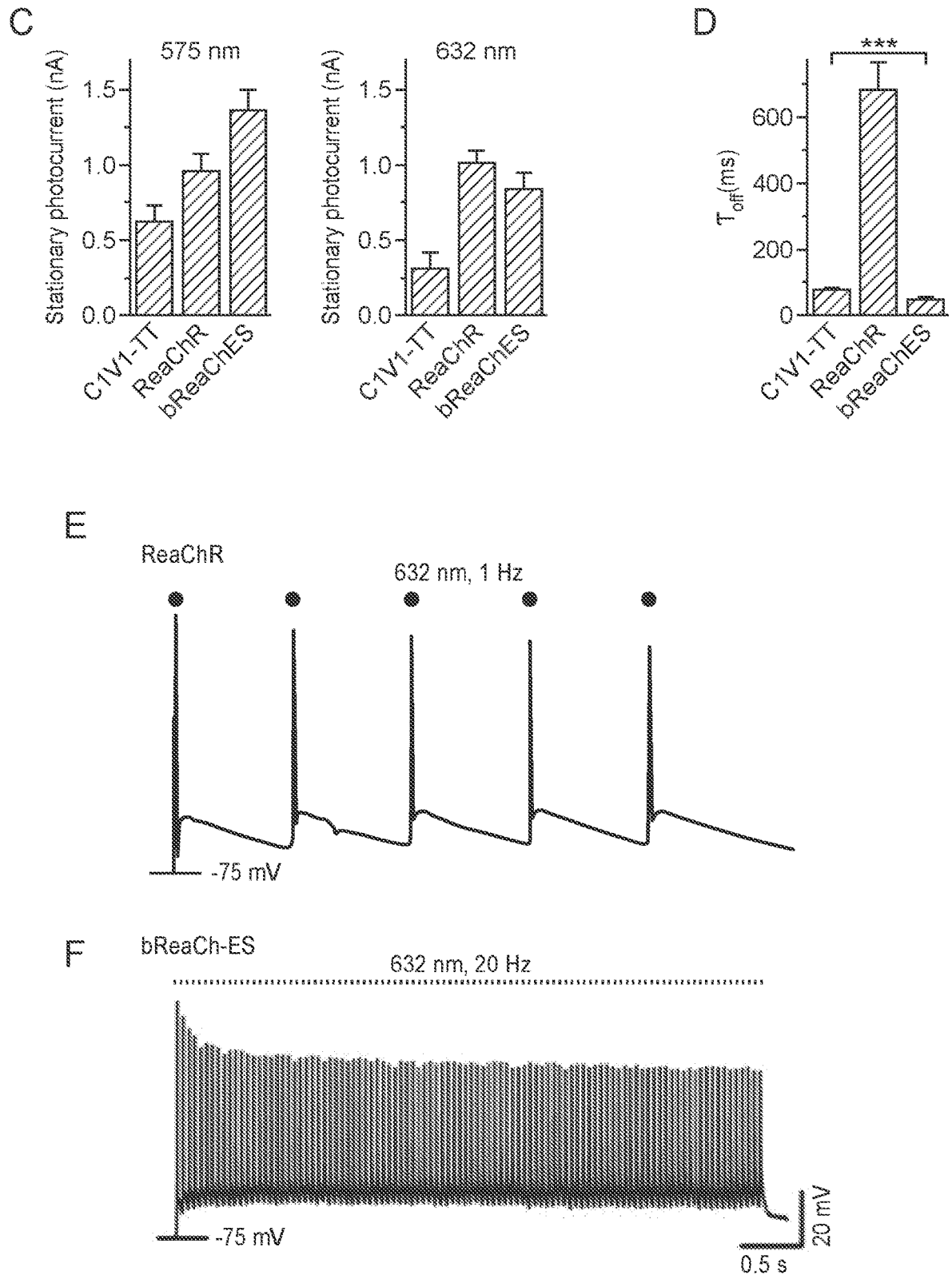
FIG. 24A-24L depict design and characterization of bReaChE-S.
Figure 24:
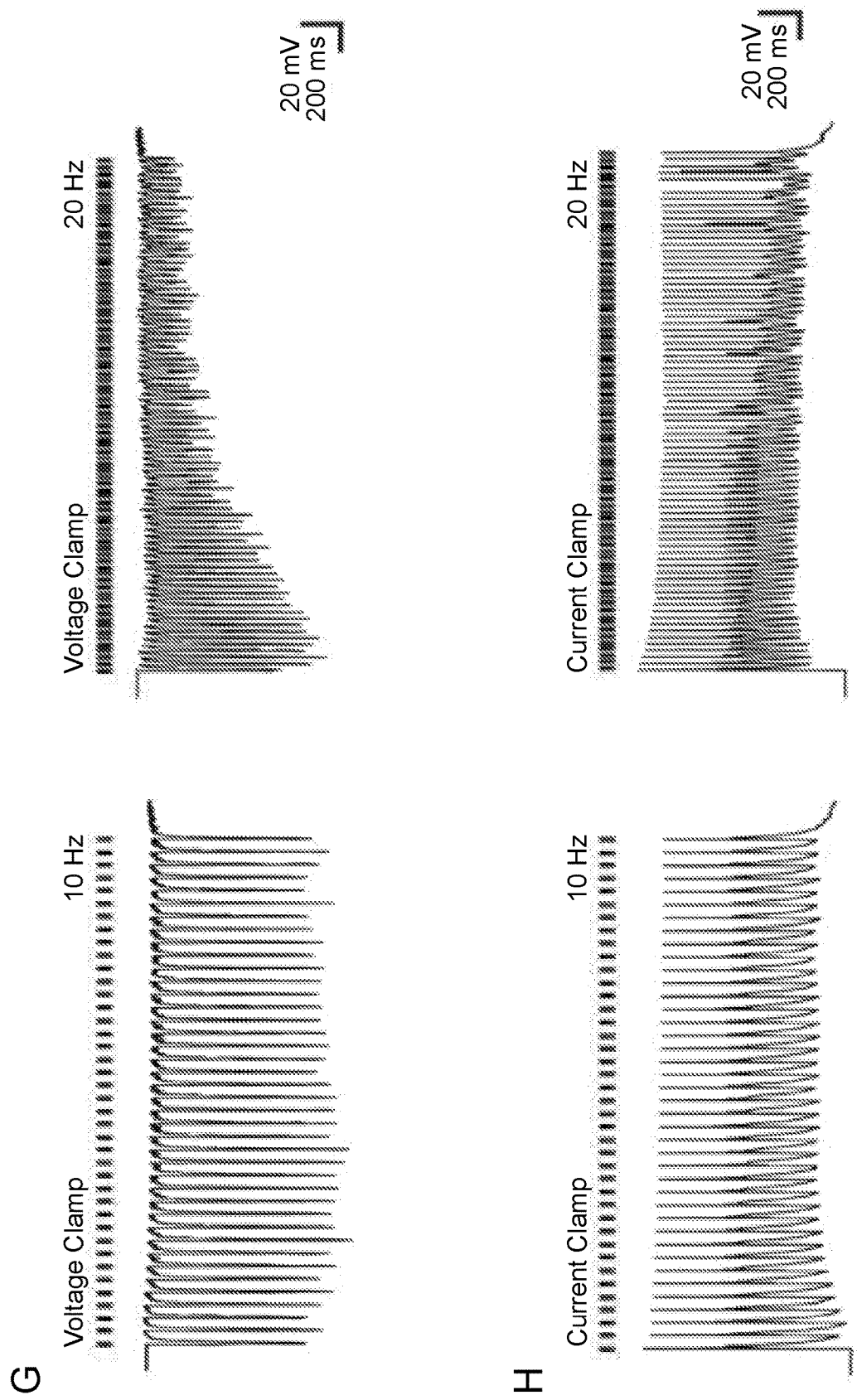
Figure 24:
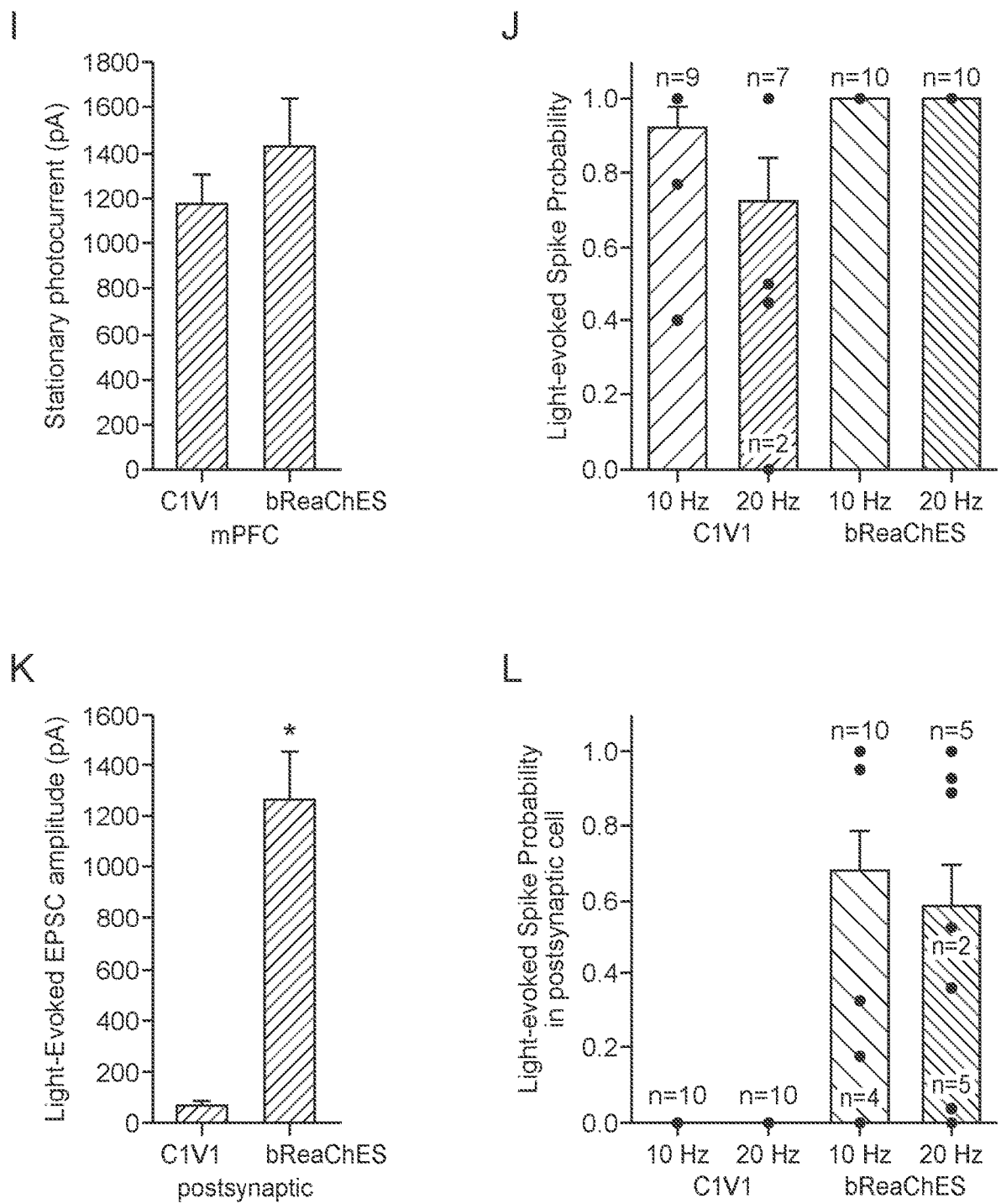

FIG. 15A-FIG. 15L. Memory formation generates highly-correlated HC neurons that represent context. a, Head-fixed virtual reality setup. Fear quantified by lick suppression (Methods). b, Lick rates in fear (black) vs neutral (gray) contexts (mean±sd; n=12, P<0.001, paired t-test). Sample day 3 raw lick profiles in fear (top) vs neutral (bottom) context (Scale: 1V, 20 s). c, Histology performed four weeks after injection/surgical implantation showing implant above GCaMP6m expressing neurons. Left: 10×; Scale: 200 μm. Right: 20×; Scale: 50 μm. d, Histograms showing number of correlated partners for each neuron in fear vs neutral contexts for a representative mouse (see FIG. 19). e, HC neurons in fear context (red) have few correlated partners in neutral context (f), n=4 mice (60±18.2 (s.d.) fear vs 18±15.8 in neutral context; P<0.01, paired t-test; see FIG. 20). g, Raster plot (above) and collapsed activity histogram (below) during memory retrieval in one mouse; Representative HC neuron timeseries overlaid (red). h, HC neuron activity onset (time 0) compared with onset activity of their correlated pairs (n=67 HC neurons, 60.3±6% leading vs 23.2±10% lagging; P<0.01, unpaired t-test). Synchronous activity (Methods) quantified (n=5, 8.1±4 events in fear vs 4.2±1.6 in neutral context; P<0.01, paired t-test), and were not accompanied by significant changes in velocity (j) or lick rate (k) (n=5 mice; n.s., paired t-test). 1, Principal component analysis from representative mouse (FIG. 23 for additional datasets). Population trajectory in fear (red) vs neutral context (blue) projected onto the respective first 3 principal components. Right: dF/F traces of HC neurons and their correlated neurons participating in each deflection. Scale: 400% dF/F, 20 s.

FIG. 16A-FIG. 16F. Physiological properties of GCaMP6m-expressing CA3 neurons. a, To ensure that expression of GCaMP6m did not alter $Ca^{2+}$-related physiological processes, a form of endocannabinoid-mediated short-term plasticity known as DSI (Depolarization-induced Suppression of Inhibition) was tracked. Schematic diagram of DSI shown; DSI is dependent on the increase of post-synaptic intracellular $Ca^{2+}$ to trigger the synthesis and release of endocannabinoids, which then signal in retrograde fashion to suppress GABA release from presynaptic inhibitory neurons expressing cannabinoid receptors (Adapted from Lee et al., (2011) J Neurosci. 31:10993-1002). Intrinsic membrane properties of the GCaMP6m-expressing CA3 cells were similar to previously-reported values for CA3 (Kohara et al. Nat Neurosci. 2014 17:269-79); mean resting potential: −72.1±1.6 mV, mean input resistance: 161.8±26.4 MΩ, n=7). b, Sample trace illustrating DSI of sIPSCs in a GCaMP6m-expressing CA3 cell following application of a depolarizing current step (from −65 mV to 0 mV for 500 ms). c, Sample trace illustrating lack of DSI of sIPSCs with inclusion of intracellular BAPTA in the patch pipette. d, Summary graph of normalized charge transfer in GCaMP6m-expressing cells with standard intracellular solution (left, normalized charge transfer of sIPSCs following DSI compared to pre-pulse baseline over the same fixed interval: charge reduced to 46.9±6.7% of baseline charge; n=7; comparable to charge transfer reported for non-GCaMP expressing cells (Varga et al. Nat Neurosci. 2010, 13:822-24)) and with addition of intracellular BAPTA (right, n=6; error bars represent s.e.m; p<0.05, paired t-test). e, Spontaneous event rate (detection described in Online Methods) of GCaMP6m-expressing neurons as a function of baseline GCaMP6m fluorescence intensity (arbitrary units spanning the range over which event-rate population data could be reliably quantified) in each cell (pooling all neurons with >=1 significant transient, from all mice, over all FOVs). Event rates were not observed to change significantly as a function of GCaMP6m expression level (Spearman's rank correlation coefficient: 0.48, P=0.3). f, Behavioral scores from mice prior to GCaMP6m virus injection and implantation of cannulae above hippocampus; lick rates for the first 2 min in fear (black) vs neutral (gray) contexts are provided. The level of learning assessed by lick suppression on day 3 retrieval (mean 0.5±0.3 for day 3 fear vs 2.7±0.3 for day 3 neutral; n=10, P<0.001, paired t-test) pre-injection/implantation was comparable to levels corresponding to post-injection/implantation (compare with FIG. 15B).

FIG. 17A-FIG. 17F. The AC-CA projection preferentially recruits HCs neurons during memory retrieval. a, left: AAV8-CaMKII::bReaChES-EYFP or AAV8-CaMKII::C1V1-EYFP injected in AC; fiber terminals visualized in CA2/CA3 (red). (20×); scale: 60 μm. right: AAV8-CaMKII::tdTomato in AC, and AAVdj-CaMKII::GCAMP6m in CA3. Histology 8 weeks after cannula implantation showing preservation of AC-CA projections (red) near GCaMP6m expressing neurons (green). 20×. Scale: 50 μm. b, 2P imaging and full-field optogenetic stimulation setup (Methods). c, Z-projection images (mean over time) at two depths (40 μm apart) from a representative mouse before and after training. Scale: 60 μm. d, CDF (proportion of cells responding) to AC-CA stimulation as a function of latency (n=4 mice: 12 trials, p=0.002, Kolmogorov-Smirnov two-tail test, K=0.2673), Sample traces in inset (red box: stim duration). Consecutive trials overlaid. e, Optical stimulation in neutral context induces significant lick suppression after training (n=4 mice, 12 total trials, mean±sd, P<0.01, paired t-test). No lick suppression before training (n.s paired t-test). f, Fraction of fear- and neutral-context HC and non-HC neurons recruited during before—(n=3 mice, 10 total trial) and after-training optical stimulation (n=4 mice, 12 total trials, P<0.001, one-way ANOVA) mean, quartile, min and max shown.

Identification of features of the functional network that differed consistently across days or contexts was first sought. Many features were indistinguishable, including mean response magnitude of active neurons, mean activity event rate, mean activity event duration, and spatial distribution of active neurons (FIG. 18C-FIG. 18F, FIG. 19A-FIG. 19J). However, a significant increase in the number of neurons active during memory retrieval in the fear context (FIG. 19B, n=5 mice) was noted; interestingly, this was accompanied by a significant decrease in mean correlated activity. Though prior studies reported increased correlated activity after learning[29-31]; a parsimonious unifying explanation could be that reduced mean correlated network activity reflects a state of greater sparsity after learning wherein few neurons engage in significantly higher correlated activity while most become de-correlated. Indeed, binning the number of correlated partners for each neuron and fitting the histograms to the distribution $ae^{-bx}$ revealed a significant distribution shift (FIG. 15D, FIG. 19D), from randomly-organized Poisson-like correlation distributions before learning, to more ordered, power law-like distributions after learning, with the emergence of a small population of neurons displaying highly correlated activity in the network (HC neurons). Indeed, at the single-neuron level, the highest levels of cell-by-cell correlation were seen in the fear context (FIG. 15D, FIG. 19D; n=5; P<0.01, paired t-test). Additional quantitative properties were assessed for differential representation of the fear and neutral contexts (FIG. 19D-FIG. 19I), revealing that the power-law exponent b provided the largest contribution to this context separation (FIG. 19C, n=5, P<0.01), consistent with the emergence of HC neurons representing aspects of fear memory retrieval. Intriguingly, HC neurons in the fear context (FIG. 15E; shown in dark dots) tended to be neurons that had a low degree of correlated partners in the neutral context (FIG. 15F; FIG. 20), suggesting that the emergence of HC neurons after learning does not stem simply from strengthening of pre-existing correlated cell assemblies.

FIG. 18A-FIG. 18F. Real-time imaging of neural ensembles in 3D hippocampal volumes: Extraction of neural sources and identification of significant transients. a, Head-fixed virtual reality setup. Mice run on an axially-fixed track ball[31] while movements and licking behavior were measured through an optical mouse and a lickometer respectively, both interfaced with the virtual-reality gaming software. For contextual fear conditioning, water-restricted mice were exposed to two contexts with distinct visual, olfactory, tactile, and auditory cues (day 1), and provided aversive air puffs in one context (fear context), but not the other (neutral context) (day 2). Fear memory retrieval in the two contexts were quantified (days 3, 30) by lick suppression. b, Sample mean intensity z projections from raw videos (Scale: 50 μm), with extracted neural sources (segmented cells) from CA2/CA3 for each of the optical sections, along with the first 50 time-series traces. Scale: 300% dF/F, 30 s. c, Identification of significant transients in dF/F traces. Histogram showing the distribution of events occurring at amplitude 2σ above noise (noise calculated on a per cell basis), over a range of event duration in seconds. The number of negative going transients at each amplitude and duration were plotted in red to the left of the ordinate, and positive going transients at each amplitude and duration are plotted in blue to the right. d, The above analysis was repeated for events that occur at an amplitude of 3σ, and e, 4σ. f, False positive rates for 2-, 3-, and 4-σ events (pooled across all neurons in all mice over all FOVs). False positive rate curves were calculated for each σ level by dividing the number of negative events at that level by the number of positive events at that level (Online Methods). Event onset was defined as the time corresponding to dF/F exceeding 2σ, and offset as the time corresponding to dF/F falling below 0.5σ. A decaying exponential was fit by least-squares to the false positive rate values, allowing for the determination of a minimum transient duration at each a level for different confidence levels.

FIG. 19A-FIG. 19J. Cell populations and graph properties of fear and neutral networks in hippocampus during retrieval. a, No context-dependent change in total event amplitude or rate was detected. Top panel: Mean GCaMP6m-detected event amplitude (average dF/F of all significant events; definition of significant event for each neuron as described in Methods) was plotted across days for mice in the fear and neutral contexts (n=5 mice, n.s. in paired t-tests). Bottom panel: Mean GCaMP6m-detected event rate plotted across days for mice in the fear and neutral contexts (n=5 mice, n.s. in paired t-tests). b, Context-dependent changes in individual-neuron and correlated behavior were observed. Top panel: number of active neurons (at least one significant GCaMP6m transient detected within first two min in context) plotted for fear and neutral contexts (n=5 mice, 378±64 for day 3 fear context vs 257±39 for day 3 neutral context; P<0.05, paired t-test, mean±s.d.). Bottom panel: mean number of correlated pairs per neuron (where pairwise Pearson's correlation coefficient>0.3) plotted for fear and neutral contexts (n=5 mice, 18.5±1.8 for day 2 fear context vs 13.4±1.4 for day 2 neutral context; 11.3±0.8 for day 3 fear context vs 13.6±0.5 for day 3 neutral context; P<0.05, paired t-test). c, Fitting histograms from FIG. 15D to an exponential distribution of the form $ae^{-bx}$ demonstrates a power-law (b>1) distribution in day 3 fear context (each red dot represents one mouse) compared to day 3 neutral context (b<1; green dots), that was consistent across all mice (n=5 mice; P<0.01, paired t-test). Many graph properties were calculated for fear vs. neutral context, but the power-law exponent of the degree distribution distinguished fear (red) from neutral (green) most powerfully (discriminants shown: coefficient of the power law exponent=0.78, coefficient of cluster coefficient=0.61, coefficient of mean path length=0.11, with 90% confidence intervals being [0.74, 1.0], [0.1, 0.65], and [0.01, 0.23] respectively). These confidence intervals were obtained using 1000 bootstrapped samples; shown is the best 3D hyperplane separation using a linear support vector machine classifier. d, Histograms of the number of correlated partner neurons existing for each neuron in fear vs neutral context on day 3 (retrieval testing) across mice. The dotted red line indicates correlation threshold (set automatically as mean+1 standard deviation in the number of correlated pairs in the network), to the right of which lie (by definition) the highly correlated or HC neurons. Similar measurements of interest in fear vs. neutral context across mice were calculated and are provided here for other graph invariant properties: e, betweenness centrality; f,g, clique properties; h, strength; i, cluster coefficient; and j, mean path length (all defined in Online Methods). For the above calculations, correlation between two neurons was defined to exist when the pairwise Pearson correlation coefficient exceeded 0.3 (Online Methods). Data are presented as individual data points corresponding to each mouse, with mean±S.D. (*)=p<0.05; ()=p<0.01; (*)=p<0.001, using paired t-tests.

FIG. 20. Functional relationships of fear context-defined HC neurons as appearing in fear vs. neutral context. a-c, Data from all additional mice (beyond the exemplar of FIG. 15E, FIG. 15F) demonstrating that HC neurons (red circles) in the fear context with a high degree of correlated partners (gray edges) when located in the neutral context have a much lower degree of correlated partners (n=4 mice including the example in FIG. 15E, FIG. 15F); mean=60 correlated pairs (standard deviation 19.4) in fear context vs mean=18 correlated pairs (standard deviation 14.2) in neutral context; p<0.01 by paired t-test). Only 4 mice are analyzed here because the exact same FOV (with cell identities) was not captured in fear vs. neutral context for one mouse.

Figure 21:
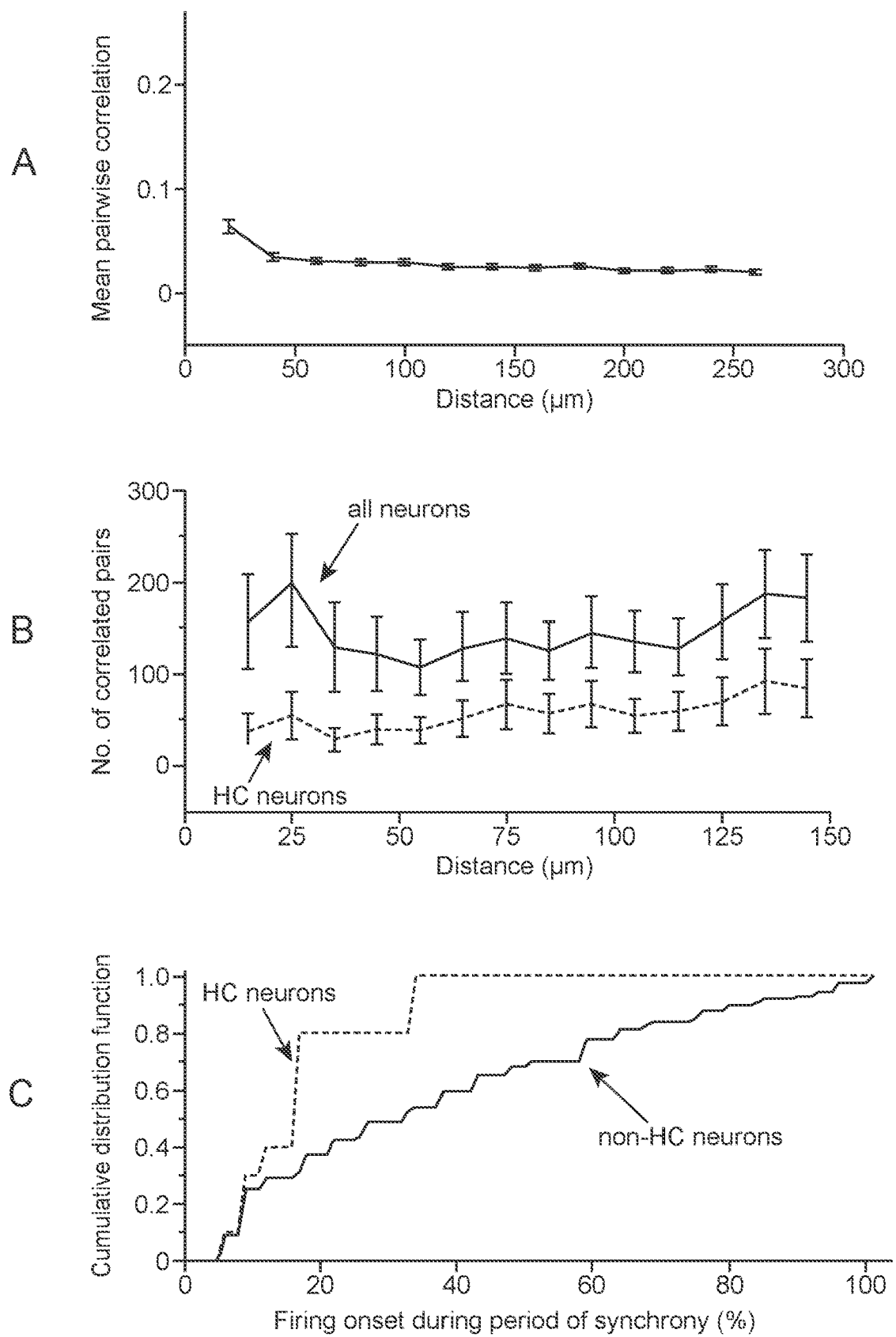
FIG. 21A-21C depict the spatial and temporal organization of HC neurons.

To better understand the significance of these HC neurons, analysis was focused on the activity of the entire network at times when the HC neurons were active. The HC neurons tended to lead rather than lag their correlated pairs (FIG. 15H), which were spatially distributed throughout the volume (FIG. 21A and FIG. 21B). Furthermore, although overall cell-by-cell correlated activity was reduced during the fear retrieval test, significantly more population-wide synchronous events (FIG. 15G and FIG. 15I), which were confirmed to be not related to motion (FIG. 15I and FIG. 15K) and consisted of essentially orthogonal groups of neurons (FIG. 15L, FIG. 23A-FIG. 23E), occurred in the fear context; HC neurons were found to lead these broad synchronous events (FIG. 21C, p<0.001, Kolmogorov-Smirnov two tail test), with 78% of HC neurons active within the first 20% of a synchronous event. This event-leading nature could be consistent with a role for HC neurons in recruiting network activity.

Importantly, the above analyses were designed to limit the effects of potential confounds of slow fluctuations in the signal (e.g., GCaMP6m and $Ca^{2+}$ kinetics) on correlations between neurons. Additionally, a fast non-negative deconvolution analysis[32], for detecting onset of activity while removing slow decay kinetics yielded consistent results as above for the increased pair-wise correlations in fear vs. neutral context, the event-leading nature of HC neurons compared to their correlated pairs, and the increased synchronous events observed in fear vs. neutral context (FIG. 22A-FIG. 22D).

FIG. 21A-FIG. 21C. Spatial and temporal organization of HC neurons. a, Plot of mean pairwise correlation versus mean pairwise distance averaged over all FOVs (all days and all contexts) from all five mice. It was possible to detect a significant but weak relationship between mean correlation and distance (Spearman's correlation=−0.66, P=0.01), which could be a reflection of fine-scale spatial clustering as might be expected of recurrent circuits in CA2/CA3, but would also likely include residual crosstalk between ROIs due to brain motion and common neuropil signal, which is expected and not significantly different from what has been previously observed in hippocampus.[3] b, Plot of number of correlated pairs versus pairwise distance for all neurons (black line), and HC neurons only (gray line). More correlated pairs were found at greater distances for HC neurons (Spearman's=0.84, P=0.002 for HC neurons; Spearman's correlation=0.23, P=0.43 for all neurons). c, Cumulative distributions showing fraction of HC neurons (y-axis) with onset times at various latencies across the time course of synchronous events (x-axis) averaged across all mice, compared to response latencies of non-HC neurons. HC neuron activity appeared significantly earlier than for non-HC neurons during synchronous events (p<0.001, Kolmogorov-Smirnov two-tail test, κ=0.664; note the horizontal resolution of the plot is inversely proportional to length of the synchrony window, and dependent on frame duration; for instance, a 10 s-long synchrony window with frame duration of 333 ms corresponds to a 3.33% resolution per frame).

FIG. 22A-FIG. 22E. Additional analyses: estimation of event onsets using fast non-negative deconvolution, and correlated pair analysis. a, Example pairings of the original GCaMP6m trace (top traces), with the deconvolved trace (bottom traces), shows reliable estimation of event onset from deconvolved data (deconvolution algorithm and parameters detailed further in Online Methods). Scale bar: 150% dF/F, 10 s. b, Original GCaMP6m traces from a representative synchronous event in one animal (left), paired with the deconvolved traces for that same synchronous event (right). Scale bar: 300% dF/F, 10 s. c, The highest-degree node (neuron with the greatest number of correlated pairs) in the day 3 fear context had significantly more correlated pairs than the highest degree node in the day 3 neutral context, significant across n=5 mice (58.8 vs 33.2 pairs, P<0.01, paired t-test). d, Temporal relationship of HC neuron activity onset (set to time 0) compared with onset activity of correlated pairs (binned into 333 ms preceding or succeeding HC activity); n=48 HC neurons. HC's were more likely to lead than lag their correlated pairs (58.5±20% leading vs 24.4±10% lagging; P<0.01, unpaired t-test). e, Significant synchronous activity quantified across five mice: number of synchronous events in the fear context was significantly greater than in the neutral context (5.8±2.9 events in fear context vs 1.2±1.1 in neutral context; P<0.01, paired t-test).

AC-CA Projections Target HC Neurons During Retrieval

These volumetric imaging studies during memory retrieval demonstrate emergence of a sparse set of HC neurons characterized by high correlations and leading of local synchronous events. Such neurons could serve as efficient points of access if preferentially recruited by top-down projections during memory retrieval. To test this idea, it was sought to stimulate AC-CA projections while simultaneously imaging the postsynaptic hippocampal network to directly observe local dynamics. By extensively modifying ReaChR to include ChETA[35]-based and other mutations, a red-shifted opsin termed bReaChES was generated with strong photocurrents, high spike-fidelity (FIG. 24A-FIG. 24K) and robust trafficking in long-range projections (FIG. 17A).

Mice were injected with GCaMP6m in CA3 and bReaChES in anterior cingulate, and implanted with a cannula above CA3 (FIG. 17A) for simultaneous 1P stimulation of projection terminals and 2P imaging of CA3 pyramidal neurons through the same window (FIG. 17B). To test the causal effect of the projection, multiple optical-stimulation trials both before and after fear conditioning, while tracking the same neurons across contexts and days were performed (FIG. 17C). While trial-to-trial variability existed in the number and identity of neurons activated, fear conditioning was found to consistently increase the fraction of cells that were time-locked to onset of optogenetic stimulus of the top-down projection (FIG. 17D, P-0.002, Kolmogorov-Smirnov two-tail test). Finally, recruitment of the memory-associated HC neurons by this projection was directly tested. To do this, it was first established that consistent with earlier results, head-fixed mice were able to learn the contextual fear conditioning task and that stimulation of the AC-CA projection induced fear memory retrieval only after training and not before (FIG. 17E). Quantification over many trials indicated that stimulation of the AC-CA projection recruited relatively few (~5%) HC neurons in either fear or neutral context before training, whereas there was a marked increase (~20%) in the fraction of HC neurons recruited after training; recruitment of non-HC neurons in the fear context, and recruitment of any neurons in the neutral context, remained unchanged and low (FIG. 17F). These results further demonstrated swift reorganization of the functional impact of the AC-CA projection, with preferential recruitment of HC neurons associated with the recently-formed contextual fear memory. Together these findings reveal a means by which top-down circuit influences could organize and engage with salient memory representations to enable efficient retrieval.

FIG. 23A-FIG. 23E. PCA of population trajectories in fear vs. neutral contexts. a, PCA of dF/F traces of all active cells for mouse 2, performed separately for fear and neutral contexts. Population trajectories in the fear context take large, nearly orthogonal, deviations from the center, while neutral context trajectories remain close to the origin. b, 3D reconstruction of the neuronal population showing that neurons participating in each synchronous event {red cells (t=39), green circles (t=92), blue circles (t=200)} are largely non-overlapping and anatomically homogenously distributed throughout the volume. There are a small fraction of neurons participate in all three events (black circles). c,d, Data are shown for another representative mouse. Similar results were seen in all other mice. e, The dF/F traces for a randomly selected set of 30 neurons participating in each of three events are shown, with the greatest amount of overlap seen between t=65 and t=210. Scale bars: 400% dF/F, 20 s.

FIG. 24A-FIG. 24K. bReaChES: Engineering a redshifted opsin for robust projection targeting. a, Schematics of ReaChe and bReaChES. ReaChR is a hybrid of segments from Channelrhopsin-1 (blue, amino acids (aa): 1-95), *Volvox-Channelrhodopsin-1* (red, aa: 96-246, 279-350) and *Volvox-Channelrhodopsin-2* (green, aa: 247-278). The VChR1 segment contains the point mutation Leu171Ile. ReaChR was modified here for enhanced expression and membrane trafficking as well as accelerated channel kinetics, resulting in bReaChES, as follows: The first 51 N-terminal residues were replaced by the first 11 N-terminal residues from Channelrhodopsin-2 (yellow, aa: 1-11) and the last 5 C-terminal residues were removed. Mutation of Glutamate-123 to serine increases speed of channel closure. b, Spectra of $C1V1_{TT}$, bReaChES and ChR2 measured between 400 and 650 nm at 0.65 $mW/mm^2$ in cultured neurons from rat hippocampus (n=6 each). c, Stationary photocurrents at 575 nm ($C1V1_{TT}$ 630±109 pA (s.e.m. throughout figure), ReaChR 963±113 pA, bReaChES 1365±128 pA) and 632 nm ($C1V1_{TT}$ 315±111 pA, ReaChR 1003±95 pA, bReaChES 841±102 pA). Current amplitudes measured at −80 mV and 5 $mW/mm^2$ light intensity respectively. d, Speed of channel closure: value of mono-exponential off-kinetics ($C1V1_{TT}$ 79±3.7 ms, n=26; ReaChR 682±86 ms, n=6; bReaChES 49±4.4 ms, n=25; P<0.0005). e,f, Representative current-clamp traces of ReaChR or bReaChES-expressing cultured neurons excited with 633 nm light (5 ms, 5 $mW/mm^2$). ReaChR kinetics were slow enough that reliable action potential generation was only possible at very low frequencies (e), while the accelerated channel closure of bReaChES allowed reliable spike generation up to 20 Hz (f). g, Representative voltage-clamp and h, current-clamp traces of postsynaptic cells responding to light stimulation (orange) of bReaChES-expressing presynaptic terminals. Pulse length: 5 ms. i, Stationary photocurrents, and j, light-evoked spike probability in opsin-expressing mPFC cells in acute slice ($C1V1_{TT}$: n=11, bReaChES: n=10). k, Light-evoked EPSC amplitude and l, spike probability in postsynaptic cells ($C1V1_{TT}$: n=10, bReaChES: n=18). Light wavelength 575 nm (25 nm bandwidth) and power density 5 $mW/mm^2$.

REFERENCES

1. Kandel E R, Dudai Y, Mayford M R. The Molecular and Systems Biology of Memory. Cell 157, 163-186 (2014).
2. Han J H, Kushner S A, Yiu A P, Cole C J, Matynia A, Brown R A, Neve R L, Guzowski J F, Silva A J, Josselyn S A. Neuronal competition and selection during memory formation. Science, 316, 457-460 (2007).
3. Han J H, Kushner S A, Yiu A P, Hsiang H L, Buch T, Waisman A, Bontempi B, Neve R L, Frankland P W, Josselyn S A. Selective erasure of a fear memory. Science 323, 1492-6 (2009).
4. Yiu A P, Mercaldo V, Yan C, Richards B, Rashid A J, Hsiang H L, Pressey J, Mahadevan V, Tran M M, Kushner S A, Woodin M A, Frankland P W, Josselyn S A. Neurons Are Recruited to a Memory Trace Based on Relative Neuronal Excitability Immediately before Training. Neuron 83, 722-35 (2014).
5. Reijmers L G, Perkins B L, Matsuo N, Mayford M. Localization of a stable neural correlate of associative memory. Science 317, 1230-1233 (2007).
6. Liu X, Ramirez S, Pang P T, Puryear C B, Govindarajan A, Deisseroth K, Tonegawa S. Optogenetic stimulation of a hippocampal engram activates fear memory recall. Nature 484, 381-385 (2012).
7. Garner A R, Rowland D C, Hwang S Y, Baumgaertel K, Roth B L, Kentros C, Mayford M. Generation of a synthetic memory trace. Science 335, 1513-1516 (2012).
8. Ramirez S, Liu X, Lin P A, Suh J, Pignatelli M, Redondo R L, Ryan T J, Tonegawa S. Creating a false memory in the hippocampus. Science 341, 387-391 (2013).
9. Tse D, Takeuchi T, Kakeyama M, Kajii Y, Okuno H, Tohyama C, Bito H, Morris R G. Schema-dependent gene activation and memory encoding in neocortex. Science. 333, 891-5 (2011).
10. Lesburgueres E et al., Early tagging of cortical networks is required for the formation of enduring associative memory. Science 331, 924 (2011).
11. Bero A W, Meng J, Cho S, Shen A H, Canter R G, Ericsson M, Tsai L H. Early remodeling of the neocortex upon episodic memory encoding. Proc Natl Acad Sci USA. 111, 11852-7 (2014).
12. Frankland P W, Bontempi B. The organization of recent and remote memories. Nat. Rev. Neurosci., 6, 119-130 (2005).
13. Ressler, K. & Mayberg, H. Targeting abnormal neural circuits in mood and anxiety disorders: from the laboratory to the clinic. *Nature Neurosci.* 10, 1116-1124 (2007).
14. Taylor, S. et al. Meta-analysis of functional neuroimaging studies of emotion perception and experience in schizophrenia. *Biol. Psychiatry* 71, 136-145 (2012).
15. Wilson, S., Sayette, M. & Fiez, J. Prefrontal responses to drug cues: a neurocognitive analysis. *Nature Neurosci.* 7, 211-214 (2004).
16. Nadel L, Moscovitch M. Memory consolidation, retrograde amnesia and the hippocampal complex. Curr. Opin. Neurobiol. 7, 217-227 (1997).
17. Winocur G, Moscovitch M, Bontempi B. Memory formation and long-term retention in humans and animals: convergence towards a transformation account of hippocampal neocortical interactions. Neuropsychologia, 48, 2339-2356 (2010).

18. Strogatz S H. Exploring complex networks. Nature 410, 268-76 (2001).
19. Barabási A L, Oltvai Z N. Network biology: understanding the cell's functional organization. Nat Rev Genet. 5, 101-13 (2004).
20. Bullmore E, Sporns O. Complex brain networks: graph theoretical analysis of structural and functional systems. Nat Rev Neurosci. 10, 186-98 (2009).
21. Hermundstad A M, Brown K S, Bassett D S, Carlson J M. Learning, memory, and the role of neural network architecture. PLoS Comput Biol. 7 (2011).
22. Wickersham, I. R., Finke, S., Conzelmann, K. K. & Callaway, E. M. Retrograde neuronal tracing with a deletion-mutant rabies virus. *Nature Methods* 2007, 4:47-49.
23. Soudais C, Laplace-Builhe C, Kissa K, Kremer E J. Preferential transduction of neurons by canine adenovirus vectors and their efficient retrograde transport in vivo. FASEB J. 2001, 15:2283-5.
24. Dombeck D A, Harvey C D, Tian L, Looger L L, Tank D W. Functional imaging of hippocampal place cells at cellular resolution during virtual navigation. Nat. Neurosci., 13, 1433-1440 (2010).
25. Mahoney W J, Ayres J J B, One-trial simultaneous and backward fear conditioning as reflected in conditioned suppression of licking in rats. Anim. Learn. Behav. 4, 357-362 (1976).
26. Bouton M E, Bolles R C. Conditioned fear assessed by freezing and by the suppression of three different baselines. Anim. Learn. Behav. 8, 429-434 (1980).
27. Lovett-Barron M, Kaifosh P, Kheirbek M A, Danielson N, Zaremba J D, Reardon T R, Turi G F, Hen R, Zemelman B V, Losonczy A. Dendritic inhibition in the hippocampus supports fear learning. Science 343, 857-63 (2014).
28. Chen T W, Wardill T J, Sun Y, Pulver S R, Renninger S L, Baohan A, Schreiter E R, Kerr R A, Orger M B, Jayaraman V, Looger L L, Svoboda K, Kim D S. Ultrasensitive fluorescent proteins for imaging neuronal activity. Nature 499, 295-300 (2013).
29. Cheng S, Frank L M. New experiences enhance coordinated neural activity in the hippocampus. Neuron. 2008 Jan. 24; 57(2):303-13.
30. Komiyama T, Sato T R, O'Connor D H, Zhang Y X, Huber D, Hooks B M, Gabitto M, Svoboda K. Learning-related fine-scale specificity imaged in motor cortex circuits of behaving mice. Nature 464, 1182-6 (2010).
31. Modi M N, Dhawale A K, Bhalla U S. CA1 cell activity sequences emerge after reorganization of network correlation structure during associative learning. Elife. 2014, 3:e01982.
32. Vogelstein, J. T., Packer, A. M., Machado, T. A., Sippy, T., Babadi, B., Yuste, R., & Paninski, L. Fast nonnegative deconvolution for spike train inference from population calcium imaging. Journal of neurophysiology, 2010, 104: 3691-3704.
33. Yizhar O, Fenno L E, Prigge M, Schneider F, Davidson T J, O'Shea D J, Sohal V S, Goshen I, Finkelstein J, Paz J T, Stehfest K, Fudim R, Ramakrishnan C, Huguenard J R, Hegemann P, Deisseroth K. Neocortical excitation/inhibition balance in information processing and social dysfunction. Nature 477, 171-8 (2011).
34. Lin J Y, Knutsen P M, Muller A, Kleinfeld D, Tsien R Y. ReaChR: a red-shifted variant of channelrhodopsin enables deep transcranial optogenetic excitation. Nat Neurosci. 16, 1499-508 (2013).
35. Gunaydin L A, Yizhar O, Berndt A, Sohal V S, Deisseroth K, Hegemann P. Ultrafast optogenetic control. Nat Neurosci. 13, 387-92 (2010).
36. Goshen I, Brodsky M, Prakash R, Wallace J, Gradinaru V, Ramakrishnan C, Deisseroth K. Dynamics of retrieval strategies for remote memories. Cell. 2011, 147:678-89.
37. Vinje W E, Gallant J L. Sparse coding and decorrelation in primary visual cortex during natural vision. Science, 287, 1273-1276 (2000).
38. Olshausen B A, Field D J. Sparse coding of sensory inputs. Curr. Opin. Neurobiol. 14, 481-487 (2004).
39. L. Yassin, B. L. Benedetti, J. S. Jouhanneau, J. A. Wen, J. F. Poulet, A. L. Barth. An embedded subnetwork of highly active neurons in the neocortex. Neuron 68, 1043-1050 (2010).
40. Gdalyahu A, Tring E, Polack P, Gruver R, Golshani P, Fanselow M S, Silva A J, Trachtenberg J T. Associative Fear Learning Enhances Sparse Network Coding in Primary Sensory Cortex. Neuron 75, 121-132 (2012).
41. Buzsaki G, Geisler C, Henze D A, Wang X-J. Interneuron Diversity series: Circuit complexity and axon wiring economy of cortical interneurons. Trends Neurosci 27, 186-193 (2004).
42. Perin R, Berger T K, Markram H. A synaptic organizing principle for cortical neuronal groups. PNAS 108, 5419-5424 (2011).
43. Bonifazi P, Goldin M, Picardo M A, Jorquera I, Cattani A, Bianconi G, Represa A, Ben-Ari Y, Cossart R. GABAergic hub neurons orchestrate synchrony in developing hippocampal networks. Science. 2009, 326:1419-24.
44. Brecht M, Schneider M, Sakmann B, Margrie T W. Whisker movements evoked by stimulation of single pyramidal cells in rat motor cortex. *Nature* 427, 704-710 (2004).
45. Houweling A R, Brecht M. Behavioural report of single neuron stimulation in somatosensory cortex. *Nature* 451, 65-68 (2008).
46. Li C Y, Poo M-M, Dan Y. Burst spiking of a single cortical neuron modifies global brain state. *Science* 324: 643-646 (2009).
47. Prakash R, Yizhar O, Grewe B, Ramakrishnan C, Wang N, Goshen I, Packer A M, Peterka D S, Yuste R, Schnitzer M J, Deisseroth K. Two-photon optogenetic toolbox for fast inhibition, excitation and bistable modulation. Nat Methods. 9, 1171-9 (2012).
48. Rickgauer J P, Deisseroth K, Tank D W. Simultaneous cellular-resolution optical perturbation and imaging of place cell firing fields. Nat Neurosci. 2014, 17:1816-24.
49. Packer A M, Russell L E, Dalgleish H W, Musser M. Simultaneous all-optical manipulation and recording of neural circuit activity with cellular resolution in vivo. Nat Methods. 2015, 12:140-6.
50. Chung K, Wallace J, Kim S Y, Kalyanasundaram S, Andalman A S, Davidson T J, Mirzabekov J J, Zalocusky K A, Mattis J, Denisin A K, Pak S, Bernstein H, Ramakrishnan C, Grosenick L, Gradinaru V, Deisseroth K. Structural and molecular interrogation of intact biological systems. Nature 497, 332-7 (2013).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant light-activated polypeptide that comprises an amino acid sequence having at least 90% amino acid sequence identity to the amino acid sequence set forth in SEQ ID NO:3, wherein the amino acid sequence comprises serine at position 123 relative to the amino acid sequence set forth in SEQ ID NO:3, and wherein the variant light-activated polypeptide exhibits at least 5-fold increased channel closure kinetics compared to a light-activated polypeptide of SEQ ID NO:1.

2. The variant light-activated polypeptide of claim 1, comprising:
   a) a heterologous membrane trafficking signal;
   b) an endoplasmic reticulum (ER) export signal; or
   c) both a heterologous membrane trafficking signal and an ER export signal.

3. The variant light-activated polypeptide of claim 1, wherein the variant light-activated polypeptide comprises an amino acid sequence having at least 90% amino acid sequence identity to the amino acid sequence set forth in one of SEQ ID NO:4, SEQ ID NO:5, and SEQ ID NO:6.

4. The variant light-activated polypeptide of claim 1, wherein variant light-activated polypeptide evokes action potentials at frequencies of from 5 Hz to 20 Hz when present in a eukaryotic cell and when activated by light of a wavelength of from 600 nm to 700 nm.

5. A nucleic acid comprising a nucleotide sequence encoding the variant light-activated polypeptide of claim 1.

6. A recombinant expression vector comprising the nucleic acid of claim 5.

7. A mammalian cell comprising the variant light-activated polypeptide of claim 1 in the cell membrane, wherein the variant light-activated polypeptide is responsive to light, wherein the variant light-activated polypeptide is capable of mediating a depolarizing current in the cell when the cell is illuminated with light of a wavelength of from about 600 nm to about 700 nm.

8. The variant light-activated polypeptide of claim 1, wherein the variant light-activated polypeptide exhibits at least 10-fold increased channel closure kinetics compared to the light-activated polypeptide of SEQ ID NO:1.

* * * * *